United States Patent [19]
Takiguchi et al.

[11] Patent Number: 5,714,614
[45] Date of Patent: Feb. 3, 1998

[54] THERMAL TRANSFER SHEET

[75] Inventors: Ryohei Takiguchi; Koumei Kafuku; Hiroshi Eguchi, all of Tokyo, Japan

[73] Assignee: Dai Nippon Printing Co., Ltd., Japan

[21] Appl. No.: 715,356

[22] Filed: Sep. 10, 1996

Related U.S. Application Data

[60] Continuation of Ser. No. 297,035, Aug. 29, 1994, abandoned, which is a division of Ser. No. 877,882, May 4, 1992, Pat. No. 5,374,601.

[30] Foreign Application Priority Data

May 10, 1991 [JP] Japan ..................... 3-133236
Feb. 28, 1992 [JP] Japan ..................... 4-75784

[51] Int. Cl.$^6$ ............. C07D 213/73; C07D 213/74; C07D 401/12
[52] U.S. Cl. ............. 546/271; 546/309; 546/312
[58] Field of Search .................. 546/271, 309, 546/312, 297, 35

[56] References Cited

U.S. PATENT DOCUMENTS

| | | | |
|---|---|---|---|
| 4,914,077 | 4/1990 | Shuttleworth et al. | 503/227 |
| 4,939,118 | 7/1990 | Etzbach et al. | 503/227 |
| 5,079,365 | 1/1992 | Sens et al. | 546/119 |
| 5,476,943 | 12/1995 | Komamura et al. | 546/271 |
| 5,612,282 | 3/1997 | Komamura et al. | 503/227 |

FOREIGN PATENT DOCUMENTS

| | | | |
|---|---|---|---|
| 0340722 | 11/1989 | European Pat. Off. | 503/227 |
| 0346729 | 12/1989 | European Pat. Off. | 503/227 |
| 0416434 | 3/1991 | European Pat. Off. | 503/227 |
| 0239292 | 11/1985 | Japan | 503/227 |
| 1489972 | 10/1977 | United Kingdom | 503/227 |

OTHER PUBLICATIONS

E. Klingsberg et al 'The chemistry of Heterocyclic compounds', 1962, Interscience Publishers, New York, USA, vol. 14, Part 3, Chapter IX; "Aminopyridines", pp. 1-178.
Chemical Abstracts, vol. 102, No. 25, 24 Jun. 1985, Columbus, Ohio, US; abstract No. 214472D, A. Matsuura et al: 'A new flurometric method for latamofex in biological materials using 2, 6-diamino-3-nitrospyridine.', p. 3; col. Right.

*Primary Examiner*—Richard L. Raymond
*Attorney, Agent, or Firm*—Parkhurst & Wendel, LLP

[57] ABSTRACT

The present invention provides a pyridine derivative represented by the following formula A or B, a dye produced by coupling the pyridine derivative A or B with an arbitray coupler and a thermal transfer sheet wherein use is made of the dye. In a thermal transfer process wherein use is made of a sublimable dye, the dye and the thermal transfer sheet according to the present invention can form a clear image having a sufficient density and an excellent light fastness.

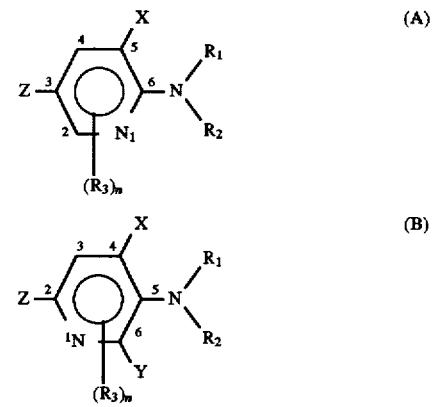

4 Claims, 4 Drawing Sheets

THERMAL TRANSFER SHEET

This is a Continuation of application Ser. No. 08/297,035 filed Aug. 29, 1994, now abandoned, which is a division of application Ser. No. 07/877,882 filed May 4, 1992, now U.S. Pat. No. 5,374,601.

BACKGROUND OF THE INVENTION

1. Field of the Art

The present invention relates to a dye intermediate, a dye and a thermal transfer sheet. More particularly, it is concerned with an intermediate capable of providing a dye excellent in the coloring density, sharpness, light fastness, safety, etc., a dye and a thermal transfer sheet excellent in the above-described properties.

2. Background Art

Various thermal transfer processes are known in the art. Among them, a sublimation transfer process has been practiced which comprises supporting a sublimable dye as a recording agent on a substrate sheet, such as paper, to form a thermal transfer sheet, putting the thermal transfer sheet on a transfer material dyeable with a sublimable dye, for example, a polyester woven fabric, and applying a thermal energy in a pattern form from the back surface of the thermal transfer sheet to transfer the sublimable dye to the transfer material.

In recent years, a proposal has been made on a process wherein various full color images are formed on paper or a plastic film through the use of the above-described sublimation type or thermal transfer system. In this case, a thermal head of a printer is used as heating means, and a number of color dots of three or four colors are transferred to the transfer material, thereby reproducing a full color image of an original by means of the multicolor dots.

Since the color material used is a dye, the image thus formed is very clear and highly transparent, so that the resultant image is excellent in the reproducibility and gradation and the quality of the image is the same as that of an image formed by the conventional offset printing and gravure printing. In this method, it is possible to form an image having a high quality comparable to a full color photographic image.

The most important problem in the thermal transfer process resides in the color density, sharpness and light fastness of the formed image, and no dye which could have sufficiently solved these problems are known in the art.

SUMMARY OF THE INVENTION

Accordingly, an object of the present invention is to provide a thermal transfer sheet which, in a thermal transfer process wherein use is made of a sublimable dye, can provide a clear image having a sufficient density, the formed image being excellent in the light fastness.

The above-described object can be attained by the present invention. Specifically, the present invention provides a pyridine derivative represented by the following formula A or B, a dye produced by coupling the pyridine derivative A or B with any coupler and a thermal transfer sheet using the dye:

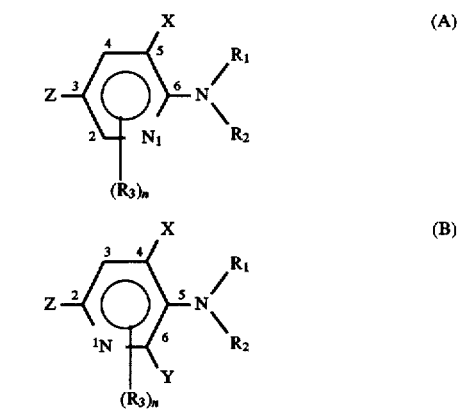

wherein Z stands for an atom or atom group having a coupling capability selected from a hydrogen atom, an amino group, a halogen atom, a nitro group and a nitroso group, $R_1$ and $R_2$ each independently stand for a hydrogen atom or a substituted or unsubstituted alkyl group, vinyl group, allyl group, aryl group, alkoxyalkyl group, aralkyl group, alkoxycarbonylalkyl group, carboxyalkyl group, alkoxycarboxyalkyl group, substituted or unsubstituted cycloalkyl group, substituted or unsubstituted acylamino group, substituted or unsubstituted alkylsulfonylamino group, substituted or unsubstituted oxycarbonyl group, substituted or unsubstituted ureido group, substituted or unsubstituted carbamoyl group, substituted or unsubstituted sulfamoyl group, substituted or unsubstituted heterocyclic group, substituted or unsubstituted acyl, substituted or unsubstituted amino group or substituted or unsubstituted sulfonyl group, provided that $R_1$ and $R_2$ may combine with each other to form a ring or $R_1$ or $R_2$ may combine with X or Y to form a ring; $R_3$ stands for a hydroxyl group, a halogen atom, a cyano group or a substituted or unsubstituted alkyl group, alkylformylamino group, alkylsulfonylamino group, formylamino group, allylformylamino group, sulfonylamino group, allylsulfonylamino group, carbamoyl group, sulfamoyl group, amino group, carboxyl group, alkoxy group or ureido group; and n is an integer of 0 to 3.

DETAILED DESCRIPTION OF THE INVENTION

A heat transfer sheet capable of providing a record image excellent in the coloring density, sharpness and light fastness is provided through the use of a dye having a particular structure.

The present invention will now be described in more detail with reference to the following preferred embodiments.

The pyridine derivative of the present invention is represented by the general formula A or B. For example, 50 g of 2-chloro-5-nitropyridine and 150 ml of diethylamine were placed in a sealed tube and heated at 120° C. for 7 hr. Pure water was added to the precipitated crystal, and the crystal was collected by filtration and recrystallized from 300 ml of methanol to give 53 g of 2-diethylamino-5-nitropyridine (yield: 86%, melting point: 75° to 76° C.).

40 g of the 2-diethylamino-5-nitropyridine was subjected to catalytic reduction in one liter of methanol through the use of 2 g of 10% Pd-C. The catalyst was removed by filtration, and the filtrate was concentrated to give 32 g of 5-amino-2-diethylaminopyridine (yield: 95% oleaginous form).

The dye of the present invention can be produced by coupling the above-described pyridine derivative A or B with any known coupler and represented by the following general formula A' or B'.

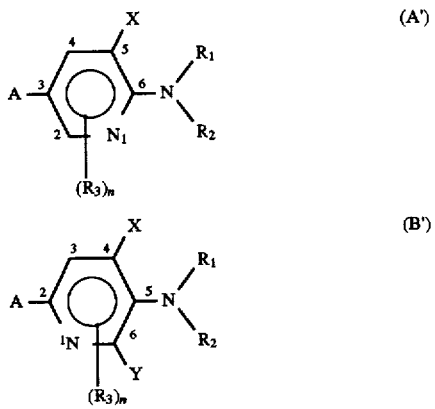

wherein $R_1$ to $R_3$, X, Y and n are as defined above and A stands for a residue of any coupler.

Several processes for producing the above-described dye will now be exemplified.

<SYNTHESIS EXAMPLE 1>

Figure 1:
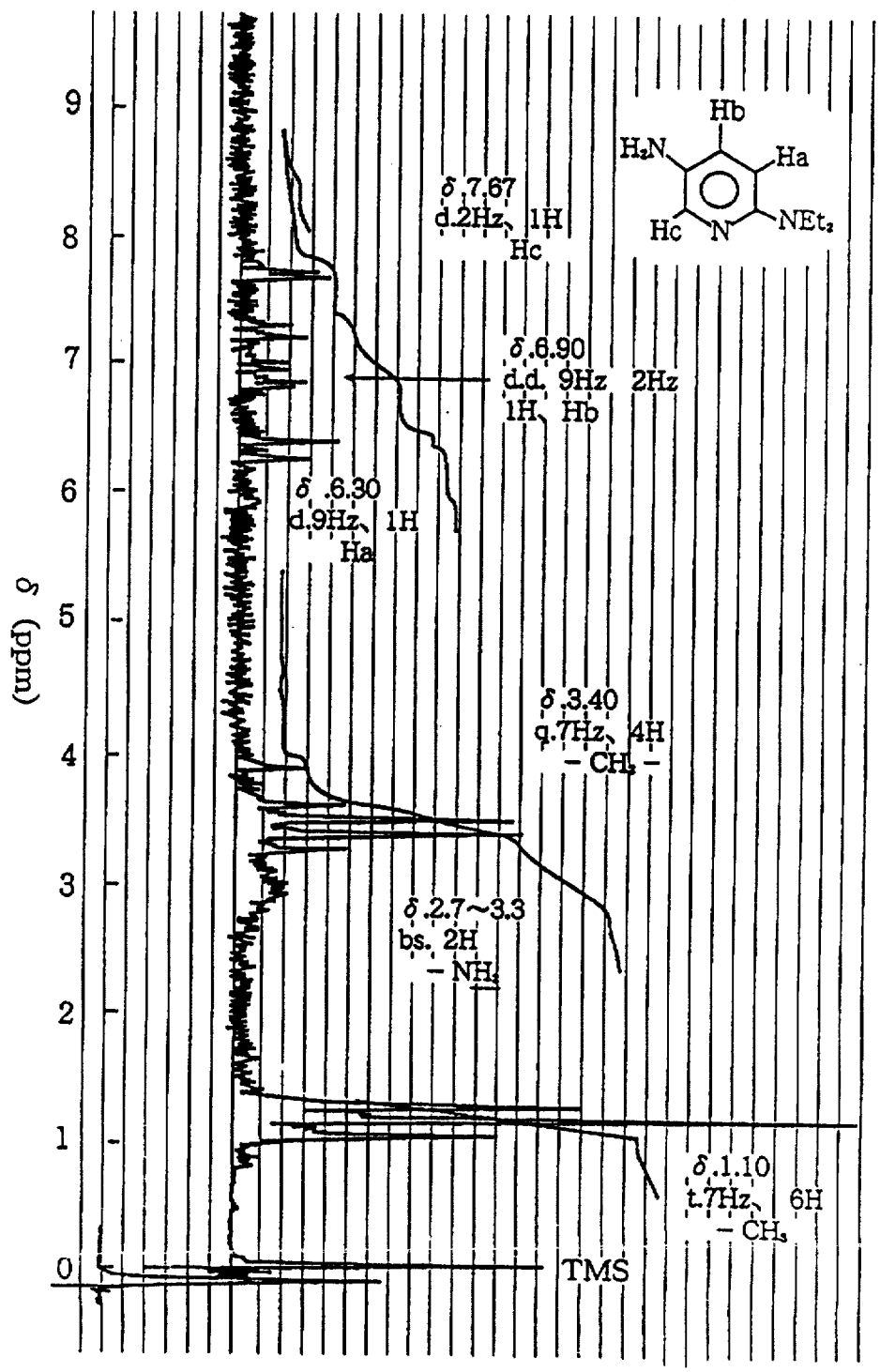
FIG. 1 is a diagram showing the results of H-NMR of the pyridine derivative of the present invention.
Figure 2:
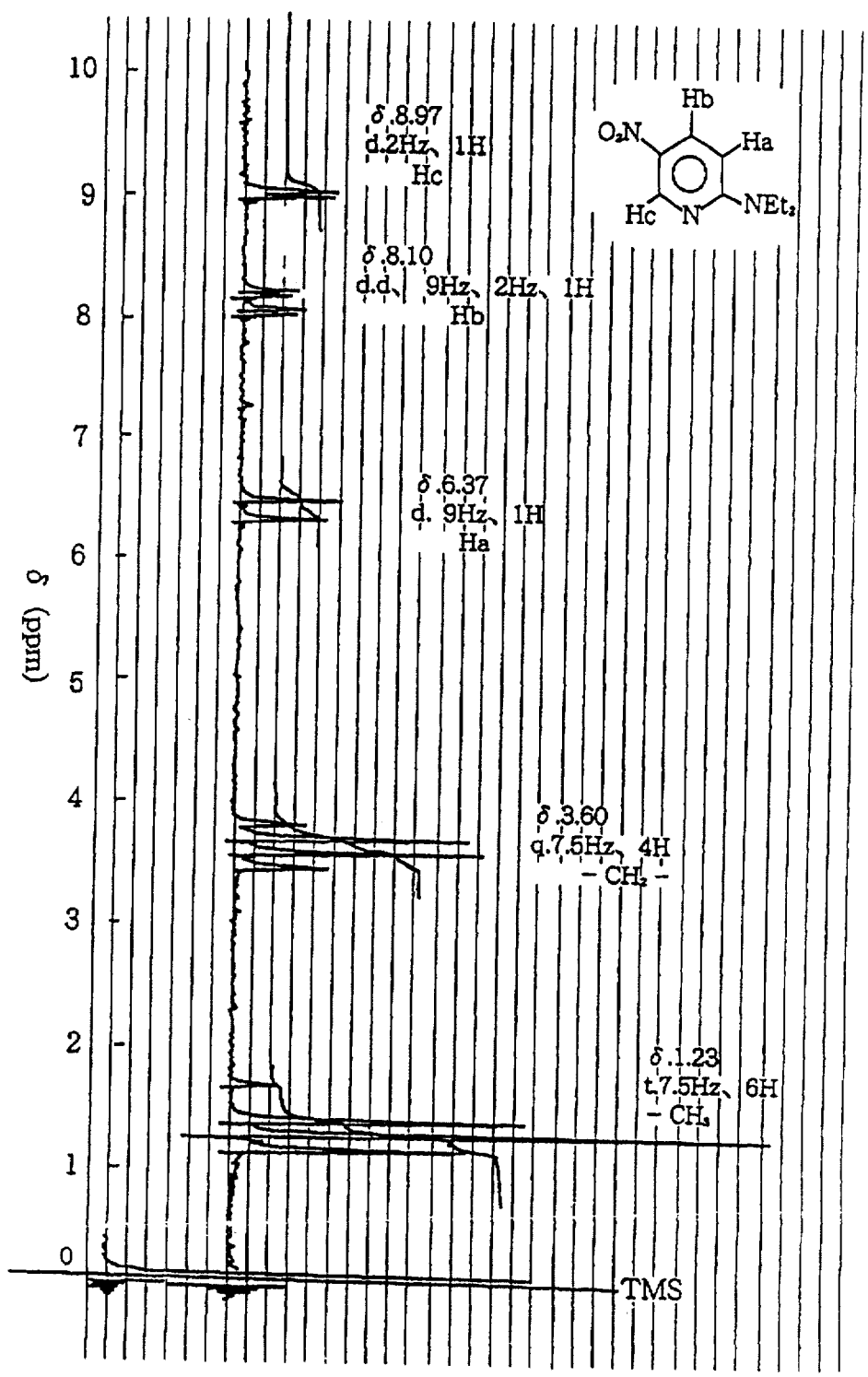
FIG. 2 is a diagram showing the results of H-NMR of the pyridine derivative of the present invention.
Figure 3:
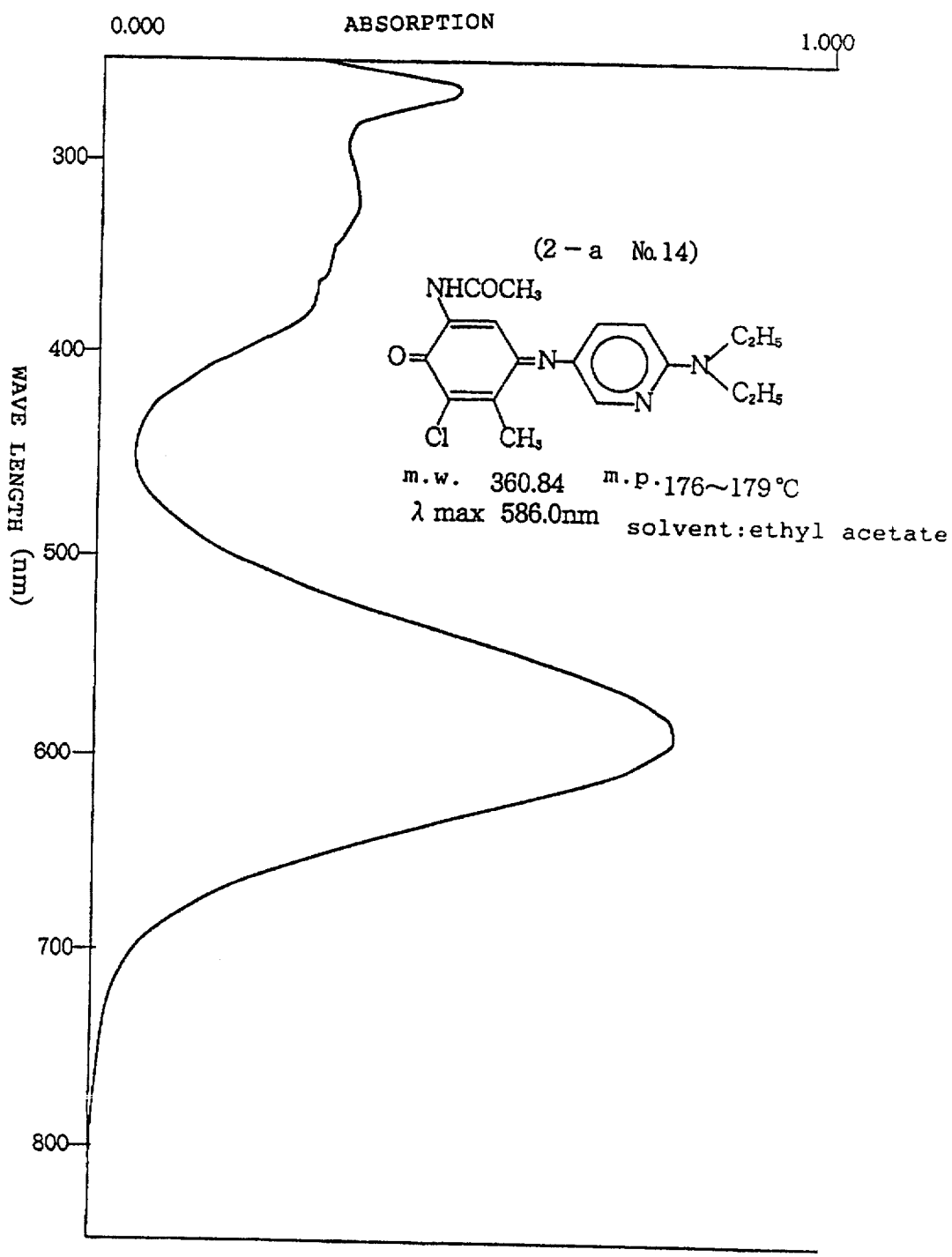
FIG. 3 is a diagram showing a visible absorption spectrum of the dye of the present invention.

7 g of 2-acetylamino-4,6-dichloro-5-methylphenol and 5 g of 5-amino-2-diethylaminopyridine were dissolved in 240 ml of ethanol. 80 ml of an aqueous solution of 15.8 g of sodium carbonate and 60 ml of an aqueous solution of 11.9 g of red prussiate were successively added to the resultant solution with stirring, and the mixture was stirred at room temperature for 2 hr. Thereafter, 300 ml of water was added thereto, and the mixture was stirred for 30 min and extracted with 400 ml of ethyl acetate. The resultant organic layer was separated, washed with water, dried and removed by distillation. The residue was purified by silica gel column chromatography and recrystallized twice from ethanol to give 0.5 g of a dye represented by the following structural formula. The ultraviolet and visible absorption spectrum is shown in FIG. 3.

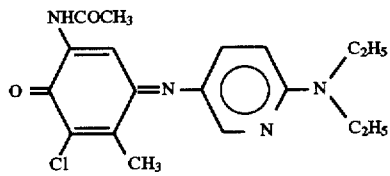

<SYNTHETIC EXAMPLE 2>

Figure 4:
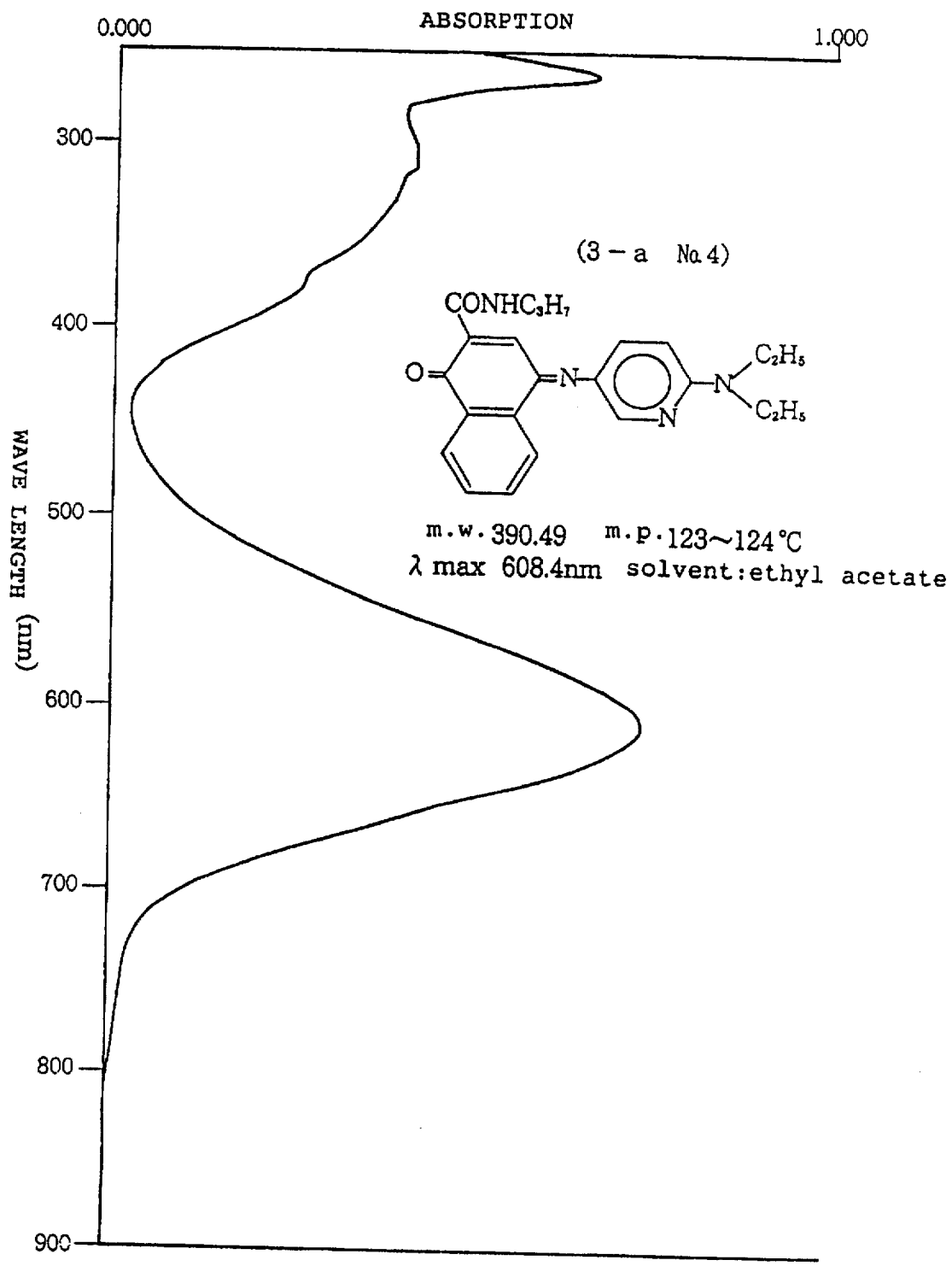
FIG. 4 is a diagram showing a visible absorption spectrum of the dye of the present invention.

5 g of 2-propylamide-1-naphthol and 7.0 g of 5-amino-2-diethylaminopyridine were dissolved in 250 ml of ethanol. 80 ml of an aqueous solution of 15.8 g of sodium carbonate and 60 ml of an aqueous solution of 11.9 g of red prussiate were successively added to the resultant solution with stirring, and the mixture was stirred at room temperature for 2 hr. Thereafter, 300 ml of water was added thereto, and the mixture was stirred for 30 min and extracted with 400 ml of ethyl acetate. The resultant organic layer was separated, washed with water, dried and removed by distillation. The residue was purified by silica gel column chromatography and recrystallized twice from ethanol to give 3.7 g of a dye represented by the following structural formula. The ultraviolet and visible absorption spectrum is shown in FIG. 4.

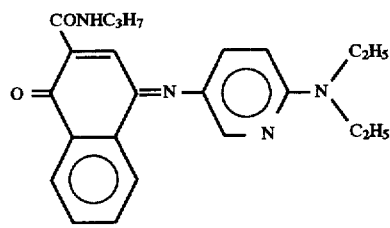

The λmax and molar extinction coefficient (ε) and melting point (mp) of dyes produced in the same manner as that described above are exemplified in Tables 1 to 3.

(1) Dyes having the following structure:

TABLE 1

| No | $R_1$ | $R_2$ | $R_3$ | $R_4$ | $R_6$ | $R_7$ | lmax | e | mp |
|---|---|---|---|---|---|---|---|---|---|
| 1-1 | $-C_2H_5$ | $-C_2H_5$ | 3$-CH_3$ | $-NHCOCH_3$ | $-CH_3$ | $-Cl$ | 610.0 | 24600 | 166 |
| 1-2 | $-C_2H_5$ | $-C_2H_5$ | 5$-CH_3$ | $-NHCOCH_3$ | $-CH_3$ | $-Cl$ | 609.6 | 20200 | 197 |
| 1-3 | $-C_2H_5$ | $-C_2H_5$ | 3,5-diCH$_3$ | $-NHCOCH_3$ | $-CH_3$ | $-Cl$ | 654.0 | 8580 | 197 |
| 1-4 | $-C_2H_5$ | $-C_2H_5$ | $-H$ | $-NHCOCH_3$ | $-CH_3$ | $-Cl$ | 586.0 | 22700 | 178 |

(2) Dyes having the following structure:

TABLE 2

![Structure 2]

| No | $R_1$ | $R_2$ | $R_3$ | $R_4$ | $R_6$ | $R_7$ | γmax | ε | mp |
|---|---|---|---|---|---|---|---|---|---|
| 2-1 | $-C_2H_5$ | $-C_2H_5$ | $-H$ | $-NHCOPh$ | $-CH_3$ | $-Cl$ | 572.0 | 29600 | 168 |

(3) Dyes having the following structure:

TABLE 3

![Structure 3]

| No | $R_1$ | $R_2$ | $R_3$ | $R_4$ | γmax | ε | mp |
|---|---|---|---|---|---|---|---|
| 3-1 | $-C_2H_5$ | $-C_2H_5$ | $-H$ | $-CONHC_3H_7$ | 608.4 | 22500 | 124 |
| 3-2 | $-C_2H_5$ | $-C_2H_5$ | $3-CH_3$ | $-CONHC_3H_7$ | 631.4 | 24200 | 103 |
| 3-3 | $-C_2H_5$ | $-C_2H_5$ | $5-CH_3$ | $-CONHC_3H_7$ | 623.6 | 20800 | 105 |
| 3-4 | $-C_2H_5$ | $-C_2H_5$ | $3-CH_3$ | $-CONHPh$ | 649.6 | 27200 | 196 |
| 3-5 | $-C_2H_5$ | $-C_2H_5$ | $3,5-diCH_3$ | $-CONHC_3H_7$ | 667.6 | 9500 | 183 |
| 3-6 | $-C_2H_5$ | $-C_2H_5$ | $3,5-diCH_3$ | $-CONHPh$ | 684.8 | 11300 | 224 |
| 3-7 | $-C_2H_5$ | $-C_2H_5$ | $5-CH_3$ | $-CONHPh$ | 642.4 | 23200 | 190 |
| 3-8 | $-C_2H_5$ | $-C_2H_5$ | $3-CH_3$ | $-CONH$-allyl | 632.7 | 24600 | 147 |
| 3-9 | $-C_2H_5$ | $-C_2H_5$ | $3-CH_3$ | $-CONH$-2-toluyl | 651.0 | 27700 | 200 |
| 3-10 | $-C_2H_5$ | $-C_2H_5$ | $3-CH_3$ | $-CONH$-4-(n-butylphenyl) | 648.4 | 27600 | 153 |
| 3-11 | $-C_2H_5$ | $-C_2H_5$ | $3-CH_3$ | $-CONH$-2-ethylphenyl | 649.6 | 27800 | 155 |
| 3-12 | $-C_2H_5$ | $-C_2H_5$ | $3-CH_3$ | $-CONH$-3,4-xylyl | 648.4 | 27600 | 174 |
| 3-13 | $-C_4H_9$ | $-C_4H_9$ | $3-CH_3$ | $-CONHPh$ | 654.8 | 29000 | 144 |
| 3-14 | $-C_4H_9$ | $-C_4H_9$ | $3-CH_3$ | $-CONH$-2,4-xylyl | 654.0 | 29100 | 151 |
| 3-15 | $-C_4H_9$ | $-C_4H_8OH$ | $3-CH_3$ | $-CONHC_3H_7$ | 636.8 | 25100 | 85 |
| 3-16 | $-C_2H_5$ | $-C_2H_5$ | $3-CH_3$ | $-CONH$-cyclohexyl | 631.2 | 25400 | 149 |
| 3-17 | $-C_2H_5$ | $-C_2H_4OH$ | $3-CH_3$ | $-CONHC_3H_7$ | 626.4 | 22500 | 156 |
| 3-18 | $-C_2H_5$ | $-C_2H_4OH$ | $3-CH_3$ | $-CONH$-3-toluyl | 645.6 | 25300 | 176 |
| 3-19 | $-C_2H_4OCOCH_3$ | $-C_2H_4OCOCH_3$ | $3-CH_3$ | $-CONHC_3H_7$ | 605.6 | 18700 | 101 |
| 3-20 | $-C_2H_4OCOCH_3$ | $-C_2H_4OCOCH_3$ | $3-CH_3$ | $-CONH$-cyclohexyl | 608.4 | 18900 | 124 |
| 3-21 | $-C_2H_4OCOCH_3$ | $-C_2H_4OCOCH_3$ | $3-CH_3$ | $-CONH$-3-toluyl | 624.8 | 20700 | 135 |
| 3-22 | $-C_2H_5$ | $-C_2H_5$ | $3-CH_3$ | $-CONHC_3H_6OH$ | 631.6 | 23600 | 120 |
| 3-23 | $-C_2H_5$ | $-C_2H_5$ | $3-CH_3$ | $-CONHC_3H_6OCOCH_3$ | 631.6 | 24000 | 111 |
| 3-24 | $-C_2H_5$ | $-C_2H_5$ | $3-CH_3$ | $-CONHC_3H_6OCOOPh$ | 632.8 | 24300 | 111 |
| 3-25 | $-C_2H_5$ | $-C_4H_8OH$ | $3-CH_3$ | $-CONHC_3H_7$ | 634.0 | 24800 | 92 |
| 3-26 | $-C_2H_5$ | $-C_4H_8OH$ | $3-CH_3$ | $-CONH$-cyclohexyl | 635.2 | 23800 | 123 |
| 3-27 | $-C_2H_5$ | $-C_2H_5$ | $-H$ | $-CONH$-3-ethylphenyl | 623.6 | 25800 | 141 |

(4) Dyes having the following structure:

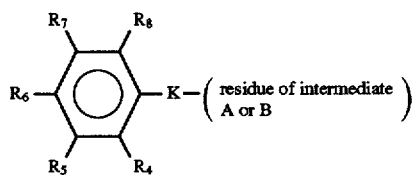

(4)

wherein K stands for $-N=N-$, $R_4$ to $R_8$ stand for a hydrogen atom, a halogen atom, a nitro group, a cyano group or a substituted or unsubstituted alkyl group, alkoxycarbonyl group, alkoxyalkyl group, alkoxycarbonylalkyl group, alkoxy group, cycloalkyl group or alkoxycarboxyalkyl group.

(4-a) Dyes having the following structure:

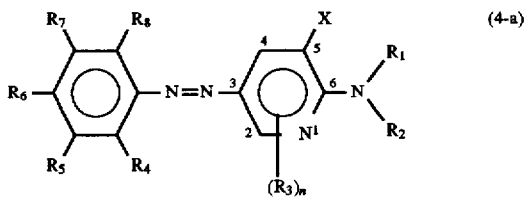

(4-a)

wherein $R_1$ to $R_8$, X and n are as defined above.

Specific examples of the dye 4-a and the performance thereof in the case of use in a thermal transfer sheet are given in the following Table 4-a.

TABLE 4-a

| No. | $R_1$ | $R_2$ | $R_3$ | $R_4$ | $R_5$ |
|---|---|---|---|---|---|
| 1 | —$C_2H_5$ | —$C_2H_5$ | —H | —CN | —H |
| 2 | —$C_2H_5$ | —$C_2H_4OH$ | 2,5-di$CH_3$ | —CN | —H |
| 3 | —$C_2H_5$ | —CH=$CH_2$ | —H | —Cl | —H |
| 4 | —$C_2H_5$ | —Ph | 2-Cl | —Br | —H |
| 5 | —$C_2H_5$ | —CH=CHO$COCH_3$ | 2-NHCO$CH_3$ | —CN | —H |
| 6 | —$C_2H_5$ | —$C_2H_4COOC_3H_7$ | 2-OH | —CN | —H |
| 7 | —$C_2H_5$ | —$C_2H_4OCOC_4H_9$ | 2-NHSO$_2CH_3$ | —Cl | —$CH_3$ |
| 8 | —$C_2H_5$ | —$C_2H_4OCOOPh$ | 2-NHCO$CH_3$ | —CN | —$CH_3$ |
| 9 | —$CH_2Ph$ | —H | 4-NHCO$CH_3$ | —CN | —Cl |
| 10 | —$C_2H_5$ | combining of $R_2$ with —$C_3H_6$—X to form ring | 4-O$C_2H_5$ | —CN | —H |
| 11 | —$C_2H_4OCOCH_3$ | —$C_2H_4OCOCH_3$ | 2-CONH$CH_3$ | —$NO_2$ | —$OCH_3$ |
| 12 | —$C_2H_5$ | —H | 2-$SO_2NHC_3H_7$ | —CN | —H |

| No. | $R_6$ | $R_7$ | $R_8$ | hue | coloring density | light fastness |
|---|---|---|---|---|---|---|
| 1 | —$C_4H_9$ | —H | —CN | orange | 1.53 | ○ |
| 2 | —O$C_2H_4OCH_3$ | —H | —CN | orange | 1.61 | ○ |
| 3 | —$NO_2$ | —H | —Cl | purple | 1.60 | Δ |
| 4 | —O$C_3H_7$ | —H | —CN | orange | 1.52 | Δ |
| 5 | —COO$C_4H_9$ | —H | —CN | orange | 1.55 | ○ |
| 6 | —$C_2H_4OC_3H_7$ | —H | —CN | orange | 1.48 | ○ |
| 7 | —$C_2H_4COOPh$ | —$CH_3$ | —Cl | orange | 1.30 | ○ |
| 8 | —H | —H | —CN | orange | 1.74 | ○ |
| 9 | —O$C_4H_9$ | —Cl | —CN | orange | 1.55 | Δ |
| 10 | -cyclohexyl | —H | —CN | orange | 1.57 | ○ |
| 11 | —CN | —H | —$NO_2$ | purple | 1.70 | Δ |
| 12 | —$NO_2$ | —H | —CN | purple | 1.62 | Δ |

(4-b) Dyes having the following structure:

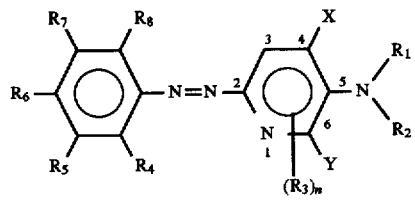

(4-b)

wherein $R_1$ to $R_8$, X, Y and n are as defined above.

Specific exampls of the dye 4-b and the performance thereof in the case of use in a thermal transfer sheet are given in the following Table 4-b.

TABLE 4-b

| No. | $R_1$ | $R_2$ | $R_3$ | $R_4$ | $R_5$ |
|---|---|---|---|---|---|
| 13 | —$C_2H_5$ | —$C_2H_5$ | —H | —CN | |
| 14 | —$C_2H_4OCOCH_3$ | —$C_2H_4OCOCH_3$ | 3-NHCO$CH_3$ | —CN | —H |
| 15 | — | — | — | — | — |
| 16 | —$C_2H_5$ | —CH=CHO$COCH_3$ | 3-NHCO$CH_3$ | —Br | —H |
| 17 | —$C_2H_4Ph$ | —H | 3-O$C_2H_5$ | —CN | —H |
| 18 | —$C_2H_5$ | —$C_2H_4OCOOPh$ | 3-OH | —$NO_2$ | —$OCH_3$ |
| 19 | —$C_2H_4$-cyclohexyl | —H | 3-Cl | —CN | —H |
| 20 | combining of $R_1$ with —$C_3H_6$—X to form ring | combining of $R_2$ with —$C_3H_6$—X to form ring | —NHSO$_2CH_3$ | —CN | —$CH_3$ |
| 21 | combining of $R_1$ with $R_2$ to form ring (—$C_5H_{10}$—) | | 3-CONH$CH_3$ | —CN | —$OCH_3$ |
| 22 | —$C_2H_5$ | —$C_2H_4COOCH_3$ | 3,6-di$CH_3$ | —CN | —H |
| 23 | —$C_2H_5$ | —$C_2H_4OH$ | 3—$CH_3$ | —CN | —Cl |
| 24 | —$C_2H_5$ | —CH=CH$CH_3$ | 6-$CH_3$ | —CN | —H |

TABLE 4-b-continued

| No. | $R_6$ | $R_7$ | $R_8$ | hue | coloring density | light fastness |
|---|---|---|---|---|---|---|
| 13 | -isoC$_3$H$_7$ | —H | —CN | red | 1.95 | Δ |
| 14 | —CH$_3$ | —H | —CN | red | 1.90 | ○ |
| 15 | — | — | — | — | — | — |
| 16 | —OC$_3$H$_7$ | —H | —CN | red | 1.92 | ○ |
| 17 | —C$_2$H$_4$OC$_3$H$_7$ | —H | —CN | red | 1.85 | Δ |
| 18 | —CN | —H | —NO$_2$ | blue | 1.98 | Δ |
| 19 | -cyclohexyl | —H | —CN | red | 1.82 | ○ |
| 20 | —C$_2$H$_4$COOPh | —CH$_3$ | —CN | red | 1.78 | ○ |
| 21 | —H | —OCH$_3$ | —CN | red | 2.07 | ○ |
| 22 | —C$_2$H$_4$-cyclohexyl | —H | —CN | red | 1.93 | ○ |
| 23 | —CH$_3$ | —Cl | —CN | red | 2.05 | ○ |
| 24 | —NO$_2$ | —H | —CN | blue | 2.10 | Δ |

(5) Dyes having the following structure:

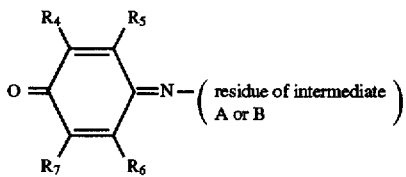

wherein $R_4$ stands for a hydrogen atom, a halogen atom or a substituted or unsubstituted alkyl group, alkoxy group, amino group, ureido group, carbamoyl group, sulfamoyl group, —NHCOR$_8$, —NHCSR$_8$, —NHCON(R$_8$)(R$_9$), —NHCSN(R$_8$)(R$_9$), —NHCOOR$_8$, —NHCSOR$_8$, —NHCONHR$_8$, —NHCSNHR$_8$, —NHSO$_2$R$_8$ or —NHSO$_2$N(R$_8$)(R$_9$) wherein R$_8$ and R$_9$ stand for a hydrogen atom, a halogen atom or a substituted or unsubstituted alkyl group, aryl group, vinyl group, allyl group, cycloalkyl group or aromatic heterocyclic group, provided that R$_8$ and R$_9$ may combine with each other to form a ring; and R$_5$ and R$_7$ stand for a hydrogen atom, a halogen atom or a substituted or unsubstituted alkyl group, alkoxy group, amino group, formylamino group, alkylformylamino group, sulfonylamino group, alkylsulfonylamino group, ureido group, carbamoyl group, sulfamoyl group or carboxyl group.

Specific examples of the dyes represented by the general formula 5 and the performance thereof in the case of use in a thermal transfer sheet which will be described later are given in the following Table 5.

TABLE 5

(5-a), (5-b), (5-c)

| No. | $R_1$ | $R_2$ | $R_3$ | $R_4$ |
|---|---|---|---|---|
| | | 5 common to a to c | | |
| 1 | —C$_2$H$_5$ | —C$_2$H$_5$ | —H | —NHCOCH$_3$ |
| 2 | —C$_2$H$_5$ | —C$_2$H$_5$ | —CH$_3$ | —NHCOC$_2$H$_5$ |
| 3 | —C$_2$H$_5$ | —C$_2$H$_5$ | —NHCOCH$_3$ | —NHCOPh |
| 4 | —C$_2$H$_5$ | —C$_2$H$_5$ | —NHCOC$_2$H$_5$ | —NHCO-cyclohexyl |
| 5 | —C$_2$H$_4$CN | —C$_2$H$_5$ | —OH | —NHCOCH$_3$ |
| 6 | —C$_2$H$_4$OH | —C$_2$H$_5$ | —CH$_3$ | —NHCOCH$_3$ |
| 7 | —C$_2$H$_4$OCH$_3$ | —C$_2$H$_5$ | —CH$_3$ | —NHCOCH$_3$ |
| 8 | —C$_2$H$_4$OCOCH$_3$ | —C$_2$H$_5$ | —CH$_3$ | —NHCOCH$_3$ |

TABLE 5-continued

| | | | | |
|---|---|---|---|---|
| 9 | $-C_2H_4OCOOPh$ | $-C_2H_5$ | $-CH_3$ | $-NHCOCH_3$ |
| 10 | $-C_2H_4OPh$ | $-C_2H_5$ | $-CH_3$ | $-NHCOCH_3$ |
| 11 | $-C_2H_4OCH_2Ph$ | $-C_2H_5$ | $-CH_3$ | $-NHCOCH_3$ |
| 12 | $-C_2H_4OC_2H_4OCH_3$ | $-C_2H_5$ | $-CH_3$ | $-NHCOCH_3$ |
| 13 | $-C_2H_4COOCH_3$ | $-C_2H_5$ | $-CH_3$ | $-NHCOCH_3$ |
| 14 | $-C_2H_5$ | $-C_2H_5$ | $-H$ | $-NHCOCH_3$ |
| 15 | $-C_2H_5$ | $-C_2H_5$ | $-CH_3$ | $-NHCOC_2H_5$ |
| 16 | $-C_2H_5$ | $-C_2H_5$ | $-CH_3$ | $-NHCOCNHCH_3$ |
| 17 | $-C_2H_5$ | $-C_2H_5$ | $-CH_3$ | $-NHSO_2CH_3$ |
| 18 | $-C_2H_5$ | $-C_2H_5$ | $-CH_3$ | $-CONHCH_3$ |
| 19 | $-C_2H_5$ | $-C_2H_5$ | $-CH_3$ | $-SO_2NHCH_3$ |
| 20 | $-C_2H_5$ | $-C_2H_5$ | $-CH_3$ | $-NHCOCH_3$ |
| 21 | $-C_2H_5$ | $-C_2H_5$ | $-CH_3$ | $-NHCOCH_3$ |
| 22 | $-C_2H_5$ | $-C_2H_5$ | $-CH_3$ | $-NHCOCH_3$ |
| 23 | $-C_2H_5$ | $-C_2H_5$ | $-C_2H_5$ | $-NHCOC_6H_{13}$ |
| 24 | $-C_2H_5$ | $-C_2H_5$ | $-NHSO_2CH_3$ | $-NHCOCH_3$ |
| 25 | $-C_2H_4OCH_3$ | $-C_2H_5$ | $-OC_2H_5$ | $-NHCOCH_3$ |
| 26 | $-C_2H_4OCOCH_3$ | $-C_2H_4OCOCH_3$ | $-CH_3$ | $-NHCOPh$ |
| 27 | $-C_2H_4OCOCH_3$ | $-C_2H_4OCOCH_3$ | $-NHCOCH_3$ | $-NHCOPh$ |
| 28 | $-C_2H_5$ | $-C_2H_5$ | $-CH_3$ | $-NHC_2H_5$ |
| 29 | $-C_2H_5$ | $-C_2H_5$ | $-NHCONHCH_3$ | $-N(C_2H_5)_2$ |
| 30 | $-C_2H_4OCH_3$ | $-C_2H_5$ | $-CH_3$ | $-Cl$ |
| 31 | $-C_2H_4OCH_3$ | $-C_2H_5$ | $-CH_3$ | $-OH$ |
| 32 | $-C_2H_4OCH_3$ | $-C_2H_5$ | $-COOCH_3$ | $-H$ |
| 33 | $-C_2H_5$ | $-H$ | $-CH_3$ | $-NHCOCH_3$ |
| 34 | $-C_2H_5$ | $-C_2H_5$ | $-CH_3$ | $-CONHCH_3$ |
| 35 | $-C_2H_5$ | $-C_2H_5$ | $-CH_3$ | $-CONHCH_3$ |
| 36 | $-C_2H_5$ | $-C_2H_5$ | $-CH_3$ | $-CONHCH_3$ |
| 37 | $-C_2H_5$ | $-C_2H_5$ | $-OH$ | $-CONHCH_3$ |
| 38 | $-C_2H_5$ | $-C_2H_5$ | $-NHCONHC_2H_5$ | $-NHCOCH_3$ |
| 39 | $-C_2H_5$ | $-C_2H_5$ | $-NHCOCH_3$ | $-CONHCH_3$ |
| 40 | $-C_2H_5$ | $-C_2H_5$ | $-NHSO_2CH_3$ | $-CONHCH_3$ |
| 41 | $-C_2H_5$ | $-C_2H_5$ | $-NHCOCH_3$ | $-CONHCH_3$ |
| 42 | $-C_2H_5$ | $-C_2H_5$ | $-CH_3$ | $-CONHCH_3$ |
| 43 | $-C_2H_5$ | $-C_2H_5$ | $-CH_3$ | $-CONHCH_3$ |
| 44 | $-C_2H_5$ | $-C_2H_5$ | $-CH_3$ | $-CONHCH_3$ |
| 45 | $-C_2H_5$ | $-C_2H_5$ | $-CH_3$ | $-CONHCH_3$ |
| 46 | $-C_2H_5$ | $-C_2H_5$ | $-CH_3$ | $-CONHCH_3$ |
| 47 | $-C_2H_5$ | $-C_2H_5$ | $-CH_3$ | $-CONHCH_3$ |
| 48 | $-C_2H_5$ | $-C_2H_5$ | $-CH_3$ | $-SO_2NHCH_3$ |
| 49 | $-C_2H_5$ | $-C_2H_5$ | $-NHCOCH_3$ | $-SO_2NHCH_3$ |
| 50 | $-C_2H_5$ | $-C_2H_5$ | $-NHCOCH_3$ | $-SO_2NHCH_3$ |
| 51 | $-C_2H_5$ | $-C_2H_5$ | $-NHSO_2CH_3$ | $-SO_2NHCH_3$ |
| 52 | $-C_2H_4OCH_3$ | $-C_2H_4OCH_3$ | $-NHCOCH_3$ | $-SO_2NHCH_3$ |
| 53 | $-C_2H_5$ | $-C_2H_5$ | $-CH_3$ | $-NHCOCH_2Ph$ |
| 54 | $-C_2H_5$ | $-C_2H_5$ | $-NHCOPh$ | $-NHCOCH_2Ph$ |
| 55 | $-C_2H_5$ | $-C_2H_5$ | $-CH_3$ | $-NHCOOC_2H_5$ |
| 56 | $-C_2H_5$ | $-C_2H_5$ | $-CH_3$ | $-NHCOOCH_2Ph$ |
| 57 | $-C_2H_5$ | $-C_2H_5$ | $-CH_3$ | $-NHCOCOC_2H_5$ |
| 58 | $-C_2H_5$ | $-C_2H_5$ | $-CH_3$ | $-NHCSOC_2H_5$ |
| 59 | $-C_2H_5$ | $-C_2H_5$ | $-CH_3$ | $-NHCO$-thienyl (2) |
| 60 | $-C_2H_5$ | $-C_2H_5$ | $-CH_3$ | $-NHCO$-thienyl (3) |
| 61 | $-C_2H_5$ | $-C_2H_5$ | $-CH_3$ | $-NHCOCH2$-thienyl (3) |
| 62 | $-C_2H_5$ | $-C_2H_5$ | $-CH_3$ | $-NHCOCH2$-thienyl (2) |
| 63 | $-C_2H_5$ | $-C_2H_5$ | $-CH_3$ | $-NHCO$-furyl (2) |
| 64 | $-C_2H_5$ | $-C_2H_5$ | $-CH_3$ | $-NHCO-Ph-CH_3$ (4) |
| 65 | $-C_2H_5$ | $-C_2H_5$ | $-CH_3$ | $-NHCO-Ph$-cyclohexyl (4) |
| 66 | $-C_2H_5$ | $-C_2H_5$ | $-CH_3$ | $-NHCO$-pyrrolyl (1) |
| 67 | $-C_2H_5$ | $-C_2H_5$ | $-CH_3$ | $-NHCO$-morpholyl (1) |
| 68 | $-C_2H_5$ | $-C_2H_5$ | $-CH_3$ | $-NHCO$-pyrrolidonyl (1) |
| 69 | $-C_2H_5$ | $-C_2H_5$ | $-CH_3$ | $-NHCO$-cyclopropane |
| 70 | $-C_2H_5$ | $-C_2H_5$ | $-CH_3$ | $-NHCOCH_3$ |
| 71 | $-C_2H_5$ | $-C_2H_5$ | $-CH_3$ | $-NHCOCH_3$ |
| 72 | $-C_2H_5$ | $-C_2H_5$ | $-CH_3$ | $-NHCOCH_3$ |
| 73 | $-C_2H_5$ | $-C_2H_5$ | $-CH_3$ | $-NHSO_2CH_3$ |
| 74 | Combining of $R_1$ with $R_2$ to form ring ($-C_5H_{10}-$) | | $-CH_3$ | $-NHCOPh$ |
| 75 | Combining of $R_1$ with $R_2$ to form ring ($-C_2H_4-O-C_2H_4-$) | | $-CH_3$ | $-NHCOPh$ |
| 76 | Combining of $R_1$ with $R_2$ to form ring ($-C_4H_8-$) | | $-CH_3$ | $-NHCOCH_3$ |

5-a,b

| | | | | |
|---|---|---|---|---|
| 77 | Combining of X with $R_1$ to form ring ($-C_3H_6-$) | $-C_2H_5$ | $-H$ | $-NHCOCH_3$ |
| 78 | Combining of X with $R_1$ to form ring ($-C_3H_6-$) | $-C_2H_5$ | $-CH_3$ | $-NHCOCH_3$ |
| 79 | Combining of X with $R_1$ to form ring ($-C_3H_6-$) | $-C_2H_5$ | $-CH_3$ | $-NHCOCH_3$ |

TABLE 5-continued

| | | | | |
|---|---|---|---|---|
| 80 | Combining of X with $R_1$ to form ring ($-C_3H_6-$) | $-H$ | $-CH_3$ | $-NHCOCH_3$ |
| 81 | Combining of X with $R_1$ to form ring ($-C_3H_6-$) | $-C_2H_4OCOCH_3$ | $-CH_3$ | $-NHCOPh$ |
| 82 | Combining of X with $R_1$ to form ring ($-C_3H_6-$) | $-C_2H_4OCH_3$ | $-CH_3$ | $-NHCOPh$ |
| 83 | Combining of X with $R_1$ to form ring ($-C_3H_6-$) | $-C_2H_4OCH_3$ | $-CH_3$ | $-NHSO_2CH_3$ |
| 84 | Combining of X with $R_1$ to form ring ($-C_3H_6-$) | $-C_2H_4OH$ | $-OH$ | $-NHCOCH_3$ |
| 85 | Combining of X with $R_1$ to form ring ($-C_3H_6-$) | $-C_2H_4CN$ | $-NHCOCH_3$ | $-NHCOCH_3$ |
| 86 | Combining of X with $R_1$ to form ring ($-C_3H_6-$) | $-CH_3$ | $-C_2H_5$ | $-NHCOOCH_3$ |
| 87 | Combining of X with $R_1$ to form ring ($-C_3H_6-$) | $-C_2H_5$ | $-CH_3$ | $-CONHCH_3$ |
| 88 | Combining of X with $R_1$ and Y with $R_2$ to form $-C_3H_6-$ | | $-CH_3$ | $-NHCOCH_3$ |
| 89 | Combining of X with $R_1$ and Y with $R_2$ to form $-C_3H_6-$ | | $-NHCOCH_3$ | $-NHCOPh$ |
| 90 | Combining of X with $R_1$ and Y with $R_2$ to form $-C_3H_6-$ | | $-CH_3$ | $-NHCOPh$ |
| 91 | Combining of X with $R_1$ and Y with $R_2$ to form $-C_3H_6-$ | | $-C_2H_5$ | $-NHCOPh$ |

5-a,b,c

| | | | | |
|---|---|---|---|---|
| 92 | $-CH=CH_2$ | $-C_2H_5$ | $-CH_3$ | $-NHCOPh$ |
| 93 | $-CH_2CH=CH_2$ | $-C_2H_5$ | $-CH_3$ | $-NHCOPh$ |
| 94 | $-Ph$ | $-C_2H_5$ | $-CH_3$ | $-NHCOPh$ |
| 95 | $-$cyclohexyl | $-C_2H_5$ | $-CH_3$ | $-NHCOPh$ |
| 96 | $-$cyclopentyl | $-C_2H_5$ | $-CH_3$ | $-NHCOPh$ |
| 97 | $-N(C_2H_5)COCH_3$ | $-C_2H_5$ | $-CH_3$ | $-NHCOPh$ |
| 98 | $-N(C_2H_5)COPh$ | $-C_2H_5$ | $-CH_3$ | $-NHCOPh$ |
| 99 | $-N(C_2H_5)SO_2CH_3$ | $-C_2H_5$ | $-CH_3$ | $-NHCOPh$ |
| 100 | $-N(C_2H_5)SO_2Ph$ | $-C_2H_5$ | $-CH_3$ | $-NHCOPh$ |
| 101 | $-NHCONHCH_3$ | $-C_2H_5$ | $-CH_3$ | $-NHCOPh$ |
| 102 | $-N(CH_3)CONHCH_3$ | $-C_2H_5$ | $-CH_3$ | $-NHCOPh$ |
| 103 | $-N(C_2H_5)CONHPh$ | $-C_2H_5$ | $-CH_3$ | $-NHCOPh$ |
| 104 | $-CONHCH_3$ | $-C_2H_5$ | $-CH_3$ | $-NHCOPh$ |
| 105 | $-CONHC_2H_5$ | $-C_2H_5$ | $-CH_3$ | $-NHCOPh$ |
| 106 | $-CON(C_2H_5)_2$ | $-C_2H_5$ | $-CH_3$ | $-NHCOPh$ |
| 107 | $-CON(C_4H_9\text{-}n)_2$ | $-C_2H_5$ | $-CH_3$ | $-NHCOPh$ |
| 108 | $-SO_2NHC_2H_5$ | $-C_2H_5$ | $-CH_3$ | $-NHCOPh$ |
| 109 | $-SO_2N(C_4H_9\text{-}n)_2$ | $-C_2H_5$ | $-CH_3$ | $-NHCOPh$ |
| 110 | $-$2-pyridyl | $-C_2H_5$ | $-CH_3$ | $-NHCOPh$ |
| 111 | $-$4-pyridyl | $-C_2H_5$ | $-CH_3$ | $-NHCOPh$ |
| 112 | $-$4-methyl-2-pyridyl | $-C_2H_5$ | $-CH_3$ | $-NHCOPh$ |
| 113 | $-$2-thienyl | $-C_2H_5$ | $-CH_3$ | $-NHCOPh$ |
| 114 | $-$3-thienyl | $-C_2H_5$ | $-CH_3$ | $-NHCOPh$ |
| 115 | $-$2-furyl | $-C_2H_5$ | $-CH_3$ | $-NHCOPh$ |
| 116 | $-$3-furyl | $-C_2H_5$ | $-CH_3$ | $-NHCOPh$ |
| 117 | $-$2-pyrrolyl | $-C_2H_5$ | $-CH_3$ | $-NHCOPh$ |
| 118 | $-$2-imidazolyl | $-C_2H_5$ | $-CH_3$ | $-NHCOPh$ |
| 119 | $-$2-indolyl | $-C_2H_5$ | $-CH_3$ | $-NHCOPh$ |
| 120 | $-$2-pyrrolidinyl | $-C_2H_5$ | $-CH_3$ | $-NHCOPh$ |
| 121 | $-$2-imidazolidinyl | $-C_2H_5$ | $-CH_3$ | $-NHCOPh$ |
| 122 | $-$2-pyrazolidinyl | $-C_2H_5$ | $-CH_3$ | $-NHCOPh$ |
| 123 | $-$2-piperidyl | $-C_2H_5$ | $-CH_3$ | $-NHCOPh$ |
| 124 | $-$4-piperidyl | $-C_2H_5$ | $-CH_3$ | $-NHCOPh$ |
| 125 | $-$morpholino | $-C_2H_5$ | $-CH_3$ | $-NHCOPh$ |
| 126 | $-COC_2H_5$ | $-C_2H_5$ | $-CH_3$ | $-NHCOPh$ |
| 127 | $-COPh$ | $-C_2H_5$ | $-CH_3$ | $-NHCOPh$ |
| 128 | $-N(C_2H_5)_2$ | $-C_2H_5$ | $-CH_3$ | $-NHCOPh$ |
| 129 | $-SO_2C_4H_9\text{-}n$ | $-C_2H_5$ | $-CH_3$ | $-NHCOPh$ |
| 130 | $-SO_2Ph$ | $-C_2H_5$ | $-CH_3$ | $-NHCOPh$ |
| 131 | $-$2-acetylaminocyclohexyl | $-C_2H_5$ | $-CH_3$ | $-NHCOC_3H_7$ |
| 132 | $-$2-tolyl | $-C_2H_5$ | $-CH_3$ | $-NHCOC_3H_7$ |
| 133 | $-$4-tolyl | $-C_2H_5$ | $-H$ | $-NHCOPh$ |
| 134 | $-$4-methyl-2-pyridyl | $-C_2H_5$ | $-CH_3$ | $-NHCOPh$ |
| 135 | $-$2-methyl-4-pyridyl | $-C_2H_5$ | $-CH_3$ | $-NHCOPh$ |
| 136 | $-CON(C_4H_9\text{-}n)_2$ | $-C_2H_5$ | $-CH_3$ | $-NHCOC_3H_7$ |
| 137 | $-NHCOOC_2H_5$ | $-C_2H_5$ | $-CH_3$ | $-NHCOC_3H_7$ |
| 138 | $-COOPh$ | $-C_2H_5$ | $-CH_3$ | $-NHCOC_3H_7$ |
| 139 | $-COOCH_2Ph$ | $-C_2H_5$ | $-CH_3$ | $-NHCOC_3H_7$ |
| 140 | $-NHCOO$-pyridyl (2) | $-C_2H_5$ | $-CH_3$ | $-NHCOPh$ |
| 141 | $-COCH_2Ph$ | $-C_2H_5$ | $-CH_3$ | $-NHCOC_3H_7$ |
| 142 | $-$3-nicotinoyl | $-C_2H_5$ | $-CH_3$ | $-NHCOPh$ |
| 143 | $-$2-nicotinoyl | $-C_2H_5$ | $-CH_3$ | $-NHCOPh$ |

TABLE 5-continued

| | | | | |
|---|---|---|---|---|
| 144 | —4-nicotinoyl | —$C_2H_5$ | —$CH_3$ | —NHCOPh |
| 145 | —2-thenoyl | —$C_2H_5$ | —$CH_3$ | —NHCOPh |
| 146 | —4-toluoyl | —$C_2H_5$ | $CH_3$ | —NHCOPh |

| No. | $R_6$ | $R_7$ | hue | coloring density | light fastness |
|---|---|---|---|---|---|
| (5-a) | | | | | |
| 1 | —H | —H | blue | 1.85 | Δ |
| 2 | —$CH_3$ | —H | blue | 1.82 | Δ |
| 3 | —H | —Cl | blue | 1.76 | Δ |
| 4 | —$C_2H_5$ | —Cl | blue | 1.68 | ○ |
| 5 | —$CH_3$ | —Cl | blue | 1.69 | ○ |
| 6 | —$CH_3$ | —Cl | blue | 1.83 | ○ |
| 7 | —$CH_3$ | —Cl | blue | 1.77 | ○ |
| 8 | —$CH_3$ | —Cl | blue | 1.72 | ○ |
| 9 | —$CH_3$ | —Cl | blue | 1.62 | ○ |
| 10 | —$CH_3$ | —Cl | blue | 1.63 | ○ |
| 11 | —$CH_3$ | —Cl | blue | 1.60 | ○ |
| 12 | —$CH_3$ | —Cl | blue | 1.73 | ○ |
| 13 | —$CH_3$ | —Cl | blue | 1.84 | ○ |
| 14 | —$CH_3$ | —Cl | blue | 1.69 | ○ |
| 15 | —$CH_3$ | —Cl | blue | 1.88 | ○ |
| 16 | —$CH_3$ | —Cl | blue | 1.80 | ○ |
| 17 | —$CH_3$ | —Cl | blue | 1.78 | ○ |
| 18 | —$CH_3$ | —Cl | blue | 1.63 | ○ |
| 19 | —$CH_3$ | —Cl | blue | 1.66 | ○ |
| 20 | —$N(CH_3)_2$ | —Cl | blue | 1.74 | ○ |
| 21 | —$N(C_2H_5)_2$ | —Cl | blue | 1.80 | ○ |
| 22 | —$NHCOCH_3$ | —Cl | blue | 1.82 | ○ |
| 23 | —$CH_3$ | —Cl | blue | 1.77 | ○ |
| 24 | —$C_2H_5$ | —Cl | blue | 1.71 | ○ |
| 25 | —$C_2H_5$ | —Cl | blue | 1.83 | ○ |
| 26 | —$CH_3$ | —Cl | blue | 1.66 | ○ |
| 27 | —$CH_3$ | —Cl | blue | 1.68 | ○ |
| 28 | —$C_2H_5$ | —Cl | blue | 1.92 | ○ |
| 29 | —$C_2H_5$ | —Cl | blue | 1.81 | ○ |
| 30 | —H | —$CH_3$ | blue | 2.00 | Δ |
| 31 | —OH | —H | blue | 1.94 | Δ |
| 32 | —H | —H | blue | 1.96 | Δ |
| 33 | —$CH_3$ | —Cl | blue | 1.94 | ○ |
| 34 | —H | —H | blue | 1.88 | Δ |
| 35 | —$CH_3$ | —H | blue | 1.92 | ○ |
| 36 | —$CH_3$ | —Cl | blue | 1.83 | ○ |
| 37 | —$CH_3$ | —Cl | blue | 1.84 | ○ |
| 38 | —$CH_3$ | —Cl | blue | 1.69 | ○ |
| 39 | —$CH_3$ | —Cl | blue | 1.68 | ○ |
| 40 | —$CH_3$ | —Cl | blue | 1.74 | ○ |
| 41 | —$NHCH_3$ | —Cl | blue | 1.77 | ○ |
| 42 | —$N(CH_3)2$ | —Cl | blue | 1.68 | ○ |
| 43 | —$NHCOCH_3$ | —Cl | blue | 1.64 | ○ |
| 44 | —NHPh | —Cl | blue | 1.63 | ○ |
| 45 | —NHPh | —H | blue | 1.69 | ○ |
| 46 | —$N(C_2H_5)_2$ | —H | blue | 1.74 | ○ |
| 47 | —$CONHCH_3$ | —Cl | blue | 1.71 | ○ |
| 48 | —$CH_3$ | —Cl | blue | 1.82 | ○ |
| 49 | —$C_2H_5$ | —Cl | blue | 1.80 | ○ |
| 50 | —H | —$CH_3$ | blue | 1.70 | Δ |
| 51 | —$C_2H_5$ | —H | blue | 1.73 | ○ |
| 52 | —$CH_3$ | —Cl | blue | 1.66 | ○ |
| 53 | —$CH_3$ | —Cl | blue | 1.78 | ○ |
| 54 | —$CH_3$ | —Cl | blue | 1.71 | ○ |
| 55 | —$CH_3$ | —Cl | blue | 1.77 | ○ |
| 56 | —$CH_3$ | —Cl | blue | 1.70 | ○ |
| 57 | —$C_2H_5$ | —$CH_3$ | blue | 1.74 | Δ |
| 58 | —$CH_3$ | —Cl | blue | 1.78 | ○ |
| 59 | —$CH_3$ | —Cl | blue | 1.77 | ○ |
| 60 | —$CH_3$ | —Cl | blue | 1.77 | ○ |
| 61 | —$CH_3$ | —Cl | blue | 1.79 | ○ |
| 62 | —$CH_3$ | —Cl | blue | 1.78 | ○ |
| 63 | —$CH_3$ | —Cl | blue | 1.74 | ○ |
| 64 | —$CH_3$ | —Cl | blue | 1.72 | ○ |
| 65 | —$CH_3$ | —Cl | blue | 1.74 | ○ |
| 66 | —$CH_3$ | —Cl | blue | 1.77 | ○ |
| 67 | —$CH_3$ | —Cl | blue | 1.68 | ○ |
| 68 | —$CH_3$ | —Cl | blue | 1.71 | ○ |
| 69 | —$CH_3$ | —Cl | blue | 1.88 | ○ |
| 70 | —Cl | —Cl | blue | 1.74 | ○ |
| 71 | —Cl | —$CH_3$ | blue | 1.83 | ○ |

TABLE 5-continued

| | | | | | |
|---|---|---|---|---|---|
| 72 | —CH₃ | —NHCOCH₃ | blue | 1.78 | Δ |
| 73 | —CH₃ | —NHCOCH₃ | blue | 1.72 | Δ |
| 74 | —CH₃ | —Cl | blue | 1.78 | ○ |
| 75 | —CH₃ | —Cl | blue | 1.74 | ○ |
| 76 | —CH₃ | —Cl | blue | 1.76 | ○ |
| 77 | —CH₃ | —Cl | blue | 1.84 | ○ |
| 78 | —H | —H | blue | 1.96 | Δ |
| 79 | —CH₃ | —H | blue | 1.90 | Δ |
| 80 | —CH₃ | —Cl | blue | 1.88 | ○ |
| 81 | —CH₃ | —Cl | blue | 1.72 | ○ |
| 82 | —CH₃ | —Cl | blue | 1.84 | ○ |
| 83 | —C₂H₅ | —Cl | blue | 1.79 | ○ |
| 84 | —CH₃ | —Cl | blue | 1.84 | ○ |
| 85 | —CH₃ | —Cl | blue | 1.72 | ○ |
| 86 | —N(C₂H₅)₂ | —Cl | blue | 1.75 | ○ |
| 87 | —CH₃ | —Cl | blue | 1.80 | ○ |
| 92 | —CH₃ | —Cl | blue | 1.66 | ○ |
| 93 | —CH₃ | —Cl | blue | 1.73 | ○ |
| 94 | —CH₃ | —Cl | blue | 1.81 | ○ |
| 95 | —CH₃ | —Cl | blue | 1.76 | ○ |
| 96 | —CH₃ | —Cl | blue | 1.53 | ○ |
| 97 | —CH₃ | —Cl | blue | 1.63 | ○ |
| 98 | —CH₃ | —Cl | blue | 1.64 | ○ |
| 99 | —CH₃ | —Cl | blue | 1.57 | ○ |
| 100 | —CH₃ | —Cl | blue | 1.82 | ○ |
| 101 | —CH₃ | —Cl | blue | 1.79 | ○ |
| 102 | —CH₃ | —Cl | blue | 1.68 | ○ |
| 103 | —CH₃ | —Cl | blue | 1.65 | ○ |
| 104 | —CH₃ | —Cl | blue | 1.55 | ○ |
| 105 | —CH₃ | —Cl | blue | 1.71 | ○ |
| 106 | —CH₃ | —Cl | blue | 1.74 | ○ |
| 107 | —CH₃ | —Cl | blue | 1.74 | ○ |
| 108 | —CH₃ | —Cl | blue | 1.68 | ○ |
| 109 | —CH₃ | —Cl | blue | 1.76 | ○ |
| 110 | —CH₃ | —Cl | blue | 1.88 | ○ |
| 111 | —CH₃ | —Cl | blue | 1.84 | ○ |
| 112 | —CH₃ | —Cl | blue | 1.83 | ○ |
| 113 | —CH₃ | —Cl | blue | 1.85 | ○ |
| 114 | —CH₃ | —Cl | blue | 1.77 | ○ |
| 115 | —CH₃ | —Cl | blue | 1.64 | ○ |
| 116 | —CH₃ | —Cl | blue | 1.58 | ○ |
| 117 | —CH₃ | —Cl | blue | 1.78 | ○ |
| 118 | —CH₃ | —Cl | blue | 1.55 | ○ |
| 119 | —CH₃ | —Cl | blue | 1.61 | ○ |
| 120 | —CH₃ | —Cl | blue | 1.72 | ○ |
| 121 | —CH₃ | —Cl | blue | 1.71 | ○ |
| 122 | —CH₃ | —Cl | blue | 1.63 | ○ |
| 123 | —CH₃ | —Cl | blue | 1.69 | ○ |
| 124 | —CH₃ | —Cl | blue | 1.52 | ○ |
| 125 | —CH₃ | —Cl | blue | 1.84 | ○ |
| 126 | —CH₃ | —Cl | blue | 1.77 | ○ |
| 127 | —CH₃ | —Cl | blue | 1.68 | ○ |
| 128 | —CH₃ | —Cl | blue | 1.75 | ○ |
| 129 | —CH₃ | —Cl | blue | 1.64 | ○ |
| 130 | —CH₃ | —Cl | blue | 1.63 | ○ |
| 131 | —CH₃ | —Cl | blue | 1.66 | ○ |
| 132 | —CH₃ | —Cl | blue | 1.69 | ○ |
| 133 | —CH₃ | —Cl | blue | 1.74 | ○ |
| 134 | —CH₃ | —Cl | blue | 1.77 | ○ |
| 135 | —CH₃ | —Cl | blue | 1.83 | ○ |
| 136 | —CH₃ | —Cl | blue | 1.82 | ○ |
| 137 | —CH₃ | —Cl | blue | 1.84 | ○ |
| 138 | —CH₃ | —Cl | blue | 1.86 | ○ |
| 139 | —CH₃ | —Cl | blue | 1.73 | ○ |
| 140 | —CH₃ | —Cl | blue | 1.71 | ○ |
| 141 | —CH₃ | —Cl | blue | 1.68 | ○ |
| 142 | —CH₃ | —Cl | blue | 1.73 | ○ |
| 143 | —CH₃ | —Cl | blue | 1.77 | ○ |
| 144 | —CH₃ | —Cl | blue | 1.65 | ○ |

(5-b)

| | | | | | |
|---|---|---|---|---|---|
| 1 | —H | —H | blue | 1.84 | Δ |
| 2 | —CH₃ | —H | blue | 1.83 | Δ |
| 3 | —H | —Cl | blue | 1.78 | Δ |
| 4 | —C₂H₅ | —Cl | blue | 1.70 | ○ |
| 5 | —CH₃ | —Cl | blue | 1.66 | ○ |
| 6 | —CH₃ | —Cl | blue | 1.81 | ○ |
| 7 | —CH₃ | —Cl | blue | 1.75 | ○ |
| 8 | —CH₃ | —Cl | blue | 1.76 | ○ |

TABLE 5-continued

| | | | | | |
|---|---|---|---|---|---|
| 9 | —CH$_3$ | —Cl | blue | 1.64 | ○ |
| 10 | —CH$_3$ | —Cl | blue | 1.60 | ○ |
| 11 | —CH$_3$ | —Cl | blue | 1.62 | ○ |
| 12 | —CH$_3$ | —Cl | blue | 1.75 | ○ |
| 13 | —CH$_3$ | —Cl | blue | 1.82 | ○ |
| 14 | —CH$_3$ | —Cl | blue | 1.70 | ○ |
| 15 | —CH$_3$ | —Cl | blue | 1.88 | ○ |
| 16 | —CH$_3$ | —Cl | blue | 1.82 | ○ |
| 17 | —CH$_3$ | —Cl | blue | 1.81 | ○ |
| 18 | —CH$_3$ | —Cl | blue | 1.66 | ○ |
| 19 | —CH$_3$ | —Cl | blue | 1.67 | ○ |
| 20 | —N(CH$_3$)$_2$ | —Cl | blue | 1.76 | ○ |
| 21 | —N(C$_2$H$_5$)$_2$ | —Cl | blue | 1.77 | ○ |
| 22 | —NHCOCH$_3$ | —Cl | blue | 1.79 | ○ |
| 23 | —CH$_3$ | —Cl | blue | 1.80 | ○ |
| 24 | —C$_2$H$_5$ | —Cl | blue | 1.70 | ○ |
| 25 | —C$_2$H$_5$ | —Cl | blue | 1.81 | ○ |
| 26 | —CH$_3$ | —Cl | blue | 1.72 | ○ |
| 27 | —CH$_3$ | —Cl | blue | 1.71 | ○ |
| 28 | —C$_2$H$_5$ | —Cl | blue | 1.84 | ○ |
| 29 | —C$_2$H$_5$ | —Cl | blue | 1.80 | ○ |
| 30 | —H | —CH$_3$ | blue | 1.90 | △ |
| 31 | —OH | —H | blue | 1.91 | △ |
| 32 | —H | —H | blue | 1.94 | △ |
| 33 | —CH$_3$ | —Cl | blue | 1.90 | ○ |
| 34 | —H | —H | blue | 1.90 | △ |
| 35 | —CH$_3$ | —H | blue | 1.88 | ○ |
| 36 | —CH$_3$ | —Cl | blue | 1.80 | ○ |
| 37 | —CH$_3$ | —Cl | blue | 1.83 | ○ |
| 38 | —CH$_3$ | —Cl | blue | 1.67 | ○ |
| 39 | —CH$_3$ | —Cl | blue | 1.69 | ○ |
| 41 | —NHCH$_3$ | —Cl | blue | 1.75 | ○ |
| 42 | —N(CH$_3$)$_2$ | —Cl | blue | 1.70 | ○ |
| 43 | —NHCOCH$_3$ | —Cl | blue | 1.66 | ○ |
| 44 | —NHPh | —Cl | blue | 1.65 | ○ |
| 45 | —NHPh | —H | blue | 1.72 | ○ |
| 46 | —N(C$_2$H$_5$)$_2$ | —H | blue | 1.76 | ○ |
| 47 | —CONHCH$_3$ | —Cl | blue | 1.73 | ○ |
| 48 | —CH$_3$ | —Cl | blue | 1.80 | ○ |
| 49 | —C$_2$H$_5$ | —Cl | blue | 1.78 | ○ |
| 50 | —H | —CH$_3$ | blue | 1.66 | △ |
| 51 | —C$_2$H$_5$ | —H | blue | 1.74 | ○ |
| 52 | —CH$_3$ | —Cl | blue | 1.70 | ○ |
| 53 | —CH$_3$ | —Cl | blue | 1.72 | ○ |
| 54 | —CH$_3$ | —Cl | blue | 1.74 | ○ |
| 55 | —CH$_3$ | —Cl | blue | 1.73 | ○ |
| 56 | —CH$_3$ | —Cl | blue | 1.74 | ○ |
| 57 | —C$_2$H$_5$ | —CH$_3$ | blue | 1.76 | △ |
| 58 | —CH$_3$ | —Cl | blue | 1.81 | ○ |
| 59 | —CH$_3$ | —Cl | blue | 1.82 | ○ |
| 60 | —CH$_3$ | —Cl | blue | 1.80 | ○ |
| 61 | —CH$_3$ | —Cl | blue | 1.74 | ○ |
| 62 | —CH$_3$ | —Cl | blue | 1.79 | ○ |
| 63 | —CH$_3$ | —Cl | blue | 1.73 | ○ |
| 64 | —CH$_3$ | —Cl | blue | 1.77 | ○ |
| 65 | —CH$_3$ | —Cl | blue | 1.72 | ○ |
| 66 | —CH$_3$ | —Cl | blue | 1.80 | ○ |
| 67 | —CH$_3$ | —Cl | blue | 1.71 | ○ |
| 68 | —CH$_3$ | —Cl | blue | 1.69 | ○ |
| 69 | —CH$_3$ | —Cl | blue | 1.87 | ○ |
| 70 | —Cl | —Cl | blue | 1.78 | ○ |
| 71 | —Cl | —CH$_3$ | blue | 1.80 | ○ |
| 72 | —CH$_3$ | —NHCOCH$_3$ | blue | 1.76 | △ |
| 73 | —CH$_3$ | —NHCOCH$_3$ | blue | 1.77 | △ |
| 74 | —CH$_3$ | —Cl | blue | 1.72 | ○ |
| 75 | —CH$_3$ | —Cl | blue | 1.75 | ○ |
| 76 | —CH$_3$ | —Cl | blue | 1.76 | ○ |
| 77 | —CH$_3$ | —Cl | blue | 1.83 | ○ |
| 78 | —H | —H | blue | 2.00 | △ |
| 79 | —CH$_3$ | —H | blue | 1.93 | △ |
| 80 | —CH$_3$ | —Cl | blue | 1.90 | ○ |
| 81 | —CH$_3$ | —Cl | blue | 1.78 | ○ |
| 82 | —CH$_3$ | —Cl | blue | 1.83 | ○ |
| 83 | —C$_2$H$_5$ | —Cl | blue | 1.80 | ○ |
| 84 | —CH$_3$ | —Cl | blue | 1.79 | ○ |
| 85 | —CH$_3$ | —Cl | blue | 1.74 | ○ |
| 86 | —N(C$_2$H$_5$)$_2$ | —Cl | blue | 1.77 | ○ |
| 87 | —CH$_3$ | —Cl | blue | 1.83 | ○ |
| 92 | —CH$_3$ | —Cl | blue | 1.81 | ○ |

TABLE 5-continued

| | | | | | |
|---|---|---|---|---|---|
| 93 | —CH₃ | —Cl | blue | 1.88 | ○ |
| 94 | —CH₃ | —Cl | blue | 1.73 | ○ |
| 95 | —CH₃ | —Cl | blue | 1.70 | ○ |
| 96 | —CH₃ | —Cl | blue | 1.84 | ○ |
| 97 | —CH₃ | —Cl | blue | 1.74 | ○ |
| 98 | —CH₃ | —Cl | blue | 1.49 | ○ |
| 99 | —CH₃ | —Cl | blue | 1.81 | ○ |
| 100 | —CH₃ | —Cl | blue | 1.76 | ○ |
| 101 | —CH₃ | —Cl | blue | 1.82 | ○ |
| 102 | —CH₃ | —Cl | blue | 1.77 | ○ |
| 103 | —CH₃ | —Cl | blue | 1.75 | ○ |
| 104 | —CH₃ | —Cl | blue | 1.82 | ○ |
| 105 | —CH₃ | —Cl | blue | 1.66 | ○ |
| 106 | —CH₃ | —Cl | blue | 1.60 | ○ |
| 107 | —CH₃ | —Cl | blue | 1.70 | ○ |
| 108 | —CH₃ | —Cl | blue | 1.63 | ○ |
| 109 | —CH₃ | —Cl | blue | 1.71 | ○ |
| 110 | —CH₃ | —Cl | blue | 1.80 | ○ |
| 111 | —CH₃ | —Cl | blue | 1.59 | ○ |
| 112 | —CH₃ | —Cl | blue | 1.60 | ○ |
| 113 | —CH₃ | —Cl | blue | 1.63 | ○ |
| 114 | —CH₃ | —Cl | blue | 1.72 | ○ |
| 115 | —CH₃ | —Cl | blue | 1.78 | ○ |
| 116 | —CH₃ | —Cl | blue | 1.75 | ○ |
| 117 | —CH₃ | —Cl | blue | 1.75 | ○ |
| 118 | —CH₃ | —Cl | blue | 1.62 | ○ |
| 119 | —CH₃ | —Cl | blue | 1.66 | ○ |
| 120 | —CH₃ | —Cl | blue | 1.69 | ○ |
| 121 | —CH₃ | —Cl | blue | 1.81 | ○ |
| 122 | —CH₃ | —Cl | blue | 1.56 | ○ |
| 123 | —CH₃ | —Cl | blue | 1.53 | ○ |
| 124 | —CH₃ | —Cl | blue | 1.73 | ○ |
| 125 | —CH₃ | —Cl | blue | 1.70 | ○ |
| 126 | —CH₃ | —Cl | blue | 1.65 | ○ |
| 127 | —CH₃ | —Cl | blue | 1.58 | ○ |
| 128 | —CH₃ | —Cl | blue | 1.59 | ○ |
| 129 | —CH₃ | —Cl | blue | 1.81 | ○ |
| 130 | —CH₃ | —Cl | blue | 1.77 | ○ |
| 131 | —CH₃ | —Cl | blue | 1.74 | ○ |
| 132 | —CH₃ | —Cl | blue | 1.69 | ○ |
| 133 | —CH₃ | —Cl | blue | 1.58 | ○ |
| 134 | —CH₃ | —Cl | blue | 1.80 | ○ |
| 135 | —CH₃ | —Cl | blue | 1.66 | ○ |
| 136 | —CH₃ | —Cl | blue | 1.74 | ○ |
| 137 | —CH₃ | —Cl | blue | 1.78 | ○ |
| 138 | —CH₃ | —Cl | blue | 1.77 | ○ |
| 139 | —CH₃ | —Cl | blue | 1.74 | ○ |
| 140 | —CH₃ | —Cl | blue | 1.70 | ○ |
| 141 | —CH₃ | —Cl | blue | 1.65 | ○ |
| 142 | —CH₃ | —Cl | blue | 1.66 | ○ |
| 143 | —CH₃ | —Cl | blue | 1.70 | ○ |
| 144 | —CH₃ | —Cl | blue | 1.75 | ○ |
| (5-c) | | | | | |
| 1 | —H | —H | blue | 1.82 | △ |
| 2 | —CH₃ | —H | blue | 1.78 | △ |
| 3 | —H | —Cl | blue | 1.80 | △ |
| 4 | —C₂H₅ | —Cl | blue | 1.70 | ○ |
| 5 | —CH₃ | —Cl | blue | 1.72 | ○ |
| 6 | —CH₃ | —Cl | blue | 1.77 | ○ |
| 7 | —CH₃ | —Cl | blue | 1.72 | ○ |
| 8 | —CH₃ | —Cl | blue | 1.68 | ○ |
| 9 | —CH₃ | —Cl | blue | 1.58 | ○ |
| 10 | —CH₃ | —Cl | blue | 1.57 | ○ |
| 11 | —CH₃ | —Cl | blue | 1.62 | ○ |
| 12 | —CH₃ | —Cl | blue | 1.64 | ○ |
| 13 | —CH₃ | —Cl | blue | 1.79 | ○ |
| 14 | —CH₃ | —Cl | blue | 1.67 | ○ |
| 15 | —CH₃ | —Cl | blue | 1.82 | ○ |
| 16 | —CH₃ | —Cl | blue | 1.77 | ○ |
| 17 | —CH₃ | —Cl | blue | 1.72 | ○ |
| 18 | —CH₃ | —Cl | blue | 1.61 | ○ |
| 19 | —CH₃ | —Cl | blue | 1.59 | ○ |
| 20 | —N(CH₃)₂ | —Cl | blue | 1.70 | ○ |
| 21 | —N(C₂H₅)₂ | —Cl | blue | 1.73 | ○ |
| 22 | —NHCOCH₃ | —Cl | blue | 1.79 | ○ |
| 23 | —CH₃ | —Cl | blue | 1.73 | ○ |
| 24 | —C₂H₅ | —Cl | blue | 1.68 | ○ |
| 25 | —C₂H₅ | —Cl | blue | 1.79 | ○ |

TABLE 5-continued

| | | | | | |
|---|---|---|---|---|---|
| 26 | −CH₃ | −Cl | blue | 1.62 | ◯ |
| 27 | −CH₃ | −Cl | blue | 1.60 | ◯ |
| 28 | −C₂H₅ | −Cl | blue | 1.83 | ◯ |
| 29 | −C₂H₅ | −Cl | blue | 1.84 | ◯ |
| 30 | −H | −CH₃ | blue | 1.86 | △ |
| 31 | −OH | −H | blue | 1.83 | △ |
| 32 | −H | −H | blue | 1.79 | △ |
| 33 | −CH₃ | −Cl | blue | 1.78 | ◯ |
| 34 | −H | −H | blue | 1.75 | △ |
| 35 | −CH₃ | −H | blue | 1.77 | ◯ |
| 36 | −CH₃ | −Cl | blue | 1.76 | ◯ |
| 37 | −CH₃ | −Cl | blue | 1.72 | ◯ |
| 38 | −CH₃ | −Cl | blue | 1.57 | ◯ |
| 39 | −CH₃ | −Cl | blue | 1.55 | ◯ |
| 40 | −CH₃ | −Cl | blue | 1.61 | ◯ |
| 41 | −NHCH₃ | −Cl | blue | 1.72 | ◯ |
| 42 | −N(CH₃)₂ | −Cl | blue | 1.60 | ◯ |
| 43 | −NHCOCH₃ | −Cl | blue | 1.62 | ◯ |
| 44 | −NHPh | −Cl | blue | 1.55 | ◯ |
| 45 | −NHPh | −H | blue | 1.58 | ◯ |
| 46 | −N(C₂H₅)₂ | −H | blue | 1.61 | ◯ |
| 47 | −CONHCH₃ | −Cl | blue | 1.68 | ◯ |
| 48 | −CH₃ | −Cl | blue | 1.77 | ◯ |
| 49 | −C₂H₅ | −Cl | blue | 1.72 | ◯ |
| 59 | −H | −CH₃ | blue | 1.61 | ◯ |
| 51 | −C₂H₅ | −H | blue | 1.62 | ◯ |
| 52 | −CH₃ | −Cl | blue | 1.58 | ◯ |
| 53 | −CH₃ | −Cl | blue | 1.71 | ◯ |
| 54 | −CH₃ | −Cl | blue | 1.62 | ◯ |
| 55 | −CH₃ | −Cl | blue | 1.60 | ◯ |
| 56 | −CH₃ | −Cl | blue | 1.63 | ◯ |
| 57 | −C₂H₅ | −CH₃ | blue | 1.66 | △ |
| 58 | −CH₃ | −Cl | blue | 1.69 | ◯ |
| 59 | −CH₃ | −Cl | blue | 1.70 | ◯ |
| 60 | −CH₃ | −Cl | blue | 1.68 | ◯ |
| 61 | −CH₃ | −Cl | blue | 1.72 | ◯ |
| 62 | −CH₃ | −Cl | blue | 1.69 | ◯ |
| 63 | −CH₃ | −Cl | blue | 1.62 | ◯ |
| 64 | −CH₃ | −Cl | blue | 1.58 | ◯ |
| 65 | −CH₃ | −Cl | blue | 1.57 | ◯ |
| 66 | −CH₃ | −Cl | blue | 1.55 | ◯ |
| 67 | −CH₃ | −Cl | blue | 1.51 | ◯ |
| 68 | −CH₃ | −Cl | blue | 1.63 | ◯ |
| 69 | −CH₃ | −Cl | blue | 1.71 | ◯ |
| 70 | −Cl | −Cl | blue | 1.73 | ◯ |
| 71 | −Cl | −CH₃ | blue | 1.72 | ◯ |
| 72 | −CH₃ | −NHCOCH₃ | blue | 1.68 | △ |
| 73 | −CH₃ | −NHCOCH₃ | blue | 1.61 | △ |
| 74 | −CH₃ | −Cl | blue | 1.69 | ◯ |
| 75 | −CH₃ | −Cl | blue | 1.63 | ◯ |
| 76 | −CH₃ | −Cl | blue | 1.60 | ◯ |
| 77 | — | — | — | — | — |
| 78 | — | — | — | — | — |
| 15 | — | — | — | — | — |
| 79 | — | — | — | — | — |
| 80 | — | — | — | — | — |
| 81 | — | — | — | — | — |
| 20 | — | — | — | — | — |
| 84 | — | — | — | — | — |
| 85 | — | — | — | — | — |
| 86 | — | — | — | — | — |
| 88 | −CH₃ | −Cl | blue | 1.75 | ◯ |
| 89 | −C₂H₅ | −Cl | blue | 1.63 | ◯ |
| 90 | −Cl | −Cl | blue | 1.66 | △ |
| 91 | −CH₃ | −Cl | blue | 1.70 | ◯ |
| 92 | −CH₃ | −Cl | blue | 1.72 | ◯ |
| 93 | −CH₃ | −Cl | blue | 1.66 | ◯ |
| 94 | −CH₃ | −Cl | blue | 1.79 | ◯ |
| 95 | −CH₃ | −Cl | blue | 1.69 | ◯ |
| 96 | −CH₃ | −Cl | blue | 1.71 | ◯ |
| 97 | −CH₃ | −Cl | blue | 1.73 | ◯ |
| 98 | −CH₃ | −Cl | blue | 1.73 | ◯ |
| 99 | −CH₃ | −Cl | blue | 1.76 | ◯ |
| 100 | −CH₃ | −Cl | blue | 1.68 | ◯ |
| 101 | −CH₃ | −Cl | blue | 1.63 | ◯ |
| 102 | −CH₃ | −Cl | blue | 1.57 | ◯ |
| 103 | −CH₃ | −Cl | blue | 1.64 | ◯ |
| 104 | −CH₃ | −Cl | blue | 1.63 | ◯ |
| 105 | −CH₃ | −Cl | blue | 1.81 | ◯ |

TABLE 5-continued

| | | | | | |
|---|---|---|---|---|---|
| 106 | —CH₃ | —Cl | blue | 1.78 | ○ |
| 107 | —CH₃ | —Cl | blue | 1.68 | ○ |
| 108 | —CH₃ | —Cl | blue | 1.64 | ○ |
| 109 | —CH₃ | —Cl | blue | 1.71 | ○ |
| 110 | —CH₃ | —Cl | blue | 1.84 | ○ |
| 111 | —CH₃ | —Cl | blue | 1.83 | ○ |
| 112 | —CH₃ | —Cl | blue | 1.80 | ○ |
| 113 | —CH₃ | —Cl | blue | 1.73 | ○ |
| 114 | —CH₃ | —Cl | blue | 1.58 | ○ |
| 115 | —CH₃ | —Cl | blue | 1.66 | ○ |
| 116 | —CH₃ | —Cl | blue | 1.53 | ○ |
| 117 | —CH₃ | —Cl | blue | 1.71 | ○ |
| 118 | —CH₃ | —Cl | blue | 1.82 | ○ |
| 119 | —CH₃ | —Cl | blue | 1.73 | ○ |
| 120 | —CH₃ | —Cl | blue | 1.66 | ○ |
| 121 | —CH₃ | —Cl | blue | 1.81 | ○ |
| 122 | —CH₃ | —Cl | blue | 1.77 | ○ |
| 123 | —CH₃ | —Cl | blue | 1.76 | ○ |
| 124 | —CH₃ | —Cl | blue | 1.73 | ○ |
| 125 | —CH₃ | —Cl | blue | 1.78 | ○ |
| 126 | —CH₃ | —Cl | blue | 1.61 | ○ |
| 127 | —CH₃ | —Cl | blue | 1.79 | ○ |
| 128 | —CH₃ | —Cl | blue | 1.78 | ○ |
| 129 | —CH₃ | —Cl | blue | 1.84 | ○ |
| 130 | —CH₃ | —Cl | blue | 1.75 | ○ |
| 131 | —CH₃ | —Cl | blue | 1.73 | ○ |
| 132 | —CH₃ | —Cl | blue | 1.55 | ○ |
| 133 | —CH₃ | —Cl | blue | 1.51 | ○ |
| 134 | —CH₃ | —Cl | blue | 1.59 | ○ |
| 135 | —CH₃ | —Cl | blue | 1.88 | ○ |
| 136 | —CH₃ | —Cl | blue | 1.86 | ○ |
| 137 | —CH₃ | —Cl | blue | 1.74 | ○ |
| 138 | —CH₃ | —Cl | blue | 1.70 | ○ |
| 139 | —CH₃ | —Cl | blue | 1.80 | ○ |
| 140 | —CH₃ | —Cl | blue | 1.69 | ○ |
| 141 | —CH₃ | —Cl | blue | 1.57 | ○ |
| 142 | —CH₃ | —Cl | blue | 1.74 | ○ |
| 143 | —CH₃ | —Cl | blue | 1.59 | ○ |
| 144 | —CH₃ | —Cl | blue | 1.70 | ○ |

(6) Dyes having the following structure:

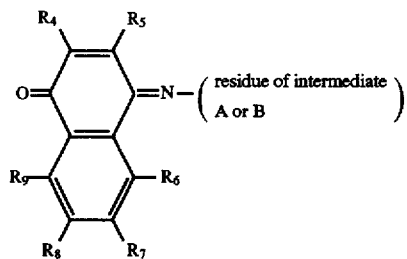

(6)

wherein $R_4$ to $R_9$ stand for a hydrogen atom, a halogen atom or a substituted or unsubstituted alkyl group, alkoxy group, amino group, ureido group, —CON($R_{10}$)($R_{11}$), —CSN($R_{10}$)($R_{11}$), —SO₂N($R_{11}$)($R_{11}$), —COOR$_{10}$ or —CSOR$_{10}$ wherein $R_{10}$ and $R_{11}$ stand for a hydrogen atom, a halogen atom or a substituted or unsubstituted alkyl group, cycloalkyl group, aryl group, vinyl group, ally group, cycloalkyl group or aromatic heterocyclic group, provided that $R_{10}$ and $R_{11}$ may combine with each other to form a ring.

Specific examples of the dyes represented by the general formula 6 and the performance thereof in the case of use in a thermal transfer sheet which will be described later are given in the following Table 6.

TABLE 6

(6-a), (6-b), (6-c) structures shown with R1, R2, R3, R4, X, Y substituents on naphthoquinone-pyridine imine scaffolds.

6 common to a to c

| No. | R₁ | R₂ | R₃ | R₄ |
|---|---|---|---|---|
| 1 | —C₂H₅ | —C₂H₅ | —H | —H |
| 2 | —C₂H₅ | —C₂H₅ | —CH₃ | —H |
| 3 | —C₂H₅ | —C₂H₅ | —CH₃ | —CH₃ |
| 4 | —C₂H₅ | —C₂H₅ | —H | —NHCOC₃H₇ |
| 5 | —C₂H₅ | —C₂H₅ | —CH₃ | —CONHCH₃ |
| 6 | —C₂H₅ | —C₂H₅ | —CH₃ | —NHSO₂CH₃ |
| 7 | —C₂H₅ | —C₂H₅ | —CH₃ | —SO₂NHCH₃ |
| 8 | —C₂H₅ | —C₂H₅ | —CH₃ | —CONH-2-toluyl |
| 9 | —C₂H₅ | —C₂H₅ | —H | —CONH-2-toluyl |
| 10 | —C₂H₅ | —C₂H₅ | —H | —CONH-3-(2-ethylpyridyl) |
| 11 | —C₂H₅ | —C₂H₅ | —NHCOCH₃ | —SO₂NHCH₃ |
| 12 | —C₂H₄OH | —C₂H₅ | —CH₃ | —CONHCH₃ |
| 13 | —C₂H₄CN | —C₂H₅ | —CH₃ | —CONHCH₃ |
| 14 | —C₂H₄OCH₃ | —C₂H₅ | —CH₃ | —CONHCH₃ |
| 15 | —C₂H₄OCOCH₃ | —C₂H₅ | —CH₃ | —CONHCH₃ |
| 16 | —C₂H₄OCOPh | —C₂H₅ | —CH₃ | —CONHCH₃ |
| 17 | —C₂H₄OCOOCH₃ | —C₂H₅ | —CH₃ | —CONHCH₃ |
| 18 | —C₂H₄OCOOPh | —C₂H₅ | —CH₃ | —CONHCH₃ |
| 19 | —C₂H₄OCOCH₃ | —C₂H₄OCOCH₃ | —CH₃ | —CONHCH₃ |
| 20 | —C₂H₄OCOCH₃ | —C₂H₄OCOCH₃ | —CH₃ | —CONHPh |
| 21 | —C₂H₅ | —C₂H₅ | —CH₃ | —CONHC₃H₆OH |
| 22 | —C₄H₉ | —C₄H₉ | —CH₃ | —CONHCH₃ |
| 23 | —C₂H₄OC₂H₄OCH₃ | —C₂H₅ | —CH₃ | —CONHCH₃ |
| 24 | —C₄H₈OH | —C₂H₅ | —CH₃ | —CONHCH₃ |
| 25 | —C₂H₄OCH₂Ph | —C₂H₅ | —NHCOCH₃ | —CONHCH₃ |
| 26 | —C₂H₄O-cyclohexyl | —C₂H₅ | —CH₃ | —CONHCH₃ |
| 27 | —C₂H₄OPh | —C₂H₅ | —CH₃ | —CONHCH₃ |
| 28 | —C₂H₄OPh | —C₂H₅ | —NHCOCH₃ | —CONHCH₃ |
| 29 | —C₂H₅ | —C₂H₅ | —CH₃ | —Cl |
| 30 | —C₂H₅ | —C₂H₅ | —H | —Cl |
| 31 | —C₂H₅ | —C₂H₅ | —NHCOCH₃ | —Cl |
| 32 | —C₂H₅ | —C₂H₅ | —NHSO₂CH₃ | —Cl |
| 33 | —C₂H₅ | —C₂H₅ | —NHCOC₂H₅ | —CONHCH₃ |
| 34 | —C₂H₄OCH₃ | —C₂H₅ | —NHCOC₂H₅ | —CONHCH₃ |
| 35 | —C₂H₄OCOCH₃ | —C₂H₅ | —NHCOC₂H₅ | —CONHCH₃ |
| 36 | —C₂H₅ | —C₂H₅ | —NHCON(C₂H₅)₂ | —CONHCH₃ |
| 37 | —C₂H₅ | —C₂H₅ | —NHCONHCH₃ | —CONHCH₃ |
| 38 | —C₂H₅ | —C₂H₅ | —NHCOCOC₂H₅ | —CONHCH₃ |
| 39 | —C₂H₅ | —C₂H₅ | —NHCOOCH₃ | —CONHCH₃ |
| 40 | —C₂H₅ | —C₂H₅ | —NHCOCH₂Ph | —CONHCH₃ |
| 41 | —C₂H₅ | —C₂H₅ | —NHCOPh | —CONHCH₃ |

TABLE 6-continued

| | | | | |
|---|---|---|---|---|
| 42 | $-C_2H_5$ | $-C_2H_5$ | $-NHSO_2C_2H_5$ | $-CONHCH_3$ |
| 43 | $-C_2H_5$ | $-C_2H_5$ | $-NHSO_2NHCH_3$ | $-CONHCH_3$ |
| 44 | $-C_2H_5$ | $-C_2H_5$ | $-CONHCOCH_3$ | $-CONHCH_3$ |
| 45 | $-C_2H_5$ X = $-$CN (a,b) Y = CN (c) | $-C_2H_5$ | $-NHCOCH_3$ | $-CONHCH_3$ |
| 46 | $-C_2H_5$ X = $-NHCOCH_3$(a,b) Y = $NHCOCH_3$(c) | $-C_2H_5$ | $-NHCOCH_3$ | $-CONHCH_3$ |
| 47 | $-C_2H_5$ X = $-$CN (a,b) Y = $-$CN (c) | $-C_2H_5$ | $-CH_3$ | $-CONHCH_3$ |
| 48 | $-C_2H_5$ X = $-NHCOCH_3$(a,b) Y = $NHCOCH_3$(c) | $-C_2H_5$ | $-CH_3$ | $-CONHCH_3$ |
| 49 | $-C_2H_5$ | $-C_2H_5$ | $-CH_3$ | $-NHCH_3$ |
| 50 | $-C_2H_5$ | $-C_2H_5$ | $-CH_3$ | $-N(CH_3)_2$ |
| 51 | $-C_2H_5$ | $-C_2H_5$ | $-NHCOCH_3$ | $-N(C_2H_5)_2$ |
| 52 | $-C_2H_5$ | $-C_2H_5$ | $-NHSO_2CH_3$ | $-N(C_2H_5)_2$ |
| 53 | $-C_2H_5$ | $-C_2H_5$ | $-OH$ | $-OH$ |
| 54 | $-C_2H_5$ | $-C_2H_5$ | $-OH$ | $-NHCOCH_3$ |
| 55 | $-C_2H_5$ | $-C_2H_5$ | $-OH$ | $-CONHCH_3$ |
| 56 | $-C_2H_5$ | $-C_2H_5$ | $-OH$ | $-NHCOPh$ |
| 57 | $-C_2H_5$ | $-C_2H_5$ | $-OH$ | $-CONHPh$ |
| 58 | $-C_2H_5$ | $-C_2H_5$ | $-OH$ | $-CONH$-cyclohexyl |
| 59 | $-C_2H_5$ | $-C_2H_5$ | $-OH$ | $-CONHCH_2Ph$ |
| 60 | $-C_2H_5$ | $-C_2H_5$ | $-OH$ | $-CONHC_2H_5$ |
| 61 | $-C_2H_5$ | $-C_2H_5$ | $-OCH_3$ | $-CONHCH_3$ |
| 62 | $-C_2H_5$ | $-C_2H_5$ | $-OCH_3$ | $-NHCOPh$ |
| 63 | $-C_2H_5$ | $-C_2H_5$ | $-OCH_3$ | $-CONHPh$ |
| 64 | $-C_2H_5$ X = $-$CN (a,b) Y = $-$CN (c) | $-C_2H_5$ | $-OCH_3$ | $-NHCOCH_3$ |
| 65 | $-C_2H_5$ | $-C_2H_5$ | $-Cl$ | $-Cl$ |
| 66 | $-C_2H_5$ | $-C_2H_5$ | $-Cl$ | $-CONHCH_3$ |
| 67 | $-C_2H_5$ $R_9 = -CH_3$ | $-C_2H_5$ | $-CH_3$ | $-CONHCH_3$ |
| 68 | $-C_2H_5$ $R_9 = -NH_2$ | $-C_2H_5$ | $-CH_3$ | $-CONHCH_3$ |
| 69 | $-C_2H_5$ $R_9 = -NHCH_3$ | $-C_2H_5$ | $-CH_3$ | $-CONHCH_3$ |
| 70 | $-C_2H_5$ $R_9 = -CH$ | $-C_2H_5$ | $-CH_3$ | $-CONHCH_3$ |
| 71 | $-C_2H_5$ | $-C_2H_5$ | $-CH_3$ | $-CONH$-thienyl(3) |
| 72 | $-C_2H_5$ | $-C_2H_5$ | $-CH_3$ | $-CONH$-thienyl(2) |
| 73 | $-C_2H_5$ | $-C_2H_5$ | $-CH_3$ | $-CONH$-furyl(2) |
| 74 | $-C_2H_5$ | $-C_2H_5$ | $-CH_3$ | $-COOCH_3$ |
| 75 | $-C_2H_5$ | $-C_2H_5$ | $-CH_3$ | $-CONHCH_2$-thienyl(2) |
| 76 | $-C_2H_5$ | $-C_2H_5$ | $-CH_3$ | $-CONHCH_2$-thienyl(3) |
| 77 | $-C_2H_5$ | $-C_2H_5$ | $-CH_3$ | $-NHCO$-thienyl(3) |
| 78 | $-C_2H_5$ | $-C_2H_5$ | $-CH_3$ | $-NHCO$-thienyl(2) |
| 79 | $-C_2H_5$ | $-C_2H_5$ | $-CH_3$ | $-NHCOCH_2$-thienyl(2) |
| 80 | $-C_2H_4OCH_3$ | $-C_2H_5$ | $-CH_3$ | $-CONH$-thienyl(2) |
| 81 | $-C_2H_4OCH_3$ | $-C_2H_4OCH_3$ | $-CH_3$ | $-CONH$-thienyl(2) |
| 82 | $-C_2H_4OCOCH_3$ | $-C_2H_5$ | $-CH_3$ | $-CONH$-thienyl(2) |
| 83 | $-C_2H_4OCOCH_3$ | $-C_2H_4OCOCH_3$ | $-CH_3$ | $-CONH$-thienyl(2) |
| 84 | $-C_2H_4CN$ | $-C_2H_5$ | $-CH_3$ | $-CONH$-thienyl(2) |
| 85 | $-C_2H_4OH$ | $-C_2H_5$ | $-CH_3$ | $-CONH$-thienyl(2) |
| 86 | $-C_2H_4OCH_3$ | $-C_2H_5$ | $-NHCOCH_3$ | $-CONH$-thienyl(2) |
| 87 | $-C_2H_4OCH_3$ | $-C_2H_4OCH_3$ | $-NHCOCH_3$ | $-CONH$-thienyl(2) |
| 88 | $-C_2H_4OCOCH_3$ X = $-$CN (a,b) Y = CN (c) | $-C_2H_5$ | $-NHCOCH_3$ | $-CONH$-thienyl(2) |
| 89 | $-C_2H_4COOCH_3$ | $-C_2H_5$ | $-NHCOCH_3$ | $-CONHCH_3$ |
| 90 | $-C_2H_4COOCH_3$ | $-C_2H_4COOCH_3$ | $-CH_3$ | $-CONHCH_3$ |
| 91 | $-C_2H_4COOCH_3$ | $-C_2H_4COOCH_3$ | $-NHCOCH_3$ | $-CONHCH_3$ |
| 92 | $-C_2H_5$ | $-C_2H_5$ | $-CH_3$ | $-CONHNHCH_3$ |
| 93 | $-C_2H_5$ | $-C_2H_5$ | $-CH_3$ | $-CONH$-piperidyl(1) |
| 94 | $-C_2H_5$ | $-C_2H_5$ | $-CH_3$ | $-CONH$-morpholyl(1) |
| 95 | $-C_2H_5$ | $-C_2H_5$ | $-CH_3$ | $-CONH$-bicyclo[2,2,1]-hepto-2-yl |
| 96 | $-C_2H_5$ | $-C_2H_5$ | $-CH_3$ | $-NHCO$-bicyclo[2,2,1]-hepto-2-yl |
| 97 | $-C_2H_5$ | $-C_2H_5$ | $-NHCOCH_3$ | $-CONH$-piperidyl(1) |
| 98 | $-C_2H_5$ | $-C_2H_5$ | $-NHCOC_2H_5$ | $-CONH$-morpholyl(1) |
| 99 | $-C_2H_5$ | $-C_2H_5$ | $-NHCOCH_3$ | $-CONH$-pyrrolidolyl(1) |
| 100 | $-C_2H_5$ | $-C_2H_5$ | $-NHCOCH_3$ | $-CO$-pyrrolidolyl(1) |
| 101 | $-C_2H_5$ | $-C_2H_5$ | $-CH_3$ | $-CO$-pyrrolidolyl(1) |
| 102 | $-C_2H_5$ | $-C_2H_5$ | $-CONHCH_3$ | $-CONHCH_3$ |
| 103 | $-C_2H_5$ | $-C_2H_5$ | $-SO_2NHCH_3$ | $-CONHCH_3$ |
| 104 | combining of $R_1$ | $-C_2H_5$ | $-CCH_3$ | $-CONHCH_3$ |

TABLE 6-continued

| | | | | |
|---|---|---|---|---|
| | with X to form ($-C_3H_6-$) in the case of (c), a ring is formed also through combining of Y with $R_2$ | | | |
| 105 | combining of $R_1$ with X to form ($-C_3H_6-$) | $-C_2H_4OCH_3$ | $-CH_3$ | $-CONHCH_3$ |
| 106 | combining of $R_1$ with X to form ($-C_3H_6-$) | $-C_2H_4OCOCH_3$ | $-CH_3$ | $-CONHCH_3$ |
| 107 | combining of $R_1$ with X to form ($-C_3H_6-$) | $-C_2H_5$ | $-NHCOCH_3$ | $-CONHCH_3$ |
| 108 | combining of $R_1$ with X to form ($-C_3H_6-$) | $-C_2H_5$ | $-CH_3$ | $-CONHPh$ |
| 109 | combining of $R_1$ with X to form ($-C_3H_6-$) | $-H$ | $-CH_3$ | $-CONHPh$ |
| 110 | combining of $R_1$ with X to form ($-C_3H_6-$) | $-C_2H_5$ | $-CC_2H_5$ | $-CONHPh$ |
| 111 | combining of $R_1$ with X to form ($-C_3H_6-$) | $-C_2H_5$ | $-OC_2H_5$ | $-NHCOPh$ |
| 112 | combining of $R_1$ with $R_2$ to form ($-C_5H_{10}-$) | | $-CH_3$ | $-CONHCH_3$ |
| 113 | combining of $R_1$ with $R_2$ to form ($-C_2H_4OC_2H_4-$) | | $-CH_3$ | $-CONHCH_3$ |
| 114 | combining of $R_1$ with $R_2$ to form ($-C_5H_{10}-$) | | $-NHCOCH_3$ | $-CONHCH_3$ |
| 115 | combining of $R_1$ with $R_2$ to form ($-C_5H_{10}-$) | | $-CH_3$ | $-CONHPh$ |
| 116 | combining of $R_1$ with $R_2$ to form ($-C_5H_{10}-$) | | $-NHCOCH_3$ | $-CONHPh$ |
| | 6-c | | | |
| 117 | combining of X with $R_1$ to form ($-C_3H_6-$), combining of Y with $R_2$ to form ($-C_3H_6-$) | | $-CH_3$ | $-CONHCH_3$ |
| 118 | combining of X with $R_1$ to form ($-C_3H_6-$), combining of Y with $R_2$ to form ($-C_3H_6-$) | | $-NHCOCH_3$ | $-CONHPh$ |
| 119 | combining of X with $R_1$ to form ($-C_3H_6-$), combining of Y with $R_2$ to form ($-C_3H_6-$) | | $-CH_3$ | $-CONHCH_2Ph$ |
| 120 | combining of X with $R_1$ to form ($-C_3H_6-$), combining of Y with $R_2$ to form ($-C_3H_6-$) | | $-NHSO_2CH_3$ | $-CONH-isoC_3H_7$ |
| | 6 a,b,c | | | |
| 121 | -cyclohexyl | $-C_2H_5$ | $-CH_3$ | $-CONHPh$ |
| 122 | $-$2-acetylaminocyclohexyl | $-C_2H_5$ | $-CH_3$ | $-CONHPh$ |
| 123 | $-$cyclopentyl | $-C_2H_5$ | $-CH_3$ | $-CONHPh$ |
| 124 | $-CH=CH_2$ | $-C_2H_5$ | $-CH_3$ | $-CONHPh$ |
| 125 | $-CH_2CH=CH_2$ | $-C_2H_5$ | $-CH_3$ | $-CONHPh$ |
| 126 | $-N(C_2H_5)COPh$ | $-C_2H_5$ | $-CH_3$ | $-CONHPh$ |
| 127 | $-N(C_2H_5)SO_2CH_3$ | $-C_2H_5$ | $-CH_3$ | $-CONHPh$ |
| 128 | $-NHCONHPh$ | $-C_2H_5$ | $-CH_3$ | $-CONHPh$ |
| 129 | $-CON(C_4H_9\text{-}n)_2$ | $-C_2H_5$ | $-CH_3$ | $-CONHPh$ |
| 130 | $-SO_2NHPh$ | $-C_2H_5$ | $-CH_3$ | $-CONHPh$ |
| 131 | $-$3-pyridyl | $-C_2H_5$ | $-CH_3$ | $-CONHPh$ |
| 132 | $-$2-thienyl | $-C_2H_5$ | $-CH_3$ | $-CONHPh$ |
| 133 | $-$phenyl | $-C_2H_5$ | $-CH_3$ | $-CONHPh$ |
| 134 | $-$2-pyrrolyl | $-C_2H_5$ | $-CH_3$ | $-CONHPh$ |
| 135 | $-$2-imidazolyl | $-C_2H_5$ | $-CH_3$ | $-CONHPh$ |
| 136 | $-$2-pyrrolidinyl | $-C_2H_5$ | $-CH_3$ | $-CONHPh$ |
| 137 | $-$2-imidazolidinyl | $-C_2H_5$ | $-CH_3$ | $-CONHPh$ |
| 138 | $-$2-pyrazolidinyl | $-C_2H_5$ | $-CH_3$ | $-CONHPh$ |
| 139 | $-$4-piperidyl | $-C_2H_5$ | $-CH_3$ | $-CONHPh$ |
| 140 | $-$morpholino | $-C_2H_5$ | $-CH_3$ | $-CONHPh$ |
| 141 | $-COPh$ | $-C_2H_5$ | $-CH_3$ | $-CONHPh$ |
| 142 | $-SO_2Ph$ | $-C_2H_5$ | $-CH_3$ | $-CONHPh$ |
| 143 | $-$2-tolyl | $-C_2H_5$ | $-CH_3$ | $-CONHPh$ |
| 144 | $-COOPh$ | $-C_2H_5$ | $-CH_3$ | $-CONHPh$ |
| 145 | $-NHCOOCH_2Ph$ | $-C_2H_5$ | $-CH_3$ | $-NHCOPh$ |
| 146 | $-COCH_2Ph$ | $-C_2H_5$ | $-CH_3$ | $-NHCOPh$ |
| 147 | $-$2-nicotinoyl | $-C_2H_5$ | $-CH_3$ | $-NHCOPh$ |
| 148 | $-$4-toluoyl | $-C_2H_5$ | $-CH_3$ | $-NHCOPh$ |

TABLE 6-continued

| No. | hue | coloring density | light fastness |
|---|---|---|---|
| | | (6-a) | |
| 1 | blue | 2.10 | Δ |
| 2 | blue | 2.21 | Δ |
| 3 | blue | 1.88 | Δ |
| 4 | blue | 1.92 | ○ |
| 5 | blue | 1.76 | ○ |
| 6 | blue | 1.81 | Δ |
| 7 | blue | 1.78 | Δ |
| 8 | blue | 1.77 | ○ |
| 9 | blue | 1.78 | ○ |
| 10 | blue | 1.63 | ○ |
| 11 | blue | 1.72 | ○ |
| 12 | blue | 1.73 | Δ |
| 13 | blue | 1.97 | Δ |
| 14 | blue | 1.84 | Δ |
| 15 | blue | 1.78 | Δ |
| 16 | blue | 1.80 | ○ |
| 17 | blue | 1.91 | ○ |
| 18 | blue | 1.82 | ○ |
| 19 | blue | 1.76 | ○ |
| 20 | blue | 1.83 | ○ |
| 21 | blue | 1.78 | ○ |
| 22 | blue | 1.78 | Δ |
| 23 | blue | 1.79 | Δ |
| 24 | blue | 1.69 | Δ |
| 25 | blue | 1.72 | Δ |
| 26 | blue | 1.74 | ○ |
| 27 | blue | 1.87 | ○ |
| 28 | blue | 1.78 | Δ |
| 29 | blue | 1.77 | ○ |
| 30 | blue | 1.77 | Δ |
| 31 | blue | 1.79 | Δ |
| 32 | blue | 1.84 | Δ |
| 33 | blue | 1.77 | Δ |
| 34 | blue | 1.80 | Δ |
| 35 | blue | 1.70 | Δ |
| 36 | blue | 1.80 | Δ |
| 37 | blue | 1.81 | Δ |
| 38 | blue | 1.73 | Δ |
| 39 | blue | 1.79 | Δ |
| 40 | blue | 1.66 | Δ |
| 41 | blue | 1.75 | Δ |
| 42 | blue | 1.54 | Δ |
| 43 | blue | 1.61 | Δ |
| 44 | blue | 1.71 | Δ |
| 45 | blue | 1.74 | Δ |
| 46 | blue | 1.69 | ○ |
| 47 | blue | 1.66 | ○ |
| 48 | blue | 1.72 | ○ |
| 49 | blue | 1.73 | Δ |
| 50 | blue | 1.81 | Δ |
| 51 | blue | 1.72 | Δ |
| 52 | blue | 1.75 | Δ |
| 53 | blue | 1.75 | Δ |
| 54 | blue | 1.72 | Δ |
| 55 | blue | 1.77 | Δ |
| 56 | blue | 1.80 | Δ |
| 57 | blue | 1.49 | Δ |
| 58 | blue | 1.78 | Δ |
| 59 | blue | 1.65 | Δ |
| 60 | blue | 1.45 | Δ |
| 61 | blue | 1.69 | ○ |
| 62 | blue | 1.66 | Δ |
| 63 | blue | 1.79 | ○ |
| 64 | blue | 1.74 | Δ |
| 65 | blue | 1.70 | Δ |
| 66 | blue | 1.77 | Δ |
| 67 | blue | 1.69 | Δ |
| 68 | blue | 1.82 | Δ |
| 69 | blue | 1.74 | Δ |
| 70 | blue | 1.70 | Δ |
| 71 | blue | 1.75 | ○ |
| 72 | blue | 1.67 | ○ |
| 73 | blue | 1.74 | Δ |
| 74 | blue | 1.72 | Δ |
| 75 | blue | 1.65 | Δ |

TABLE 6-continued

| | | | |
|---|---|---|---|
| 76 | blue | 1.82 | ○ |
| 77 | blue | 1.75 | Δ |
| 78 | blue | 1.83 | Δ |
| 79 | blue | 1.73 | Δ |
| 80 | blue | 1.81 | Δ |
| 81 | blue | 1.74 | Δ |
| 82 | blue | 1.82 | Δ |
| 83 | blue | 1.79 | Δ |
| 84 | blue | 1.79 | Δ |
| 85 | — | — | — |
| 86 | — | — | — |
| 87 | blue | 1.77 | Δ |
| 88 | — | — | — |
| 89 | — | — | — |
| 90 | blue | 1.69 | ○ |
| 91 | — | — | — |
| 92 | — | — | — |
| 93 | blue | 1.65 | Δ |
| 94 | — | — | — |
| 95 | — | — | — |
| 96 | blue | 1.57 | Δ |
| 97 | blue | 1.62 | Δ |
| 98 | blue | 1.70 | Δ |
| 99 | — | — | — |
| 100 | — | — | — |
| 101 | blue | 1.73 | Δ |
| 102 | — | — | — |
| 103 | — | — | — |
| 104 | blue | 1.77 | ○ |
| 105 | blue | 1.77 | Δ |
| 106 | — | — | — |
| 107 | — | — | — |
| 108 | — | — | — |
| 109 | — | — | — |
| 110 | — | — | — |
| 111 | — | — | — |
| 112 | — | — | — |
| 113 | — | — | — |
| 114 | — | — | — |
| 115 | — | — | — |
| 116 | — | — | — |
| 117 | — | — | — |
| 118 | — | — | — |
| 119 | — | — | — |
| 120 | — | — | — |
| 121 | blue | 1.72 | ○ |
| 122 | blue | 1.78 | ○ |
| 123 | blue | 1.75 | ○ |
| 124 | blue | 1.68 | ○ |
| 125 | blue | 1.74 | ○ |
| 126 | blue | 1.70 | ○ |
| 127 | blue | 1.67 | ○ |
| 128 | blue | 1.71 | ○ |
| 129 | blue | 1.74 | ○ |
| 130 | blue | 1.77 | ○ |
| 131 | blue | 1.85 | ○ |
| 132 | blue | 1.82 | ○ |
| 133 | blue | 1.73 | ○ |
| 134 | blue | 1.57 | ○ |
| 135 | blue | 1.59 | ○ |
| 136 | blue | 1.63 | ○ |
| 137 | blue | 4.61 | ○ |
| 138 | blue | 1.70 | ○ |
| 139 | blue | 1.71 | ○ |
| 140 | blue | 1.80 | ○ |
| 141 | blue | 1.78 | ○ |
| 142 | blue | 1.65 | ○ |
| 143 | blue | 1.73 | ○ |
| 144 | blue | 1.75 | ○ |
| 145 | blue | 1.66 | ○ |
| 146 | blue | 1.77 | ○ |
| 147 | blue | 1.70 | ○ |
| 148 | blue | 1.80 | ○ |
| (6-b) | | | |
| 1 | blue | 2.02 | ○ |
| 2 | blue | 1.95 | ○ |
| 3 | blue | 1.98 | ○ |
| 4 | blue | 2.12 | ○ |

TABLE 6-continued

| | | | |
|---|---|---|---|
| 5 | blue | 1.83 | ○ |
| 6 | blue | 1.97 | ○ |
| 7 | — | — | — |
| 8 | blue | 1.83 | Δ |
| 9 | blue | 1.84 | Δ |
| 10 | blue | 1.92 | Δ |
| 11 | — | — | — |
| 12 | blue | 2.02 | ○ |
| 13 | blue | 2.09 | ○ |
| 14 | blue | 1.99 | ○ |
| 15 | — | — | — |
| 16 | blue | 1.79 | ○ |
| 17 | — | — | — |
| 18 | blue | 1.87 | ○ |
| 19 | blue | 1.76 | ○ |
| 20 | blue | 1.77 | Δ |
| 21 | blue | 1.74 | Δ |
| 22 | blue | 1.83 | Δ |
| 23 | blue | 1.69 | Δ |
| 24 | blue | 1.84 | ○ |
| 25 | blue | 1.82 | ○ |
| 26 | blue | 1.95 | ○ |
| 27 | blue | 1.86 | ○ |
| 28 | blue | 1.97 | ○ |
| 29 | blue | 1.96 | Δ |
| 30 | blue | 1.72 | Δ |
| 31 | blue | 1.70 | Δ |
| 32 | — | — | — |
| 33 | blue | 1.69 | Δ |
| 34 | blue | 1.84 | Δ |
| 35 | blue | 1.99 | Δ |
| 36 | blue | 1.69 | Δ |
| 37 | blue | 1.83 | Δ |
| 38 | blue | 1.63 | Δ |
| 39 | blue | 1.87 | Δ |
| 40 | blue | 1.88 | Δ |
| 41 | blue | 1.80 | Δ |
| 42 | blue | 1.79 | Δ |
| 43 | — | — | — |
| 44 | blue | 1.65 | Δ |
| 45 | blue | 1.89 | Δ |
| 46 | blue | 1.91 | Δ |
| 47 | blue | 1.65 | Δ |
| 48 | blue | 1.71 | Δ |
| 49 | blue | 1.79 | Δ |
| 50 | blue | 1.77 | Δ |
| 51 | blue | 1.81 | Δ |
| 52 | — | — | — |
| 53 | blue | 1.80 | Δ |
| 54 | — | — | — |
| 55 | blue | 1.82 | Δ |
| 56 | — | — | — |
| 57 | blue | 1.78 | ○ |
| 58 | blue | 1.70 | ○ |
| 59 | blue | 1.65 | ○ |
| 60 | blue | 1.69 | ○ |
| 61 | blue | 1.80 | Δ |
| 62 | — | — | — |
| 63 | blue | 1.78 | Δ |
| 64 | blue | 1.72 | Δ |
| 65 | blue | 1.63 | Δ |
| 66 | blue | 1.68 | Δ |
| 67 | blue | 1.72 | ○ |
| 68 | — | — | — |
| 69 | — | — | — |
| 70 | — | — | — |
| 71 | blue | 1.69 | Δ |
| 72 | blue | 1.73 | ○ |
| 73 | blue | 1.73 | Δ |
| 74 | blue | 1.79 | Δ |
| 75 | blue | 1.76 | Δ |
| 76 | — | — | — |
| 77 | — | — | — |
| 78 | blue | 1.83 | ○ |
| 79 | blue | 1.81 | ○ |
| 80 | blue | 1.84 | ○ |
| 81 | — | — | — |
| 82 | blue | 1.80 | ○ |
| 83 | blue | 1.87 | ○ |

TABLE 6-continued

| | | | |
|---|---|---|---|
| 84 | blue | 1.68 | ◯ |
| 85 | blue | 1.71 | ◯ |
| 86 | — | — | ◯ |
| 87 | blue | 1.85 | — |
| 88 | blue | 1.80 | △ |
| 89 | blue | 1.84 | △ |
| 90 | blue | 1.81 | ◯ |
| 91 | blue | 1.90 | △ |
| 92 | blue | 1.77 | ◯ |
| 93 | blue | 1.78 | ◯ |
| 94 | blue | 1.71 | ◯ |
| 95 | — | — | — |
| 96 | — | — | — |
| 97 | — | — | — |
| 98 | blue | 1.67 | △ |
| 99 | — | — | — |
| 100 | — | — | — |
| 101 | — | — | — |
| 102 | blue | 1.88 | ◯ |
| 103 | blue | 1.72 | ◯ |
| 104 | blue | 1.92 | ◯ |
| 105 | blue | 1.91 | ◯ |
| 106 | blue | 1.86 | ◯ |
| 107 | blue | 1.84 | ◯ |
| 108 | — | — | — |
| 121 | blue | 1.77 | ◯ |
| 122 | blue | 1.80 | ◯ |
| 123 | blue | 1.79 | ◯ |
| 124 | blue | 1.75 | ◯ |
| 125 | blue | 1.65 | ◯ |
| 126 | blue | 1.61 | ◯ |
| 127 | blue | 1.68 | ◯ |
| 128 | blue | 1.60 | ◯ |
| 129 | blue | 1.57 | ◯ |
| 130 | blue | 1.63 | ◯ |
| 131 | blue | 1.74 | ◯ |
| 132 | blue | 1.79 | ◯ |
| 133 | blue | 1.77 | ◯ |
| 134 | blue | 1.82 | ◯ |
| 135 | blue | 1.81 | ◯ |
| 136 | blue | 1.64 | ◯ |
| 137 | blue | 1.62 | ◯ |
| 138 | blue | 1.74 | ◯ |
| 139 | blue | 1.75 | ◯ |
| 140 | blue | 1.75 | ◯ |
| 141 | blue | 1.80 | ◯ |
| 142 | blue | 1.79 | ◯ |
| 143 | blue | 1.65 | ◯ |
| 144 | blue | 1.72 | ◯ |
| 145 | blue | 1.65 | ◯ |
| 146 | blue | 1.66 | ◯ |
| 147 | blue | 1.71 | ◯ |
| 148 | blue | 1.75 | ◯ |
| (6-c) | | | |
| 1 | blue | 1.90 | △ |
| 2 | blue | 1.72 | ◯ |
| 3 | blue | 1.82 | △ |
| 4 | blue | 1.82 | ◯ |
| 5 | blue | 1.77 | ◯ |
| 6 | — | — | — |
| 7 | blue | 1.84 | ◯ |
| 8 | blue | 1.94 | △ |
| 9 | — | — | — |
| 10 | blue | 1.98 | ◯ |
| 11 | blue | 1.96 | △ |
| 12 | blue | 1.80 | ◯ |
| 13 | blue | 1.77 | △ |
| 14 | blue | 1.82 | ◯ |
| 15 | — | — | — |
| 16 | — | — | — |
| 17 | — | — | — |
| 18 | blue | 2.04 | △ |
| 19 | blue | 2.11 | ◯ |
| 20 | blue | 1.73 | ◯ |
| 21 | blue | 1.73 | △ |
| 22 | blue | 1.70 | ◯ |
| 23 | blue | 1.72 | △ |
| 24 | blue | 1.76 | △ |

TABLE 6-continued

| | | | |
|---|---|---|---|
| 25 | blue | 2.11 | △ |
| 26 | — | — | — |
| 27 | blue | 1.87 | △ |
| 28 | blue | 2.18 | △ |
| 29 | — | — | — |
| 30 | — | — | — |
| 31 | — | — | — |
| 32 | blue | 1.64 | ○ |
| 33 | blue | 1.99 | △ |
| 34 | blue | 1.70 | △ |
| 35 | blue | 1.60 | △ |
| 36 | — | — | — |
| 37 | blue | 1.75 | △ |
| 38 | blue | 1.83 | △ |
| 39 | blue | 1.91 | △ |
| 40 | — | — | — |
| 41 | blue | 1.92 | △ |
| 42 | blue | 1.78 | △ |
| 43 | — | — | — |
| 44 | — | — | — |
| 45 | blue | 1.88 | △ |
| 46 | blue | 1.79 | △ |
| 47 | blue | 2.02 | △ |
| 48 | blue | 1.73 | △ |
| 49 | blue | 1.95 | ○ |
| 50 | — | — | — |
| 51 | — | — | — |
| 52 | — | — | — |
| 53 | — | — | — |
| 54 | blue | 1.86 | ○ |
| 55 | blue | 1.68 | △ |
| 56 | blue | 1.78 | △ |
| 57 | — | — | — |
| 58 | — | — | — |
| 59 | blue | 2.14 | △ |
| 60 | blue | 2.17 | △ |
| 61 | blue | 1.82 | △ |
| 62 | blue | 1.95 | ○ |
| 63 | blue | 1.69 | △ |
| 64 | — | — | — |
| 65 | blue | 1.75 | △ |
| 66 | blue | 1.72 | △ |
| 67 | blue | 1.78 | ○ |
| 68 | — | — | — |
| 69 | blue | 1.81 | △ |
| 70 | — | — | — |
| 71 | blue | 1.77 | △ |
| 72 | blue | 1.97 | ○ |
| 73 | blue | 1.68 | ○ |
| 74 | blue | 1.79 | ○ |
| 75 | — | — | — |
| 76 | — | — | — |
| 77 | blue | 2.08 | △ |
| 78 | blue | 1.77 | ○ |
| 79 | — | — | — |
| 80 | — | — | — |
| 81 | blue | 1.92 | ○ |
| 82 | blue | 2.06 | △ |
| 83 | blue | 1.77 | △ |
| 84 | blue | 1.84 | △ |
| 85 | blue | 1.72 | ○ |
| 86 | blue | 1.77 | ○ |
| 87 | blue | 1.86 | ○ |
| 88 | blue | 1.63 | ○ |
| 89 | — | — | — |
| 90 | — | — | — |
| 91 | blue | 1.66 | △ |
| 92 | blue | 1.92 | △ |
| 93 | blue | 1.87 | △ |
| 94 | — | — | — |
| 95 | blue | 1.95 | △ |
| 96 | blue | 2.12 | △ |
| 97 | blue | 2.00 | △ |
| 98 | — | — | — |
| 99 | blue | 1.77 | △ |
| 100 | blue | 2.01 | △ |
| 101 | — | — | — |
| 102 | blue | 1.95 | △ |
| 103 | blue | 1.87 | ○ |

TABLE 6-continued

| | | | |
|---|---|---|---|
| 104 | — | — | — |
| 105 | blue | 1.86 | O |
| 106 | blue | 1.84 | O |
| 107 | — | — | — |
| 108 | — | — | — |
| 109 | blue | 1.81 | Δ |
| 110 | — | — | — |
| 111 | blue | 1.84 | Δ |
| 112 | — | — | — |
| 113 | — | — | — |
| 114 | — | — | — |
| 115 | — | — | — |
| 116 | blue | 1.77 | O |
| 117 | blue | 1.98 | Δ |
| 118 | blue | 1.71 | Δ |
| 119 | blue | 1.92 | Δ |
| 120 | blue | 1.94 | Δ |
| 121 | blue | 1.65 | O |
| 122 | blue | 1.68 | O |
| 123 | blue | 1.71 | O |
| 124 | blue | 1.72 | O |
| 125 | blue | 1.66 | O |
| 126 | blue | 1.69 | O |
| 127 | blue | 1.70 | O |
| 128 | blue | 1.73 | O |
| 129 | blue | 1.77 | O |
| 130 | blue | 1.82 | O |
| 131 | blue | 1.86 | O |
| 132 | blue | 1.58 | O |
| 133 | blue | 1.72 | O |
| 134 | blue | 1.73 | O |
| 135 | blue | 1.79 | O |
| 136 | blue | 1.71 | O |
| 137 | blue | 1.61 | O |
| 138 | blue | 1.70 | O |
| 139 | blue | 1.74 | O |
| 140 | blue | 1.68 | O |
| 141 | blue | 1.77 | O |
| 142 | blue | 1.69 | O |
| 143 | blue | 1.80 | O |
| 144 | blue | 1.71 | O |
| 145 | blue | 1.81 | O |
| 146 | blue | 1.83 | O |
| 147 | blue | 1.78 | O |
| 148 | blue | 1.77 | O |

(7) Dyes having the following structure:

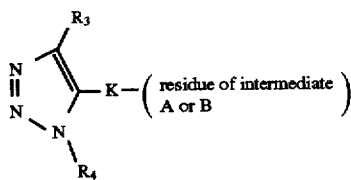

(7)

wherein K stands for —N=N—, $R_4$ stands for a hydrogen atoms, a halogen atoms, a substituted or unsubstituted alkyl group, cycloalkyl group, allyl group, aryl group, aralkyl group or aromatic heterocyclic group, $R_5$ stands for a cyano group, a nitro group or a substituted or unsubstituted formylamino group, sulfonylamino group, alkoxycarbonyl group, carbamoyl group, sulfamoyl group or ureido group.

Specific examples of the dyes represented by the general formula 7 and the performance thereof in the case of use in a thermal transfer sheet which will be described later are given in the following Table 7.

TABLE 7

(7-1)

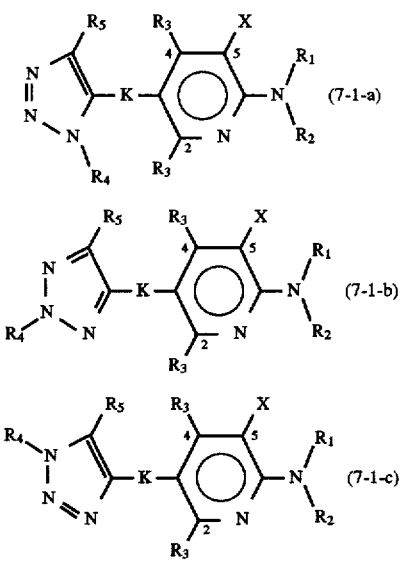

| No. | $R_1$ | $R_2$ | 2-$R_3$ | 4-$R_3$ |
|---|---|---|---|---|
| | | 7-1 common to a to c | | |
| 1 | $-C_2H_5$ | $-C_2H_5$ | $-H$ | $-H$ |
| 2 | $-CH_2CH=CH_2$ | $-C_2H_5$ | $-CH_3$ | $-H$ |
| 3 | $-C_2H_4CN$ | $-C_2H_5$ | $-NHCOCH_3$ | $-H$ |
| 4 | $-C_2H_4OH$ | $-C_2H_5$ | $-NHSO_2CH_3$ | $-H$ |
| 5 | $-C_2H_4OCH_3$ | $-C_2H_5$ | $-NHCOC_2H_5$ | $-H$ |
| 6 | $-C_2H_4COOCH_3$ | $-C_2H_5$ | $-CH_3$ | $-H$ |
| 7 | $-C_2H_4OCOCH_3$ | $-C_2H_5$ | $-CH_3$ | $-H$ |
| 8 | $-C_2H_4OCH_2Ph$ | $-C_2H_5$ | $-H$ | $-H$ |
| 9 | $-CH_2OCOOPh$ | $-C_2H_5$ | $-OCH_3$ | $-H$ |
| 10 | $-C_2H_4OCH_3$ | $-C_2H_5$ | $-NHCOC_2H_5$ | $-H$ |
| 11 | $-C_2H_4OCOCH_3$ | $-C_2H_5$ | $-OH$ | $-H$ |
| 12 | $-C_2H_5$ | $-C_2H_5$ | $-H$ | $-H$ |
| 13 | $-C_2H_5$ | $-C_2H_5$ | $-H$ | $-H$ |
| 14 | $-C_2H_5$ | $-C_2H_5$ | $-H$ | $-H$ |
| 15 | $-C_2H_5$ | $-C_2H_5$ | $-CH_3$ | $-H$ |
| 16 | $-C_2H_5$ | $-C_2H_5$ | $-C_2H_5$ | $-H$ |
| 17 | $-C_2H_5$ | $-C_2H_5$ | $-CH_3$ | $-H$ |
| 18 | $-C_2H_5$ | $-C_2H_5$ | $-CH_3$ | |
| 19 | $-C_2H_4OCH_3$ | $-C_2H_4OCH_3$ | $-NHCOCH_3$ | $-H$ |
| 20 | $-CH_2Ph$ | $-CH_3$ | $-OC_2H_5$ | $-H$ |
| 21 | $-C_2H_5$ | $-C_2H_5$ | $-CH_3$ | |
| 22 | $-C_2H_5$ | $-C_2H_5$ | $-NHSO_2CH_3$ | $-CH_3$ |
| 23 | $-C_2H_5$ | $-C_2H_5$ | $-NHCOCH_3$ | 5-NHCOCH$_3$ |
| 24 | $-C_2H_4OCOCH_3$ | $-C_2H_4OCOCH_3$ | $-CH_3$ | $-H$ |
| 25 | $-C_2H_5$ | $-H$ | $-CH_3$ | $-H$ |
| 26 | $-C_2H_5$ | $-C_2H_5$ | $-H$ | $-H$ |
| 27 | $-C_2H_5$ | $-C_2H_5$ | $-H$ | $-H$ |
| 28 | $-C_2H_5$ | $-C_2H_5$ | $-NHCOCH_3$ | $-H$ |
| 29 | $-CH_2CH=CH_2$ | $-C_2H_4OCH_3$ | $-CH_3$ | $-H$ |
| 30 | $-C_2H_4$-cyclohexyl | $-C_2H_5$ | $-NHCOCH_3$ | $-H$ |
| 31 | combining of $R_1$ with X to form $-C_3H_6-$ | $-C_2H_5$ | $-CH_3$ | $-H$ |
| 32 | combining of $R_1$ with X to form $-C_3H_6-$ | $-C_2H_5$ | $-NHCOCH_3$ | $-H$ |
| 33 | combining of $R_1$ with X to form $-C_3H_6-$ | $-C_2H_5$ | $-NHSO_2CH_3$ | $-H$ |
| 34 | combining of $R_1$ with $R_2$ to form $-C_5H_{10}-$ | | $-CH_3$ | $-H$ |
| 35 | combining of $R_1$ with $R_2$ to form $-C_5H_{10}-$ | | $-NHCOCH_3$ | $-H$ |
| 36 | combining of $R_1$ with $R_2$ to form $-C_5H_{10}-$ | | $-NHSO_2CH_3$ | $-H$ |
| 37 | combining of $R_1$ with $R_2$ to form $-C_5H_{10}-$ | | $-H$ | $-H$ |
| 38 | combining of $R_1$ with $R_2$ to form $-C_2H_4OC_2H_4-$ | | $-H$ | $-H$ |
| 39 | combining of $R_1$ with $R_2$ to form $-C_2H_4OC_2H_4-$ | | $-CH_3$ | $-H$ |

TABLE 7-continued

| No. | R₁ | R₂ | R₃ | |
|---|---|---|---|---|
| 40 | combining of R₁ with R₂ to form —C₂H₄OC₂H₄— | | —NHCOCH₃ | —H |
| 41 | combining of R₁ with R₂ to form —C₂H₄OC₂H₄— | | —NHSO₂CH₃ | —H |
| 42 | combining of R₁ with R₂ to form —C₄H₈— | | —NHCOCH₃ | —H |
| 43 | —C₂H₄OCOOC₂H₅ | —CH₃ | —CH₃ | —H |
| 44 | —C₂H₅ | —C₂H₅ | —NHCOCH₃ | —H |
| 45 | —C₂H₄OC₂H₄OC₂H₅ | —C₂H₅ | —CH₃ | —H |
| 46 | —C₂H₅ | —C₂H₅ | —CH₃ | —H |
| 47 | —C₂H₅ | —C₂H₅ | —CH₃ | —H |
| 48 | —C₂H₅ | —C₂H₅ | —NHCOCH₃ | 5-OCH₃ |
| 49 | —C₂H₅ | —C₂H₅ | —CH₃ | 5-CH₃ |

7-1 b,c

| No. | R₁ | R₂ | R₃ | |
|---|---|---|---|---|
| 50 | —C₂H₅ | —C₂H₅ | —CH₃ | —H |
| 51 | —C₂H₅ | —C₂H₅ | —CH₃ | —H |
| 52 | —C₂H₅ | —C₂H₅ | —CH₃ | —H |
| 53 | —C₂H₅ | —C₂H₅ | —CH₃ | —H |
| 54 | —C₂H₅ | —C₂H₅ | —CH₃ | —H |
| 55 | —C₂H₅ | —C₂H₅ | —NHCOCH₃ | —H |
| 56 | —C₂H₄OCOCH₃ | —C₂H₅ | —NHCOCH₃ | —H |

| No. | R₄ | R₅ | hue | coloring density | light fastness |
|---|---|---|---|---|---|
| | | | (7-1-a K: —N=N—) | | |
| 1 | —CH₂Ph | —CN | orange | 2.14 | ○ |
| 2 | —CH₂Ph | —CN | orange | 2.02 | Δ |
| 3 | —CH₂Ph | —CN | orange | 2.20 | Δ |
| 4 | —CH₂Ph | —CN | orange | 1.98 | Δ |
| 5 | —CH₂Ph | —CN | orange | 1.97 | ○ |
| 6 | —CH₂Ph | —CN | orange | 1.88 | ○ |
| 7 | —CH₂Ph | —CN | orange | 1.94 | ○ |
| 8 | —CH₂Ph | —CN | orange | 1.87 | Δ |
| 9 | —CH₂Ph | —CN | orange | 1.79 | ○ |
| 10 | —CH₂Ph | —CN | orange | 1.94 | ○ |
| 11 | —CH₂Ph | —CN | orange | 1.70 | ○ |
| 12 | —CH₂Ph | —NO₂ | orange | 1.93 | Δ |
| 13 | —CH₂Ph | —COOH | yellowish orange | 1.80 | Δ |
| 14 | —CH₂Ph | —COOC₂H₅ | yellowish orange | 1.75 | Δ |
| 15 | —CH₂Ph | —CN | orange | 1.96 | ○ |
| 16 | —CH₂Ph | —SO₂NHCH₃ | yellowish orange | 2.01 | ○ |
| 17 | —CH₂Ph | —CONHCH₃ | yellowish orange | 1.94 | ○ |
| 18 | —CH₂Ph | —CN | orange | 1.83 | ○ |
| 19 | —CH₂Ph | —CN | orange | 1.92 | ○ |
| 20 | —CH₂Ph | —CN | orange | 1.88 | ○ |
| 21 | —CH₂CH=CH₂ | —CN | orange | 1.96 | Δ |
| 22 | —nC₄H₉ | —CN | orange | 1.87 | Δ |
| 23 | —nC₄H₉ | —CN | orange | 1.73 | ○ |
| 24 | —nC₄H₉ | —CN | orange | 2.00 | ○ |
| 25 | —nC₄H₉ | —CN | orange | 1.83 | Δ |
| 26 | —Ph | —CN | orange | 1.72 | ○ |
| 27 | 2-thienyl | —CN | orange | 1.77 | ○ |
| 28 | —isoC₃H₇ | —CN | orange | 1.79 | Δ |
| 29 | —nC₄H₉ | —CN | orange | 1.77 | ○ |
| 30 | —nC₄H₉ | —CN | orange | 1.71 | Δ |
| 31 | —nC₄H₉ | —CN | orange | 1.79 | ○ |
| 32 | —nC₄H₉ | —CN | orange | 1.81 | ○ |
| 33 | —nC₄H₉ | —CN | orange | 1.82 | ○ |
| 34 | —nC₄H₉ | —CN | orange | 1.65 | ○ |
| 35 | —nC₄H₉ | —CN | orange | 1.90 | ○ |
| 36 | —nC₄H₉ | —CN | orange | 1.76 | ○ |
| 37 | —nC₄H₉ | —CN | orange | 1.86 | ○ |
| 38 | —nC₄H₉ | —CN | orange | 1.91 | ○ |
| 39 | —nC₄H₉ | —CN | orange | 1.80 | ○ |
| 40 | —nC₄H₉ | —CN | orange | 1.79 | ○ |
| 41 | —nC₄H₉ | —CN | orange | 1.79 | ○ |
| 42 | —nC₄H₉ | —CN | orange | 1.94 | ○ |
| 43 | —tert-C₄H₉ | —CN | orange | 1.75 | ○ |
| 44 | —C₆H₁₃ | —CN | orange | 1.84 | ○ |
| 45 | —nC₄H₉ | —CN | orange | 1.89 | ○ |
| 46 | 2-thiazolyl | —CN | orange | 1.87 | Δ |
| 47 | 3-thienyl | —CN | orange | 1.70 | Δ |
| 48 | —nC₄H₉ | —CN | orange | 1.75 | Δ |
| 49 | —nC₄H₉ | —CN | orange | 1.69 | Δ |
| | | | (7-1-b K: —N=N—) | | |
| 1 | —CH₂Ph | —CN | orange | 2.12 | ○ |
| 2 | —CH₂Ph | —CN | orange | 2.03 | — |
| 3 | —CH₂Ph | —CN | orange | 2.10 | ○ |
| 4 | —CH₂Ph | —CN | orange | 1.90 | ○ |

TABLE 7-continued

| | | | | | |
|---|---|---|---|---|---|
| 5 | —CH₂Ph | —CN | orange | 1.99 | ◯ |
| 6 | —CH₂Ph | —CN | orange | 1.90 | ◯ |
| 7 | —CH₂Ph | —CN | orange | 1.96 | ◯ |
| 8 | —CH₂Ph | —CN | orange | 1.80 | ◯ |
| 9 | —CH₂Ph | —CN | orange | 1.83 | ◯ |
| 10 | —CH₂Ph | —CN | orange | 1.90 | ◯ |
| 11 | —CH₂Ph | —CN | orange | 1.73 | ◯ |
| 12 | —CH₂Ph | —NO₂ | orange | 1.90 | △ |
| 13 | —CH₂Ph | —COOH | yellowish orange | 1.75 | ◯ |
| 14 | —CH₂Ph | —COOC₂H₅ | yellowish orange | 1.78 | △ |
| 15 | —CH₂Ph | —CN | orange | 1.90 | ◯ |
| 16 | —CH₂Ph | —SO₂NHCH₃ | yellowish orange | 1.96 | ◯ |
| 17 | —CH₂Ph | —CONHCH₃ | yellowish orange | 1.90 | ◯ |
| 18 | —CH₂Ph | —CN | orange | 1.81 | ◯ |
| 19 | —CH₂Ph | —CN | orange | 1.75 | ◯ |
| 20 | —CH₂Ph | —CN | orange | 1.83 | △ |
| 21 | —CH₂—CH═CH₂ | —CN | orange | 1.91 | ◯ |
| 22 | —nC₄H₉ | —CN | orange | 1.83 | ◯ |
| 23 | —nC₄H₉ | —CN | orange | 1.76 | ◯ |
| 24 | —nC₄H₉ | —CN | orange | 1.95 | ◯ |
| 25 | —nC₄H₉ | —CN | orange | 1.80 | ◯ |
| 26 | —Ph | —CN | orange | 1.71 | △ |
| 27 | 2-thienyl | —CN | orange | 1.79 | ◯ |
| 28 | —isoC₃H₇ | —CN | orange | 1.82 | △ |
| 29 | —nC₄H₉ | —CN | orange | 1.72 | ◯ |
| 30 | —nC₄H₉ | —CN | orange | 1.65 | ◯ |
| 31 | —nC₄H₉ | —CN | orange | 1.70 | ◯ |
| 32 | —nC₄H₉ | —CN | orange | 1.76 | ◯ |
| 33 | —nC₄H₉ | —CN | orange | 1.74 | ◯ |
| 34 | —nC₄H₉ | —CN | orange | 1.66 | ◯ |
| 35 | —nC₄H₉ | —CN | orange | 1.91 | ◯ |
| 36 | —nC₄H₉ | —CN | orange | 1.76 | ◯ |
| 37 | —nC₄H₉ | —CN | orange | 1.86 | △ |
| 38 | —nC₄H₉ | —CN | orange | 1.96 | △ |
| 39 | —nC₄H₉ | —CN | orange | 1.85 | △ |
| 40 | —nC₄H₉ | —CN | orange | 1.72 | ◯ |
| 41 | —nC₄H₉ | —CN | orange | 1.73 | ◯ |
| 42 | —nC₄H₉ | —CN | orange | 1.90 | ◯ |
| 43 | —tert-C₄H₉ | —CN | orange | 1.78 | ◯ |
| 44 | —C₆H₁₃ | —CN | orange | 1.80 | ◯ |
| 45 | —nC₄H₉ | —CN | orange | 1.81 | ◯ |
| 46 | 2-thiazolyl | —CN | orange | 1.83 | △ |
| 47 | 3-thienyl | —CN | orange | 1.71 | ◯ |
| 48 | —nC₄H₉ | —CN | orange | 1.79 | △ |
| 49 | —nC₄H₉ | —CN | orange | 1.71 | △ |
| (7-1-c K: —N═N—) | | | | | |
| 1 | —CH₂Ph | —CN | red | 2.10 | ◯ |
| 2 | —CH₂Ph | —CN | red | 1.97 | ◯ |
| 3 | —CH₂Ph | —CN | red | 2.00 | ◯ |
| 4 | —CH₂Ph | —CN | red | 1.73 | △ |
| 5 | —CH₂Ph | —CN | red | 1.90 | ◯ |
| 6 | —CH₂Ph | —CN | red | 1.81 | ◯ |
| 7 | —CH₂Ph | —CN | red | 1.85 | ◯ |
| 8 | —CH₂Ph | —CN | red | 1.69 | △ |
| 9 | —CH₂Ph | —CN | red | 1.70 | ◯ |
| 10 | —CH₂Ph | —CN | red | 1.90 | ◯ |
| 11 | —CH₂Ph | —CN | red | 1.74 | △ |
| 12 | —CH₂Ph | —NO₂ | red | 1.68 | ◯ |
| 13 | — | — | — | — | — |
| 14 | — | — | — | — | — |
| 15 | —CH₂Ph | —CN | red | 1.96 | ◯ |
| 16 | — | — | — | — | — |
| 17 | —CH₂Ph | —CONHCH₃ | red | 1.81 | ◯ |
| 18 | —CH₂Ph | —CN | red | 1.76 | ◯ |
| 19 | —CH₂Ph | —CN | red | 1.85 | ◯ |
| 20 | —CH₂Ph | —CN | red | 1.80 | △ |
| 21 | —CH₂—CH═CH₂ | —CN | red | 1.90 | ◯ |
| 22 | —nC₄H₉ | —CN | red | 1.82 | △ |
| 23 | —nC₄H₉ | —CN | red | 1.70 | ◯ |
| 24 | —nC₄H₉ | —CN | red | 1.86 | ◯ |
| 25 | —nC₄H₉ | —CN | red | 1.80 | ◯ |
| 26 | —Ph | —CN | red | 1.78 | ◯ |
| 27 | 2-thienyl | —CN | red | 1.77 | ◯ |
| 28 | — | — | — | — | — |
| 29 | —nC₄H₉ | —CN | red | 1.71 | ◯ |
| 30 | —nC₄H₉ | —CN | red | 1.74 | ◯ |
| 31 | —nC₄H₉ | —CN | red | 1.75 | △ |
| 32 | —nC₄H₉ | —CN | red | 1.78 | ◯ |

TABLE 7-continued

| No. | R | | | | |
|---|---|---|---|---|---|
| 33 | —nC$_4$H$_9$ | —CN | red | 1.84 | Δ |
| 34 | —nC$_4$H$_9$ | —CN | red | 1.62 | ○ |
| 35 | — | — | — | — | — |
| 36 | — | — | — | — | — |
| 37 | —nC$_4$H$_9$ | —CN | red | 1.80 | ○ |
| 38 | —nC$_4$H$_9$ | —CN | red | 1.70 | Δ |
| 39 | —nC$_4$H$_9$ | —CN | red | 1.74 | ○ |
| 40 | —nC$_4$H$_9$ | —CN | red | 1.76 | ○ |
| 41 | — | — | — | — | — |
| 42 | —nC$_4$H$_9$ | —CN | red | 1.84 | ○ |
| 43 | —nC$_4$H$_9$ | —CN | red | 1.73 | Δ |
| 44 | —C$_6$H$_{13}$ | —CN | red | 1.86 | ○ |
| 45 | —nC$_4$H$_9$ | —CN | red | 1.80 | Δ |
| 46 | 2-thiazolyl | —CN | red | 1.80 | ○ |
| 47 | 3-thienyl | —CN | red | 1.71 | ○ |
| 48 | —nC$_4$H$_9$ | —CN | red | 1.73 | ○ |
| 49 | —nC$_4$H$_9$ | —CN | red | 1.75 | ○ |
| 50 | — | — | — | — | — |
| 51 | 2-benzothiazolyl | —CN | red | 1.74 | ○ |
| 52 | 2-pyridyl | —CN | red | 1.68 | Δ |
| 53 | — | — | — | — | — |
| 54 | — | — | — | — | — |
| 55 | 2-(4,5-dicyano)thiazolyl | —CN | red | 1.73 | Δ |
| 56 | —Ph | —CN | red | 1.76 | ○ |

(7-2)

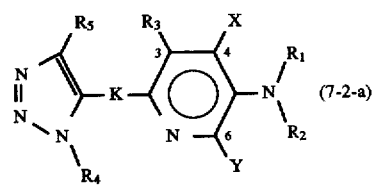

(7-2-a)

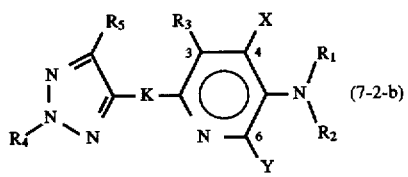

(7-2-b)

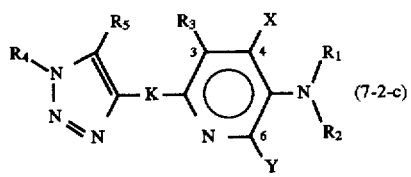

(7-2-c)

| No. | R$_1$ | R$_2$ | 3-R$_3$ | X or Y |
|---|---|---|---|---|
| | | 7-2 common to a to c | | |
| 1 | —C$_2$H$_5$ | —C$_2$H$_5$ | —H | —H |
| 2 | —CH$_2$CH=CH$_2$ | —C$_2$H$_5$ | —CH$_3$ | —H |
| 3 | —C$_2$H$_4$CN | —C$_2$H$_5$ | —NHCOCH$_3$ | —H |
| 4 | —C$_2$H$_4$OH | —C$_2$H$_5$ | —NHSO$_2$CH$_3$ | —H |
| 5 | —C$_2$H$_4$OCH$_3$ | —C$_2$H$_5$ | —NHCOC$_2$H$_5$ | —H |
| 6 | —C$_2$H$_4$COOCH$_3$ | —C$_2$H$_5$ | —CH$_3$ | —H |
| 7 | —C$_2$H$_4$OCOCH$_3$ | —C$_2$H$_5$ | —CH$_3$ | —H |
| 8 | —CH$_2$OCH$_2$Ph | —C$_2$H$_5$ | —H | —H |
| 9 | —CH$_2$OCOOPh | —C$_2$H$_5$ | —OCH$_3$ | —H |
| 10 | —C$_2$H$_4$OCH$_3$ | —C$_2$H$_5$ | —NHCOC$_2$H$_5$ | —H |
| 11 | —C$_2$H$_4$OCOCH$_3$ | —C$_2$H$_5$ | —CH | —H |
| 12 | —C$_2$H$_5$ | —C$_2$H$_5$ | —H | —H |
| 13 | —C$_2$H$_5$ | —C$_2$H$_5$ | —H | —H |
| 14 | —C$_2$H$_5$ | —C$_2$H$_5$ | —H | —H |
| 15 | —C$_2$H$_5$ | —C$_2$H$_5$ | —CH$_3$ | —H |
| 16 | —C$_2$H$_5$ | —C$_2$H$_5$ | —C$_2$H$_5$ | —H |
| 17 | —C$_2$H$_5$ | —C$_2$H$_5$ | —CH$_3$ | —H |
| 18 | —C$_2$H$_5$ | —C$_2$H$_5$ | —CH$_3$ | X,Y = —OH |
| 19 | —C$_2$H$_4$OCH$_3$ | —C$_2$H$_4$OCH$_3$ | —NHCOCH$_3$ | —H |
| 20 | —CH$_2$Ph | —CH$_3$ | —OC$_2$H$_5$ | —H |
| 21 | —C$_2$H$_5$ | —C$_2$H$_5$ | —CH$_3$ | —H |

TABLE 7-continued

| | | | | |
|---|---|---|---|---|
| 22 | —C₂H₅ | —C₂H₅ | —NHSO₂CH₃ | —CH₃ |
| 23 | —C₂H₅ | —C₂H₅ | —NHCOCH₃ | Y = —OH |
| 24 | —C₂H₅ | —C₂H₅ | —NHCOCH₃ | Y = —NHCOCH₃ |
| 25 | —C₂H₄OCOCH₃ | —C₂H₄OCOCH₃ | —CH₃ | —H |
| 26 | —C₂H₅ | —H | —CH₃ | —H |
| 27 | —C₂H₅ | —C₂H₅ | —H | —H |
| 28 | —C₂H₅ | —C₂H₅ | —H | —H |
| 29 | —C₂H₅ | —C₂H₅ | —CH₃ | —H |
| 30 | —C₂H₅ | —C₂H₅ | —NHCOCH₃ | —H |
| 31 | —CH₂CH=CH₂ | —C₂H₄OCH₃ | —CH₃ | —H |
| 32 | —C₂H₄O-cyclohexyl | —C₂H₅ | —NHCOCH₃ | —H |
| 33 | combining of R₁ with X to form —C₃H₆— | —C₂H₅ | —CH₃ | —H |
| 34 | combining of R₁ with X to form —C₃H₆— | —C₂H₅ | —NHCOCH₃ | —H |
| 35 | combining of R₁ with X to form —C₃H₆— | —C₂H₅ | —NHSO₂CH₃ | —H |
| 36 | combining of R₁ with R₂ to form —C₅H₁₀— | | —CH₃ | —H |
| 37 | combining of R₁ with R₂ to form —C₅H₁₀— | | —NHCOCH₃ | —H |
| 38 | combining of R₁ with R₂ to form —C₅H₁₀— | | —CH₃ | —H |
| 39 | combining of R₁ with R₂ to form —C₂H₄OC₂H₄— | | —NHCOCH₃ | —H |
| 40 | combining of R₁ with R₂ to form —C₂H₄OC₂H₄— | | —CH₃ | X = —CN |
| 41 | combining of R₁ with R₂ to form —C₄H₈— | | —NHCOCH₃ | —H |
| 42 | —C₂H₄OCOOC₂H₅ | —CH₃ | —CH₃ | —H |
| 43 | —C₂H₅ | —C₂H₅ | —NHCOCH₃ | —H |
| 44 | —C₂H₄OC₂H₄OC₂H₅ | —C₂H₅ | —CH₃ | —H |
| 45 | —C₂H₅ | —C₂H₅ | —CH₃ | —H |
| 46 | —C₂H₅ | —C₂H₅ | —NHCOCH₃ | X = —OC₂H₅ |
| 47 | —C₂H₅ | —C₂H₅ | —CH₃ | X = —CH₃ |
| 48 | —C₂H₅ | —C₂H₅ | —CH₃ | X,Y = —CH₃ |
| 49 | —C₂H₅ | —C₂H₅ | —NHCOCH₃ | Y = —CN |
| 50 | —C₂H₅ | —C₂H₅ | —CH₃ | X,Y = —CN |
| 51 | combining of R₁ with X to form —C₃H₆— | combining of R₂ with Y to form —C₃H₆— | —CH₃ | |
| 52 | combining of R₁ with X to form —C₃H₆— | combining of R₂ with Y to form —C₃H₆— | —NHCOCH₃ | |
| 53 | combining of R₁ with X to form —C₃H₆— | combining of R₂ with Y to form —C₃H₆— | —NHSO₂CH₃ | |

7-2 b to c

| | | | | |
|---|---|---|---|---|
| 54 | —C₂H₅ | —C₂H₅ | —CH₃ | —H |
| 55 | —C₂H₅ | —C₂H₅ | —CH₃ | —H |
| 56 | —C₂H₅ | —C₂H₅ | —NHCOCH₃ | —H |
| 57 | —C₂H₅ | —C₂H₅ | —CH₃ | —H |
| 58 | —C₂H₅ | —C₂H₅ | —CH₃ | Y = —CN |
| 59 | —C₂H₅ | —C₂H₅ | —NHCOCH₃ | —H |
| 60 | —C₂H₄OCOCH₃ | —C₂H₅ | —NHCOCH₃ | —H |

| No. | R₄ | R₅ | hue | coloring density | light fastness |
|---|---|---|---|---|---|
| (7-2-a K: —N=N—) | | | | | |
| 1 | —CH₂Ph | —CN | red | 1.90 | ○ |
| 2 | —CH₂Ph | —CN | red | 1.88 | ○ |
| 3 | —CH₂Ph | —CN | red | 2.02 | ○ |
| 4 | —CH₂Ph | —CN | red | 1.96 | ○ |
| 5 | —CH₂Ph | —CN | red | 2.11 | ○ |
| 6 | —CH₂Ph | —CN | red | 1.91 | ○ |
| 7 | —CH₂Ph | —CN | red | 1.88 | ○ |
| 8 | —CH₂Ph | —CN | red | 1.82 | ○ |
| 9 | —CH₂Ph | —CN | red | 1.77 | Δ |
| 10 | —CH₂Ph | —CN | red | 1.74 | ○ |
| 11 | —CH₂Ph | —CN | red | 1.97 | Δ |
| 12 | —CH₂Ph | —NO₂ | red | 1.72 | Δ |
| 13 | —CH₂Ph | —COOH | red | 1.80 | ○ |
| 14 | —CH₂Ph | —COOC₂H₅ | red | 1.77 | Δ |
| 15 | —CH₂Ph | —CN | red | 1.88 | ○ |
| 16 | —CH₂Ph | —SO₂NHCH₃ | red | 1.81 | Δ |
| 17 | —CH₂Ph | —CONHCH₃ | red | 1.89 | ○ |
| 18 | —CH₂Ph | —CN | red | 1.84 | ○ |
| 19 | —CH₂Ph | —CN | red | 1.87 | ○ |
| 20 | —CH₂Ph | —CN | red | 1.76 | Δ |
| 21 | —CH=CH₂ | —CN | red | 1.82 | Δ |

TABLE 7-continued

| | | | | | |
|---|---|---|---|---|---|
| 22 | —CH₂Ph | —CN | red | 1.87 | ○ |
| 23 | —CH₂Ph | —CN | red | 1.91 | ○ |
| 24 | —nC₄H₉ | —CN | red | 1.87 | ○ |
| 25 | —nC₄H₉ | —CN | red | 1.80 | ○ |
| 26 | —nC₄H₉ | —CN | red | 1.76 | ○ |
| 27 | —Ph | —CN | red | 1.70 | ○ |
| 28 | 2-thienyl | —CN | red | 1.73 | ○ |
| 29 | 3-thienyl | —CN | red | 1.64 | ○ |
| 30 | —isoC₃H₇ | —CN | red | 1.71 | ○ |
| 31 | —nC₄H₉ | —CN | red | 1.89 | △ |
| 32 | —nC₄H₉ | —CN | red | 1.80 | △ |
| 33 | —nC₄H₉ | —CN | red | 1.92 | ○ |
| 34 | —nC₄H₉ | —CN | red | 1.87 | ○ |
| 35 | —nC₄H₉ | —CN | red | 1.80 | △ |
| 36 | —nC₄H₉ | —CN | red | 1.94 | △ |
| 37 | —nC₄H₉ | —CN | red | 1.70 | ○ |
| 38 | —nC₄H₉ | —CN | red | 1.76 | ○ |
| 39 | —nC₄H₉ | —CN | red | 1.97 | ○ |
| 40 | —nC₄H₉ | —CN | red | 1.77 | ○ |
| 41 | —nC₄H₉ | —CN | red | 1.82 | ○ |
| 42 | —tert-C₄H₉ | —CN | red | 2.06 | ○ |
| 43 | —C₆H₁₃ | —CN | red | 1.84 | ○ |
| 44 | —nC₄H₉ | —CN | red | 1.76 | △ |
| 45 | 2-thiazolyl | —CN | red | 1.81 | △ |
| 46 | —nC₄H₉ | —CN | red | 1.73 | △ |
| 47 | —nC₄H₉ | —CN | red | 1.82 | ○ |
| 48 | —nC₄H₉ | —CN | red | 1.77 | ○ |
| 49 | —nC₄H₉ | —CN | red | 1.80 | ○ |
| 50 | —nC₄H₉ | —CN | red | 1.90 | ○ |
| 51 | —nC₄H₉ | —CN | red | 1.83 | △ |
| 52 | —nC₄H₉ | —CN | red | 1.87 | △ |
| 53 | —nC₄H₉ | —CN | red | 1.89 | △ |
| | | (7-2-b K: —N=N—) | | | |
| 1 | —CH₂Ph | —CN | red | 1.89 | △ |
| 2 | —CH₂Ph | —CN | red | 1.82 | △ |
| 3 | — | — | — | — | — |
| 4 | —CH₂Ph | —CN | red | 1.76 | △ |
| 5 | — | — | — | — | — |
| 6 | — | — | — | — | — |
| 7 | —CH₂Ph | —CN | red | 1.70 | ○ |
| 8 | —CH₂Ph | —CN | red | 1.72 | ○ |
| 9 | —CH₂Ph | —CN | red | 1.68 | △ |
| 10 | —CH₂Ph | —CN | red | 1.76 | ○ |
| 11 | —CH₂Ph | —CN | red | 1.80 | △ |
| 12 | —CH₂Ph | —NO₂ | red | 1.71 | △ |
| 13 | —CH₂Ph | —COOH | red | 1.79 | △ |
| 14 | — | — | — | — | — |
| 15 | —CH₂Ph | —CN | red | 1.80 | ○ |
| 16 | — | — | — | — | — |
| 17 | —CH₂Ph | —CONHCH₃ | red | 1.74 | |
| 18 | —CH₂Ph | —CN | red | 1.58 | △ |
| 19 | —CH₂Ph | —CN | red | 1.78 | ○ |
| 20 | —CH₂Ph | —CN | red | 1.79 | ○ |
| 21 | — | — | — | — | — |
| 22 | —CH₂Ph | —CN | red | 1.81 | ○ |
| 23 | —CH₂Ph | —CN | red | 1.70 | △ |
| 24 | —nC₄H₉ | —CN | red | 1.77 | ○ |
| 25 | —nC₄H₉ | —CN | red | 1.89 | ○ |
| 26 | — | — | — | — | — |
| 27 | —Ph | —CN | red | 1.85 | ○ |
| 28 | 2-thienyl | —CN | red | 1.69 | ○ |
| 29 | 3-thienyl | —CN | red | 1.72 | △ |
| 30 | — | — | — | — | — |
| 31 | — | — | — | — | — |
| 32 | —nC₄H₉ | —CN | red | 1.64 | △ |
| 33 | —nC₄H₉ | —CN | red | 1.70 | ○ |
| 34 | —nC₄H₉ | —CN | red | 1.73 | ○ |
| 35 | —nC₄H₉ | —CN | red | 1.82 | △ |
| 36 | —nC₄H₉ | —CN | red | 1.69 | ○ |
| 37 | —nC₄H₉ | —CN | red | 1.71 | ○ |
| 38 | — | — | — | — | — |
| 39 | — | — | — | — | — |
| 41 | —nC₄H₉ | —CN | red | 1.78 | ○ |
| 42 | — | — | — | — | — |
| 43 | —C₆H₁₃ | —CN | red | 1.80 | ○ |
| 44 | —nC₄H₉ | —CN | red | 1.82 | ○ |
| 45 | 2-thiazolyl | —CN | red | 1.77 | △ |
| 46 | —nC₄H₉ | —CN | red | 1.68 | △ |

TABLE 7-continued

| | | | | | |
|---|---|---|---|---|---|
| 47 | $-nC_4H_9$ | $-CN$ | red | 1.76 | ○ |
| 48 | $-nC_4H_9$ | $-CN$ | red | 1.71 | ○ |
| 49 | $-nC_4H_9$ | $-CN$ | red | 1.74 | ○ |
| 50 | $-nC_4H_9$ | $-CN$ | red | 1.80 | ○ |
| 51 | $-nC_4H_9$ | $-CN$ | red | 1.81 | △ |
| 52 | $-nC_4H_9$ | $-CN$ | red | 1.82 | ○ |
| 53 | $-nC_4H_9$ | $-CN$ | red | 1.83 | ○ |
| 54 | 1-naphthyl | $-CN$ | red | 1.70 | ○ |
| 55 | — | — | — | — | — |
| 56 | 2-pyridyl | $-CN$ | red | 1.65 | ○ |
| 57 | 2-furyl | $-CN$ | red | 1.69 | ○ |
| 58 | — | — | — | — | — |
| 59 | 2-(4,5-dicyano)thiazolyl | $-CN$ | red | 1.73 | ○ |
| 60 | $-Ph$ | $-CN$ | red | 1.79 | ○ |
| (7-2-c K: $-N=N-$) | | | | | |
| 1 | $-CH_2Ph$ | $-CN$ | red | 1.76 | △ |
| 2 | $-CH_2Ph$ | $-CN$ | red | 1.87 | ○ |
| 3 | — | — | — | — | — |
| 5 | — | — | — | — | — |
| 6 | $-CH_2Ph$ | $-CN$ | red | 1.79 | ○ |
| 7 | $-CH_2Ph$ | $-CN$ | red | 1.82 | ○ |
| 8 | $-CH_2Ph$ | $-CN$ | red | 1.73 | ○ |
| 9 | — | — | — | — | — |
| 10 | $-CH_2Ph$ | $-CN$ | red | 2.06 | ○ |
| 11 | $-CH_2Ph$ | $-CN$ | red | 1.69 | △ |
| 12 | $-CH_2Ph$ | $-NO_2$ | red | 1.73 | △ |
| 13 | $-CH_2Ph$ | $-COOH$ | red | 1.68 | △ |
| 14 | — | — | — | — | — |
| 15 | $-CH_2Ph$ | $-CN$ | red | 1.77 | ○ |
| 16 | — | — | — | — | — |
| 17 | $-CH_2Ph$ | $-CONHCH_3$ | red | 1.78 | ○ |
| 18 | $-CH_2Ph$ | $-CN$ | red | 1.70 | △ |
| 19 | $-CH_2Ph$ | $-CN$ | red | 1.89 | ○ |
| 20 | $-CH_2Ph$ | $-CN$ | red | 1.65 | △ |
| 21 | — | — | — | — | — |
| 22 | $-C_4H_9$ | $-CN$ | red | 1.80 | △ |
| 23 | $-C_4H_9$ | $-CN$ | red | 1.91 | △ |
| 24 | $-nC_4H_9$ | $-CN$ | red | 1.92 | ○ |
| 25 | $-nC_4H_9$ | $-CN$ | red | 1.82 | ○ |
| 26 | $-nC_4H_9$ | $-CN$ | red | 1.84 | ○ |
| 27 | — | — | — | — | — |
| 28 | 2-thienyl | $-CN$ | red | 1.78 | △ |
| 29 | 3-thienyl | $-CN$ | red | 1.73 | △ |
| 30 | $-isoC_4H_9$ | $-CN$ | red | 1.87 | ○ |
| 31 | $-nC_4H_9$ | $-CN$ | red | 1.77 | △ |
| 32 | — | — | — | — | — |
| 33 | $-nC_4H_9$ | $-CN$ | red | 1.72 | ○ |
| 34 | — | — | — | — | — |
| 35 | $-nC_4H_9$ | $-CN$ | red | 1.73 | △ |
| 36 | $-nC_4H_9$ | $-CN$ | red | 1.81 | ○ |
| 37 | — | — | — | — | — |
| 38 | — | — | — | — | — |
| 39 | $-nC_4H_9$ | $-CN$ | red | 1.75 | ○ |
| 40 | $-nC_4H_9$ | $-CN$ | red | 1.75 | △ |
| 41 | — | — | — | — | — |
| 42 | $-tert-C_4H_9$ | $-CN$ | red | 1.77 | △ |
| 43 | — | — | — | — | — |
| 44 | $-nC_4H_9$ | $-CN$ | red | 1.78 | △ |
| 45 | 2-thiazolyl | $-CN$ | red | 1.83 | ○ |
| 46 | $-nC_4H_9$ | $-CN$ | red | 1.84 | ○ |
| 47 | $-nC_4H_9$ | $-CN$ | red | 1.82 | ○ |
| 48 | $-nC_4H_9$ | $-CN$ | red | 1.71 | ○ |
| 49 | $-nC_4H_9$ | $-CN$ | red | 1.70 | △ |
| 50 | $-nC_4H_9$ | $-CN$ | red | 1.76 | △ |
| 51 | $-nC_4H_9$ | $-CN$ | red | 1.67 | ○ |
| 52 | $-nC_4H_9$ | $-CN$ | red | 1.82 | ○ |
| 53 | $-nC_4H_9$ | $-CN$ | red | 1.80 | △ |
| 54 | — | — | — | — | — |
| 55 | 2-benzothiazolyl | $-CN$ | red | 1.76 | ○ |
| 57 | — | — | — | — | — |
| 58 | $-Ph$ | $-CN$ | red | 1.70 | △ |
| 59 | 2-(4,5-dicyano)thiazolyl | $-CN$ | red | 1.80 | ○ |
| 60 | $-Ph$ | $-CN$ | red | 1.83 | ○ |

(8) Dyes having the following structure:

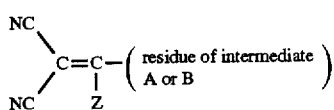

wherein Z stands for a hydrogen atom or a cyano group.

(8) Specific examples of the dyes represented by the general formula 8 and the performance thereof in the case of use in a thermal transfer sheet which will be described later are given in the following Table 8.

TABLE 8

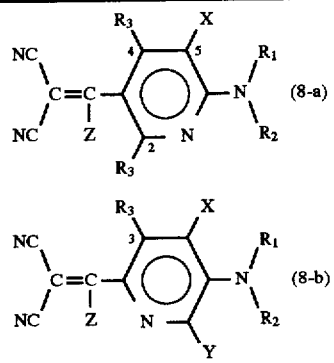

| No. | $R_1$ | $R_2$ | 2,3-$R_3$ | 4-$R_3$ | X | Y |
|---|---|---|---|---|---|---|
| | | 8-common to a to b | | | | |
| 1 | $-C_2H_5$ | $-C_2H_5$ | $-H$ | $-H$ | | |
| 2 | $-C_2H_5$ | $-C_2H_5$ | $-CH_3$ | $-H$ | | |
| 3 | $-C_2H_5$ | $-C_2H_5$ | $-NHCOCH_3$ | $-H$ | | |
| 4 | $-C_2H_4CN$ | $-C_2H_5$ | $-NHCOCH_3$ | $-H$ | | |
| 5 | $-C_2H_4OH$ | $-C_2H_5$ | $-NHSO_2CH_3$ | $-H$ | | |
| 6 | $-C_2H_4OCH_3$ | $-C_2H_5$ | $-NHCOC_2H_5$ | $-H$ | | |
| 7 | $-C_2H_4COOCH_3$ | $-C_2H_5$ | $-CH_3$ | $-H$ | | |
| 8 | $-C_2H_4OCOCH_3$ | $-C_2H_5$ | $-CH_3$ | $-H$ | | |
| 9 | $-C_2H_4OCH_2Ph$ | $-C_2H_5$ | $-CH_3$ | $-H$ | | |
| 10 | $-C_2H_4OCH_2Ph$ | $-C_2H_5$ | $-OH$ | $-H$ | | |
| 11 | $-CH_2OCOOPh$ | $-C_2H_5$ | $-OCH_3$ | $-H$ | | |
| 12 | $-C_2H_4OCH_3$ | $-C_2H_5$ | $-NHCOC_2H_5$ | $-H$ | | |
| 13 | $-C_2H_4OCOCH_3$ | $-C_2H_5$ | $-OH$ | $-H$ | | |
| 14 | $-C_2H_5$ | $-C_2H_5$ | $-H$ | $-H$ | $-CN$ | |
| 15 | $-C_2H_5$ | $-C_2H_5$ | $-NHCOCH_3$ | $-H$ | $-CN$(a) alone | $-CN$(b) alone |
| 16 | $-C_2H_5$ | $-C_2H_5$ | $-NHSO_2CH_3$ | $-H$ | $-CN$(a) alone | $-CN$(b) alone |
| 17 | $-CH_2CH=CH_2$ | $-C_2H_4OMe$ | $-CH_3$ | $-H$ | | |
| 18 | $-CH_2CH=CH_2$ | $-C_2H_5$ | $-NHCOCH_3$ | $-H$ | | |
| 19 | $-C_2H_4OPh$ | $-C_2H_5$ | $-CH_3$ | $-H$ | | |
| 20 | $-C_2H_5$ | $-C_2H_5$ | $-CH_3$ | $-H$ | $-CN$(b) alone | $-CN$(b) alone |
| 21 | $-MI_2H_5$ | $-C_2H_5$ | $-NHCOCH_3$ | $-H$ | $-CN$(a) alone | $-CN$(b) alone |
| 22 | $-C_2H_4O-$ (4-cyclohexylphenyl) | $-C_2H_5$ | $-NHCOCH_3$ | $-H$ | | |
| 23 | $-C_2H_5$ | $-C_2H_5$ | $-NHCOCH_3$ | | $-NHCOCH_3$ (a) alone | $-NHCOCH_3$ (b) alone |
| 24 | $-C_2H_5$ | $-C_2H_5$ | $-CH_3$ | | $-CH_3$ | |
| 25 | combining of $R_1$ with $R_2$ to form $-C_5H_{10}-$ | | $-NHCOCH_3$ | | | |
| 26 | combining of $R_1$ with $R_2$ to form $-C_5H_{10}-$ | | $-CH_3$ | | | |
| 27 | combining of $R_1$ with $R_2$ to form $-C_5H_{10}-$ | | $-NHCOCH_3$ | | $-CN$(a) alone | $-CN$(b) alone |
| 28 | combining of $R_1$ with $R_2$ to form $-C_2H_4OC_2H_4-$ | | $-NHCOCH_3$ | | | |
| 29 | combining of $R_1$ with $R_2$ to form $-C_2H_4OC_2H_4-$ | | $-CH_3$ | | | |
| | | 8-a alone | | | | |
| 30 | combining of $R_1$ with X to form $-C_3H_6-$ | $-C_2H_5$ | $-NHCOCH_3$ | | | |
| 31 | combining of $R_1$ with X to | $-C_2H_5$ | $-CH_3$ | | | |

TABLE 8-continued

| No. | | | | |
|---|---|---|---|---|
| 32 | combining of R₁ with X to form —C₃H₆— | —C₂H₄OCOCH₃ | —NHCOCH₃ | |
| 33 | combining of R₁ with X to form —C₃H₆— | —C₂H₄OCH₃ | —OH | |

8-b alone

| No. | | | | |
|---|---|---|---|---|
| 34 | combining of R₁ with X to form —C₃H₆— | —C₂H₅ | —NHCOCH₃ | |
| 35 | combining of R₁ with X to form —C₃H₆— | —C₂H₅ | —CH₃ | |
| 36 | combining of R₁ with X to form —C₃H₆— | —C₂H₄OCH₃ | —NHCOCH₃ | |
| 37 | combining of R₁ with X to form —C₃H₆— | —C₂H₄OCOCH₃ | —NHCOCH₃ | |
| 38 | combining of R₁ with X to form —C₃H₆— | —C₂H₅ | —CH₃ | —CH₃ |
| 39 | combining of R₁ with X or R₂ and Y to form —C₃H₆— | | NHCOCH₃ | |
| 40 | combining of R₁ with X or R₂ with Y to form —C₃H₆— | | —CH₃ | |

| No. | hue | coloring density | light fastness |
|---|---|---|---|
| | | (8-a Z: H) | |
| 1 | yellow | 2.10 | Δ |
| 2 | yellow | 2.07 | ○ |
| 3 | yellow | 1.95 | ○ |
| 4 | yellow | 1.92 | ○ |
| 5 | yellow | 1.89 | ○ |
| 6 | yellow | 1.93 | ○ |
| 7 | yellow | 1.95 | ○ |
| 8 | yellow | 1.95 | ○ |
| 9 | yellow | 1.86 | ○ |
| 10 | yellow | 1.82 | Δ |
| 11 | yellow | 1.80 | ○ |
| 12 | yellow | 1.93 | ○ |
| 13 | yellow | 1.90 | ○ |
| 14 | yellow | 1.97 | Δ |
| 15 | yellow | 1.91 | ○ |
| 16 | yellow | 1.93 | ○ |
| 17 | yellow | 1.94 | ○ |
| 18 | yellow | 1.88 | ○ |
| 19 | yellow | 1.85 | ○ |
| 20 | yellow | 1.92 | ○ |
| 21 | yellow | 1.97 | ○ |
| 22 | yellow | 1.96 | ○ |
| 23 | yellow | 1.82 | ○ |
| 24 | yellow | 2.03 | ○ |
| 25 | yellow | 1.93 | ○ |
| 26 | yellow | 2.06 | ○ |
| 27 | yellow | 1.84 | ○ |
| 28 | yellow | 1.90 | ○ |
| 29 | yellow | 2.02 | ○ |
| 30 | yellow | 1.91 | ○ |
| 31 | yellow | 2.07 | ○ |
| 32 | yellow | 1.85 | ○ |
| 33 | yellow | 1.89 | Δ |
| 34 | — | — | — |
| 35 | — | — | — |
| 36 | — | — | — |
| 37 | — | — | — |
| 38 | — | — | — |
| 39 | — | — | — |
| 40 | — | — | — |
| | | (8-a Z: CN) | |
| 1 | red | 1.97 | Δ |
| 2 | red | 1.98 | ○ |
| 3 | red | 1.93 | ○ |
| 4 | red | 1.87 | ○ |

TABLE 8-continued

| | | | |
|---|---|---|---|
| 5 | red | 1.82 | ○ |
| 6 | red | 1.83 | ○ |
| 7 | red | 1.87 | ○ |
| 8 | red | 1.86 | ○ |
| 9 | red | 1.81 | ○ |
| 10 | red | 1.77 | Δ |
| 11 | red | 1.73 | ○ |
| 12 | red | 1.82 | ○ |
| 13 | red | 1.80 | Δ |
| 14 | red | 1.92 | Δ |
| 15 | red | 1.85 | ○ |
| 16 | red | 1.84 | ○ |
| 17 | red | 1.90 | Δ |
| 18 | red | 1.83 | ○ |
| 19 | red | 1.79 | ○ |
| 20 | red | 1.90 | ○ |
| 21 | red | 1.92 | ○ |
| 22 | red | 1.90 | ○ |
| 23 | red | 1.84 | ○ |
| 24 | red | 1.97 | Δ |
| 25 | red | 1.88 | ○ |
| 26 | red | 1.97 | ○ |
| 27 | red | 1.80 | ○ |
| 28 | red | 1.74 | ○ |
| 29 | red | 1.91 | ○ |
| 30 | red | 1.83 | ○ |
| 31 | red | 1.99 | ○ |
| 32 | red | 1.77 | ○ |
| 33 | red | 1.80 | Δ |
| 34 | — | — | — |
| 35 | — | — | — |
| 36 | — | — | — |
| 37 | — | — | — |
| 38 | — | — | — |
| 39 | — | — | — |
| 40 | — | — | — |
| (8-b Z: H) | | | |
| 1 | yellow | 2.07 | Δ |
| 2 | yellow | 2.03 | Δ |
| 3 | yellow | 1.98 | ○ |
| 4 | yellow | 1.90 | ○ |
| 5 | yellow | 1.85 | ○ |
| 6 | yellow | 1.90 | ○ |
| 7 | yellow | 1.99 | ○ |
| 8 | yellow | 2.00 | ○ |
| 9 | yellow | 1.82 | ○ |
| 10 | yellow | 1.79 | Δ |
| 11 | yellow | 1.83 | ○ |
| 12 | yellow | 1.91 | ○ |
| 13 | yellow | 1.95 | Δ |
| 14 | yellow | 2.00 | Δ |
| 15 | yellow | 1.94 | ○ |
| 16 | yellow | 1.89 | ○ |
| 17 | yellow | 1.91 | ○ |
| 18 | yellow | 1.90 | ○ |
| 19 | yellow | 1.88 | ○ |
| 20 | yellow | 1.85 | Δ |
| 21 | yellow | 1.94 | ○ |
| 22 | yellow | 2.02 | ○ |
| 23 | yellow | 1.88 | ○ |
| 24 | yellow | 2.05 | ○ |
| 25 | yellow | 1.99 | ○ |
| 26 | yellow | 2.10 | ○ |
| 27 | yellow | 1.87 | ○ |
| 28 | yellow | 1.93 | ○ |
| 29 | yellow | 2.00 | Δ |
| 30 | — | — | — |
| 31 | — | — | — |
| 32 | — | — | — |
| 33 | — | — | — |
| 34 | yellow | 1.87 | ○ |
| 35 | yellow | 1.96 | ○ |
| 36 | yellow | 1.90 | ○ |
| 37 | yellow | 1.86 | ○ |
| 38 | yellow | 2.01 | ○ |
| 39 | yellow | 1.83 | ○ |
| 40 | yellow | 1.92 | ○ |

TABLE 8-continued

(8-b Z: CN)

| | | | |
|---|---|---|---|
| 1 | red | 2.15 | Δ |
| 2 | red | 2.07 | Δ |
| 3 | red | 2.02 | ○ |
| 4 | red | 1.98 | ○ |
| 5 | red | 1.93 | ○ |
| 6 | red | 2.01 | ○ |
| 7 | red | 2.08 | ○ |
| 8 | red | 2.13 | ○ |
| 9 | red | 1.94 | ○ |
| 10 | red | 1.91 | Δ |
| 11 | red | 1.84 | ○ |
| 12 | red | 1.98 | ○ |
| 13 | red | 2.03 | Δ |
| 14 | red | 2.18 | Δ |
| 15 | red | 2.04 | ○ |
| 16 | red | 1.93 | ○ |
| 17 | red | 1.98 | Δ |
| 18 | red | 1.95 | ○ |
| 19 | red | 1.93 | ○ |
| 20 | red | 1.91 | Δ |
| 21 | red | 2.03 | ○ |
| 22 | red | 2.10 | ○ |
| 23 | red | 1.99 | ○ |
| 24 | red | 2.12 | Δ |
| 25 | red | 2.08 | ○ |
| 26 | red | 2.18 | ○ |
| 27 | red | 2.00 | ○ |
| 28 | red | 2.06 | ○ |
| 29 | red | 2.11 | Δ |
| 30 | — | — | — |
| 31 | — | — | — |
| 32 | — | — | — |
| 33 | — | — | — |
| 34 | red | 1.94 | ○ |
| 35 | red | 2.03 | Δ |
| 36 | red | 1.99 | ○ |
| 37 | red | 1.94 | ○ |
| 38 | red | 2.15 | Δ |
| 39 | red | 1.93 | ○ |
| 40 | red | 2.04 | ○ |

(9) Dyes having the following structure:

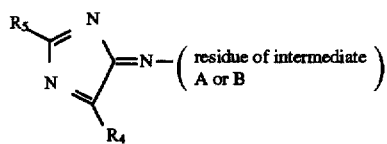

(9)

wherein $R_4$ and $R_5$ stand for a hydrogen atoms, a cyano group, a nitro group or a substituted or unsubstituted alkyl group, aryl group or aromatic heterocyclic group, a formylamino group, a sulfonylamino group, an alkoxycarbonyl group, a carbamoyl group or a sulfamoyl group.

Specific examples of the dyes represented by the general formula 9 and the performance thereof in the case of use in a thermal transfer sheet which will be described later are given in the following Table 9.

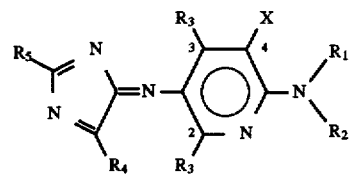

(9-a)

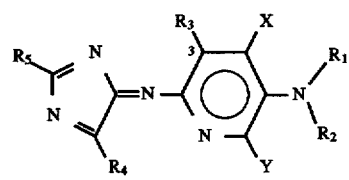

(9-b)

wherein $R_1$ to $R_5$, X, Y and n are as defined above.

TABLE 9

| No | $R_1$ | $R_2$ | 2,3-$R_3$ | 4-$R_3$ | X | Y |
|---|---|---|---|---|---|---|
| | | | 9- common to a to b | | | |
| 1 | —$C_2H_5$ | —$C_2H_5$ | | | —$CH_3$ | |
| 2 | —$C_2H_5$ | —$C_2H_5$ | | | —$NHCOCH_3$ | |
| 3 | —$C_2H_5$ | —$C_2H_5$ | | | —$NHSO_2CH_3$ | |
| 4 | —$C_2H_5$ | —$C_2H_5$ | | | —H | |

TABLE 9-continued

| | | | | | |
|---|---|---|---|---|---|
| 5 | —$C_2H_4OCH_3$ | —$C_2H_5$ | —$CH_3$ | | |
| 6 | —$C_2H_4OCH_3$ | —$C_2H_5$ | —$NHCOCH_3$ | | |
| 7 | —$C_2H_4OCOCH_3$ | —$C_2H_5$ | —$NHCOCH_3$ | | |
| 8 | —$C_2H_4OCOOCH_3$ | —$C_2H_5$ | —$CH_3$ | | |
| 9 | —$C_2H_4OCOOPh$ | —$CH_3$ | —$NHCOCH_3$ | | |
| 10 | —$C_2H_4OCH_2Ph$ | —$C_2H_5$ | —$CH_3$ | | |
| 11 | —$C_2H_5$ | —$C_2H_5$ | —$NHCOCH_3$ | —$NHCOCH_3$ (a) alone | —$NHCOCH_3$ (b) alone |
| 12 | —$C_2H_4CN$ | —$C_2H_5$ | —$CH_3$ | | |
| 13 | —$C_2H_4OCH_3$ | —$C_2H_4OCH_3$ | —$CH_3$ | | |
| 14 | —$CH_2CH=CH_2$ | —$C_2H_5$ | —H | | |
| 15 | —$C_2H_4OCO$—$CH_3$ | —$C_2H_4OCO$—$CH_3$ | —$NHCOCH_3$ | | |
| 16 | —$C_2H_5$ | —$C_2H_5$ | —$CH_3$ | —$CH_3$ | |
| 17 | combining of $R_1$ with $R_2$ to form —$C_5H_{10}$— | | —$CH_3$ | | |
| 18 | combining of $R_1$ with $R_2$ to form —$C_2H_4OC_2H_4$— | | —$NHCOCH_3$ | -2-furyl | —Ph |
| | 9-a alone | | | | |
| 19 | combining of $R_1$ with X to form —$C_3H_6$— | —$C_2H_5$ | —$CH_3$ | | |
| 20 | combining of $R_1$ with X to form —$C_3H_6$— | —$C_2H_4OCO$—$CH_3$ | —$NHCOCH_3$ | | |
| | 9-b alone | | | | |
| 21 | combining of $R_1$ with Y to form —$C_3H_6$— | —$C_2H_5$ | —$CH_3$ | | |
| 22 | combining of $R_1$ with Y to form —$C_3H_6$— | —$C_2H_4OCO$—$CH_3$ | —$NHCOCH_3$ | | |
| 23 | combining of $R_1$ with X or $R_2$ with Y to form —$C_3H_6$— | | —$NHCOCH_3$ | | |
| 24 | combining of $R_1$ with X or $R_2$ with Y to form —$C_3H_6$— | | —$NHSO_2CH_3$ | | |

| No. | $R_4$ | $R_5$ | hue | coloring density | light fastness |
|---|---|---|---|---|---|
| | | | (9-a) | | |
| 1 | —Ph | —Ph | blue | 2.20 | △ |
| 2 | —Ph | —Ph | blue | 2.03 | ○ |
| 3 | —Ph | —Ph | blue | 2.04 | ○ |
| 4 | —Ph | —Ph | blue | 2.18 | △ |
| 5 | —Ph | —Ph | blue | 2.14 | △ |
| 6 | —Ph | —Ph | blue | 1.99 | ○ |
| 7 | —Ph | —Ph | blue | 1.93 | ○ |
| 8 | —Ph | —Ph | blue | 2.07 | △ |
| 9 | —Ph | —Ph | blue | 1.90 | ○ |
| 10 | —Ph | —Ph | blue | 1.98 | △ |
| 11 | —Ph | —Ph | blue | 1.90 | ○ |
| 12 | —Ph | —Ph | blue | 2.10 | △ |
| 13 | —Ph | —Ph | blue | 2.04 | △ |
| 14 | —Ph | —Ph | blue | 2.16 | △ |
| 15 | —Ph | —Ph | blue | 2.08 | ○ |
| 16 | —Ph | —Ph | blue | 2.18 | △ |
| 17 | 2-thienyl | 2-thienyl | blue | 2.17 | ○ |
| 18 | 3-thienyl | 2-thienyl | blue | 1.87 | ○ |
| 19 | 2-thienyl | 3-thienyl | blue | 2.12 | ○ |
| 20 | 3-thienyl | 3-thienyl | blue | 1.92 | ○ |
| 21 | — | — | — | — | — |
| 22 | — | — | — | — | — |
| 23 | — | — | — | — | — |
| 24 | — | — | — | — | — |
| | | | (9-b) | | |
| 1 | —Ph | —Ph | blue | 1.98 | △ |
| 2 | —Ph | —Ph | blue | 1.84 | ○ |
| 3 | —Ph | —Ph | blue | 1.86 | ○ |
| 4 | —Ph | —Ph | blue | 1.93 | △ |
| 5 | —Ph | —Ph | blue | 1.95 | △ |
| 6 | —Ph | —Ph | blue | 1.77 | ○ |
| 7 | —Ph | —Ph | blue | 1.72 | ○ |
| 8 | —Ph | —Ph | blue | 1.90 | △ |
| 9 | —Ph | —Ph | blue | 1.71 | ○ |
| 10 | —Ph | —Ph | blue | 1.74 | △ |

TABLE 9-continued

| 11 | —Ph | —Ph | blue | 1.70 | ○ |
| 12 | —Ph | —Ph | blue | 1.92 | △ |
| 13 | —Ph | —Ph | blue | 1.88 | △ |
| 14 | —Ph | —Ph | blue | 1.94 | △ |
| 15 | —Ph | —Ph | blue | 1.88 | ○ |
| 16 | —Ph | —Ph | blue | 1.91 | △ |
| 17 | 2-thienyl | 2-thienyl | blue | 1.72 | ○ |
| 18 | 3-thienyl | 2-thienyl | blue | 1.73 | ○ |
| 19 | — | — | — | — | — |
| 20 | — | — | — | — | — |
| 21 | —Ph | 3-thienyl | blue | 1.68 | ○ |
| 22 | —Ph | 2-thienyl | blue | 1.69 | ○ |
| 23 | 3-thienyl | —Ph | blue | 1.70 | ○ |
| 24 | 2-thienyl | —Ph | blue | 1.66 | ○ |

(10) Dyes having the following structure:

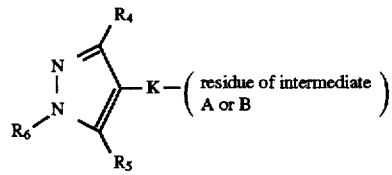  (10-1)

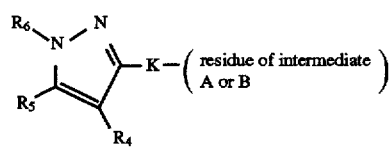  (10-2)

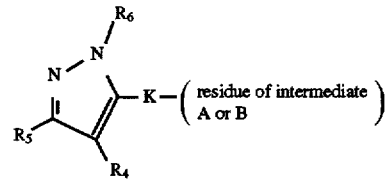  (10-3)

wherein K stands for —N=N—; $R_4$ and $R_5$ stand for a hydrogen atom, a halogen atom, a hydroxyl group, a cyano group, a nitro group or a substituted or unsubstituted alkyl group, allyl group, aryl group, aralkyl group, alkoxyalkyl group, alkoxy group, heterocyclic group, aralkylalkoxyalkyl group, carbamoyl group, sulfamoyl group, oxycarbonylalkyl group, oxycarbonyl group, carboxyalkyl group, formylamino group, sulfonylamino group or amino group; $R_6$ stands for a hydrogen atom or a substituted or unsubstituted alkyl group, allyl group, aryl group, aralkyl group, alkoxyalkyl group, aralkyloxyalkyl group, allyloxyalkyl group, aryloxyalkyl group, alkoxycarbonylalkyl group, carboxyalkyl group, heterocyclic group, carbamoyl group, sulfamoyl group or cycloalkyl group.

Specific examples of the dye represented by the general formula 10 and the performance thereof in the case of use in a thermal transfer sheet are given in the following Table 10.

TABLE 10

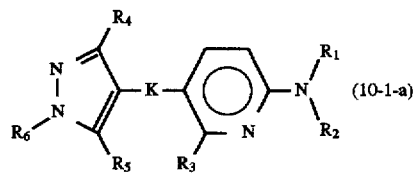  (10-1-a)

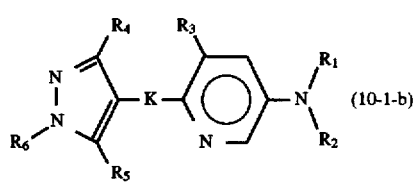  (10-1-b)

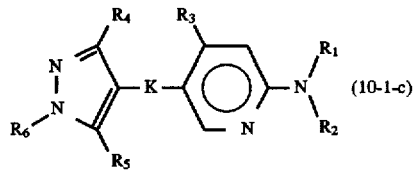  (10-1-c)

TABLE 10-continued

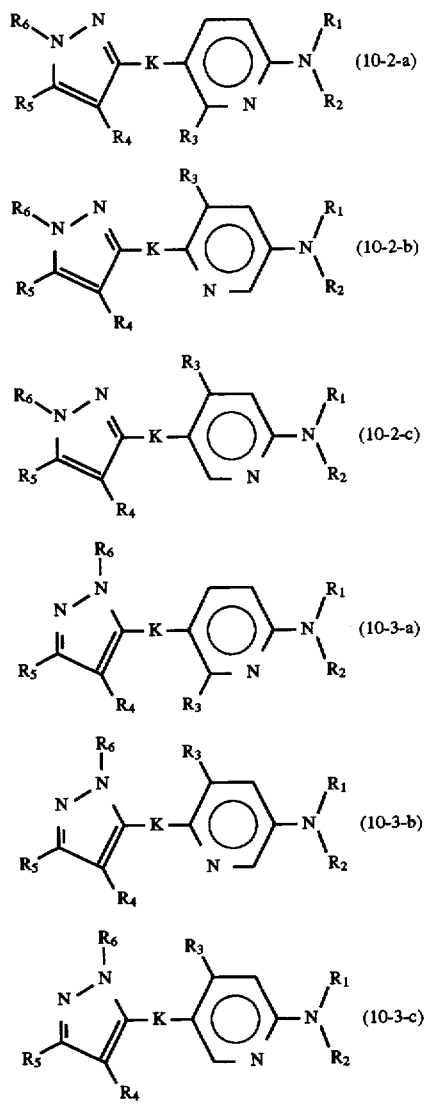

| No. | $R_1$ | $R_2$ | $R_3$ | $R_4$ | $R_5$ | $R_6$ | hue | coloring density | light fastness |
|---|---|---|---|---|---|---|---|---|---|
| (10-1-a K: $-N=N-$) | | | | | | | | | |
| 1 | $-C_2H_5$ | $-C_2H_5$ | $-H$ | $-CH_3$ | $-H$ | $-Ph$ | red | 1.81 | △ |
| 2 | $-C_2H_5$ | $-C_2H_5$ | $-NHCOCH_3$ | $-CN$ | $-nC_4H_9$ | $-Ph$ | red | 1.87 | ◯ |
| 3 | $-C_2H_4OCH_3$ | $-C_2H_5$ | $-NHSO_2CH_3$ | $-CN$ | $-CH_3$ | $-Ph$ | red | 1.76 | △ |
| 4 | $-C_2H_4OCOCH_3$ | $-C_2H_5$ | $-CH_3$ | $-CN$ | $-CH_3$ | $-Ph$ | red | 1.87 | △ |
| 5 | $-C_2H_4OCH_3$ | $-C_2H_4OMe$ | $-NHCOCH_3$ | $-CN$ | $-Ph$ | $-nC_4H_9$ | red | 1.97 | ◯ |
| 6 | $-C_2H_4CN$ | $-CH_3$ | $-CH_3$ | $-CN$ | $-Ph$ | $-nC_4H_9$ | red | 1.92 | △ |
| 7 | $-C_2H_4OCH_2Ph$ | $-C_2H_5$ | $-NHCOCH_3$ | $-CN$ | $-Ph$ | $-nC_4H_9$ | red | 1.82 | ◯ |
| 8 | $-C_2H_5$ | $-C_2H_5$ | $-NHSO_2CH_3$ | $-NO_2$ | $-Ph$ | $-nC_4H_9$ | red | 1.88 | △ |
| 9 | $-C_2H_4OCH_3$ | $-C_2H_5$ | $-NHCOC_2H_5$ | $-NO_2$ | $-nC_4H_9$ | $-Ph$ | red | 1.80 | △ |
| 10 | $-C_2H_5$ | $-C_2H_5$ | $-NHCOCH_3$ | $-nC_4H_9$ | $-CN$ | $-Ph$ | red | 1.81 | △ |
| 11 | $-C_2H_5$ | $-CH_3$ | $-CH_3$ | $-nC_4H_9$ | $-CN$ | $-CH_2-Ph$ | red | 1.78 | △ |
| 12 | $-C_2H_4OCH_3$ | $-C_2H_5$ | $-NHCOCH_3$ | $-nC_4H_9$ | $-CN$ | $-Ph$ | red | 1.72 | ◯ |
| 13 | $-C_2H_4OCOCH_3$ | $-C_2H_5$ | $-CH_3$ | $-nC_4H_9$ | $-CN$ | $-CH_2-Ph$ | red | 1.89 | △ |
| (10-2-a K: $-N=N-$) | | | | | | | | | |
| 1 | $-C_2H_5$ | $-C_2H_5$ | $-CH_3$ | $-CN$ | $-nC_4H_9$ | $-CH_2Ph$ | red | 1.80 | ◯ |
| 2 | $-C_2H_5$ | $-C_2H_5$ | $-NHCOCH_3$ | $-CN$ | $-nC_4H_9$ | $-CH_2Ph$ | red | 1.83 | ◯ |
| 3 | $-C_2H_4OCH_3$ | $-C_2H_5$ | $-NHSO_2CH_3$ | $-CN$ | $-CH_3$ | $-CH_2Ph$ | red | 1.76 | △ |
| 4 | $-C_2H_4OCOCH_3$ | $-C_2H_5$ | $-CH_3$ | $-CN$ | $-CH_3$ | $-CH_2Ph$ | red | 1.70 | △ |
| 5 | $-C_2H_4OCH_3$ | $-C_2H_4OMe$ | $-NHCOCH_3$ | $-CN$ | $-Ph$ | $-nC_4H_9$ | red | 1.73 | △ |
| 6 | $-C_2H_4CN$ | $-CH_3$ | $-CH_3$ | $-CN$ | $-Ph$ | $-nC_4H_9$ | red | 1.82 | △ |

TABLE 10-continued

| | | | | | | | | | |
|---|---|---|---|---|---|---|---|---|---|
| 7 | —$C_2H_4OCH_2Ph$ | —$C_2H_5$ | —$NHCOCH_3$ | —CN | —Ph | —$nC_4H_9$ | red | 1.87 | Δ |
| 8 | — | — | — | — | — | — | — | — | — |
| 9 | — | — | — | — | — | — | — | — | — |
| (10-2-a K: —N=N—) | | | | | | | | | |
| 1 | —$C_2H_5$ | —$C_2H_5$ | —$CH_3$ | —CN | —$nC_4H_9$ | —Ph | red | 1.84 | ○ |
| 2 | —$C_2H_5$ | —$C_2H_5$ | —$NHCOCH_3$ | —CN | —$nC_4H_9$ | —Ph | red | 1.83 | ○ |
| 3 | —$C_2H_4OCH_3$ | —$C_2H_5$ | —$NHSO_2CH_3$ | —CN | —$CH_3$ | —Ph | red | 1.77 | Δ |
| 4 | —$C_2H_4OCOCH_3$ | —$C_2H_5$ | —$CH_3$ | —CN | —$CH_3$ | —Ph | red | 1.82 | ○ |
| 5 | —$C_2H_4OCH_3$ | —$C_2H_4OMe$ | —$NHCOCH_3$ | —CN | —Ph | —$nC_4H_9$ | red | 1.90 | ○ |
| 6 | —$C_2H_4CN$ | —$CH_3$ | —$CH_3$ | —CN | —Ph | —$nC_4H_9$ | red | 1.88 | ○ |
| 7 | —$C_2H_4OCH_2Ph$ | —$C_2H_5$ | —$NHCOCH_3$ | —CN | —Ph | —$nC_4H_9$ | red | 1.84 | Δ |
| 8 | —$C_2H_5$ | —$C_2H_5$ | —$NHSO_2CH_3$ | —$NO_2$ | —Ph | —$nC_4H_9$ | red | 1.80 | Δ |
| 9 | —$C_2H_4OCH_3$ | —$C_2H_5$ | —$NHCOC_2H_5$ | —$NO_2$ | —$nC_4H_9$ | —Ph | red | 1.76 | Δ |
| 10 | —$C_2H_5$ | —$C_2H_5$ | —$NHCOCH_3$ | —CN | —CN | —Ph | red | 1.89 | ○ |
| (10-1-b K: —N=N—) | | | | | | | | | |
| 1 | —$C_2H_5$ | —$C_2H_5$ | —$CH_3$ | —CN | —$nC_4H_9$ | —Ph | red | 1.78 | Δ |
| 2 | —$C_2H_5$ | —$C_2H_5$ | —$NHCOCH_3$ | —CN | —$nC_4H_9$ | —Ph | red | 1.83 | ○ |
| 3 | —$C_2H_4OCH_3$ | —$C_2H_5$ | —$NHSO_2CH_3$ | —CN | —$CH_3$ | —Ph | red | 1.73 | Δ |
| 4 | —$C_2H_4OCOCH_3$ | —$C_2H_5$ | —$CH_3$ | —CN | —$CH_3$ | —Ph | red | 1.89 | ○ |
| 5 | —$C_2H_4OCH_3$ | —$C_2H_4OMe$ | —$NHCOCH_3$ | —CN | —Ph | —$nC_4H_9$ | red | 1.92 | ○ |
| 6 | —$C_2H_4CN$ | —$CH_3$ | —$CH_3$ | —CN | —Ph | —$nC_4H_9$ | red | 1.96 | Δ |
| 7 | —$C_2H_4OCH_2Ph$ | —$C_2H_5$ | —$NHCOCH_3$ | —CN | —Ph | —$nC_4H_9$ | red | 1.80 | ○ |
| 8 | —$C_2H_5$ | —$C_2H_5$ | —$NHSO_2CH_3$ | —$NO_2$ | —Ph | —$nC_4H_9$ | red | 1.73 | Δ |
| 9 | —$C_2H_4OCH_3$ | —$C_2H_5$ | —$NHCOC_2H_5$ | —$NO_2$ | —$nC_4H_9$ | —Ph | red | 1.75 | Δ |
| 10 | —$C_2H_5$ | —$C_2H_5$ | —$NHCOCH_3$ | —CN | —CN | —$CH_2Ph$ | red | 1.84 | ○ |
| (10-2-b K: —N=N—) | | | | | | | | | |
| 1 | —$C_2H_5$ | —$C_2H_5$ | —$CH_3$ | —CN | —$nC_4H_9$ | —Ph | red | 1.77 | Δ |
| 2 | —$C_2H_5$ | —$C_2H_5$ | —$NHCOCH_3$ | —CN | —$nC_4H_9$ | —Ph | red | 1.80 | ○ |
| 3 | —$C_2H_4OCH_3$ | —$C_2H_5$ | —$NHSO_2CH_3$ | —CN | —$CH_3$ | —Ph | red | 1.79 | Δ |
| 4 | —$C_2H_4OCOCH_3$ | —$C_2H_5$ | —$CH_3$ | —CN | —$CH_3$ | —Ph | red | 1.82 | Δ |
| 5 | —$C_2H_4OCH_3$ | —$C_2H_4OMe$ | —$NHCOCH_3$ | —CN | —Ph | —$nC_4H_9$ | red | 1.87 | ○ |
| 6 | —$C_2H_4CN$ | —$CH_3$ | —$CH_3$ | —CN | —Ph | —$nC_4H_9$ | red | 1.90 | Δ |
| 7 | —$C_2H_4OCH_2Ph$ | —$C_2H_5$ | —$NHCOCH_3$ | —CN | —Ph | —$nC_4H_9$ | red | 1.77 | ○ |
| 8 | —$C_2H_5$ | —$C_2H_5$ | —$NHSO_2CH_3$ | —$NO_2$ | —Ph | —$nC_4H_9$ | red | 1.70 | ○ |
| 9 | —$C_2H_4OCH_3$ | —$C_2H_5$ | —$NHCOC_2H_5$ | —$NO_2$ | —$nC_4H_9$ | —Ph | red | 1.72 | ○ |
| (10-1-c K: —N=N—) | | | | | | | | | |
| 1 | —$C_2H_5$ | —$C_2H_5$ | —$CH_3$ | —CN | —$nC_4H_9$ | —Ph | red | 1.18 | Δ |
| 2 | —$C_2H_5$ | —$C_2H_5$ | —$NHCOCH_3$ | —CN | —$nC_4H_9$ | —Ph | red | 1.85 | ○ |
| 3 | —$C_2H_4OCH_3$ | —$C_2H_5$ | —$NHSO_2CH_3$ | —CN | —$CH_3$ | —Ph | red | 1.78 | Δ |
| 4 | —$C_2H_4OCOCH_3$ | —$C_2H_5$ | —$CH_3$ | —CN | —$CH_3$ | —Ph | red | 1.89 | Δ |
| 5 | —$C_2H_4OCH_3$ | —$C_2H_4OMe$ | —$NHCOCH_3$ | —CN | —Ph | —$nC_4H_9$ | red | 1.90 | ○ |
| 6 | —$C_2H_4CN$ | —$CH_3$ | —$CH_3$ | —CN | —Ph | —$nC_4H_9$ | red | 1.91 | Δ |
| 7 | —$C_2H_4OCH_2Ph$ | —$C_2H_5$ | —$NHCOCH_3$ | —CN | —Ph | —$nC_4H_9$ | red | 1.78 | ○ |
| 8 | —$C_2H_5$ | —$C_2H_5$ | —$NHSO_2CH_3$ | —N92 | —Ph | —$nC_4H_9$ | red | 1.84 | Δ |
| 9 | —$C_2H_4OCH_3$ | —$C_2H_5$ | —$NHCOC_2H_5$ | —$NO_2$ | —$nC_4H_9$ | —Ph | red | 1.75 | Δ |
| 10 | —$C_2H_5$ | —$C_2H_5$ | —$NHCOCH_3$ | —$nC_4H_9$ | —CN | —Ph | red | 1.82 | ○ |
| (10-2-c K: —N=N—) | | | | | | | | | |
| 1 | —$C_2H_5$ | —$C_2H_5$ | —$CH_3$ | —CN | —$nC_4H_9$ | —Ph | red | 1.78 | ○ |
| 2 | —$C_2H_5$ | —$C_2H_5$ | —$NHCOCH_3$ | —CN | —$nC_4H_9$ | —Ph | red | 1.84 | ○ |
| 3 | —$C_2H_4OCH_3$ | —$C_2H_5$ | —$NHSO_2CH_3$ | —CN | —$CH_3$ | —Ph | red | 1.78 | Δ |
| 4 | —$C_2H_4OCOCH_3$ | —$C_2H_5$ | —$CH_3$ | —CN | —$CH_3$ | —Ph | red | 1.75 | Δ |
| 5 | —$C_2H_4OCH_3$ | —$C_2H_4OMe$ | —$NHCOCH_3$ | —CN | —Ph | —$nC_4H_9$ | red | 1.70 | ○ |
| 6 | —$C_2H_4CN$ | —$CH_3$ | —$CH_3$ | —CN | —Ph | —$nC_4H_9$ | red | 1.84 | Δ |
| 7 | —$C_2H_4OCH_2Ph$ | —$C_2H_5$ | —$NHCOCH_3$ | —CN | —Ph | —$nC_4H_9$ | red | 1.85 | Δ |
| 8 | —$C_2H_5$ | —$C_2H_5$ | —$NHSO_2CH_3$ | —$NO_2$ | —Ph | —$nC_4H_9$ | red | 1.72 | ○ |
| 9 | —$C_2H_4OCH_3$ | —$C_2H_5$ | —$NHCOC_2H_5$ | —$NO_2$ | —$nC_4H_9$ | —Ph | red | 1.75 | Δ |
| (10-3-c K: —N=N—) | | | | | | | | | |
| 1 | —$C_2H_5$ | —$C_2H_5$ | —$CH_3$ | —CN | —$nC_4H_9$ | —Ph | red | 1.85 | ○ |
| 2 | —$C_2H_5$ | —$C_2H_5$ | —$NHCOCH_3$ | —CN | —$nC_4H_9$ | —Ph | red | 1.82 | ○ |
| 3 | —$C_2H_4OCH_3$ | —$C_2H_5$ | —$NHSO_2CH_3$ | —CN | —$CH_3$ | —Ph | red | 1.82 | Δ |
| 4 | —$C_2H_4OCOCH_3$ | —$C_2H_5$ | —$CH_3$ | —CN | —$CH_3$ | —Ph | red | 1.77 | Δ |
| 5 | —$C_2H_4OCH_3$ | —$C_2H_4OMe$ | —$NHCOCH_3$ | —CN | —Ph | —$nC_4H_9$ | red | 1.90 | Δ |
| 6 | —$C_2H_4CN$ | —$CH_3$ | —$CH_3$ | —CN | —Ph | —$nC_4H_9$ | red | 1.84 | Δ |
| 7 | —$C_2H_4OCH_2Ph$ | —$C_2H_5$ | —$NHCOCH_3$ | —CN | —Ph | —$nC_4H_9$ | red | 1.78 | Δ |
| 8 | —$C_2H_5$ | —$C_2H_5$ | —$NHSO_2CH_3$ | —$NO_2$ | —Ph | —$nC_4H_9$ | red | 1.76 | Δ |
| 9 | —$C_2H_4OCH_3$ | —$C_2H_5$ | —$NHCOC_2H_5$ | —$NO_2$ | —$nC_4H_9$ | —Ph | red | 1.87 | Δ |

(11) Dyes having the following structure:

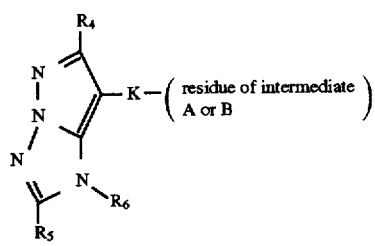
(11-1)

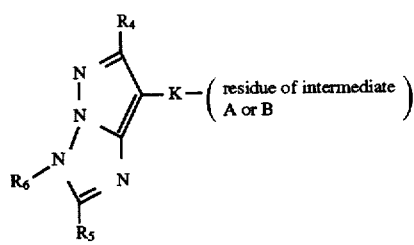
(11-2)

wherein K stands for —N=N—; $R_4$ and $R_5$ stand for a hydrogen atom, a halogen atom, a cyano group, a nitro group or a substituted or unsubstituted amino group, formylamino group, sulfonylamino group, alkyl group, allyl group, aryl group, aralkyl group, alkoxyalkyl group, aralkyloxyalkyl group, allyloxyalkyl group, aryloxyalkyl group, carbamoyl group, sulfamoyl group, oxycarbonyl group or heterocyclic group; $R_6$ stands for a hydrogen atom or a substituted or unsubstituted alkyl group, allyl group, aryl group, aralkyl group, alkoxyalkyl group, aralkyloxyalkyl group, allyloxyalkyl group, aryloxyalkyl group, alkoxycarbonylalkyl group, carboxyalkyl group, heterocyclic group, carbamoyl group, sulfamoyl group or cycloalkyl group.

Specific examples of the dye represented by the general formula 11 and the performance thereof in the case of use in a thermal transfer sheet are given in the following Table 11.

TABLE 11

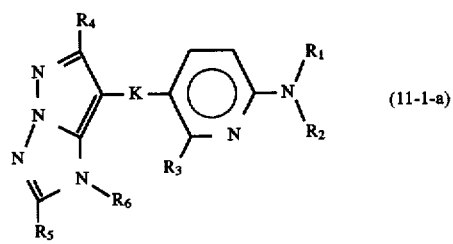
(11-1-a)

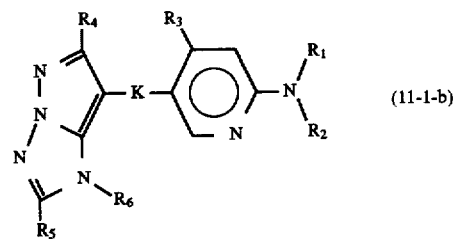
(11-1-b)

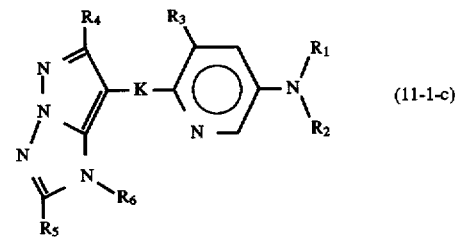
(11-1-c)

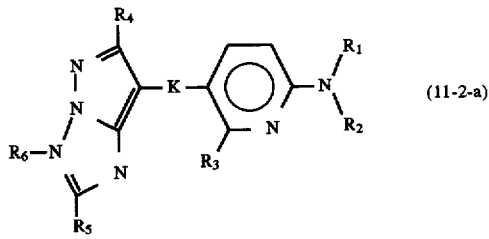
(11-2-a)

TABLE 11-continued

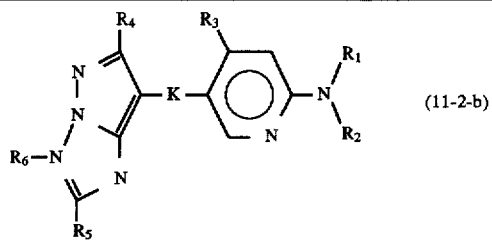

(11-2-b)

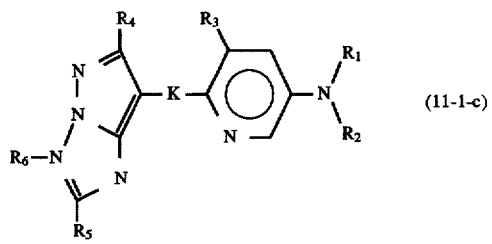

(11-1-c)

| No. | R₁ | R₂ | R₃ | R₄ | R₅ | R₆ |
|-----|----|----|----|----|----|----|
| 1 | —C₂H₅ | —C₂H₅ | —CH₃ | —CN | —Ph | —nC₄H₉ |
| 2 | —C₂H₅ | —C₂H₅ | —NHCOCH₃ | —CN | —Ph | —nC₄H₉ |
| 3 | —C₂H₅ | —C₂H₅ | —NHSO₂CH₃ | —CN | —Ph | —nC₄H₉ |
| 4 | —C₂H₄OH | —C₂H₅ | —H | —CN | —Ph | —nC₄H₉ |
| 5 | —C₂H₄CN | —C₂H₅ | —NHCOCH₃ | —CN | —Ph | —nC₄H₉ |
| 6 | —C₂H₄OCH₃ | —C₂H₅ | —CH₃ | —CN | —Ph | —nC₄H₉ |
| 7 | —C₂H₄OCOCH₃ | —C₂H₅ | —NHCOCH₃ | —NO₂ | —Ph | —nC₄H₉ |
| 8 | —C₂H₄OCOCH₃ | —C₂H₄OCOCH₃ | —CH₃ | —CN | —Ph | —nC₄H₉ |
| 9 | —C₂H₄OCH₃ | —C₂H₄OMe | —NHCOCH₃ | —CN | —Ph | —nC₄H₉ |
| 10 | —C₂CH=CH₂ | —C₂H₅ | —NHCOCH₃ | —CN | —Ph | —isoC₃H₇ |
| 11 | —C₂H₄OCOOCH₃ | —C₂H₅ | —CH₃ | —CN | —Ph | —nC₄H₉ |

| No. | hue | coloring density | light fastness |
|-----|-----|------------------|----------------|
| 11-1-a K: —N=N— | | | |
| 1 | red | 1.64 | ○ |
| 2 | red | 1.81 | ○ |
| 3 | red | 1.77 | ○ |
| 4 | red | 1.74 | Δ |
| 5 | red | 1.79 | Δ |
| 6 | red | 1.83 | ○ |
| 7 | red | 1.72 | ○ |
| 8 | red | 1.69 | ○ |
| 9 | red | 1.73 | ○ |
| 10 | red | 1.76 | Δ |
| 11 | red | 1.70 | Δ |
| 11-1-b K: —N=N— | | | |
| 1 | red | 1.65 | ○ |
| 2 | red | 1.83 | ○ |
| 3 | red | 1.75 | ○ |
| 4 | red | 1.76 | Δ |
| 5 | red | 1.78 | Δ |
| 6 | red | 1.83 | ○ |
| 7 | red | 1.71 | ○ |
| 8 | red | 1.65 | ○ |
| 9 | red | 1.74 | ○ |
| 10 | red | 1.76 | Δ |
| 11 | red | 1.74 | Δ |
| 11-1-c K: —N=N— | | | |
| 1 | red | 1.73 | ○ |
| 2 | red | 1.91 | ○ |
| 3 | red | 1.75 | ○ |
| 4 | red | 1.81 | Δ |
| 5 | red | 1.86 | ○ |
| 6 | red | 1.73 | ○ |
| 7 | red | 1.80 | ○ |
| 8 | red | 1.70 | Δ |
| 9 | red | 1.77 | ○ |
| 10 | red | 1.84 | Δ |
| 11 | red | 1.81 | ○ |

TABLE 11-continued

11-2-a K: —N=N—

| | | | |
|---|---|---|---|
| 1 | red | 1.74 | ○ |
| 2 | red | 1.83 | ○ |
| 3 | red | 1.79 | ○ |
| 4 | red | 1.84 | Δ |
| 5 | red | 1.89 | ○ |
| 6 | red | 1.83 | Δ |
| 7 | red | 1.73 | ○ |
| 8 | red | 1.71 | ○ |
| 9 | red | 1.79 | ○ |
| 10 | red | 1.75 | ○ |
| 11 | red | 1.73 | Δ |

11-2-b K: —N=N—

| | | | |
|---|---|---|---|
| 1 | red | 1.72 | ○ |
| 2 | red | 1.83 | ○ |
| 3 | red | 1.79 | ○ |
| 4 | red | 1.81 | Δ |
| 5 | red | 1.91 | ○ |
| 6 | red | 1.87 | Δ |
| 7 | red | 1.76 | ○ |
| 8 | red | 1.72 | ○ |
| 9 | red | 1.77 | ○ |
| 10 | red | 1.73 | ○ |
| 11 | red | 1.76 | Δ |

11-2-c K: —N=N—

| | | | |
|---|---|---|---|
| 1 | red | 1.74 | ○ |
| 2 | red | 1.79 | ○ |
| 3 | red | 1.81 | ○ |
| 4 | red | 1.84 | Δ |
| 5 | red | 1.87 | ○ |
| 6 | red | 1.81 | ○ |
| 7 | red | 1.71 | Δ |
| 8 | red | 1.73 | Δ |
| 9 | red | 1.68 | ○ |
| 10 | red | 1.74 | ○ |
| 11 | red | 1.77 | Δ |

(12) Dyes having the following structure:

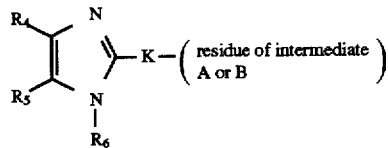

(12)

wherein K stands for —N=N—; $R_4$ and $R_5$ stand for a hydrogen atom, a halogen atom, a cyano group, a nitro group or a substituted or unsubstituted amino group, formylamino group, sulfonylamino group, alkyl group, allyl group, aryl group, aralkyl group, alkoxyalkyl group, aralkyloxyalkyl group, aryloxyalkyl group, carbamoyl group, sulfamoyl group, oxycarbonyl group, heterocyclic group or alkoxycarbonyl group; $R_6$ stands for a hydrogen atom or a substituted or unsubstituted alkyl group, allyl group, aryl group, aralkyl group, alkoxyalkyl group, aralkyloxyalkyl group, allyloxyalkyl group, aryloxyalkyl group, alkoxycarbonylalkyl group, carboxyalkyl group, heterocyclic group, carbamoyl group, sulfamoyl group or cycloalkyl group.

Specific examples of the dye represented by the general formula 12 and the performance thereof in the case of use in a thermal transfer sheet are given in the following Table 12.

TABLE 12

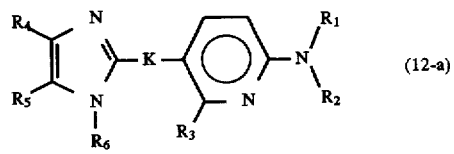

(12-a)

TABLE 12-continued

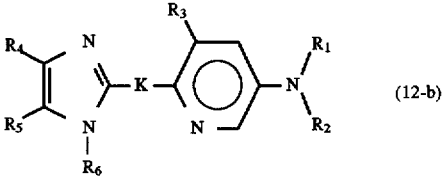

(12-b)

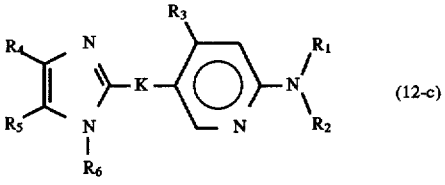

(12-c)

| No. | R₁ | R₂ | R₃ | R₄ | R₅ | R₆ |
|---|---|---|---|---|---|---|
| 1 | —C₂H₅ | —C₂H₅ | —NHCOCH₃ | —CN | —CN | —nC₄H₉ |
| 2 | —C₂H₅ | —C₂H₅ | —CH₃ | —CN | —CN | —Ph |
| 3 | —C₂H₄OCH₃ | —C₂H₅ | —NHCOC₂H₅ | —CN | —CN | —nC₄H₉ |
| 4 | —C₂H₄CN | —C₂H₅ | —CH₃ | —CN | —CN | —nC₄H₉ |
| 5 | —C₂H₄OCOCH₃ | —C₂H₅ | —NHSO2CH₃ | —CN | —CN | —nC₄H₉ |
| 6 | —C₂H₄OCH₃ | —C₂H₄OMe | —NHCOCH₃ | —CN | —CN | —nC₄H₉ |
| 7 | —C₂H₄OCOOCH₃ | —C₂H₅ | —H | —CN | —CN | —nC₆H₁₃ |
| 8 | —C₂H₄OCOCH₃ | —C₂H₄OCOCH₃ | —CH₃ | —CN | —CN | cyclohexyl |
| 9 | —C₂H₄OH | —C₂H₅ | —NHCOCH₃ | —CN | —CN | —Ph |

| No. | hue | coloring density | light fastness |
|---|---|---|---|
| 9-a K: —N=N— | | | |
| 1 | reddish orange | 1.85 | ○ |
| 2 | reddish orange | 1.90 | Δ |
| 3 | reddish orange | 1.84 | ○ |
| 4 | reddish orange | 1.82 | Δ |
| 5 | reddish orange | 1.77 | ○ |
| 6 | reddish orange | 1.75 | ○ |
| 7 | reddish orange | 1.80 | Δ |
| 8 | reddish orange | 1.71 | ○ |
| 9 | reddish orange | 1.82 | ○ |
| 9-b K: —N=N— | | | |
| 1 | red | 1.92 | ○ |
| 2 | red | 2.01 | Δ |
| 3 | red | 1.95 | ○ |
| 4 | red | 1.90 | Δ |
| 5 | red | 1.87 | ○ |
| 6 | red | 1.85 | ○ |
| 7 | red | 1.92 | Δ |
| 8 | red | 1.93 | ○ |
| 9 | red | 2.00 | ○ |
| 9-c K: —N=N— | | | |
| 1 | reddish orange | 1.84 | ○ |
| 2 | reddish orange | 1.91 | Δ |
| 3 | reddish orange | 1.85 | ○ |
| 4 | reddish orange | 1.80 | Δ |
| 5 | reddish orange | 1.77 | ○ |
| 6 | reddish orange | 1.76 | ○ |
| 7 | reddish orange | 1.78 | ○ |
| 8 | reddish orange | 1.70 | ○ |
| 9 | reddish orange | 1.80 | ○ |

(13) Dyes having the following structure:

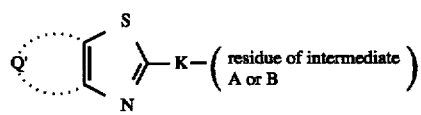

(13)

wherein K stands for —N=N—; and Q' stands for a ring comprising carbon, hydrogen, nitrogen, oxygen and sulfur and examples thereof include the following rings:

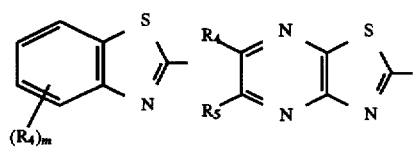

wherein $R_4$ and $R_5$ stand for a hydrogen atom, a halogen atom, a hydroxyl group, a cyano group, a nitro group, an amino group, an amide group or a substituted or unsubstituted alkyl group, allyl group, aryl group, aralkyl group, alkoxyalkyl group, alkoxy group, heterocyclic group, oxycarbonyl group, carboxyl group, carbamoyl group, sulfamoyl group, formylamino group or sulfonylamino group; $R_6$ stands for a hydrogen atom or a substituted or unsubstituted alkyl group, allyl group, aryl group, aralkyl group, heterocyclic group, alkoxyalkyl group, oxycarbonylalkyl group, carboxyalkyl group, carbamoyl group, sulfamoyl group or cycloalkyl group; and m is an integer of 0 to 4.

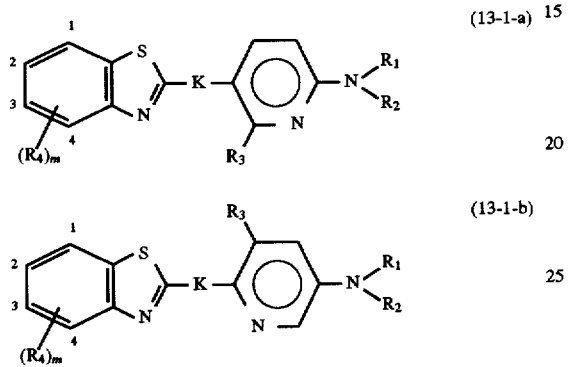

(13-1-a)

(13-1-b)

-continued

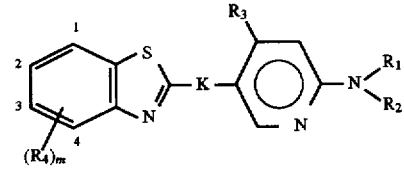

(13-1-c)

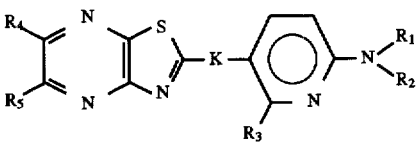

(13-2-a)

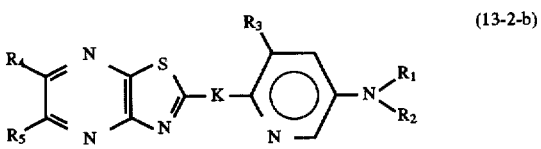

(13-2-b)

(13-2-c)

Specific examples of the dye represented by the general formula 13 and the performance thereof in the case of use in a thermal transfer sheet are given in the following Table 13.

TABLE 13

| No. | $R_1$ | $R_2$ | $R_3$ | $R_4$ | hue | coloring density | light fastness |
|---|---|---|---|---|---|---|---|
| | | | 13-1-a K: —N=N— | | | | |
| 1 | —$C_2H_5$ | —$C_2H_5$ | —H | —H | red | 1.92 | Δ |
| 2 | —$C_2H_5$ | —$C_2H_4OH$ | —$CH_3$ | 2,3-di (isoC3H7) | red | 1.82 | ○ |
| 3 | —$C_2H_5$ | —CH=$CH_2$ | —H | 2-$C_2H_4Ph$ | red | 1.78 | Δ |
| 4 | —$C_2H_5$ | —Ph | —Cl | 4-$OC_4H_9$ | red | 1.80 | Δ |
| 5 | —$C_2H_5$ | —CH=$CHOCOCH_3$ | —$NHCOCH_3$ | 2-$NHCOCH_3$ | red | 1.75 | ○ |
| 6 | —$C_2H_5$ | —$C_2H_4COOCH_3$ | —OH | —H | red | 1.83 | ○ |
| 7 | —$C_2H_5$ | —$C_2H_4OCOC_4H_9$ | —$NHSO2CH3$ | 2-$SO_2NHCH_3$ | red | 1.72 | ○ |
| 8 | —$C_2H_5$ | —$C_2H_4OCOOPh$ | —$NHCOCH_3$ | 3-CN | red | 1.77 | Δ |
| 9 | —$C_2H_5$ | —H | —$NHCOCH_3$ | 2-$NO_2$ | red | 1.75 | Δ |
| 10 | —$C_2H_5$ | —CH2Ph | —$OC_2H_5$ | 1-$COOC_3H_7$ | red | 1.81 | Δ |
| 11 | —$C_2H_4$—$COCH_3$ | —$C_2H_4OCOCH_3$ | —$CONHCH_3$ | 1-Ph | red | 1.76 | ○ |
| 12 | —$C_2H_5$ | —$C_2H_4OCOPh$ | —SO2NHC3H7 | 1-CH=CH($CH_3$) | red | 1.74 | ○ |
| | | | 13-1-b K: —N=N— | | | | |
| 1 | —$C_2H_5$ | —$C_2H_5$ | —H | —H | red | 1.91 | Δ |
| 2 | —$C_2H_5$ | —$C_2H_4OH$ | —$CH_3$ | 2,3-di (isoC3H7) | red | 1.88 | ○ |
| 3 | —$C_2H_5$ | —CH=$CH_2$ | —H | 2-$C_2H_4Ph$ | red | 1.78 | Δ |
| 4 | —$C_2H_5$ | —Ph | —Cl | 4-$OC_4H_9$ | red | 1.80 | Δ |
| 5 | —$C_2H_5$ | —CH=$CHOCOCH_3$ | —$NHCOCH_3$ | 2-$NHCOCH_3$ | red | 1.74 | ○ |
| 6 | —$C_2H_5$ | —$C_2H_4COOCH_3$ | —OH | —H | red | 1.77 | ○ |
| 7 | —$C_2H_5$ | —$C_2H_4OCOC_4H_9$ | —$NHSO2CH3$ | 2-$SO_2NHCH_3$ | red | 1.77 | Δ |
| 8 | —$C_2H_5$ | —$C_2H_4OCOOPh$ | —$NHCOCH_3$ | 3-CN | red | 1.77 | Δ |
| 9 | —$C_2H_5$ | —H | —$NHCOCH_3$ | 2-$NO_2$ | red | 1.80 | Δ |
| 10 | —$C_2H_5$ | —CH2Ph | —$OC_2H_5$ | 1-$COOC_3H_7$ | red | 1.83 | Δ |
| 11 | —$C_2H_4$—$COCH_3$ | —$C_2H_4OCOCH_3$ | —$CONHCH_3$ | 1-Ph | red | 1.82 | ○ |
| 12 | —$C_2H_5$ | —$C_2H_4OCOPh$ | —SO2NHC3H7 | 1-CH=CH($CH_3$) | red | 1.79 | ○ |
| | | | 13-1-c K: —N=N— | | | | |
| 1 | —$C_2H_5$ | —$C_2H_5$ | —H | —H | red | 1.93 | Δ |
| 2 | —$C_2H_5$ | —$C_2H_4OH$ | —$CH_3$ | 2,3-di (isoC3H7) | red | 1.80 | ○ |
| 3 | —$C_2H_5$ | —CH=$CH_2$ | —H | 2-$C_2H_4Ph$ | red | 1.77 | Δ |
| 4 | —$C_2H_5$ | —Ph | —Cl | 4-$OC_4H_9$ | red | 1.81 | Δ |
| 5 | —$C_2H_5$ | —CH=$CHOCOCH_3$ | —$NHCOCH_3$ | 2-$NHCOCH_3$ | red | 1.74 | ○ |
| 6 | —$C_2H_5$ | —$C_2H_4COOCH_3$ | —OH | —H | red | 1.82 | ○ |
| 7 | —$C_2H_5$ | —$C_2H_4OCOC_4H_9$ | —$NHSO2CH3$ | 2-$SO_2NHCH_3$ | red | 1.77 | ○ |
| 8 | —$C_2H_5$ | —$C_2H_4OCOOPh$ | —$NHCOCH_3$ | 3-CN | red | 1.76 | Δ |

TABLE 13-continued

| | | | | | | | |
|---|---|---|---|---|---|---|---|
| 9 | —C₂H₅ | —H | —NHCOCH3 | 2-NO₂ | red | 1.75 | Δ |
| 10 | —C₂H₅ | —CH2Ph | —OC₂H₅ | 1-COOC₃H₇ | red | 1.79 | Δ |
| 11 | —C₂H₄O—COCH₃ | —C₂H₄OCOCH₃ | —CONHCH3 | 1-Ph | red | 1.78 | ○ |
| 12 | —C₂H₅ | —C₂H₄OCOOPh | —SO2NHC3H7 | 1-CH=CH(CH₃) | red | 1.72 | ○ |

| NO. | R₁ | R₂ | R₃ | R₄ | R₅ |
|---|---|---|---|---|---|
| (13-2-a K: —N=N—) | | | | | |
| 1 | —C₂H₅ | —C₂H₅ | —H | —H | —H |
| 2 | —C₂H₅ | —C₂H₄OH | —CH3 | —H | —C₂H₅ |
| 3 | —C₂H₅ | —CH=CH₂ | —H | —CH3 | —CH3 |
| 4 | —C₂H₅ | —Ph | —Cl | —CH3 | —OC₂H₅ |
| 5 | —C₂H₅ | —CH=CHOCOCH₃ | —NHCOCH3 | —CH₃ | —C₂H₄Ph |
| 6 | —C₂H₅ | —C₂H₄COOCH₃ | —OH | —CH3 | —NHCOCH3 |
| 7 | —C₂H₅ | —C₂H₄OCOC₄H₉ | —NHSO2CH3 | —H | —NHCOCH₃ |
| 8 | —C₂H₅ | —C₂H₄OCOOPh | —NHCOCH3 | —H | —CN |
| 9 | —C₂H₅ | —H | —NHCOCH3 | —H | —NO₂ |
| 10 | —C₂H₅ | —CH2Ph | —OC₂H₅ | —H | —Cl |
| 11 | —C₂H₄OCOCH₃ | —C₂H₄OCOCH₃ | —CONHCH3 | —H | —Ph |
| 12 | —C₂H₅ | —C₂H₄OCOPh | —SO2NHC3H7 | —H | —CH=CH₂ |

| No. | hue | coloring density | light fastness |
|---|---|---|---|
| 1 | red | 1.89 | Δ |
| 2 | red | 1.87 | ○ |
| 3 | red | 1.80 | Δ |
| 4 | red | 1.83 | Δ |
| 5 | red | 1.81 | ○ |
| 6 | red | 1.92 | ○ |
| 7 | red | 1.83 | ○ |
| 8 | red | 1.79 | ○ |
| 9 | red | 1.75 | ○ |
| 10 | red | 1.80 | Δ |
| 11 | red | 1.77 | ○ |
| 12 | red | 1.74 | ○ |

| NO. | R₁ | R₂ | R₃ | R₄ | R₅ |
|---|---|---|---|---|---|
| (13-2-b K: —N=N—) | | | | | |
| 1 | —C₂H₅ | —C₂H₅ | —H | —H | —H |
| 2 | —C₂H₅ | —C₂H₄OH | —CH3 | —H | —C₂H₅ |
| 3 | —C₂H₅ | —CH=CH₂ | —H | —CH3 | —CH3 |
| 4 | —C₂H₅ | —Ph | —Cl | —CH3 | —OC₂H₅ |
| 5 | —C₂H₅ | —CH=CHOCOCH₃ | —NHCOCH₃ | —CH₃ | —C₂H₄Ph |
| 6 | —C₂H₅ | —C₂H₄COOCH₃ | —OH | —CH3 | —NHCOCH3 |
| 7 | —C₂H₅ | —C₂H₄OCOC₄H₉ | —NHSO2CH₃ | —H | —NHCOCH₃ |
| 8 | —C₂H₅ | —C₂H₄OCOOPh | —NHCOCH₃ | —H | —CN |
| 9 | —C₂H₅ | —H | —NHCOCH₃ | —H | —NO₂ |
| 10 | —C₂H₅ | —CH₂Ph | —OC₂H₅ | —H | —Cl |
| 11 | —C₂H₄OCOCH₃ | —C₂H₄OCOCH₃ | —CONHCH₃ | —H | —Ph |
| 12 | —C₂H₅ | —C₂H₄OCOPh | —SO₂NHC₃H₇ | —H | 'CH=CH₂ |

| No. | hue | coloring density | light fastness |
|---|---|---|---|
| 1 | red | 1.93 | Δ |
| 2 | red | 1.84 | ○ |
| 3 | red | 1.76 | Δ |
| 4 | red | 1.81 | Δ |
| 5 | red | 1.74 | ○ |
| 6 | red | 1.80 | ○ |
| 7 | red | 1.72 | ○ |
| 8 | red | 1.75 | Δ |
| 9 | red | 1.71 | Δ |
| 10 | red | 1.80 | Δ |
| 11 | red | 1.80 | ○ |
| 12 | red | 1.72 | ○ |

| NO. | R₁ | R₂ | R₃ | R₄ | R₅ |
|---|---|---|---|---|---|
| 13-2-c K: —N=N— | | | | | |
| 1 | —C₂H₅ | —C₂H₅ | —H | —H | —H |
| 2 | —C₂H₅ | —C₂H₄OH | —CH₃ | —H | —C₂H₅ |
| 3 | —C₂H₅ | —CH=CH₂ | —H | —CH3 | —CH3 |
| 4 | —C₂H₅ | —Ph | —Cl | —CH3 | —OC₂H₅ |
| 5 | —C₂H₅ | —CH=CHOCOCH₃ | —NHCOCH₃ | —CH₃ | —C₂H₄Ph |
| 6 | —C₂H₅ | —C₂H₄COOCH₃ | —OH | —CH3 | —NHCOCH₃ |

TABLE 13-continued

| | | | | | |
|---|---|---|---|---|---|
| 7 | —$C_2H_5$ | —$C_2H_4OCOC_4H_9$ | —$NHSO_2CH_3$ | —H | —$NHCOCH_3$ |
| 8 | —$C_2H_5$ | —$C_2H_4OCOOPh$ | —$NHCOCH_3$ | —H | —CN |
| 9 | —$C_2H_5$ | —H | —$NHCOCH_3$ | —H | —$NO_2$ |
| 10 | —$C_2H_5$ | —CH2Ph | —$OC_2H_5$ | —H | —Cl |
| 11 | —$C_2H_4OCOCH_3$ | —$C_2H_4OCOCH_3$ | —$CONHCH_3$ | —H | —Ph |
| 12 | —$C_2H_5$ | —$C_2H_4OCOPh$ | —$SO2NHC_3H_7$ | —H | —CH=$CH_2$ |

| NO. | hue | coloring density | light fastness |
|---|---|---|---|
| 1 | red | 1.93 | Δ |
| 2 | red | 1.85 | ○ |
| 3 | red | 1.80 | Δ |
| 4 | red | 1.70 | Δ |
| 5 | red | 1.77 | ○ |
| 6 | red | 1.80 | ○ |
| 7 | red | 1.70 | ○ |
| 8 | red | 1.76 | Δ |
| 9 | red | 1.74 | Δ |
| 10 | red | 1.80 | Δ |
| 11 | red | 1.80 | ○ |
| 12 | red | 1.72 | ○ |

(14) Dyes having the following structure:

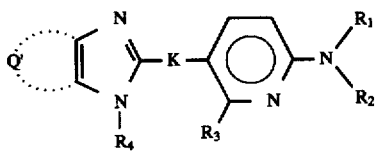
(14-a)

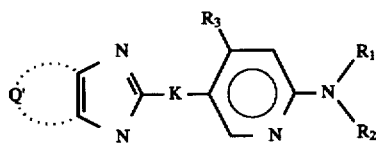
(14-b)

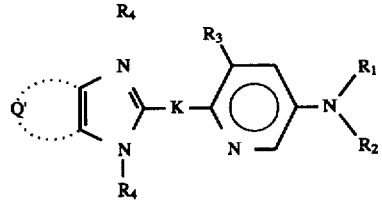
(14-c)

wherein K stands for —N=N—; and Q' stands for a ring comprising carbon, hydrogen, nitrogen, oxygen and sulfur and examples thereof include the following rings:

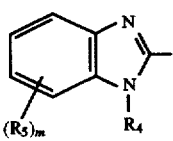
(11-1)

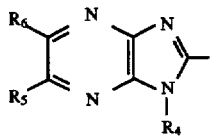
(11-2)

wherein $R_4$ stands for a hydrogen atom or a substituted or unsubstituted alkyl group, allyl group, aryl group, aralkyl group, heterocyclic group, alkoxyalkyl group, oxycarbonylalkyl group, carboxyalkyl group, carbamoyl group, sulfamoyl group or cycloalkyl group; and $R_5$ and $R_6$ stand for a hydrogen atom, a halogen atom, a cyano group, a nitro group or a substituted or unsubstituted amino group, formylamino group, sulfonylamino group, ureido group, alkyl group, allyl group, vinyl group, aryl group, aralkyl group, alkoxyalkyl group, aralkyloxyalkyl group, allyloxyalkyl group, aryloxyalkyl group, carbamoyl group, sulfamoyl group, oxycarbonyl group, carboxy group, alkoxycarbonylalkyl group, carboxyalkyl group, heterocyclic group, alkoxycarboxyalkyl group, thioalkyl group, mercapto group or cycloalkyl group.

TABLE 14

(common to all the compounds 14)

| No. | $R_1$ | $R_2$ | $R_3$ | $R_4$ | $R_5$ |
|---|---|---|---|---|---|
| 1 | —$C_2H_5$ | —$C_2H_5$ | —$NHCOCH_3$ | —$nC_4H_9$ | —H |
| 2 | —$C_2H_4OCOCH_3$ | —$C_2H_5$ | —$NHSO_2CH_3$ | —$nC_4H_9$ | —H |
| 3 | —$C_2H_4OCH_3$ | —$C_2H_5$ | —$NHCOC_2H_5$ | —$nC_4H_9$ | —H |
| 4 | —$C_2H_4OCH_2Ph$ | —$C_2H_5$ | —$CH_3$ | —$nC_4H_9$ | —H |
| 5 | —$C_2H_4CN$ | —$C_2H_5$ | —$CH_3$ | —$nC_4H_9$ | —H |

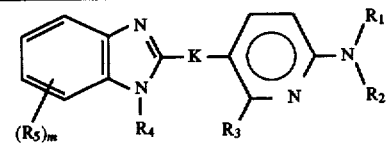
(14-1-a)

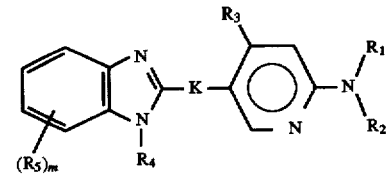
(14-1-b)

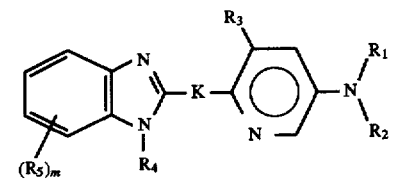
(14-1-c)

| No. | hue | coloring density | light fastness |
|---|---|---|---|
| | | 14-1-a K: —N=N— | |
| 1 | purplish red | 1.76 | ○ |
| 2 | purplish red | 1.70 | Δ |
| 3 | purplish red | 1.79 | ○ |
| 4 | purplish red | 1.67 | ○ |
| 5 | purplish red | 1.72 | Δ |

TABLE 14-continued (common to all the compounds 14)

14-1-b K: —N=N—

| | | | |
|---|---|---|---|
| 1 | purplish red | 1.78 | ○ |
| 2 | purplish red | 1.70 | Δ |
| 3 | purplish red | 1.81 | ○ |
| 4 | purplish red | 1.65 | ○ |
| 5 | purplish red | 1.73 | Δ |

14-1-c K: —N=N—

| | | | |
|---|---|---|---|
| 1 | purplish red | 1.80 | ○ |
| 2 | purplish red | 1.75 | ○ |
| 3 | purplish red | 1.82 | ○ |
| 4 | purplish red | 1.69 | ○ |
| 5 | purplish red | 1.75 | ○ |

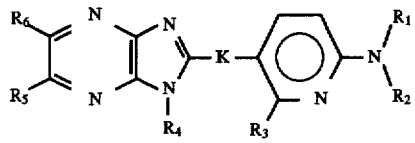

(14-2-a)

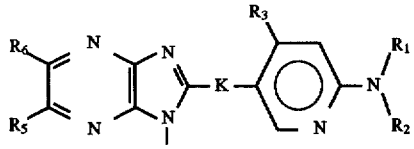

(14-2-b)

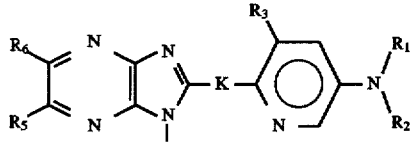

(14-2-c)

where in all the compounds a to c, $R_6$ is —H.

14-2-a K: —N=N—

| | | | |
|---|---|---|---|
| 1 | purplish red | 1.92 | ○ |
| 2 | purplish red | 1.85 | ○ |
| 3 | purplish red | 1.96 | ○ |
| 4 | purplish red | 1.89 | ○ |
| 5 | purplish red | 1.80 | Δ |

14-2-b K: —N=N—

| | | | |
|---|---|---|---|
| 1 | purplish red | 1.74 | ○ |
| 2 | purplish red | 1.72 | Δ |
| 3 | purplish red | 1.83 | ○ |
| 4 | purplish red | 1.69 | Δ |
| 5 | purplish red | 1.72 | Δ |

14-2-c K: —N=N—

| | | | |
|---|---|---|---|
| 1 | purplish red | 1.79 | ○ |
| 2 | purplish red | 1.84 | ○ |
| 3 | purplish red | 1.89 | ○ |
| 4 | purplish red | 1.73 | ○ |
| 5 | purplish red | 1.75 | ○ |

(15) Dyes represented by the following structural formulae:

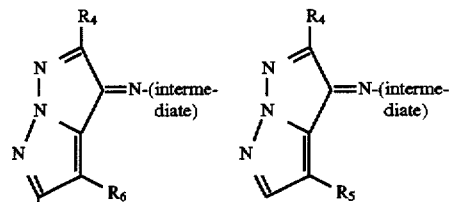

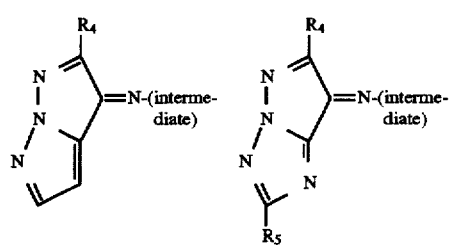

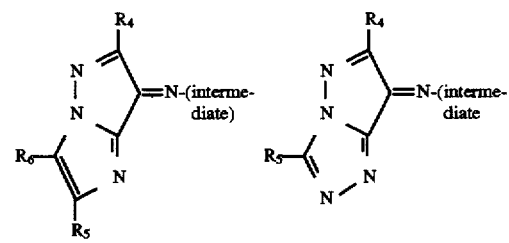

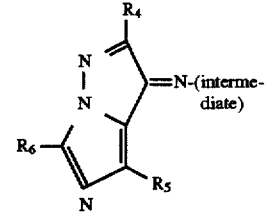

(intermediate: a residue of intermediate A or B) wherein $R_4$ to $R_6$ will be defined below.

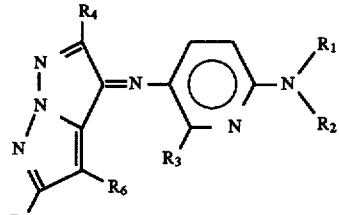

(15-1-a)

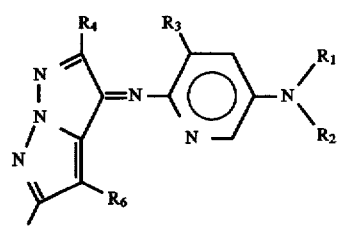

(15-1-b)

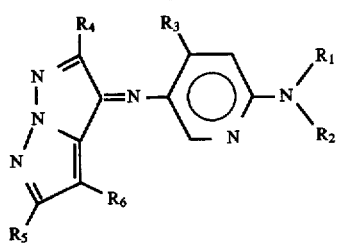 (15-1-c)
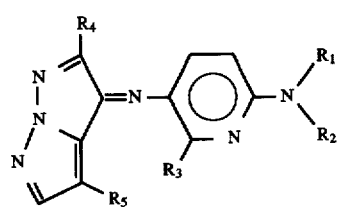 (15-2-a)
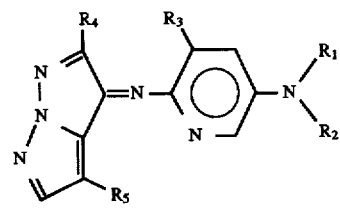 (15-2-b)
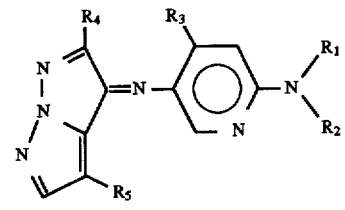 (15-2-c)
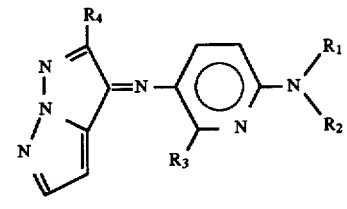 (15-3-a)
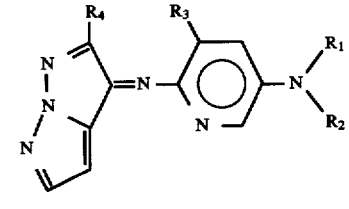 (15-3-b)
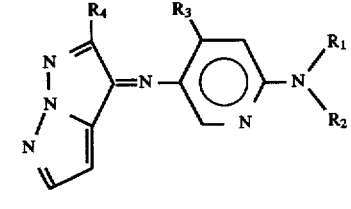 (15-3-c)
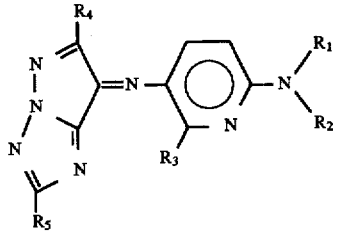 (15-4-a)
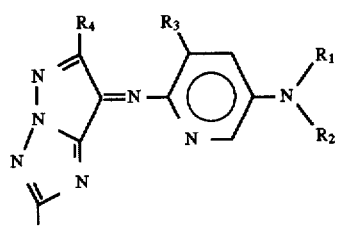 (15-4-b)
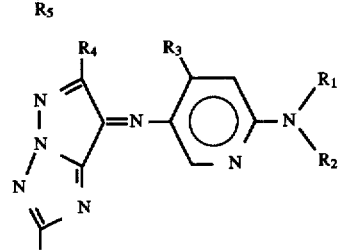 (15-4-c)
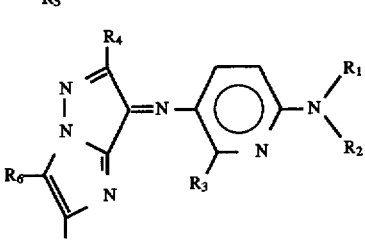 (15-5-a)
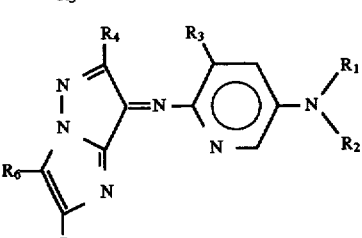 (15-5-b)
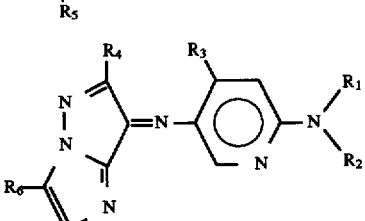 (15-5-c)
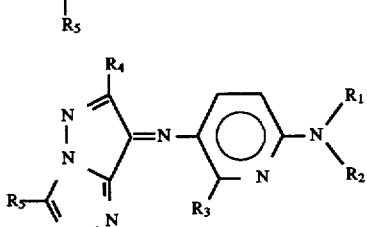 (15-6-a)

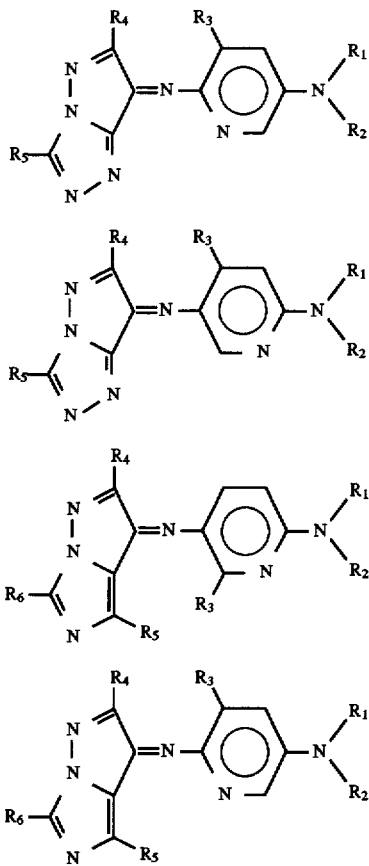

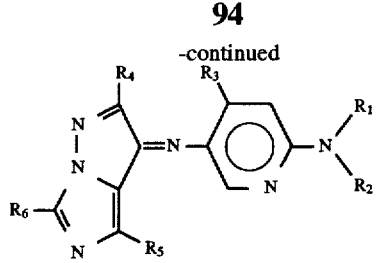

Definition of $R_4$, $R_5$ and $R_6$:

A hydrogen atom, a halogen atom, a cyano group, a nitro group or a substituted or unsubstituted alkyl group, allyl group, aryl group, aralkyl group, alkoxyalkyl group, aralkyloxyalkyl group, thioalkyl group, allyloxyalkyl group, aryloxyalkyl group, carbamoyl group, sulfamoyl group, oxycarbonyl group, amino group, formylamino group, sulfonylamino group, alkoxycarbonylalkyl group, heterocyclic group, cycloalkyl group, alkylthio group, alkylsulfinyl group or alkylsulfonyl group.

Definition of $R_7$:

A hydrogen atom, a halogen atom or a substituted or unsubstituted alkyl group, allyl group, aryl group, aralkyl group, alkoxyalkyl group, aralkyloxyalkyl group, aryloxyalkyl group, heterocyclic group or cycloalkyl group.

Definition of $R_8$:

A hydrogen atom, a halogen atom, a cyano group, a nitro group or a substituted or unsubstituted alkylcarbonyl group, amino group, arylcarbonyl group, aralkylcarbonyl group, oxycarbonyl group, heterocyclic carbonyl group, aryl group or allyl group or a substituted or unsubstituted alkyl group, allyl group, carbamoyl group, formylamino group, sulfonylamino group, sulfamoyl group or cycloalkyl group.

Specific examples of the dye represented by the general formula 15 and the performance thereof in the case of use in a thermal transfer sheet are given in the following Table 15.

TABLE 15

(15-1-a)

| No. | $R_1$ | $R_2$ | $R_3$ | $R_4$ | $R_5$ | $R_6$ |
|---|---|---|---|---|---|---|
| 1 | —$C_2H_5$ | —$C_2H_5$ | —H | —CN | —$C_4H_9$ | —H |
| 2 | —$C_2H_5$ | —$C_2H_4OH$ | —$CH_3$ | —CN | —$C_4H_9$ | —H |
| 3 | —$C_2H_5$ | —CH=$CH_2$ | —H | —CN | —$C_4H_9$ | —H |
| 4 | —$C_2H_5$ | —Ph | —Cl | —CN | —Ph | —H |
| 5 | —$C_2H_5$ | —CH=CHOCOCH$_3$ | —NHCOCH$_3$ | —CN | —Ph | —$CH_3$ |
| 6 | —$C_2H_5$ | —$C_2H_4COOCH_3$ | —OH | —$NO_2$ | —$C_4H_9$ | —H |
| 7 | —$C_2H_5$ | —$C_2H_4OCOC_4H_9$ | —$NHSO_3CH_3$ | —$NO_2$ | —$C_4H_9$ | —H |
| 8 | —$C_2H_5$ | —$C_2H_4OCOOPh$ | —NHCOCH$_3$ | —CN | —$C_4H_9$ | —$CH_3$ |
| 9 | —$C_2H_5$ | —H | —NHCOCH$_3$ | —$NO_2$ | —Ph | —H |
| 10 | —$C_2H_5$ | —CH2Ph | —$OC_2H_5$ | —CN | —Ph | —H |
| 11 | —$C_2H_4OCOCH_3$ | —$C_2H_4OCOOCH_3$ | —CONHCH$_3$ | —$CH_3$ | —$C_4H_9$ | —$CH_3$ |
| 12 | —$C_2H_5$ | —$C_2H_4OCOOPh$ | —$SO_2NHC_3H_7$ | —$CH_3$ | —$C_4H_9$ | —H |

| NO. | hue | coloring density | light fastness |
|---|---|---|---|
| 1 | red | 1.95 | Δ |
| 2 | red | 1.92 | ○ |
| 3 | red | 1.93 | Δ |
| 4 | red | 1.87 | Δ |
| 5 | red | 1.88 | Δ |
| 6 | red | 1.90 | ○ |
| 7 | red | 1.81 | ○ |
| 8 | red | 1.80 | ○ |
| 9 | red | 1.81 | ○ |
| 10 | red | 1.84 | Δ |
| 11 | red | 1.89 | ○ |
| 12 | red | 1.83 | ○ |

TABLE 15-continued (15-1-b)

| NO. | $R_1$ | $R_2$ | $R_3$ | $R_4$ | $R_5$ | $R_6$ |
|---|---|---|---|---|---|---|
| 1 | —$C_2H_5$ | —$C_2H_5$ | —H | —CN | —$C_4H_9$ | —H |
| 2 | —$C_2H_5$ | '$C_2H_4$OH | —$CH_3$ | —CN | —$C_4H_9$ | —H |
| 3 | —$C_2H_5$ | —CH=$CH_2$ | —H | —CN | —$C_4H_9$ | —H |
| 4 | —$C_2H_5$ | —Ph | —Cl | —CN | —Ph | —H |
| 5 | —$C_2H_5$ | —CH=CHOCCCH$_3$ | —NHCOCH$_3$ | —CN | —Ph | —CH$_3$ |
| 6 | —$C_2H_5$ | —$C_2H_4$COOCH$_3$ | —OH | —NO$_2$ | —$C_4H_9$ | —H |
| 7 | —$C_2H_5$ | —$C_2H_4$OCOC$_4H_9$ | —NHSO2CH$_3$ | —NO$_2$ | —$C_4H_9$ | —H |
| 8 | —$C_2H_5$ | —$C_2H_4$OCOOPh | —NHCOCH$_3$ | —CN | —$C_4H_9$ | —CH$_3$ |
| 9 | —$C_2H_5$ | —H | —NHCOCH$_3$ | —NO$_2$ | —Ph | —H |
| 10 | —$C_2H_5$ | —CH$_2$Ph | —OC$_2H_5$ | —CN | —Ph | —H |
| 11 | —$C_2H_4$OCOCH$_3$ | —$C_2H_4$OCOOCH$_3$ | —CONHCH$_3$ | —CH$_3$ | —$C_4H_9$ | —CH$_3$ |
| 12 | —$C_2H_5$ | —$C_2H_4$OCOOPh | —SO2NHC$_3H_7$ | —CH$_3$ | —$C_4H_9$ | —H |

| NO. | hue | coloring density | light fastness |
|---|---|---|---|
| 1 | red | 2.05 | Δ |
| 2 | red | 2.04 | ○ |
| 3 | red | 2.10 | Δ |
| 4 | red | 1.97 | ○ |
| 5 | red | 1.99 | ○ |
| 7 | red | 2.00 | ○ |
| 8 | red | 1.95 | ○ |
| 9 | red | 1.97 | ○ |
| 10 | red | 1.97 | Δ |
| 11 | red | 2.01 | ○ |
| 12 | red | 1.93 | ○ |

(15-1-c)

| NO. | $R_1$ | $R_2$ | $R_3$ | $R_4$ | $R_5$ | $R_6$ |
|---|---|---|---|---|---|---|
| 1 | —$C_2H_5$ | —$C_2H_5$ | —H | —CN | —$C_4H_9$ | —H |
| 2 | —$C_2H_5$ | —$C_2H_4$OH | —$CH_3$ | —CN | —$C_4H_9$ | —H |
| 3 | —$C_2H_5$ | —CH=$CH_2$ | —H | —CN | —$C_4H_9$ | —H |
| 4 | —$C_2H_5$ | —Ph | —Cl | —CN | —Ph | —H |
| 5 | —$C_2H_5$ | —CH=CHOCOCH$_3$ | —NHCOCH$_3$ | —CN | —Ph | —CH$_3$ |
| 6 | —$C_2H_5$ | —$C_2H_4$COOCH$_3$ | —OH | —NO$_2$ | —$C_4H_9$ | —H |
| 7 | —$C_2H_5$ | —$C_2H_4$OCOC$_4H_9$ | —NHSO$_3$CH$_3$ | —NO$_2$ | —$C_4H_9$ | —H |
| 8 | —$C_2H_5$ | —$C_2H_4$OCOOPh | —NHCOCH$_3$ | —CN | —$C_4H_9$ | —CH$_3$ |
| 9 | —$C_2H_5$ | —H | —NHCOCH$_3$ | —NO$_2$ | —Ph | —H |
| 10 | —$C_2H_5$ | —CH$_2$Ph | —OC$_2H_5$ | —CN | —Ph | —H |
| 11 | —$C_2H_4$OCOCH$_3$ | —$C_2H_4$OCOOCH$_3$ | —CONHCH$_3$ | —CH$_3$ | —$C_4H_9$ | —CH$_3$ |
| 12 | —$C_2H_5$ | —$C_2H_4$OCOOPh | —SO$_2$NHC$_3H_7$ | —CH$_3$ | —$C_4H_9$ | —H |

| NO. | hue | coloring density | light fastness |
|---|---|---|---|
| 1 | red | 1.94 | Δ |
| 2 | red | 1.90 | ○ |
| 3 | red | 1.94 | Δ |
| 4 | red | 1.88 | Δ |
| 5 | red | 1.86 | ○ |
| 6 | red | 1.71 | ○ |
| 7 | red | 1.82 | ○ |
| 8 | red | 1.84 | ○ |
| 9 | red | 1.83 | ○ |
| 10 | red | 1.85 | ○ |
| 11 | red | 1.90 | Δ |
| 12 | red | 1.81 | ○ |

(15-2-a)

| No. | $R_1$ | $R_2$ | $R_3$ | $R_4$ | $R_5$ |
|---|---|---|---|---|---|
| 1 | —$C_2H_5$ | —$C_2H_5$ | —H | —CN | —$C_4H_9$ |
| 2 | —$C_2H_5$ | —$C_2H_4$OH | —CH$_3$ | —CN | —$C_4H_9$ |
| 3 | —$C_2H_5$ | —CH=$CH_2$ | —H | —CN | —$C_4H_9$ |
| 4 | —$C_2H_5$ | —Ph | —Cl | —CN | —Ph |
| 5 | —$C_2H_5$ | —CH=CHOCOCH$_3$ | —NHCOCH$_3$ | —CN | —Ph |
| 6 | —$C_2H_5$ | —$C_2H_4$COOCH$_3$ | —OH | —NO$_2$ | —$C_4H_9$ |
| 7 | —$C_2H_5$ | —$C_2H_4$OCOC$_4H_9$ | —NHSO$_2$CH$_3$ | —NO$_2$ | —$C_4H_9$ |
| 8 | —$C_2H_5$ | —$C_2H_4$OCOOPh | —NHCOCH$_3$ | —CN | —$C_4H_9$ |
| 9 | —$C_2H_5$ | —H | —NHCOCH$_3$ | —NO$_2$ | —Ph |
| 10 | —$C_2H_5$ | —CH$_2$Ph | —OC$_2H_5$ | —CN | —Ph |

TABLE 15-continued

| | | | | | |
|---|---|---|---|---|---|
| 11 | —C$_2$H$_4$OCOCH$_3$ | —C$_2$H$_4$OCOOCH$_3$ | —CONHCH$_3$ | —CH$_3$ | —C$_4$H$_9$ |
| 12 | —C$_2$H$_5$ | —C$_2$H$_4$OCOOPh | —SO2NHC$_3$H$_7$ | —CH$_3$ | —C$_4$H$_9$ |

| No. | hue | coloring density | light fastness |
|---|---|---|---|
| 1 | red | 1.93 | Δ |
| 2 | red | 1.91 | ○ |
| 3 | red | 1.89 | Δ |
| 4 | red | 1.85 | Δ |
| 5 | red | 1.87 | ○ |
| 6 | red | 1.92 | ○ |
| 7 | red | 1.83 | ○ |
| 8 | red | 1.77 | ○ |
| 9 | red | 1.78 | ○ |
| 10 | red | 1.85 | Δ |
| 11 | red | 1.90 | ○ |
| 12 | red | 1.85 | ○ |

(15-2-b)

| No. | R$_1$ | R$_2$ | R$_3$ | R$_4$ | R$_5$ |
|---|---|---|---|---|---|
| 1 | —C$_2$H$_5$ | —C$_2$H$_5$ | —H | —CN | —C$_4$H$_9$ |
| 2 | —C$_2$H$_5$ | —C$_2$H$_4$OH | —CH$_3$ | —CN | —C$_4$H$_9$ |
| 3 | —C$_2$H$_5$ | —CH=CH$_2$ | —H | —CN | —C$_4$H$_9$ |
| 4 | —C$_2$H$_5$ | —Ph | —Cl | —CN | —Ph |
| 5 | —C$_2$H$_5$ | —CH=CHOCOCH$_3$ | —NHCOCH$_3$ | —CN | —Ph |
| 6 | —C$_2$H$_5$ | —C$_2$H$_4$COOCH$_3$ | —OH | —NO$_2$ | —C$_4$H$_9$ |
| 7 | —C$_2$H$_5$ | —C$_2$H$_4$OCOC$_4$H$_9$ | —NHSO$_2$CH$_3$ | —NO$_2$ | —C$_4$H$_9$ |
| 8 | —C$_2$H$_5$ | —C$_2$H$_4$OCOOPh | —NHCOCH$_3$ | —CN | —C$_4$H$_9$ |
| 9 | —C$_2$H$_5$ | —H | —NHCOCH$_3$ | —NO$_2$ | —Ph |
| 10 | —C$_2$H$_5$ | —CH$_2$Ph | —OC$_2$H$_5$ | —CN | —Ph |
| 11 | —C$_2$H$_4$OCOCH$_3$ | —C$_2$H$_4$OCOOCH$_3$ | —CONHCH$_3$ | —CH$_3$ | —C$_4$H$_9$ |
| 12 | —C$_2$H$_5$ | —C$_2$H$_4$OCOOPh | —SO2NHC$_3$H$_7$ | —CH$_3$ | —C$_4$H$_9$ |

| NO. | hue | coloring density | light fastness |
|---|---|---|---|
| 1 | red | 2.07 | Δ |
| 3 | red | 2.12 | Δ |
| 4 | red | 2.00 | ○ |
| 5 | red | 1.98 | ○ |
| 6 | red | 1.99 | ○ |
| 7 | red | 2.03 | Δ |
| 8 | red | 1.97 | ○ |
| 9 | red | 2.01 | ○ |
| 10 | red | 2.04 | Δ |
| 11 | red | 1.98 | ○ |
| 12 | red | 1.95 | ○ |

(15-2-c)

| NO. | R$_1$ | R$_2$ | R$_3$ | R$_4$ | R$_5$ |
|---|---|---|---|---|---|
| 1 | —C$_2$H$_5$ | —C$_2$H$_5$ | —H | —CN | —C$_4$H$_9$ |
| 2 | —C$_2$H$_5$ | —C$_2$H$_4$OH | —CH$_3$ | —CN | —C$_4$H$_9$ |
| 3 | —C$_2$H$_5$ | —CH=CH$_2$ | —H | —CN | —C$_4$H$_9$ |
| 4 | —C$_2$H$_5$ | —Ph | —Cl | —CN | —Ph |
| 5 | —C$_2$H$_5$ | —CH=CHOCOCH$_3$ | —NHCOCH$_3$ | —CN | —Ph |
| 6 | —C$_2$H$_5$ | —C$_2$H$_4$COOCH$_3$ | —OH | —NO$_2$ | —C$_4$H$_9$ |
| 7 | —C$_2$H$_5$ | —C$_2$H$_4$OCOC$_4$H$_9$ | —NHSO$_2$CH$_3$ | —NO$_2$ | —C$_4$H$_9$ |
| 8 | —C$_2$H$_5$ | —C$_2$H$_4$OCOOPh | —NHCOCH$_3$ | —CN | —C$_4$H$_9$ |
| 9 | —C$_2$H$_5$ | —H | —NHCOCH$_3$ | —NO$_2$ | —Ph |
| 10 | —C$_2$H$_5$ | —CH$_2$Ph | —OC$_2$H$_5$ | —CN | —Ph |
| 11 | —C$_2$H$_4$OCOCH$_3$ | —C$_2$H$_4$OCOOCH$_3$ | —CONHCH$_3$ | —CH$_3$ | —C$_4$H$_9$ |
| 12 | —C$_2$H$_5$ | —C$_2$H$_4$OCOOPh | —SO2NHC$_3$H$_7$ | #H3 | —C$_4$H$_9$ |

| NO. | hue | coloring density | light fastness |
|---|---|---|---|
| 1 | red | 1.96 | Δ |
| 2 | red | 1.88 | ○ |
| 3 | red | 1.91 | Δ |
| 4 | red | 1.90 | Δ |
| 5 | red | 1.83 | ○ |
| 6 | red | 1.88 | ○ |
| 7 | red | 1.85 | ○ |
| 8 | red | 1.87 | ○ |
| 9 | red | 1.80 | ○ |
| 10 | red | 1.82 | Δ |

TABLE 15-continued

| | | | | | |
|---|---|---|---|---|---|
| 11 | red | 1.95 | ○ | | |
| 12 | red | 1.83 | Δ | | |

| No. | $R_1$ | $R_2$ | $R_3$ | hue | coloring density | light fastness |
|---|---|---|---|---|---|---|

(15-3-a)

| No. | $R_1$ | $R_2$ | $R_3$ | hue | coloring density | light fastness |
|---|---|---|---|---|---|---|
| 1 | —$C_2H_5$ | —$C_2H_5$ | —H | red | 1.95 | Δ |
| 2 | —$C_2H_5$ | —$C_2H_4OH$ | —$CH_3$ | red | 1.89 | ○ |
| 3 | —$C_2H_5$ | —CH=$CH_2$ | —H | red | 1.87 | Δ |
| 4 | —$C_2H_5$ | —Ph | —Cl | red | 1.90 | ○ |
| 5 | —$C_2H_5$ | —CH=CHOCO$CH_3$ | —NHCO$CH_3$ | red | 1.91 | ○ |
| 6 | —$C_2H_5$ | —$C_2H_4COOCH_3$ | —OH | red | 1.89 | ○ |
| 7 | —$C_2H_5$ | —$C_2H_4OCOC_4H_9$ | —NHSO$_2CH_3$ | red | 1.79 | ○ |
| 8 | —$C_2H_5$ | —$C_2H_4OCOOPh$ | —NHCO$CH_3$ | red | 1.83 | ○ |
| 9 | —$C_2H_5$ | —H | —NHCO$CH_3$ | red | 1.84 | ○ |
| 10 | —$C_2H_5$ | —$CH_2Ph$ | —$OC_2H_5$ | red | 1.82 | Δ |
| 11 | —$C_2H_4OCOCH_3$ | —$C_2H_4OCOOCH_3$ | —CONHCH$_3$ | red | 1.90 | ○ |
| 12 | —$C_2H_5$ | —$C_2H_4OCOOPh$ | —SO$_2$NHC$_3H_7$ | red | 1.83 | ○ |

(15-3-b)

| No. | $R_1$ | $R_2$ | $R_3$ | hue | coloring density | light fastness |
|---|---|---|---|---|---|---|
| 1 | —$C_2H_5$ | —$C_2H_5$ | —H | red | 2.07 | Δ |
| 2 | —$C_2H_5$ | —$C_2H_4OH$ | —$CH_3$ | red | 2.01 | ○ |
| 3 | —$C_2H_5$ | —CH=$CH_2$ | —H | red | 2.13 | Δ |
| 4 | —$C_2H_5$ | —Ph | —Cl | red | 1.94 | Δ |
| 5 | —$C_2H_5$ | —CH=CHOCO$CH_3$ | —NHCO$CH_3$ | red | 1.97 | ○ |
| 6 | —$C_2H_5$ | —$C_2H_4COOCH_3$ | —OH | red | 1.99 | Δ |
| 7 | —$C_2H_5$ | —$C_2H_4OCOC_4H_9$ | —NHSO$_2CH_3$ | red | 2.05 | ○ |
| 8 | —$C_2H_5$ | —$C_2H_4OCOOPh$ | —NHCO$CH_3$ | red | 1.97 | ○ |
| 9 | —$C_2H_5$ | —H | —NHCO$CH_3$ | red | 2.00 | ○ |
| 10 | —$C_2H_5$ | —$CH_2Ph$ | —$OC_2H_5$ | red | 1.96 | Δ |
| 11 | —$C_2H_4OCOCH_3$ | —$C_2H_4OCOOCH_3$ | —CONHCH$_3$ | red | 2.05 | ○ |
| 12 | —$C_2H_5$ | —$C_2H_4OCOOPh$ | —SO2NHC$_3H_7$ | red | 1.97 | Δ |

(15-3-c)

| No. | $R_1$ | $R_2$ | $R_3$ | hue | coloring density | light fastness |
|---|---|---|---|---|---|---|
| 1 | —$C_2H_5$ | —$C_2H_5$ | —H | red | 1.95 | Δ |
| 2 | —$C_2H_5$ | —$C_2H_4OH$ | —$CH_3$ | red | 1.92 | ○ |
| 3 | —$C_2H_5$ | —CH=$CH_2$ | —H | red | 1.91 | Δ |
| 4 | —$C_2H_5$ | —Ph | —Cl | red | 1.90 | ○ |
| 5 | —$C_2H_5$ | —CH=CHOCO$CH_3$ | —NHCO$CH_3$ | red | 1.91 | ○ |
| 6 | —$C_2H_5$ | —$C_2H_4COOCH_3$ | —OH | red | 1.88 | ○ |
| 7 | —$C_2H_5$ | —$C_2H_4OCOC_4H_9$ | —NHSO$_2CH_3$ | red | 1.85 | ○ |
| 8 | —$C_2H_5$ | —$C_2H_4OCOOPh$ | —NHCO$CH_3$ | red | 1.81 | ○ |
| 9 | —$C_2H_5$ | —H | —NHCO$CH_3$ | red | 1.86 | ○ |
| 10 | —$C_2H_5$ | —$CH_2Ph$ | —$OC_2H_5$ | red | 1.85 | Δ |
| 11 | —$C_2H_4OCOCH_3$ | —$C_2H_4OCOOCH_3$ | —CONHCH$_3$ | red | 1.92 | ○ |
| 12 | —$C_2H_5$ | —$C_2H_4OCOOPh$ | —SO2NHC$_3H_7$ | red | 1.83 | ○ |

(15-4-a)

| No. | $R_1$ | $R_2$ | $R_3$ | $R_4$ | $R_5$ |
|---|---|---|---|---|---|
| 1 | —$C_2H_5$ | —$C_2H_5$ | —H | —CN | —$C_4H_9$ |
| 2 | —$C_2H_5$ | —$C_2H_4OH$ | —$CH_3$ | —CN | —$C_4H_9$ |
| 3 | —$C_2H_5$ | —CH=$CH_2$ | —H | —CN | —$C_4H_9$ |
| 4 | —$C_2H_5$ | —Ph | —Cl | —CN | —Ph |
| 5 | —$C_2H_5$ | —CH=CHOCO$CH_3$ | —NHCO$CH_3$ | —CN | —Ph |
| 6 | —$C_2H_5$ | —$C_2H_4COOCH_3$ | —OH | —$NO_2$ | —$C_4H_9$ |
| 7 | —$C_2H_5$ | —$C_2H_4OCOC_4H_9$ | —NHSO$_2CH_3$ | —$NO_2$ | —$C_4H_9$ |
| 8 | —$C_2H_5$ | —$C_2H_4OCOOPh$ | —NHCO$CH_3$ | —CN | —$C_4H_9$ |
| 9 | —$C_2H_5$ | —H | —NHCO$CH_3$ | —$NO_2$ | —Ph |
| 10 | —$C_2H_5$ | —$CH_2Ph$ | —$OC_2H_5$ | —CN | —Ph |
| 11 | —$C_2H_4OCOCH_3$ | —$C_2H_4OCOOCH_3$ | —CONHCH$_3$ | —$CH_3$ | —$C_4H_9$ |
| 12 | —$C_2H_5$ | —$C_2H_4OCOOPh$ | —SO2NHC$_3H_7$ | —$CH_3$ | —$C_4H_9$ |

| NO. | hue | coloring density | light fastness |
|---|---|---|---|
| 1 | red | 1.90 | ○ |
| 2 | red | 1.93 | ○ |
| 3 | red | 1.91 | Δ |
| 4 | red | 1.88 | Δ |
| 5 | red | 1.86 | ○ |
| 6 | red | 1.89 | ○ |
| 7 | red | 1.83 | ○ |
| 8 | red | 1.78 | ○ |
| 9 | red | 1.84 | ○ |
| 10 | red | 1.85 | Δ |

TABLE 15-continued

| | | | |
|---|---|---|---|
| 11 | red | 1.90 | ○ |
| 12 | red | 1.83 | ○ |

(15-4-b)

| NO. | $R_1$ | $R_2$ | $R_3$ | $R_4$ | $R_5$ |
|---|---|---|---|---|---|
| 1 | —$C_2H_5$ | —$C_2H_5$ | —H | —CN | —$C_4H_9$ |
| 2 | —$C_2H_5$ | —$C_2H_4OH$ | —$CH_3$ | —CN | —$C_4H_9$ |
| 3 | —$C_2H_5$ | —CH=$CH_2$ | —H | —CN | —$C_4H_9$ |
| 4 | —$C_2H_5$ | —Ph | —Cl | —CN | —Ph |
| 5 | —$C_2H_5$ | —CH=$CHOCOCH_3$ | —$NHCOCH_3$ | —CN | —Ph |
| 6 | —$C_2H_5$ | —$C_2H_4COOCH_3$ | —OH | —$NO_2$ | —$C_4H_9$ |
| 7 | —$C_2H_5$ | —$C_2H_4OCOC_4H_9$ | —$NHSO_2CH_3$ | —$NO_2$ | —$C_4H_9$ |
| 8 | —$C_2H_5$ | —$C_2H_4OCOOPh$ | —$NHCOCH_3$ | —CN | —$C_4H_9$ |
| 9 | —$C_2H_5$ | —H | —$NHCOCH_3$ | —$NO_2$ | —Ph |
| 10 | —$C_2H_5$ | —$CH_2Ph$ | —$OC_2H_5$ | —CN | —Ph |
| 11 | —$C_2H_4OCOCH_3$ | —$C_2H_4OCOOCH_3$ | —$CONHCH_3$ | —$CH_3$ | —$C_4H_9$ |
| 12 | —$C_2H_5$ | —$C_2H_4OCOOPh$ | —$SO_2NHC_3H_7$ | —$CH_3$ | —$C_4H_9$ |

| No. | hue | coloring density | light fastness |
|---|---|---|---|
| 1 | red | 2.01 | △ |
| 2 | red | 2.05 | ○ |
| 3 | red | 2.18 | ○ |
| 4 | red | 2.04 | △ |
| 5 | red | 2.00 | ○ |
| 6 | red | 1.97 | ○ |
| 7 | red | 1.98 | ○ |
| 8 | red | 1.97 | ○ |
| 9 | red | 1.98 | ○ |
| 10 | red | 2.00 | △ |
| 11 | red | 2.03 | ○ |
| 12 | red | 1.95 | ○ |

(15-4-c)

| No. | $R_1$ | $R_2$ | $R_3$ | $R_4$ | $R_5$ |
|---|---|---|---|---|---|
| 1 | —$C_2H_5$ | —$C_2H_5$ | —H | —CN | —$C_4H_9$ |
| 2 | —$C_2H_5$ | —$C_2H_4OH$ | —$CH_3$ | —CN | —$C_4H_9$ |
| 3 | —$C_2H_5$ | —CH=$CH_2$ | —H | —CN | —$C_4H_9$ |
| 4 | —$C_2H_5$ | —Ph | —Cl | —CN | —Ph |
| 5 | —$C_2H_5$ | —CH=$CHOCOCH_3$ | —$NHCOCH_3$ | —CN | —Ph |
| 6 | —$C_2H_5$ | —$C_2H_4COOCH_3$ | —OH | —$NO_2$ | —$C_4H_9$ |
| 7 | —$C_2H_5$ | —$C_2H_4OCOC_4H_9$ | —$NHSO_2CH_3$ | —$NO_2$ | —$C_4H_9$ |
| 8 | —$C_2H_5$ | —$C_2H_4OCOOPh$ | —$NHCOCH_3$ | —CN | —$C_4H_9$ |
| 9 | —$C_2H_5$ | —H | —$NHCOCH_3$ | —$NO_2$ | —Ph |
| 10 | —$C_2H_5$ | —$CH_2Ph$ | —$OC_2H_5$ | —CN | —Ph |
| 11 | —$C_2H_4OCOCH_3$ | —$C_2H_4OCOOCH_3$ | —$CONHCH_3$ | —$CH_3$ | —$C_4H_9$ |
| 12 | —$C_2H_5$ | —$C_2H_4OCOOPh$ | —$SO_2NHC_3H_7$ | —$CH_3$ | —$C_4H_9$ |

| No. | hue | coloring density | light fastness |
|---|---|---|---|
| 1 | red | 1.95 | △ |
| 2 | red | 1.93 | ○ |
| 3 | red | 1.91 | △ |
| 4 | red | 1.90 | △ |
| 5 | red | 1.82 | ○ |
| 6 | red | 1.90 | ○ |
| 7 | red | 1.83 | △ |
| 8 | red | 1.86 | ○ |
| 9 | red | 1.84 | ○ |
| 10 | red | 1.87 | △ |
| 11 | red | 1.91 | ○ |
| 12 | red | 1.84 | ○ |

(15-5-a)

| No. | $R_1$ | $R_2$ | $R_3$ | $R_4$ | $R_5$ | $R_6$ |
|---|---|---|---|---|---|---|
| 1 | —$C_2H_5$ | —$C_2H_5$ | —H | —CN | —$C_4H_9$ | —H |
| 2 | —$C_2H_5$ | —$C_2H_4OH$ | —$CH_3$ | —CN | —$C_4H_9$ | —H |
| 3 | —$C_2H_5$ | —CH=$CH_2$ | —H | —CN | —$C_4H_9$ | —H |
| 4 | —$C_2H_5$ | —Ph | —Cl | —CN | —Ph | —H |
| 5 | —$C_2H_5$ | —CH=$CHOCOCH_3$ | —$NHCOCH_3$ | —CN | —Ph | —H |
| 6 | —$C_2H_5$ | —$C_2H_4COOCH_3$ | —OH | —$NO_2$ | —$C_4H_9$ | —H |
| 7 | —$C_2H_5$ | —$C_2H_4OCOC_4H_9$ | —$NHSO_2CH_3$ | —$NO_2$ | —$C_4H_9$ | —H |
| 8 | —$C_2H_5$ | —$C_2H_4OCOOPh$ | —$NHCOCH_3$ | —CN | —$C_4H_9$ | —H |

TABLE 15-continued

| No. | $R_1$ | $R_2$ | $R_3$ | $R_4$ | $R_5$ | $R_6$ |
|---|---|---|---|---|---|---|
| 9 | —$C_2H_5$ | —H | —NHCOCH$_3$ | —NO$_2$ | —Ph | —H |
| 10 | —$C_2H_5$ | —CH$_2$Ph | —OC$_2$H$_5$ | —CN | —Ph | —H |
| 11 | —$C_2H_4$OCOCH$_3$ | —$C_2H_4$OCOOCH$_3$ | —CONHCH$_3$ | —CH$_3$ | —C$_4$H$_9$ | —H |
| 12 | —$C_2H_5$ | —$C_2H_4$OCOOPh | —SO$_2$NHC$_3$H$_7$ | —CH$_3$ | —C$_4$H$_9$ | —H |

| No. | hue | coloring density | light fastness |
|---|---|---|---|
| 1 | red | 1.97 | △ |
| 2 | red | 1.94 | ○ |
| 3 | red | 1.89 | △ |
| 4 | red | 1.90 | △ |
| 5 | red | 1.91 | ○ |
| 6 | red | 1.87 | ○ |
| 7 | red | 1.85 | ○ |
| 8 | red | 1.76 | ○ |
| 9 | red | 1.82 | ○ |
| 10 | red | 1.81 | △ |
| 11 | red | 1.93 | △ |
| 12 | red | 1.79 | △ |

(15-5-b)

| No. | $R_1$ | $R_2$ | $R_3$ | $R_4$ | $R_5$ | $R_6$ |
|---|---|---|---|---|---|---|
| 1 | —$C_2H_5$ | —$C_2H_5$ | —H | —CN | —C$_4$H$_9$ | —H |
| 2 | —$C_2H_5$ | —$C_2H_4$OH | —CH$_3$ | —CN | —C$_4$H$_9$ | —H |
| 3 | —$C_2H_5$ | —CH=CH$_2$ | —H | —CN | —C$_4$H$_9$ | —H |
| 4 | —$C_2H_5$ | —Ph | —Cl | —CN | —Ph | —H |
| 5 | —$C_2H_5$ | —CH=CHOCOCH$_3$ | —NHCOCH$_3$ | —CN | —Ph | —H |
| 6 | —$C_2H_5$ | —$C_2H_4$COOCH$_3$ | —OH | —NO$_2$ | —C$_4$H$_9$ | —H |
| 7 | —$C_2H_5$ | —$C_2H_4$OCOC$_4$H$_9$ | —NHSO$_2$CH$_3$ | —NO$_2$ | —C$_4$H$_9$ | —H |
| 8 | —$C_2H_5$ | —$C_2H_4$OCOOPh | —NHCOCH$_3$ | —CN | —C$_4$H$_9$ | —H |
| 9 | —$C_2H_5$ | —H | —NHCOCH$_3$ | —NO$_2$ | —Ph | —H |
| 10 | —$C_2H_5$ | —CH$_2$Ph | —OC$_2$H$_5$ | —CN | —Ph | —H |
| 11 | —$C_2H_4$OCOCH$_3$ | —$C_2H_4$OCOOCH$_3$ | —CONHCH$_3$ | —CH$_3$ | —C$_4$H$_9$ | —H |
| 12 | —$C_2H_5$ | —$C_2H_4$OCOOPh | —SO$_2$NHC$_3$H$_7$ | —CH$_3$ | —C$_4$H$_9$ | —H |

(15-5-c)

| No. | hue | coloring density | light fastness |
|---|---|---|---|
| 1 | red | 2.01 | △ |
| 2 | red | 1.97 | ○ |
| 3 | red | 2.06 | △ |
| 4 | red | 1.94 | △ |
| 5 | red | 2.00 | ○ |
| 6 | red | 2.01 | △ |
| 7 | red | 1.95 | ○ |
| 8 | red | 1.91 | ○ |
| 9 | red | 1.92 | ○ |
| 10 | red | 2.00 | △ |
| 11 | red | 1.95 | ○ |
| 12 | red | 1.89 | ○ |

| No. | $R_1$ | $R_2$ | $R_3$ | $R_4$ | $R_5$ | $R_6$ |
|---|---|---|---|---|---|---|
| 1 | —$C_2H_5$ | —$C_2H_5$ | —H | —CN | —C$_4$H$_9$ | —H |
| 2 | —$C_2H_5$ | —$C_2H_4$OH | —CH$_3$ | —CN | —C$_4$H$_9$ | —H |
| 3 | —$C_2H_5$ | —CH=CH$_2$ | —H | —CN | —C$_4$H$_9$ | —H |
| 4 | —$C_2H_5$ | —Ph | —Cl | —CN | —Ph | —H |
| 5 | —$C_2H_5$ | —CH=CHOCOCH$_3$ | —NHCOCH$_3$ | —CN | —Ph | —H |
| 6 | —$C_2H_5$ | —$C_2H_4$COOCH$_3$ | —OH | —NO$_2$ | —C$_4$H$_9$ | —H |
| 7 | —$C_2H_5$ | —$C_2H_4$OCOC$_4$H$_9$ | —NHSO$_2$CH$_3$ | —NO$_2$ | —C$_4$H$_9$ | —H |
| 8 | —$C_2H_5$ | —$C_2H_4$OCOOPh | —NHCOCH$_3$ | —CN | —C$_4$H$_9$ | —H |
| 9 | —$C_2H_5$ | —H | —NHCOCH$_3$ | —NO$_2$ | —Ph | —H |
| 10 | —$C_2H_5$ | —CH$_2$Ph | —OC$_2$H$_5$ | —CN | —Ph | —H |
| 11 | —$C_2H_4$OCOCH$_3$ | —$C_2H_4$OCOCH$_3$ | —CONHCH$_3$ | —CH$_3$ | —C$_4$H$_9$ | —H |
| 12 | —$C_2H_5$ | —$C_2H_4$OCOOPh | —SO$_2$NHC$_3$H$_7$ | —CH$_3$ | —C$_4$H$_9$ | —H |

| No. | hue | Coloring density | light fastness |
|---|---|---|---|
| 1 | red | 1.91 | △ |
| 2 | red | 1.87 | ○ |
| 3 | red | 1.96 | ○ |
| 4 | red | 1.90 | △ |
| 5 | red | 1.89 | ○ |
| 6 | red | 1.87 | △ |
| 7 | red | 1.84 | ○ |
| 8 | red | 1.79 | ○ |

TABLE 15-continued

| | | | | |
|---|---|---|---|---|
| 9 | red | 1.85 | | ○ |
| 10 | red | 1.90 | | Δ |
| 11 | red | 1.91 | | ○ |
| 12 | red | 1.79 | | ○ |

(15-6-a)

| No. | $R_1$ | $R_2$ | $R_3$ | $R_4$ | $R_5$ |
|---|---|---|---|---|---|
| 1 | —$C_2H_5$ | —$C_2H_5$ | —H | —CN | —$C_4H_9$ |
| 2 | —$C_2H_5$ | —$C_2H_4OH$ | —$CH_3$ | —CN | —$C_4H_9$ |
| 3 | —$C_2H_5$ | —CH=$CH_2$ | —H | —CN | —$C_4H_9$ |
| 4 | —$C_2H_5$ | —Ph | —Cl | —CN | —Ph |
| 5 | —$C_2H_5$ | —CH=CHOC$OCH_3$ | —$NHCOCH_3$ | —CN | —Ph |
| 6 | —$C_2H_5$ | —$C_2H_4COOCH_3$ | —OH | —$NO_2$ | —$C_4H_9$ |
| 7 | —$C_2H_5$ | —$C_2H_4OCOC_4H_9$ | —$NHSO_2CH_3$ | —$NO_2$ | —$C_4H_9$ |
| 8 | —$C_2H_5$ | —$C_2H_4OCOOPh$ | —$NHCOCH_3$ | —CN | —$C_4H_9$ |
| 9 | —$C_2H_5$ | —H | —$NHCOCH_3$ | —$NO_2$ | —Ph |
| 10 | —$C_2H_5$ | —$CH_2Ph$ | —$OC_2H_5$ | —CN | —Ph |
| 11 | —$C_2H_4OCOCH_3$ | —$C_2H_4OCOOCH_3$ | —$CONHCH_3$ | —$CH_3$ | —$C_4H_9$ |
| 12 | —$C_2H_5$ | $C_2H_4OCOPh$ | —$SO_2NHC_3H_7$ | —$CH_3$ | —$C_4H_9$ |

| No. | hue | coloring density | light fastness |
|---|---|---|---|
| 1 | red | 1.93 | Δ |
| 2 | red | 1.89 | ○ |
| 3 | red | 1.87 | Δ |
| 4 | red | 1.90 | ○ |
| 5 | red | 1.92 | ○ |
| 6 | red | 1.87 | ○ |
| 7 | red | 1.84 | ○ |
| 8 | red | 1.79 | ○ |
| 9 | red | 1.83 | ○ |
| 10 | red | 1.86 | Δ |
| 11 | red | 1.91 | ○ |
| 12 | red | 1.85 | ○ |

(15-6-b)

| No. | $R_1$ | $R_2$ | $R_3$ | $R_4$ | $R_5$ |
|---|---|---|---|---|---|
| 1 | —$C_2H_5$ | —$C_2H_5$ | —H | —CN | —$C_4H_9$ |
| 2 | —$C_2H_5$ | —$C_2H_4OH$ | —$CH_3$ | —CN | —$C_4H_9$ |
| 3 | —$C_2H_5$ | —CH=$CH_2$ | —H | —CN | —$C_4H_9$ |
| 4 | —$C_2H_5$ | —Ph | —Cl | —CN | —Ph |
| 5 | —$C_2H_5$ | —CH=CHOC$OCH_3$ | —$NHCOCH_3$ | —CN | —Ph |
| 6 | —$C_2H_5$ | —$C_2H_4COOCH_3$ | —OH | —$NO_2$ | —$C_4H_9$ |
| 7 | —$C_2H_5$ | —$C_2H_4OCOC_4H_9$ | —$NHSO_2CH_3$ | —$NO_2$ | —$C_4H_9$ |
| 8 | —$C_2H_5$ | —$C_2H_4OCOOPh$ | —$NHCOCH_3$ | —CN | —$C_4H_9$ |
| 9 | —$C_2H_5$ | —H | —$NHCOCH_3$ | —$NO_2$ | —Ph |
| 10 | —$C_2H_5$ | —$CH_2Ph$ | —$OC_2H_5$ | —CN | —Ph |
| 11 | —$C_2H_4OCOCH_3$ | —$C_2H_4OCOOCH_3$ | —$CONHCH_3$ | —$CH_3$ | —$C_4H_9$ |
| 12 | —$C_2H_5$ | —$C_2H_4OCOPh$ | —$SO_2NHC_3H_7$ | —$CH_3$ | —$C_4H_9$ |

| No. | hue | coloring density | light fastness |
|---|---|---|---|
| 1 | red | 2.07 | Δ |
| 2 | red | 2.01 | ○ |
| 3 | red | 2.14 | Δ |
| 4 | red | 2.03 | Δ |
| 5 | red | 2.00 | ○ |
| 6 | red | 1.97 | ○ |
| 7 | red | 1.98 | Δ |
| 8 | red | 2.00 | ○ |
| 9 | red | 2.01 | ○ |
| 10 | red | 2.04 | Δ |
| 11 | red | 1.98 | ○ |
| 12 | red | 1.95 | ○ |

(15-6-a)

| No. | $R_1$ | $R_2$ | $R_3$ | $R_4$ | $R_5$ |
|---|---|---|---|---|---|
| 1 | —$C_2H_5$ | —$C_2H_5$ | —H | —CN | —$C_4H_9$ |
| 2 | —$C_2H_5$ | —$C_2H_4OH$ | —$CH_3$ | —CN | —$C_4H_9$ |
| 3 | —$C_2H_5$ | —CH=$CH_2$ | —H | —CN | —$C_4H_9$ |
| 4 | —$C_2H_5$ | —Ph | —Cl | —CN | —Ph |
| 5 | —$C_2H_5$ | —CH=CHOC$OCH_3$ | —$NHCOCH_3$ | —CN | —Ph |
| 6 | —$C_2H_5$ | —$C_2H_4COOCH_3$ | —OH | —$NO_2$ | —$C_4H_9$ |

TABLE 15-continued

| No. | R₁ | R₂ | R₃ | R₄ | R₅ |
|---|---|---|---|---|---|
| 7 | —C₂H₅ | —C₂H₄OCOC₄H₉ | —NHSO₂CH₃ | —NO₂ | —C₄H₉ |
| 8 | —C₂H₅ | —C₂H₄OCOOPh | —NHCOCH₃ | —CN | —C₄H₉ |
| 9 | —C₂H₅ | —H | —NHCOCH₃ | —NO₂ | —Ph |
| 10 | —C₂H₅ | —CH₂Ph | —OC₂H₅ | —CN | —Ph |
| 11 | —C₂H₄OCOCH₃ | —C₂H₄OCOCH₃ | —CONHCH₃ | —CH₃ | —C₄H₉ |
| 12 | —C₂H₅ | —C₂H₄OCOPh | —SO₂NHC₃H₇ | —CH₃ | —C₄H₉ |

(15-6-c)

| No. | hue | coloring density | light fastness |
|---|---|---|---|
| 1 | red | 1.91 | Δ |
| 2 | red | 1.98 | ○ |
| 3 | red | 1.90 | Δ |
| 4 | red | 1.85 | ○ |
| 5 | red | 1.87 | ○ |
| 6 | red | 1.90 | ○ |
| 7 | red | 1.83 | Δ |
| 8 | red | 1.80 | ○ |
| 9 | red | 1.79 | ○ |
| 10 | red | 1.87 | Δ |
| 11 | red | 1.88 | ○ |
| 12 | red | 1.84 | ○ |

(15-7-a)

| No. | R₁ | R₂ | R₃ | R₄ | R₅ | R₆ |
|---|---|---|---|---|---|---|
| 1 | —C₂H₅ | —C₂H₅ | —H | —CN | —C₄H₉ | —H |
| 2 | —C₂H₅ | —C₂H₄OH | —CH₃ | —CN | —C₄H₉ | —H |
| 3 | —C₂H₅ | —CH=CH₂ | —H | —CN | —C₄H₉ | —H |
| 4 | —C₂H₅ | —Ph | —Cl | —CN | —Ph | —H |
| 5 | —C₂H₅ | —CH=CHOCOCH₃ | —NHCOCH₃ | —CN | —Ph | —H |
| 6 | —C₂H₅ | —C₂H₄COOCH₃ | —OH | —NO₂ | —C₄H₉ | —H |
| 7 | —C₂H₅ | —C₂H₄OCOC₄H₉ | —NHSO₂CH₃ | —NO₂ | —C₄H₉ | —H |
| 8 | —C₂H₅ | —C₂H₄OCOOPh | —NHCOCH₃ | —CN | —C₄H₉ | —H |
| 9 | —C₂H₅ | —H | —NHCOCH₃ | —NO₂ | —Ph | —H |
| 10 | —C₂H₅ | —CH₂Ph | —OC₂H₅ | —CN | —Ph | —H |
| 11 | —C₂H₄OCOCH₃ | —C₂H₄OCOCH₃ | —CONHCH₃ | —CH₃ | —C₄H₉ | —H |
| 12 | —C₂H₅ | —C₂H₄OCOPh | —SO₂NHC₃H₇ | —CH₃ | —C₄H₉ | —H |

| No. | hue | coloring density | light fastness |
|---|---|---|---|
| 1 | red | 1.97 | Δ |
| 2 | red | 1.90 | ○ |
| 3 | red | 1.89 | Δ |
| 4 | red | 1.82 | Δ |
| 5 | red | 1.91 | ○ |
| 6 | red | 1.86 | ○ |
| 7 | red | 1.84 | ○ |
| 8 | red | 1.81 | ○ |
| 9 | red | 1.77 | ○ |
| 10 | red | 1.85 | Δ |
| 11 | red | 1.90 | Δ |
| 12 | red | 1.87 | ○ |

(15-7-b)

| No. | R₁ | R₂ | R₃ | R₄ | R₅ | R₆ |
|---|---|---|---|---|---|---|
| 1 | —C₂H₅ | —C₂H₅ | —H | —CN | —C₄H₉ | —H |
| 2 | —C₂H₅ | —C₂H₄OH | —CH₃ | —CN | —C₄H₉ | —H |
| 3 | —C₂H₅ | —CH=CH₂ | —H | —CN | —C₄H₉ | —H |
| 4 | —C₂H₅ | —Ph | —Cl | —CN | —Ph | —H |
| 5 | —C₂H₅ | —CH=CHOCOCH₃ | —NHCOCH₃ | —CN | —Ph | —H |
| 6 | —C₂H₅ | —C₂H₄COOCH₃ | —OH | —NO₂ | —C₄H₉ | —H |
| 7 | —C₂H₅ | —C₂H₄OCOC₄H₉ | —NHSO₂CH₃ | —NO₂ | —C₄H₉ | —H |
| 8 | —C₂H₅ | —C₂H₄OCOOPh | —NHCOCH₃ | —CN | —C₄H₉ | —H |
| 9 | —C₂H₅ | —H | —NHCOCH₃ | —NO₂ | —Ph | —H |
| 10 | —C₂H₅ | —CH₂Ph | —OC₂H₅ | —CN | —Ph | —H |
| 11 | —C₂H₄OCOCH₃ | —C₂H₄OCOCH₃ | —CONHCH₃ | —CH₃ | —C₄H₉ | —H |
| 12 | —C₂H₅ | —C₂H₄OCOPh | —SO₂NHC₃H₇ | —CH₃ | —C₄H₉ | —H |

| No. | hue | coloring density | light fastness |
|---|---|---|---|
| 1 | red | 2.03 | Δ |
| 2 | red | 2.01 | ○ |
| 3 | red | 2.17 | Δ |
| 4 | red | 2.06 | Δ |

TABLE 15-continued

| | | | |
|---|---|---|---|
| 5 | red | 1.92 | ◯ |
| 6 | red | 1.99 | ◯ |
| 7 | red | 2.04 | ◯ |
| 8 | red | 1.89 | ◯ |
| 9 | red | 1.93 | ◯ |
| 10 | red | 1.91 | Δ |
| 11 | red | 1.94 | Δ |
| 12 | red | 1.96 | ◯ |

(15-7-c)

| No. | $R_1$ | $R_2$ | $R_3$ | $R_4$ | $R_5$ | $R_6$ |
|---|---|---|---|---|---|---|
| 1 | —$C_2H_5$ | —$C_2H_5$ | —H | —CN | —$C_4H_9$ | —H |
| 2 | —$C_2H_5$ | —$C_2H_4OH$ | —$CH_3$ | —CN | —$C_4H_9$ | —H |
| 3 | —$C_2H_5$ | —CH=$CH_2$ | —H | —CN | —$C_4H_9$ | —H |
| 4 | —$C_2H_5$ | —Ph | —Cl | —CN | —Ph | —H |
| 5 | —$C_2H_5$ | —CH=$CHOCOCH_3$ | —$NHCOCH_3$ | —CN | —Ph | —H |
| 6 | —$C_2H_5$ | —$C_2H_4COOCH_3$ | —OH | —$NO_2$ | —$C_4H_9$ | —H |
| 7 | —$C_2H_5$ | —$C_2H_4OCOC_4H_9$ | —$NHSO_3CH_3$ | —$NO_2$ | —$C_4H_9$ | —H |
| 8 | —$C_2H_5$ | —$C_2H_4OCOOPh$ | —$NHCOCH_3$ | —CN | —$C_4H_9$ | —H |
| 9 | —$C_2H_5$ | —H | —$NHCOCH_3$ | —$NO_2$ | —Ph | —H |
| 10 | —$C_2H_5$ | —$CH_2Ph$ | —$OC_2H_5$ | —CN | —Ph | —H |
| 11 | —$C_2H_4OCOCH_3$ | —$C_2H_4OCOCH_3$ | —$CONHCH_3$ | —$CH_3$ | —$C_4H_9$ | —H |
| 12 | —$C_2H_5$ | —$C_2H_4OCOPh$ | —$SO_2NHC_3H_7$ | —$CH_3$ | —$C_4H_9$ | —H |

| No. | hue | coloring density | light fastness |
|---|---|---|---|
| 1 | red | 1.97 | Δ |
| 2 | red | 1.90 | ◯ |
| 3 | red | 1.89 | Δ |
| 4 | red | 1.82 | Δ |
| 5 | red | 1.91 | ◯ |
| 6 | red | 1.86 | ◯ |
| 7 | red | 1.84 | ◯ |
| 8 | red | 1.81 | ◯ |
| 9 | red | 1.77 | ◯ |
| 10 | red | 1.85 | Δ |
| 11 | red | 1.90 | Δ |
| 12 | red | 1.87 | ◯ |

(16) Dyes represented by the following structural formula:

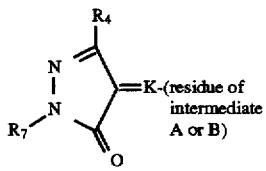

(16)

wherein K stands for =CH—, =C(CN)— or =N— and $R_4$ and $R_7$ will be defined below.

Specific examples of the dye represented by the general formula 16 and the performance thereof in the case of use in a thermal transfer sheet are given in the following Table 16.

TABLE 16

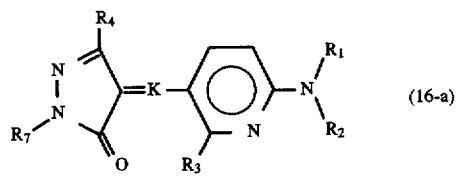 (16-a)

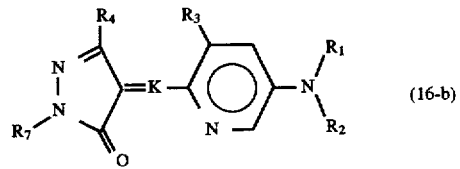 (16-b)

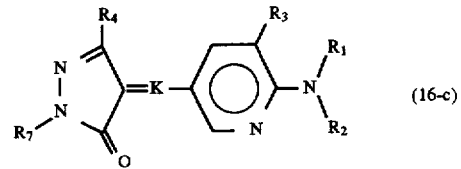 (16-c)

| No. | $R_1$ | $R_2$ | $R_3$ | $R_4$ | $R_7$ | hue | coloring density | light fastness |
|---|---|---|---|---|---|---|---|---|
| (16-a K: =N—) | | | | | | | | |
| 1 | $-C_2H_5$ | $-C_2H_5$ | $-H$ | $-CN$ | $-Ph$ | orange | 1.83 | △ |
| 2 | $-C_2H_5$ | $-C_2H_4OH$ | $-CH_3$ | $-CN$ | $-Ph$ | orange | 1.81 | ○ |
| 3 | $-C_2H_5$ | $-CH=CH_2$ | $-H$ | $-CN$ | 2-benzthiazolyl | orange | 1.84 | △ |
| 4 | $-C_2H_5$ | $-Ph$ | $-Cl$ | $-CN$ | 2-benzthiazolyl | orange | 1.75 | △ |
| 5 | $-C_2H_5$ | $-CH=CHOCOCH_3$ | $-NHCOCH_3$ | $-C_2H_5$ | 2-benzthiazolyl | orange | 1.72 | ○ |
| 6 | $-C_2H_5$ | $-C_2H_4COOCH_3$ | $-OH$ | $-NO_2$ | 2-benzthiazolyl | orange | 1.74 | ○ |
| 7 | $-C_2H_5$ | $-C_2H_4OCOC_4H_9$ | $-NHSO_2CH_3$ | $-NO_2$ | 2-thienyl | orange | 1.72 | ○ |
| 8 | $-C_2H_5$ | $-C_2H_4OCOOPh$ | $-NHCOCH_3$ | $-CN$ | 2-thienyl | orange | 1.70 | ○ |
| 9 | $-C_2H_5$ | $-H$ | $-NHCOCH_3$ | $-NO_2$ | 2-thienyl | orange | 1.79 | ○ |
| 10 | $-C_2H_5$ | $-CH_2Ph$ | $-OC_2H_5$ | $-CN$ | $-Ph$ | orange | 1.82 | △ |
| 11 | $-C_2H_4OCOCH_3$ | $-C_2H_4OCOCH_3$ | $-CONHCH_3$ | $-CH_3$ | $-Ph$ | orange | 1.73 | ○ |
| 12 | $-C_2H_5$ | $-C_2H_4OCOph$ | $-SO_2NHC_3H_7$ | $-CH_3$ | $-Ph$ | orange | 1.76 | ○ |
| (16-a K: =CH—) | | | | | | | | |
| 1 | $-C_2H_5$ | $-C_2H_5$ | $-H$ | $-CN$ | $-Ph$ | orange | 1.82 | △ |
| 2 | $-C_2H_5$ | $-C_2H_4OH$ | $-CH_3$ | $-CN$ | $-Ph$ | orange | 1.81 | ○ |
| 3 | $-C_2H_5$ | $-CH=CH_2$ | $-H$ | $-CN$ | 2-benzthiazolyl | orange | 1.79 | △ |
| 4 | $-C_2H_5$ | $-Ph$ | $-Cl$ | $-CN$ | 2-benzthiazolyl | orange | 1.76 | △ |
| 5 | $-C_2H_5$ | $-CH=CHOCOCH_3$ | $-NHCOCH_3$ | $-C_2H_5$ | 2-benzthiazolyl | orange | 1.71 | ○ |
| 6 | $-C_2H_5$ | $-C_2H_4COOCH_3$ | $-OH$ | $-NO_2$ | 2-benzthiazolyl | orange | 1.76 | ○ |
| 7 | $-C_2H_5$ | $-C_2H_4OCOC_4H_9$ | $-NHSO_2CH_3$ | $-NO_2$ | 2-thienyl | orange | 1.69 | ○ |
| 8 | $-C_2H_5$ | $-C_2H_4OCOOPh$ | $-NHCOCH_3$ | $-CN$ | 2-thienyl | orange | 1.73 | ○ |
| 9 | $-C_2H_5$ | $-H$ | $-NHCOCH_3$ | $-NO_2$ | 2-thienyl | orange | 1.82 | ○ |
| 10 | $-C_2H_5$ | $-CH_2Ph$ | $-OC_2H_5$ | $-CN$ | $-Ph$ | orange | 1.85 | △ |
| 11 | $-C_2H_4OCOCH_3$ | $-C_2H_4OCOCH_3$ | $-CONHCH_3$ | $-CH_3$ | $-Ph$ | orange | 1.75 | ○ |
| 12 | $-C_2H_5$ | $-C_2H_4OCOPh$ | $-SO_2NHC_3H_7$ | $-CH_3$ | $-Ph$ | orange | 1.77 | ○ |
| (16-b K: =N—) | | | | | | | | |
| 1 | $-C_2H_5$ | $-C_2H_5$ | $-H$ | $-CN$ | $-Ph$ | orange | 1.79 | △ |
| 2 | $-C_2H_5$ | $-C_2H_4OH$ | $-CH_3$ | $-CN$ | $-Ph$ | orange | 1.83 | ○ |
| 3 | $-C_2H_5$ | $-CH=CH_2$ | $-H$ | $-CN$ | 2-benzthiazolyl | orange | 1.86 | △ |
| 4 | $-C_2H_5$ | $-Ph$ | $-Cl$ | $-CN$ | 2-benzthiazolyl | orange | 1.77 | △ |
| 5 | $-C_2H_5$ | $-CH=CHOCOCH_3$ | $-NHCOCH_3$ | $-C_2H_5$ | 2-benzthiazolyl | orange | 1.74 | ○ |
| 6 | $-C_2H_5$ | $-C_2H_4COOCH_3$ | $-OH$ | $-NO_2$ | 2-benzthiazolyl | orange | 1.76 | ○ |
| 7 | $-C_2H_5$ | $-C_2H_4OCOC_4H_9$ | $-NHSO_2CH_3$ | $-NO_2$ | 2-thienyl | orange | 1.74 | ○ |
| 8 | $-C_2H_5$ | $-C_2H_4OCOOPh$ | $-NHCOCH_3$ | $-CN$ | 2-thienyl | orange | 1.75 | ○ |
| 9 | $-C_2H_5$ | $-H$ | $-NHCOCH_3$ | $-NO_2$ | 2-thienyl | orange | 1.73 | ○ |
| 10 | $-C_2H_5$ | $-CH_2Ph$ | $-OC_2H_5$ | $-CN$ | $-Ph$ | orange | 1.84 | △ |
| 11 | $-C_2H_4OCOCH_3$ | $-C_2H_4OCOCH_3$ | $-CONHCH_3$ | $-CH_3$ | $-Ph$ | orange | 1.75 | ○ |
| 12 | $-C_2H_5$ | $-C_2H_4OCOPh$ | $-SO_2NHC_3H_7$ | $-CH_3$ | $-Ph$ | orange | 1.75 | ○ |
| (16-b K: =CH—) | | | | | | | | |
| 1 | $-C_2H_5$ | $-C_2H_5$ | $-H$ | $-CN$ | $-Ph$ | orange | 1.79 | △ |
| 2 | $-C_2H_5$ | $-C_2H_4OH$ | $-CH_3$ | $-CN$ | $-Ph$ | orange | 1.85 | ○ |
| 3 | $-C_2H_5$ | $-CH=CH_2$ | $-H$ | $-CN$ | 2-benzthiazolyl | orange | 1.82 | △ |
| 4 | $-C_2H_5$ | $-Ph$ | $-Cl$ | $-CN$ | 2-benzthiazolyl | orange | 1.76 | △ |
| 5 | $-C_2H_5$ | $-CH=CHOCOCH_3$ | $-NHCOCH_3$ | $-C_2H_5$ | 2-benzthiazolyl | orange | 1.74 | ○ |
| 6 | $-C_2H_5$ | $-C_2H_4COOCH_3$ | $-OH$ | $-NO_2$ | 2-benzthiazolyl | orange | 1.78 | ○ |

TABLE 16-continued

|   |   |   |   |   |   |   |   |   |
|---|---|---|---|---|---|---|---|---|
| 7 | $-C_2H_5$ | $-C_2H_4OCOC_4H_9$ | $-NHSO_2CH_3$ | $-NO_2$ | 2-thienyl | orange | 1.71 | ○ |
| 8 | $-C_2H_5$ | $-C_2H_4OCOOPh$ | $-NHCOCH_3$ | $-CN$ | 2-thienyl | orange | 1.73 | ○ |
| 9 | $-C_2H_5$ | $-H$ | $-NHCOCH_3$ | $-NO_2$ | 2-thienyl | orange | 1.74 | ○ |
| 10 | $-C_2H_5$ | $-CH_2Ph$ | $-OC_2H_5$ | $-CN$ | $-Ph$ | orange | 1.81 | △ |
| 11 | $-C_2H_4OCOCH_3$ | $-C_2H_4OCOCH_3$ | $-CONHCH_3$ | $-CH_3$ | $-Ph$ | orange | 1.77 | ○ |
| 12 | $-C_2H_5$ | $-C_2H_4OCOPh$ | $-SO_2NHC_3H_7$ | $-CH_3$ | $-Ph$ | orange | 1.72 | ○ |

(16-c K: =N—)

|   |   |   |   |   |   |   |   |   |
|---|---|---|---|---|---|---|---|---|
| 1 | $-C_2H_5$ | $-C_2H_5$ | $-H$ | $-CN$ | $-Ph$ | orange | 1.78 | △ |
| 2 | $-C_2H_5$ | $-C_2H_4OH$ | $-CH_3$ | $-CN$ | $-Ph$ | orange | 1.85 | ○ |
| 3 | $-C_2H_5$ | $-CH=CH_2$ | $-H$ | $-CN$ | 2-benzthiazolyl | orange | 1.81 | △ |
| 4 | $-C_2H_5$ | $-Ph$ | $-Cl$ | $-CN$ | 2-benzthiazolyl | orange | 1.78 | △ |
| 5 | $-C_2H_5$ | $-CH=CHOCOCH_3$ | $-NHCOCH_3$ | $-C_2H_5$ | 2-benzthiazolyl | orange | 1.73 | ○ |
| 6 | $-C_2H_5$ | $-C_2H_4COOCH_3$ | $-OH$ | $-NO_2$ | 2-benzthiazolyl | orange | 1.69 | ○ |
| 7 | $-C_2H_5$ | $-C_2H_4OCOC_4H_9$ | $-NHSO_2CH_3$ | $-NO_2$ | 2-thienyl | orange | 1.74 | ○ |
| 8 | $-C_2H_5$ | $-C_2H_4OCOOPh$ | $-NHCOCH_3$ | $-CN$ | 2-thienyl | orange | 1.74 | ○ |
| 9 | $-C_2H_5$ | $-H$ | $-NHCOCH_3$ | $-NO_2$ | 2-thienyl | orange | 1.75 | ○ |
| 10 | $-C_2H_5$ | $-CH_2Ph$ | $-OC_2H_5$ | $-CN$ | $-Ph$ | orange | 1.79 | △ |
| 11 | $-C_2H_4OCOCH_3$ | $-C_2H_4OCOCH_3$ | $-CONHCH_3$ | $-CH_3$ | $-Ph$ | orange | 1.75 | ○ |
| 12 | $-C_2H_5$ | $-C_2H_4OCOPh$ | $-SO_2NHC_3H_7$ | $-CH_3$ | $-Ph$ | orange | 1.80 | ○ |

(16-c K: =CH—)

|   |   |   |   |   |   |   |   |   |
|---|---|---|---|---|---|---|---|---|
| 1 | $-C_2H_5$ | $-C_2H_5$ | $-H$ | $-CN$ | $-Ph$ | orange | 1.79 | △ |
| 2 | $-C_2H_5$ | $-C_2H_4OH$ | $-CH_3$ | $-CN$ | $-Ph$ | orange | 1.80 | ○ |
| 3 | $-C_2H_5$ | $-CH=CH_2$ | $-H$ | $-CN$ | 2-benzthiazolyl | orange | 1.79 | △ |
| 4 | $-C_2H_5$ | $-Ph$ | $-Cl$ | $-CN$ | 2-benzthiazolyl | orange | 1.77 | △ |
| 5 | $-C_2H_5$ | $-CH=CHOCOCH_3$ | $-NHCOCH_3$ | $-C_2H_5$ | 2-benzthiazolyl | orange | 1.69 | ○ |
| 6 | $-C_2H_5$ | $-C_2H_4COOCH_3$ | $-OH$ | $-NO_2$ | 2-benzthiazolyl | orange | 1.78 | ○ |
| 7 | $-C_2H_5$ | $-C_2H_4OCOC_4H_9$ | $-NHSO_2CH_3$ | $-NO_2$ | 2-thienyl | orange | 1.74 | ○ |
| 8 | $-C_2H_5$ | $-C_2H_4OCOOPh$ | $-NHCOCH_3$ | $-CN$ | 2-thienyl | orange | 1.74 | ○ |
| 9 | $-C_2H_5$ | $-H$ | $-NHCOCH_3$ | $-NO_2$ | 2-thienyl | orange | 1.73 | ○ |
| 10 | $-C_2H_5$ | $-CH_2Ph$ | $-OC_2H_5$ | $-CN$ | $-Ph$ | orange | 1.79 | △ |
| 11 | $-C_2H_4OCOCH_3$ | $-C_2H_4OCOCH_3$ | $-CONHCH_3$ | $-CH_3$ | $-Ph$ | orange | 1.77 | ○ |
| 12 | $-C_2H_5$ | $-C_2H_4OCOPh$ | $-SO_2NHC_3H_7$ | $-CH_3$ | $-Ph$ | orange | 1.80 | ○ |

(16-a K: =C(CN)—)

|   |   |   |   |   |   |   |   |   |
|---|---|---|---|---|---|---|---|---|
| 1 | $-C_2H_5$ | $-C_2H_5$ | $-H$ | $-CN$ | $-Ph$ | red | 1.91 | △ |
| 2 | $-C_2H_5$ | $-C_2H_4OH$ | $-CH_3$ | $-CN$ | $-Ph$ | red | 1.92 | ○ |
| 3 | $-C_2H_5$ | $-CH=CH_2$ | $-H$ | $-CN$ | 2-benzthiazolyl | red | 1.87 | △ |
| 4 | $-C_2H_5$ | $-Ph$ | $-Cl$ | $-CN$ | 2-benzthiazolyl | red | 1.86 | △ |
| 5 | $-C_2H_5$ | $-CH=CHOCOCH_3$ | $-NHCOCH_3$ | $-C_2H_5$ | 2-benzthiazolyl | red | 1.82 | ○ |
| 6 | $-C_2H_5$ | $-C_2H_4COOCH_3$ | $-OH$ | $-NO_2$ | 2-benzthiazolyi | red | 1.93 | ○ |
| 7 | $-C_2H_5$ | $-C_2H_4OCOC_4H_9$ | $-NHSO_2CH_3$ | $-NO_2$ | 2-thienyl | red | 1.84 | ○ |
| 8 | $-C_2H_5$ | $-C_2H_4OCOOPh$ | $-NHCOCH_3$ | $-CN$ | 2-thienyl | red | 1.86 | ○ |
| 9 | $-C_2H_5$ | $-H$ | $-NHCOCH_3$ | $-NO_2$ | 2-thienyl | red | 1.84 | ○ |
| 10 | $-C_2H_5$ | $-CH_2Ph$ | $-OC_2H_5$ | $-CN$ | $-Ph$ | red | 1.85 | △ |
| 11 | $-C_2H_4OCOCH_3$ | $-C_2H_4OCOCH_3$ | $-CONHCH_3$ | $-CH_3$ | $-Ph$ | red | 1.91 | ○ |
| 12 | $-C_2H_5$ | $-C_2H_4OCOPh$ | $-SO_2NHC_3H_7$ | $-CH_3$ | $-Ph$ | red | 1.86 | ○ |

(16-b K: =C(CN)—)

|   |   |   |   |   |   |   |   |   |
|---|---|---|---|---|---|---|---|---|
| 1 | $-C_2H_5$ | $-C_2H_5$ | $-H$ | $-CN$ | $-Ph$ | red | 1.99 | △ |
| 2 | $-C_2H_5$ | $-C_2H_4OH$ | $-CH_3$ | $-CN$ | $-Ph$ | red | 2.03 | ○ |
| 3 | $-C_2H_5$ | $-CH=CH_2$ | $-H$ | $-CN$ | 2-benzthiazolyl | red | 2.00 | △ |
| 4 | $-C_2H_5$ | $-Ph$ | $-Cl$ | $-C_2H_5$ | 2-benzthiazolyl | red | 1.96 | △ |
| 5 | $-C_2H_5$ | $-CH=CHOCOCH_3$ | $-NHCOCH_3$ | $-CN$ | 2-benzthiazolyl | red | 1.92 | ○ |
| 6 | $-C_2H_5$ | $-C_2H_4COOCH_3$ | $-OH$ | $-NO_2$ | 2-benzthiazolyl | red | 2.07 | ○ |
| 7 | $-C_2H_5$ | $-C_2H_4OCOC_4H_9$ | $-NHSO_2CH_3$ | $-NO_2$ | 2-thienyl | red | 1.93 | ○ |
| 8 | $-C_2H_5$ | $-C_2H_4OCOOPh$ | $-NHCOCH_3$ | $-CN$ | 2-thienyl | red | 1.91 | ○ |
| 9 | $-C_2H_5$ | $-H$ | $-NHCOCH_3$ | $-NO_2$ | 2-thienyl | red | 1.89 | ○ |
| 10 | $-C_2H_5$ | $-CH_2Ph$ | $-OC_2H_5$ | $-CN$ | $-Ph$ | red | 1.94 | △ |
| 11 | $-C_2H_4OCOCH_3$ | $-C_2H_4OCOCH_3$ | $-CONHCH_3$ | $-CH_3$ | $-Ph$ | red | 2.04 | ○ |
| 12 | $-C_2H_5$ | $-C_2H_4OCOPh$ | $-SO_2NHC_3H_7$ | $-CH_3$ | $-Ph$ | red | 1.97 | ○ |

(16-c K: =C(CN)—)

|   |   |   |   |   |   |   |   |   |
|---|---|---|---|---|---|---|---|---|
| 1 | $-C_2H_5$ | $-C_2H_5$ | $-H$ | $-CN$ | $-Ph$ | red | 1.89 | △ |
| 2 | $-C_2H_5$ | $-C_2H_4OH$ | $-CH_3$ | $-CN$ | $-Ph$ | red | 1.94 | ○ |
| 3 | $-C_2H_5$ | $-CH=CH_2$ | $-H$ | $-CN$ | 2-benzthiazolyl | red | 1.90 | △ |
| 4 | $-C_2H_5$ | $-Ph$ | $-Cl$ | $-CN$ | 2-benzthiazolyl | red | 1.92 | △ |
| 5 | $-C_2H_5$ | $-CH=CHOCOCH_3$ | $-NHCOCH_3$ | $-C_2H_5$ | 2-benzthiazolyl | red | 1.88 | ○ |
| 6 | $-C_2H_5$ | $-C_2H_4COOCH_3$ | $-OH$ | $-NO_2$ | 2-benzthiazolyl | red | 1.96 | ○ |
| 7 | $-C_2H_5$ | $-C_2H_4OCOC_4H_9$ | $-NHSO_2CH_3$ | $-NO_2$ | 2-thienyl | red | 1.87 | ○ |
| 8 | $-C_2H_5$ | $-C_2H_4OCOOPh$ | $-NHCOCH_3$ | $-CN$ | 2-thienyl | red | 1.84 | ○ |
| 9 | $-C_2H_5$ | $-H$ | $-NHCOCH_3$ | $-NO_2$ | 2-thienyl | red | 1.86 | ○ |
| 10 | $-C_2H_5$ | $-CH_2Ph$ | $-OC_2H_5$ | $-CN$ | $-Ph$ | red | 1.87 | △ |
| 11 | $-C_2H_4OCOCH_3$ | $-C_2H_4OCOCH_3$ | $-CONHCH_3$ | $-CH_3$ | $-Ph$ | red | 1.93 | ○ |
| 12 | $-C_2H_5$ | $-C_2H_4OCOPh$ | $-SO_2NHC_3H_7$ | $-CH_3$ | $-Ph$ | red | 1.84 | ○ |

(17) Dyes represented by the following structural formula:

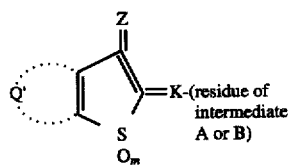
(17)

wherein K stands for =CH—, =C(CN)— or =N—, Z stands for =O or =C(CN)(R$_8$), Q' stands for a ring comprising carbon, hydrogen, nitrogen, oxygen and sulfur, m is an integer of 0 to 2. Examples of the ring include the following.

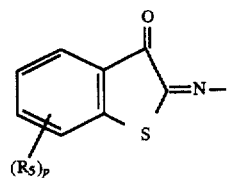

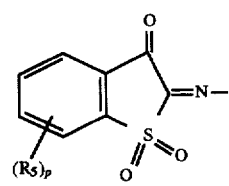

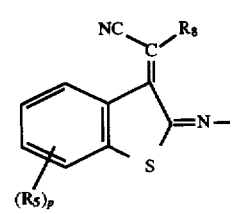

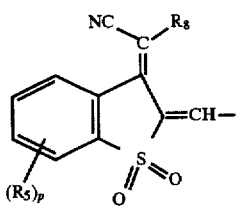

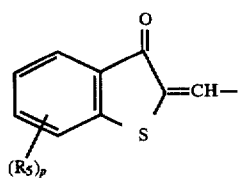

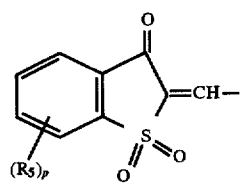

wherein R$_5$'s may be the same or different, R$_5$ and R$_8$ will be defined below and p is an integer of 0 to 4.

Specific examples of the dye represented by the general formula 17 and the performance thereof in the case of use in a thermal transfer sheet are given in the following Table 17.

TABLE 17

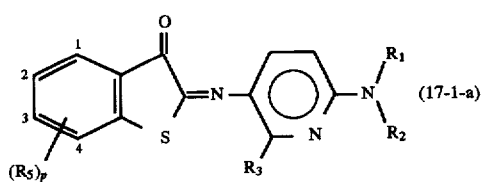
(17-1-a)

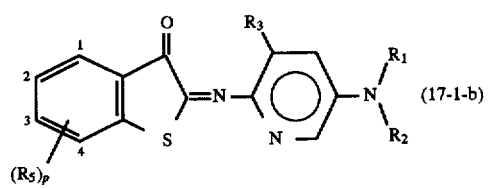
(17-1-b)

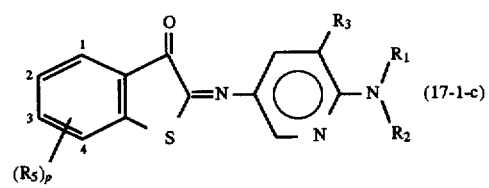
(17-1-c)

TABLE 17-continued
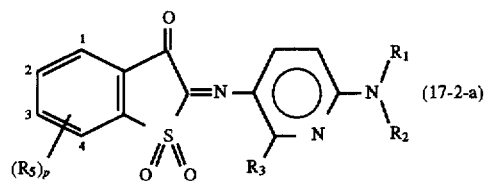 (17-2-a)
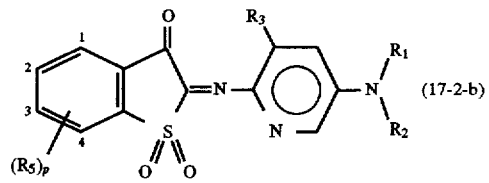 (17-2-b)
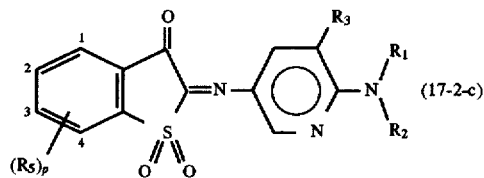 (17-2-c)
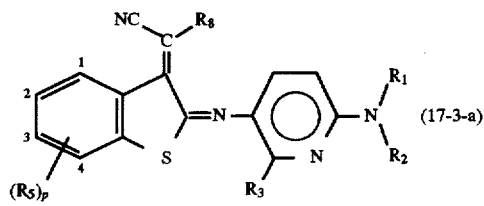 (17-3-a)
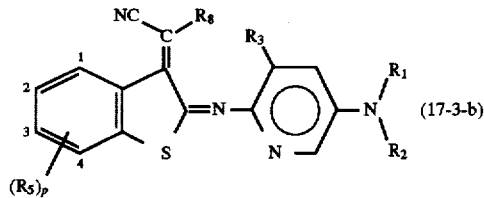 (17-3-b)
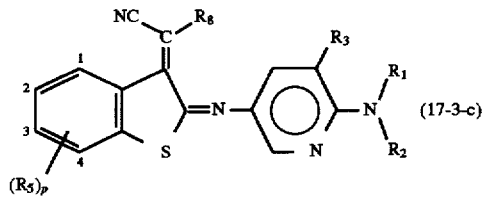 (17-3-c)
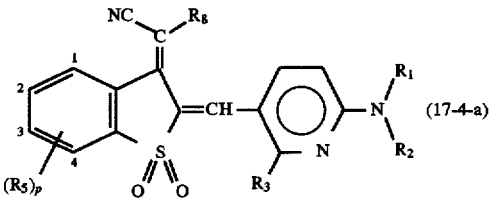 (17-4-a)
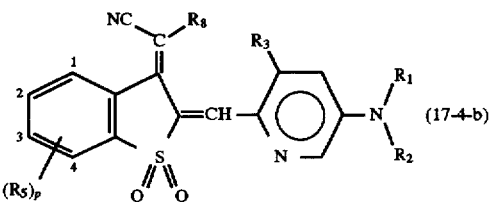 (17-4-b)

TABLE 17-continued

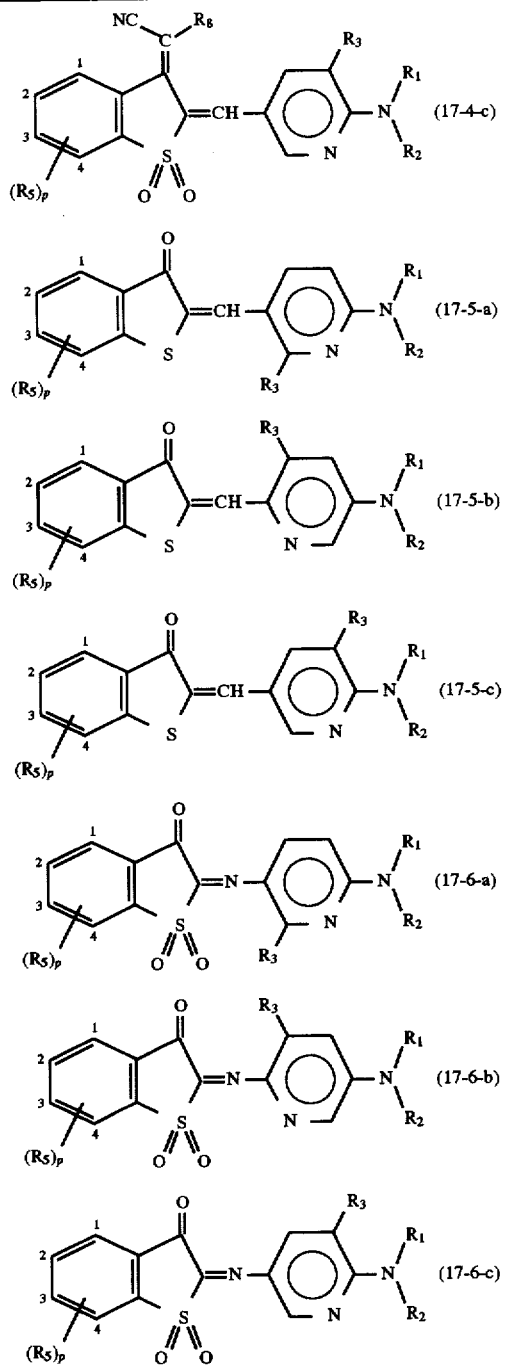

| No. | R₁ | R₂ | R₃ | R₅ | R₈ | hue | coloring density | light fastness |
|-----|----|----|----|----|----|-----|------------------|----------------|
| (17-1-a) | | | | | | | | |
| 1 | —C₂H₅ | —C₂H₅ | —H | —H | | purplish red | 1.92 | Δ |
| 2 | —C₂H₅ | —C₂H₄OH | —CH₃ | 2-CH₃ | | purplish red | 1.94 | ○ |
| 3 | —C₂H₅ | —CH=CH₂ | —H | 2-OPh | | purplish red | 1.87 | Δ |
| 4 | —C₂H₅ | —Ph | —Cl | 2,3-C₂H₅ | | purplish red | 1.90 | Δ |
| 5 | —C₂H₅ | —CH=CHOCOCH₃ | —NHCOCH₃ | 2-COOPh | | purplish red | 1.88 | ○ |
| 6 | —C₂H₅ | —C₂H₄COOCH₃ | —OH | 2-C₂H₅ 3-Cl | | purplish red | 1.87 | ○ |
| 7 | —C₂H₅ | —C₂H₄OCOC₄H₉ | —NHSO₂CH₃ | 2-CN 4-CH₃ | | purplish red | 1.85 | Δ |
| 8 | —C₂H₅ | —C₂H₄OCOOPh | —NHCOCH₃ | 4-C₂H₄COO—CH₃ | | purplish red | 1.90 | ○ |

TABLE 17-continued (17-1-b)

| | | | | | | | |
|---|---|---|---|---|---|---|---|
| 1 | —C₂H₅ | —C₂H₅ | —H | —H | purplish red | 1.94 | △ |
| 2 | —C₂H₅ | —C₂H₄OH | —CH₃ | 2-CH₃ | purplish red | 1.95 | ○ |
| 3 | —C₂H₅ | —CH=CH₂ | —H | 2-OPh | purplish red | 1.90 | △ |
| 4 | —C₂H₅ | —Ph | —Cl | 2,3-C₂H₅ | purplish red | 1.92 | △ |
| 5 | —C₂H₅ | —CH=CHOCOCH₃ | —NHCOCH₃ | 2-COOPh | purplish red | 1.87 | ○ |
| 6 | —C₂H₅ | —C₂H₄COOCH₃ | —OH | 2-C₂H₅ 3-Cl | purplish red | 1.90 | ○ |
| 7 | —C₂H₅ | —C₂H₄OCOC₄H₉ | —NHSO₂CH₃ | 2-CN 4-CH₃ | purplish red | 1.86 | △ |
| 8 | —C₂H₅ | —C₂H₄OCOOPh | —NHCOCH₃ | 4-C₂H₄COO—CH₃ | purplish red | 1.90 | ○ |

(17-1-c)

| | | | | | | | |
|---|---|---|---|---|---|---|---|
| 1 | —C₂H₅ | —C₂H₅ | —H | —H | purplish red | 1.91 | △ |
| 2 | —C₂H₅ | —C₂H₄OH | —CH₃ | 2-CH₃ | purplish red | 1.95 | ○ |
| 3 | —C₂H₅ | —CH=CH₂ | —H | 2-OPh | purplish red | 1.86 | △ |
| 4 | —C₂H₅ | —Ph | —Cl | 2,3-C₂H₅ | purplish red | 1.92 | △ |
| 5 | —C₂H₅ | —CH=CHOCOCH₃ | —NHCOCH₃ | 2-COOPh | purplish red | 1.91 | ○ |
| 6 | —C₂H₅ | —C₂H₄COOCH₃ | —OH | 2-C₂H₅ 3-Cl | purplish red | 1.86 | ○ |
| 7 | —C₂H₅ | —C₂H₄OCOC₄H₉ | —NHSO₂CH₃ | 2-CN 4-CH₃ | purplish red | 1.84 | △ |
| 8 | —C₂H₅ | —C₂H₄OCOOPh | —NHCOCH₃ | 4-C₂H₄COO—CH₃ | purplish red | 1.90 | ○ |

(17-2-a)

| | | | | | | | |
|---|---|---|---|---|---|---|---|
| 1 | —C₂H₅ | —C₂H₅ | —H | —H | purplish red | 1.88 | △ |
| 2 | —C₂H₅ | —C₂H₄OH | —CH₃ | 2-CH₃ | purplish red | 1.90 | ○ |
| 3 | —C₂H₅ | —CH=CH₂ | —H | 2-OPh | purplish red | 1.91 | △ |
| 4 | —C₂H₅ | —Ph | —Cl | 2,3-C₂H₅ | purplish red | 1.92 | △ |
| 5 | —C₂H₅ | —CH=CHOCOCH₃ | —NHCOCH₃ | 2-COOPh | purplish red | 1.86 | ○ |
| 6 | —C₂H₅ | —C₂H₄COOCH₃ | —OH | 2-C₂H₅ 3-Cl | purplish red | 1.84 | ○ |
| 7 | —C₂H₅ | —C₂H₄OCOC₄H₉ | —NHSO₂CH₃ | 2-CN 4-CH₃ | purplish red | 1.91 | △ |
| 8 | —C₂H₅ | —C₂H₄OCOOPh | —NHCOCH₃ | 4-C₂H₄COO—CH₃ | purplish red | 1.90 | ○ |

(17-2-b)

| | | | | | | | |
|---|---|---|---|---|---|---|---|
| 1 | —C₂H₅ | —C₂H₅ | —H | —H | purplish red | 1.94 | △ |
| 2 | —C₂H₅ | —C₂H₄OH | —CH₃ | 2-CH₃ | purplish red | 1.91 | ○ |
| 3 | —C₂H₅ | —CH=CH₂ | —H | 2-OPh | purplish red | 1.90 | △ |
| 4 | —C₂H₅ | —Ph | —Cl | 2,3-C₂H₅ | purplish red | 1.87 | △ |
| 5 | —C₂H₅ | —CH=CHOCOCH₃ | —NHCOCH₃ | 2-COOPh | purplish red | 1.86 | ○ |
| 6 | —C₂H₅ | —C₂H₄COOCH₃ | —OH | 2-C₂H₅ 3-Cl | purplish red | 1.85 | ○ |
| 7 | —C₂H₅ | —C₂H₄OCOC₄H₉ | —NHSO₂CH₃ | 2-CN 4-CH₃ | purplish red | 1.88 | △ |
| 8 | —C₂H₅ | —C₂H₄OCOOPh | —NHCOCH₃ | 4-C₂H₄COO—CH₃ | purplish red | 1.90 | ○ |

(17-2-c)

| | | | | | | | |
|---|---|---|---|---|---|---|---|
| 1 | —C₂H₅ | —C₂H₅ | —H | —H | purplish red | 1.90 | △ |
| 2 | —C₂H₅ | —C₂H₄OH | —CH₃ | 2-CH₃ | purplish red | 1.92 | ○ |
| 3 | —C₂H₅ | —CH=CH₂ | —H | 2-OPh | purplish red | 1.91 | △ |
| 4 | —C₂H₅ | —Ph | —Cl | 2,3-C₂H₅ | purplish red | 1.89 | △ |
| 5 | —C₂H₅ | —CH=CHOCOCH₃ | —NHCOCH₃ | 2-COOPh | purplish red | 1.91 | ○ |
| 6 | —C₂H₅ | —C₂H₄COOCH₃ | —OH | 2-C₂H₅ 3-Cl | purplish red | 1.86 | ○ |
| 7 | —C₂H₅ | —C₂H₄OCOC₄H₉ | —NHSO₂CH₃ | 2-CN 4-CH₃ | purplish red | 1.87 | △ |
| 8 | —C₂H₅ | —C₂H₄OCOOPh | —NHCOCH₃ | 4-C₂H₄COO—CH₃ | purplish red | 1.90 | ○ |

(17-3-a)

| | | | | | | | | |
|---|---|---|---|---|---|---|---|---|
| 1 | —C₂H₅ | —C₂H₅ | —H | —H | —H | blue | 1.94 | ○ |
| 2 | —C₂H₅ | —C₂H₄OH | —CH₃ | 2-CH₃ | —H | blue | 1.96 | ○ |
| 3 | —C₂H₅ | —CH=CH₂ | —H | 2-OPh | —CN | blue | 1.90 | △ |
| 4 | —C₂H₅ | —Ph | —Cl | —H | —CN | blue | 1.92 | △ |
| 5 | —C₂H₅ | —CH=CHOCOCH₃ | —NHCOCH₃ | 2-C₂H₅ 3-Cl | —CN | blue | 1.91 | ○ |
| 6 | —C₂H₅ | —C₂H₄COOCH₃ | —OH | 2-COOCH₃ | —CN | blue | 1.88 | ○ |
| 7 | —C₂H₅ | —C₂H₄OCOC₄H₉ | —NHSO₂CH₃ | 2-C₂H₄Ph | —CN | blue | 1.86 | ○ |
| 8 | —C₂H₅ | —C₂H₄OCOOPh | —NHCOCH₃ | 4-Ph | —CN | blue | 1.90 | ○ |

(17-3-b)

| | | | | | | | | |
|---|---|---|---|---|---|---|---|---|
| 1 | —C₂H₅ | —C₂H₅ | —H | —H | —H | blue | 1.92 | ○ |
| 2 | —C₂H₅ | —C₂H₄OH | —CH₃ | —H | —H | blue | 1.95 | ○ |
| 3 | —C₂H₅ | —CH=CH₂ | —H | —CN | —CN | blue | 1.91 | △ |
| 4 | —C₂H₅ | —Ph | —Cl | —CN | —CN | blue | 1.93 | △ |
| 5 | —C₂H₅ | —CH=CHOCOCH₃ | —NHCOCH₃ | —CN | —CN | blue | 1.90 | ○ |
| 6 | —C₂H₅ | —C₂H₄COOCH₃ | —OH | —CN | —CN | blue | 1.87 | ○ |
| 7 | —C₂H₅ | —C₂H₄OCOC₄H₉ | —NHSO₂CH₃ | —CN | —CN | blue | 1.92 | ○ |
| 8 | —C₂H₅ | —C₂H₄OCOOPh | —NHCOCH₃ | —CN | —CN | blue | 1.90 | ○ |

(17-3-c)

| | | | | | | | | |
|---|---|---|---|---|---|---|---|---|
| 1 | —C₂H₅ | —C₂H₅ | —H | —H | —H | blue | 1.93 | ○ |
| 2 | —C₂H₅ | —C₂H₄OH | —CH₃ | —H | —H | blue | 1.96 | ○ |
| 3 | —C₂H₅ | —CH=CH₂ | —H | —CN | —CN | blue | 1.92 | △ |
| 4 | —C₂H₅ | —Ph | —Cl | —CN | —CN | blue | 1.94 | △ |
| 5 | —C₂H₅ | —CH=CHOCOCH₃ | —NHCOCH₃ | —CN | —CN | blue | 1.92 | ○ |
| 6 | —C₂H₅ | —C₂H₄COOCH₃ | —OH | —CN | —CN | blue | 1.85 | ○ |
| 7 | —C₂H₅ | —C₂H₄OCOC₄H₉ | —NHSO₂CH₃ | —CN | —CN | blue | 1.91 | ○ |
| 8 | —C₂H₅ | —C₂H₄OCOOPh | —NHCOCH₃ | —CN | —CN | blue | 1.90 | ○ |

TABLE 17-continued (17-4-a)

| | | | | | | | | |
|---|---|---|---|---|---|---|---|---|
| 1 | −C₂H₅ | −C₂H₅ | −H | −H | −H | blue | 2.12 | △ |
| 2 | −C₂H₅ | −C₂H₄OH | −CH₃ | −H | −H | blue | 2.14 | ○ |
| 3 | −C₂H₅ | −CH=CH₂ | −H | −CN | −CN | blue | 2.07 | △ |
| 4 | −C₂H₅ | −Ph | −Cl | −CN | −CN | blue | 2.11 | △ |
| 5 | −C₂H₅ | −CH=CHOCOCH₃ | −NHCOCH₃ | −CN | −CN | blue | 2.00 | ○ |
| 6 | −C₂H₅ | −C₂H₄COOCH₃ | −OH | −CN | −CN | blue | 1.98 | ○ |
| 7 | −C₂H₅ | −C₂H₄OCOC₄H₉ | −NHSO₂CH₃ | −CN | −CN | blue | 2.04 | ○ |
| 8 | −C₂H₅ | −C₂H₄OCOOPh | −NHCOCH₃ | −CN | −CN | blue | 1.92 | △ |

(17-4-b)

| | | | | | | | | |
|---|---|---|---|---|---|---|---|---|
| 1 | −C₂H₅ | −C₂H₅ | −H | −H | −H | blue | 2.14 | △ |
| 2 | −C₂H₅ | −C₂H₄OH | −CH₃ | −H | −H | blue | 2.07 | ○ |
| 3 | −C₂H₅ | −CH=CH₂ | −H | −CN | −CN | blue | 2.03 | △ |
| 4 | −C₂H₅ | −Ph | −Cl | −CN | −CN | blue | 2.11 | △ |
| 5 | −C₂H₅ | −CH=CHOCOCH₃ | −NHCOCH₃ | −CN | −CN | blue | 2.06 | ○ |
| 6 | −C₂H₅ | −C₂H₄COOCH₃ | −OH | −CN | −CN | blue | 1.97 | ○ |
| 7 | −C₂H₅ | −C₂H₄OCOC₄H₉ | −NHSO₂CH₃ | −CN | −CN | blue | 1.98 | ○ |
| 8 | −C₂H₅ | −C₂H₄OCOOPh | −NHCOCH₃ | −CN | −CN | blue | 1.94 | △ |

(17-4-c)

| | | | | | | | | |
|---|---|---|---|---|---|---|---|---|
| 1 | −C₂H₅ | −C₂H₅ | −H | −H | −H | blue | 2.16 | △ |
| 2 | −C₂H₅ | −C₂H₄OH | −CH₃ | −H | −H | blue | 2.17 | ○ |
| 3 | −C₂H₅ | −CH=CH₂ | −H | −CN | −CN | blue | 2.03 | △ |
| 4 | −C₂H₅ | −Ph | −Cl | −CN | −CN | blue | 2.07 | △ |
| 5 | −C₂H₅ | −CH=CHOCOCH₃ | −NHCOCH₃ | −CN | −CN | blue | 1.99 | ○ |
| 6 | −C₂H₅ | −C₂H₄COOCH₃ | −OH | −CN | −CN | blue | 2.02 | ○ |
| 7 | −C₂H₅ | −C₂H₄OCOC₄H₉ | −NHSO₂CH₃ | −CN | −CN | blue | 2.08 | ○ |
| 8 | −C₂H₅ | −C₂H₄OCOOPh | −NHCOCH₃ | −CN | −CN | blue | 2.01 | △ |

(17-5-a)

| | | | | | | | | |
|---|---|---|---|---|---|---|---|---|
| 1 | −C₂H₅ | −C₂H₅ | −H | −H | −H | red | 2.04 | △ |
| 2 | −C₂H₅ | −C₂H₄OH | −CH₃ | 2-CH₃ | −H | red | 2.01 | ○ |
| 3 | −C₂H₅ | −CH=CH₂ | −H | 2-OPh | −CN | red | 1.93 | △ |
| 4 | −C₂H₅ | −Ph | −Cl | 2,3-C₂H₅ | −CN | red | 1.97 | △ |
| 5 | −C₂H₅ | −CH=CHOCOCH₃ | −NHCOCH₃ | 2-COOPh | −CN | red | 1.91 | ○ |
| 6 | −C₂H₅ | −C₂H₄COOCH₃ | −OH | 2-C₂H₅ 3-Cl | −CN | red | 1.97 | ○ |
| 7 | −C₂H₅ | −C₂H₄OCOC₄H₉ | −NHSO₂CH₃ | 2-CN 4-CH₃ | −CN | red | 1.96 | △ |
| 8 | −C₂H₅ | −C₂H₄OCOOPh | −NHCOCH₃ | 4-C₂H₄COO−CH₃ | −CN | red | 2.02 | ○ |

(17-5-b)

| | | | | | | | | |
|---|---|---|---|---|---|---|---|---|
| 1 | −C₂H₅ | −C₂H₅ | −H | −H | −H | red | 2.05 | △ |
| 2 | −C₂H₅ | −C₂H₄OH | −CH₃ | 2-CH₃ | −H | red | 1.99 | ○ |
| 3 | −C₂H₅ | −CH=CH₂ | −H | 2-OPh | −CN | red | 1.97 | △ |
| 4 | −C₂H₅ | −Ph | −Cl | 2,3-C₂H₅ | −CN | red | 1.94 | △ |
| 5 | −C₂H₅ | −CH=CHOCOCH₃ | −NHCOCH₃ | 2-COOPh | −CN | red | 1.92 | ○ |
| 6 | −C₂H₅ | −C₂H₄COOCH₃ | −OH | 2-C₂H₅ 3-Cl | −CN | red | 2.03 | ○ |
| 7 | −C₂H₅ | −C₂H₄OCOC₄H₉ | −NHSO₂CH₃ | 2-CN 4-CH₃ | −CN | red | 2.00 | △ |
| 8 | −C₂H₅ | −C₂H₄OCOOPh | −NHCOCH₃ | 4-C₂H₄COO−CH₃ | −CN | red | 1.94 | ○ |

(17-5-c)

| | | | | | | | | |
|---|---|---|---|---|---|---|---|---|
| 1 | −C₂H₅ | −C₂H₅ | −H | −H | −H | red | 2.06 | △ |
| 2 | −C₂H₅ | −C₂H₄OH | −CH₃ | 2-CH₃ | −H | red | 2.02 | ○ |
| 3 | −C₂H₅ | −CH=CH₂ | −H | 2-OPh | −CN | red | 1.99 | △ |
| 4 | −C₂H₅ | −Ph | −Cl | 2,3-C₂H₅ | −CN | red | 1.97 | △ |
| 5 | −C₂H₅ | −CH=CHOCOCH₃ | −NHCOCH₃ | 2-COOPh | −CN | red | 1.94 | ○ |
| 6 | −C₂H₅ | −C₂H₄COOCH₃ | −OH | 2-C₂H₅ 3-Cl | −CN | red | 2.01 | ○ |
| 7 | −C₂H₅ | −C₂H₄OCOC₄H₉ | −NHSO₂CH₃ | 2-CN 4-CH₃ | −CN | red | 2.06 | △ |
| 8 | −C₂H₅ | −C₂H₄OCOOPh | −NHCOCH₃ | 4-C₂H₄COO−CH₃ | −CN | red | 1.98 | ○ |

(17-6-a)

| | | | | | | | | |
|---|---|---|---|---|---|---|---|---|
| 1 | −C₂H₅ | −C₂H₅ | −H | −H | −H | red | 2.04 | △ |
| 2 | −C₂H₅ | −C₂H₄OH | −CH₃ | 2-CH₃ | −H | red | 2.01 | ○ |
| 3 | −C₂H₅ | −CH=CH₂ | −H | 2-OPh | −CN | red | 1.97 | △ |
| 4 | −C₂H₅ | −Ph | −Cl | 2,3-C₂H₅ | −CN | red | 1.95 | △ |
| 5 | −C₂H₅ | −CH=CHOCOCH₃ | −NHCOCH₃ | 2-COOPh | −CN | red | 1.96 | ○ |
| 6 | −C₂H₅ | −C₂H₄COOCH₃ | −OH | 2-C₂H₅ 3-Cl | −CN | red | 1.97 | ○ |
| 7 | −C₂H₅ | −C₂H₄OCOC₄H₉ | −NHSO₂CH₃ | 2-CN 4-CH₃ | −CN | red | 2.04 | △ |
| 8 | −C₂H₅ | −C₂H₄OCOOPh | −NHCOCH₃ | 4-C₂H₄COO−CH₃ | −CN | red | 2.02 | ○ |

(17-6-b)

| | | | | | | | | |
|---|---|---|---|---|---|---|---|---|
| 1 | −C₂H₅ | −C₂H₅ | −H | −H | −H | red | 2.06 | △ |
| 2 | −C₂H₅ | −C₂H₄OH | −CH₃ | 2-CH₃ | −H | red | 2.04 | ○ |
| 3 | −C₂H₅ | −CH=CH₂ | −H | 2-OPh | −CN | red | 2.00 | △ |
| 4 | −C₂H₅ | −Ph | −Cl | 2,3-C₂H₅ | −CN | red | 1.98 | △ |
| 5 | −C₂H₅ | −CH=CHOCOCH₃ | −NHCOCH₃ | 2-COOPh | −CN | red | 1.99 | ○ |
| 6 | −C₂H₅ | −C₂H₄COOCH₃ | −OH | 2-C₂H₅ 3-Cl | −CN | red | 1.95 | ○ |
| 7 | −C₂H₅ | −C₂H₄OCOC₄H₉ | −NHSO₂CH₃ | 2-CN 4-CH₃ | −CN | red | 2.09 | △ |

TABLE 17-continued

| 8 | —C₂H₅ | —C₂H₄OCOOPh | —NHCOCH₃ | 4-C₂H₄COO—CH₃ (17-6-c) | —CN | red | 2.03 | ○ |
|---|---|---|---|---|---|---|---|---|
| 1 | —C₂H₅ | —C₂H₅ | —H | —H | —H | red | 2.10 | Δ |
| 2 | —C₂H₅ | —C₂H₄OH | —CH₃ | 2-CH₃ | —H | red | 2.11 | ○ |
| 3 | —C₂H₅ | —CH=CH₂ | —H | 2-OPh | —CN | red | 2.07 | Δ |
| 4 | —C₂H₅ | —Ph | —Cl | 2,3-C₂H₅ | —CN | red | 1.99 | Δ |
| 5 | —C₂H₅ | —CH=CHOCOCH₃ | —NHCOCH₃ | 2-COOPh | —CN | red | 2.04 | ○ |
| 6 | —C₂H₅ | —C₂H₄COOCH₃ | —OH | 2-C₂H₅ 3-Cl | —CN | red | 2.02 | ○ |
| 7 | —C₂H₅ | —C₂H₄OCOC₄H₉ | —NHSO₂CH₃ | 2-CN 4-CH₃ | —CN | red | 2.06 | Δ |
| 8 | —C₂H₅ | —C₂H₄OCOOPh | —NHCOCH₃ | 4-C₂H₄COO—CH₃ | —CN | red | 2.11 | ○ |

(18) Dyes represented by the following formulae:

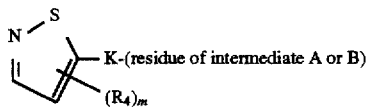
(18-1)

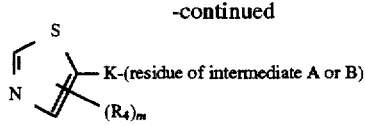
(18-2)

wherein K stands for —N=N— and m is an integer of 0 to 2.

TABLE 18

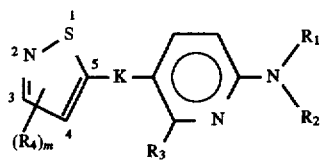
(18-1-a)

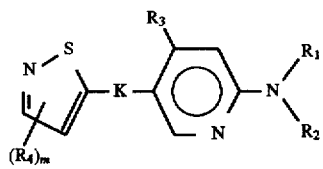
(18-1-b)

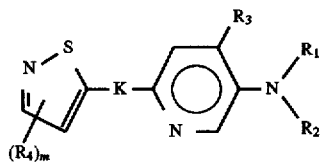
(18-1-c)

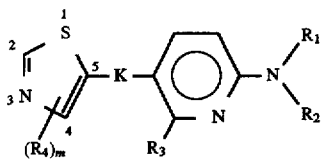
(18-2-a)

TABLE 18-continued

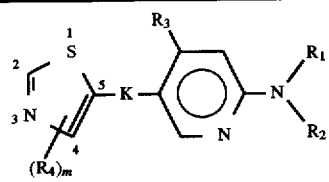

(18-2-b)

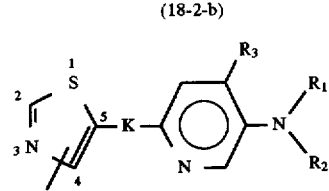

(18-2-c)

(18-1)

| No. | $R_1$ | $R_2$ | $R_3$ | 3-$R_4$ | 4-$R_4$ |
|---|---|---|---|---|---|
| 1 | —$C_2H_5$ | —$C_2H_5$ | —$NHCOCH_3$ | —$CH_3$ | —CN |
| 2 | —$C_2H_4OCOCH_3$ | —$C_2H_5$ | —$NHSO_2CH_3$ | —$CH_3$ | —CN |
| 3 | —$C_2H_4OCH_3$ | —$C_2H_5$ | —$NHCOC_2H_5$ | —$CH_3$ | —CN |
| 4 | —$C_2H_5$ | —$C_2H_5$ | —$CH_3$ | —$CH_3$ | —CN |
| 5 | —$C_2H_4OCH_3$ | —$C_2H_5$ | —H | —$CH_3$ | —CN |
| 6 | —$C_2H_4OCH_2Ph$ | —$C_2H_5$ | —$NHCOCH_3$ | —$CH_3$ | —CN |
| 7 | —$C_2H_4CN$ | —$C_2H_5$ | —$CH_3$ | —$C_2H_5$ | —CN |
| 8 | —$C_2H_4OCOCH_3$ | —$C_2H_4OCOCH_3$ | —$NHCOCH_3$ | —$CH_3$ | —CN |
| 9 | —$C_2H_5$ | —$C_2H_5$ | —$NHCOCH_3$ | —$SC_2H_5$ | —CN |

| No. | hue | coloring density | light fastness |
|---|---|---|---|
| \multicolumn{4}{c}{18-1-a K: —N=N—} | | | |
| 1 | red | 2.18 | ○ |
| 2 | red | 2.06 | ○ |
| 3 | red | 2.01 | ○ |
| 4 | red | 2.09 | ○ |
| 5 | red | 1.83 | Δ |
| 6 | red | 1.92 | ○ |
| 7 | red | 2.02 | ○ |
| 8 | red | 1.87 | ○ |
| 9 | red | 1.89 | Δ |
| \multicolumn{4}{c}{18-1-b K: —N=N—} | | | |
| 1 | red | 2.06 | ○ |
| 2 | red | 2.08 | ○ |
| 3 | red | 2.10 | ○ |
| 4 | red | 2.01 | Δ |
| 5 | red | 1.80 | Δ |
| 6 | red | 1.85 | ○ |
| 7 | red | 1.97 | Δ |
| 8 | red | 1.79 | ○ |
| 9 | red | 1.92 | Δ |
| \multicolumn{4}{c}{18-1-c K: —N=N—} | | | |
| 1 | red | 1.97 | ○ |
| 2 | red | 1.90 | Δ |
| 3 | red | 1.93 | ○ |
| 4 | red | 1.87 | Δ |
| 5 | red | 1.81 | Δ |
| 6 | red | 1.94 | ○ |
| 7 | red | 1.97 | Δ |
| 8 | red | 1.83 | Δ |
| 9 | red | 1.79 | ○ |

(18-2)

| No. | $R_1$ | $R_2$ | $R_3$ | 2-$R_4$ | 4-$R_4$ |
|---|---|---|---|---|---|
| 1 | —$C_2H_5$ | —$C_2H_5$ | —$NHCOCH_3$ | —$SC_2H_5$ | —CN |
| 2 | —$C_2H_4OCOCH_3$ | —$C_2H_5$ | —$NHSO_2CH_3$ | —$SC_2H_5$ | —CN |
| 3 | —$C_2H_4OCH_3$ | —$C_2H_5$ | —$NHCOC_2H_5$ | —$SC_2H_5$ | —CN |
| 4 | —$C_2H_5$ | —$C_2H_5$ | —H | —$SC_2H_5$ | —CN |

TABLE 18-continued

| | | | | |
|---|---|---|---|---|
| 5 | −C₂H₄OCH₃ | −C₂H₄OCH₃ | −NHCOCH₃ | −SC₂H₅ −CN |
| 6 | −C₂H₄CN | −C₂H₅ | −CH₃ | −SC₂H₅ −CN |
| 7 | −C₂H₄OCOCH₃ | −C₂H₄OCOCH₃ | −NHCOCH₃ | −SC₂H₅ −CN |
| 8 | −C₂H₅ | −C₂H₅ | −CH₃ | −CH₃ −CN |
| 9 | −C₂H₄OCOCH₃ | −C₂H₅ | −CH₃ | −CH₃ −CN |
| No. | hue | coloring density | | light fastness |

| | | | |
|---|---|---|---|
| | | 18-2-a K: —N=N— | |
| 1 | red | 1.97 | ○ |
| 2 | red | 1.83 | ○ |
| 3 | red | 1.91 | ○ |
| 4 | red | 2.13 | ○ |
| 5 | red | 1.89 | ○ |
| 6 | red | 1.84 | ○ |
| 7 | red | 1.77 | ○ |
| 8 | red | 2.19 | Δ |
| 9 | red | 2.11 | Δ |
| | | 18-2-b K: —N=N— | |
| 1 | red | 1.98 | ○ |
| 2 | red | 1.85 | ○ |
| 3 | red | 1.91 | ○ |
| 4 | red | 2.10 | ○ |
| 5 | red | 1.86 | ○ |
| 6 | red | 1.81 | ○ |
| 7 | red | 1.74 | ○ |
| 8 | red | 2.11 | Δ |
| 9 | red | 2.07 | Δ |
| | | 18-2-c K: —N=N— | |
| 1 | red | 1.92 | ○ |
| 2 | red | 1.80 | ○ |
| 3 | red | 1.87 | ○ |
| 4 | red | 2.09 | Δ |
| 5 | red | 1.83 | ○ |
| 6 | red | 1.78 | Δ |
| 7 | red | 1.79 | ○ |
| 8 | red | 2.10 | Δ |
| 9 | red | 1.93 | Δ |

(19) Dyes represented by the following structure:

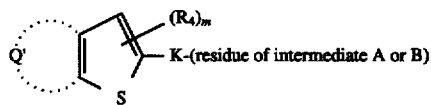
(19)

wherein K stands for —N=N, Q' is absent or a ring comprising carbon, hydrogen, nitrogen, oxygen and sulfur and m is an integer of 0 to 3. Examples of the ring include the following.

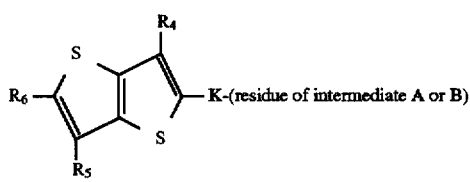
(19-1)

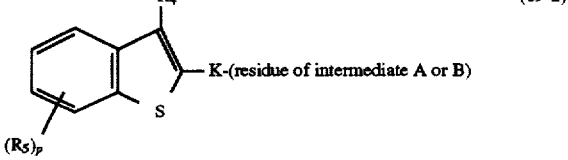
(19-2)

wherein $R_4$, $R_5$ and $R_6$ which may be the same or different will be defined later and p is an integer of 0 to 4.

Specific examples of the dye represented by the general formula 19 and the performance thereof in the case of use in a thermal transfer sheet are given in the following Table 19.

TABLE 19
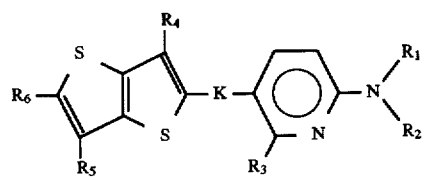
(19-1-a)
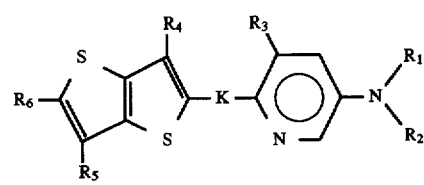
(19-1-b)
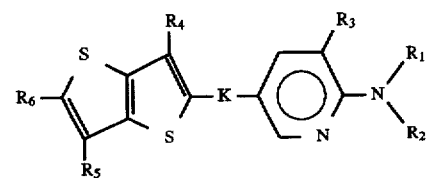
(19-1-c)
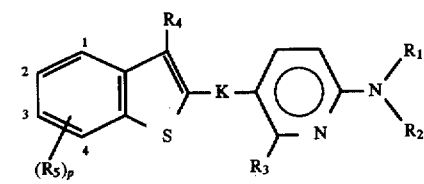
(19-2-a)
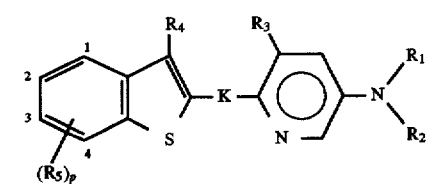
(19-2-b)
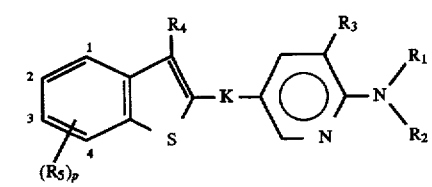
(19-2-c)
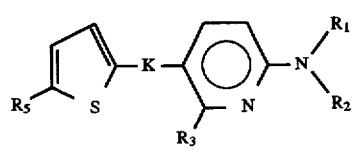
(19-3-a)

TABLE 19-continued

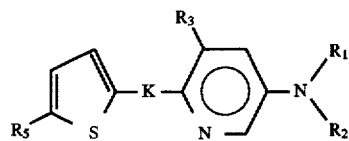

(19-3-b)

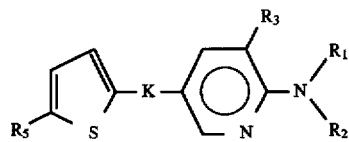

(19-3-c)

| No. | R₁ | R₂ | R₃ | R₄ | R₅ | R₆ | hue | coloring density | light fastness |
|---|---|---|---|---|---|---|---|---|---|
| | | | | (19-1-a K: —N=N—) | | | | | |
| 1 | —C₂H₅ | —C₂H₅ | —H | —CN | —H | —H | red | 1.97 | Δ |
| 2 | —C₂H₅ | —C₂H₄OH | —CH₃ | —CN | —H | —CH₃ | red | 1.94 | O |
| 3 | —C₂H₅ | —CH=CH₂ | —H | —NO₂ | —H | —H | red | 1.93 | Δ |
| 4 | —C₂H₅ | —Ph | —Cl | —CH₃ | —H | —OCOCH₃ | red | 1.89 | Δ |
| 5 | —C₂H₅ | —CH=CHOCOCH₃ | —NHCOCH₃ | —C₄H₉ | —CH₃ | —H | red | 1.94 | O |
| 6 | —C₂H₅ | —C₂H₄COOCH₃ | —OH | —Ph | —H | —H | red | 1.87 | Δ |
| 7 | —C₂H₅ | —C₂H₄OCOCH₃ | —NHSO₂CH₃ | —Ph | —C₂H₅ | —Cl | red | 1.84 | O |
| 8 | —C₂H₅ | —C₂H₄OCOOPh | —NHCOCH₃ | —Ph | —Cl | —CH₃ | red | 1.86 | O |
| | | | | (19-1-b K: —N=N—) | | | | | |
| 1 | —C₂H₅ | —C₂H₅ | —H | —CN | —H | —H | red | 1.94 | Δ |
| 2 | —C₂H₅ | —C₂H₄OH | —CH₃ | —CN | —H | —CH₃ | red | 1.92 | O |
| 3 | —C₂H₅ | —CH=CH₂ | —H | —NO₂ | —H | —H | red | 1.95 | Δ |
| 4 | —C₂H₅ | —Ph | —Cl | —CH₃ | —H | —COCH₃ | red | 1.91 | Δ |
| 5 | —C₂H₅ | —CH=CHOCOCH₃ | —NHCOCH₃ | —C₄H₉ | —CH₃ | —H | red | 1.96 | O |
| 6 | —C₂H₅ | —C₂H₄COOCH₃ | —OH | —Ph | —H | —H | red | 1.93 | Δ |
| 7 | —C₂H₅ | —C₂H₄OCOCH₃ | —NHSO₂CH₃ | —Ph | —C₂H₅ | —Cl | red | 1.87 | O |
| 8 | —C₂H₅ | —C₂H₄OCOOPh | —NHCOCH₃ | —Ph | —Cl | —CH₃ | red | 1.94 | O |
| | | | | (19-1-c K: —N=N—) | | | | | |
| 1 | —C₂H₅ | —C₂H₅ | —H | —CN | —H | —H | red | 1.94 | Δ |
| 1 | —C₂H₅ | —C₂H₅ | —H | —CN | —H | —H | red | 1.94 | Δ |
| 2 | —C₂H₅ | —C₂H₄OH | —CH₃ | —CN | —H | —CH₃ | red | 1.91 | O |
| 3 | —C₂H₅ | —CH=CH₂ | —H | —NO₂ | —H | —H | red | 1.88 | Δ |
| 4 | —C₂H₅ | —Ph | —Cl | —CH₃ | —H | —COCH₃ | red | 1.87 | Δ |
| 5 | —C₂H₅ | —CH=CHOCOCH₃ | —NHCOCH₃ | —C₄H₉ | —CH₃ | —H | red | 1.91 | O |
| 6 | —C₂H₅ | —C₂H₄COOCH₃ | —OH | —Ph | —H | —H | red | 1.86 | Δ |
| 7 | —C₂H₅ | —C₂H₄OCOCH₃ | —NHSO₂CH₃ | —Ph | —OC₂H₅ | —Cl | red | 1.82 | O |
| 8 | —C₂H₅ | —C₂H₄OCOOPh | —NHCOCH₃ | —Ph | —Cl | —CH₃ | red | 1.84 | O |
| | | | | (19-2-a K: —N=N—) | | | | | |
| 1 | —C₂H₅ | —C₂H₅ | —H | —CN | —H | | red | 1.96 | O |
| 2 | —C₂H₅ | —C₂H₄OH | —CH₃ | —CN | —CH₃ | | red | 1.95 | O |
| 3 | —C₂H₅ | —CH=CH₂ | —H | —NO₂ | —H | | red | 1.94 | Δ |
| 4 | —C₂H₅ | —Ph | —Cl | CH₃ | 2—OC₂H₅ | | red | 1.91 | Δ |
| 5 | —C₂H₅ | —CH=CHOCOCH₃ | —NHCOCH₃ | —C₄H₉ | 2, 3—diC₂H₅ | | red | 1.93 | O |
| 6 | —C₂H₅ | —C₂H₄COOCH₃ | —OH | —Ph | 2—Cl, 3—CH₃ | | red | 1.87 | O |
| 7 | —C₂H₅ | —C₂H₄OCOCH₃ | —NHSO₂CH₃ | —Ph | 4—OCOC₂H₅ | | red | 1.81 | O |
| 8 | —C₂H₅ | —C₂H₄OCOOPh | —NHCOCH₃ | —Ph | 3—CH₃, 4—Ph | | red | 1.84 | O |
| | | | | (19-2-b K: —N=N—) | | | | | |
| 1 | —C₂H₅ | —C₂H₅ | —H | —CN | —H | | red | 1.94 | O |
| 2 | —C₂H₅ | —C₂H₄OH | —CH₃ | —CN | —CH₃ | | red | 1.92 | O |
| 3 | —C₂H₅ | —CH=CH₂ | —H | —NO₂ | —H | | red | 1.96 | Δ |
| 4 | —C₂H₅ | —Ph | —Cl | —CH₃ | 2-C₂H₅ | | red | 1.90 | Δ |
| 5 | —C₂H₅ | —CH=CHOCOCH₃ | —NHCOCH₃ | —C₄H₉ | 2, 3—diC₂H₅ | | red | 1.91 | O |
| 6 | —C₂H₅ | —C₂H₄COOCH₃ | —OH | —Ph | 2—Cl, 3—CH₃ | | red | 1.88 | O |
| 7 | —C₂H₅ | —C₂H₄OCOCH₃ | —NHSO₂CH₃ | —Ph | 4—OCOC₂H₅ | | red | 1.82 | O |
| 8 | —C₂H₅ | —C₂H₄OCOOPh | —NHCOCH₃ | —Ph | 3—CH₃,4—Ph | | red | 1.87 | O |
| | | | | (19-2-c K: —N=N—) | | | | | |
| 1 | —C₂H₅ | —C₂H₅ | —H | —CN | —H | | red | 1.94 | O |
| 2 | —C₂H₅ | —C₂H₄OH | —CH₃ | —CN | —CH₃ | | red | 1.91 | O |
| 3 | —C₂H₅ | —CH=CH₂ | —H | —NO₂ | —H | | red | 1.95 | Δ |
| 4 | —C₂H₅ | —Ph | —Cl | CH₃ | 2-C₂H₅ | | red | 1.90 | Δ |

TABLE 19-continued

| | | | | | | | |
|---|---|---|---|---|---|---|---|
| 5 | $-C_2H_5$ | $-CH=CHOCOCH_3$ | $-NHCOCH_3$ | $-C_4H_9$ | 2,3-diC$_2$H$_5$ | red | 1.92 | ○ |
| 6 | $-C_2H_5$ | $-C_2H_4CCOCH_3$ | $-OH$ | $-Ph$ | 2-Cl,3-CH$_3$ | red | 1.91 | ○ |
| 7 | $-C_2H_5$ | $-C_2H_4OCOCH_3$ | $-NHSO_2CH_3$ | $-Ph$ | 4-OCOC$_2$H$_5$ | red | 1.87 | ○ |
| 8 | $-C_2H_5$ | $-C_2H_4OCOOPh$ | $-NHCOCH_3$ | $-Ph$ | 3-CH$_3$,4-Ph | red | 1.90 | ○ |

(19-3-a K: —N=N—)

| 1 | $-C_2H_5$ | $-C_2H_5$ | $-H$ | $-CN$ | red | 1.95 | △ |
|---|---|---|---|---|---|---|---|
| 2 | $-C_2H_5$ | $-C_2H_4OH$ | $-CH_3$ | $-SC_2H_5$ | red | 1.92 | ○ |
| 3 | $-C_2H_5$ | $-CH=CH_2$ | $-H$ | $-NO_2$ | red | 1.91 | △ |
| 4 | $-C_2H_5$ | $-Ph$ | $-Cl$ | $-CN$ | red | 1.87 | △ |
| 5 | $-C_2H_5$ | $-CH=CHOCOCH_3$ | $-NHCOCH_3$ | $-CN$ | red | 1.92 | ○ |
| 6 | $-C_2H_5$ | $-C_2H_4COOCH_3$ | $-OH$ | $-CN$ | red | 1.83 | ○ |
| 7 | $-C_2H_5$ | $-C_2H_4OCOCH_3$ | $-NHSO_2CH_3$ | $-CN$ | red | 1.81 | △ |
| 8 | $-C_2H_5$ | $-C_2H_4OCOOPh$ | $-NHCOCH_3$ | $-CN$ | red | 1.85 | ○ |

(19-3-b K: —N=N—)

| 1 | $-C_2H_5$ | $-C_2H_5$ | $-H$ | $-CN$ | red | 2.05 | △ |
|---|---|---|---|---|---|---|---|
| 2 | $-C_2H_5$ | $-C_2H_4OH$ | $-CH_3$ | $-SC_2H_5$ | red | 2.01 | ○ |
| 3 | $-C_2H_5$ | $-CH=CH_2$ | $-H$ | $-NO_2$ | red | 2.00 | △ |
| 4 | $-C_2H_5$ | $-Ph$ | $-Cl$ | $-CN$ | red | 1.98 | △ |
| 5 | $-C_2H_5$ | $-CH=CHOCOCH_3$ | $-NHCOCH_3$ | $-CN$ | red | 1.92 | ○ |
| 6 | $-C_2H_5$ | $-C_2H_4COCH_3$ | $-OH$ | $-CN$ | red | 1.95 | ○ |
| 7 | $-C_2H_5$ | $-C_2H_4OCOCH_3$ | $-NHSO_2CH_3$ | $-CN$ | red | 1.93 | △ |
| 8 | $-C_2H_5$ | $-C_2H_4OCOOPh$ | $-NHCOCH_3$ | $-CN$ | red | 1.91 | ○ |

(19-3-c K: —N=N—)

| 1 | $-C_2H_5$ | $-C_2H_5$ | $-H$ | $-CN$ | red | 1.99 | △ |
|---|---|---|---|---|---|---|---|
| 2 | $-C_2H_5$ | $-C_2H_4OH$ | $-CH_3$ | $-SC_2H_5$ | red | 2.00 | ○ |
| 3 | $-C_2H_5$ | $-CH=CH_2$ | $-H$ | $-NO_2$ | red | 1.91 | △ |
| 4 | $-C_2H_5$ | $-Ph$ | $-Cl$ | $-CN$ | red | 1.87 | △ |
| 5 | $-C_2H_5$ | $-CH=CHOCOCH_3$ | $-NHCOCH_3$ | $-CN$ | red | 1.94 | ○ |
| 6 | $-C_2H_5$ | $-C_2H_4COOCH_3$ | $-OH$ | $-CN$ | red | 1.86 | ○ |
| 7 | $-C_2H_5$ | $-C_2H_4OCOCH_3$ | $-NHSO_2CH_3$ | $-CN$ | red | 1.85 | △ |
| 8 | $-C_2H_5$ | $-C_2H_4OCOOPh$ | $-NHCOCH_3$ | $-CN$ | red | 1.86 | ○ |

(20) Dyes represented by the following structural formula:

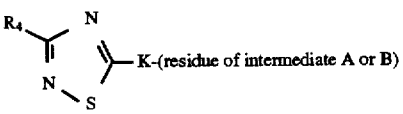

(20-1)

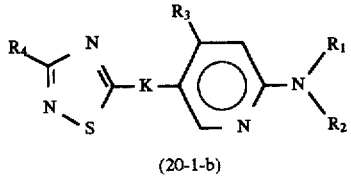

(20-2)

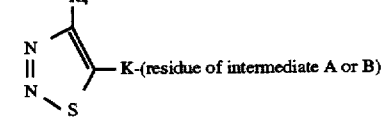

(20-3)

wherein K stands for —N=N— and $R_4$ will be defined below.

Specific examples of the dye represented by the general formula 20 and the performance thereof in the case of use in a thermal transfer sheet are given in the following Table 20.

TABLE 20

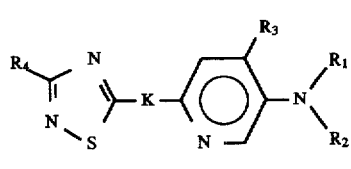

(20-1-a)

TABLE 20-continued

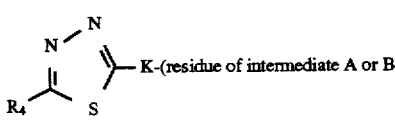

(20-1-b)

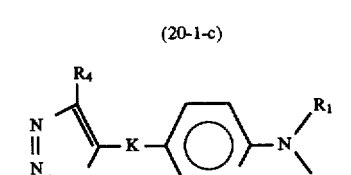

(20-1-c)

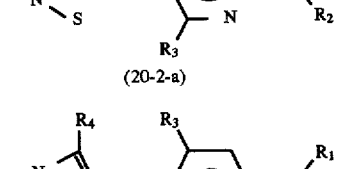

(20-2-a)

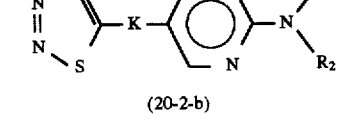

(20-2-b)

TABLE 20-continued (20-2-c)

(20-3-a)

(20-3-b)

(20-3-c)

__(20-1)__

| No. | R₁ | R₂ | R₃ | R₄ |
|---|---|---|---|---|
| 1 | —C₂H₅ | —C₂H₅ | —CH₃ | —CN |
| 2 | —C₂H₅ | —C₂H₅ | —NHCOCH₃ | —CN |
| 3 | —C₂H₄OCOCH₃ | —C₂H₅ | —NHSO₂CH₃ | —CN |
| 4 | —C₂H₄OCH₃ | —C₂H₅ | —NHCOC₂H₅ | —CN |
| 5 | —C₂H₄CN | —C₂H₅ | —CH₃ | —CN |
| 6 | —C₂H₄OCOCH₃ | —C₂H₄OCOCH₃ | —NHCOCH₃ | —CN |
| 7 | —C₂H₅ | —C₂H₅ | —NHCOCH₃ | —C₄H₉ |
| 8 | —C₂H₅ | —C₂H₅ | —CH₃ | —C₄H₉ |
| 9 | —C₂H₄OCOCH₃ | —C₂H₅ | —NHCOCH₃ | —Ph |
| 10 | —C₂H₄OCOCH₃ | —C₂H₅ | —NHCOCH₃ | —Ph |

__20-1-a K: —N=N—__

| No. | hue | coloring density | light fastness |
|---|---|---|---|
| 1 | red | 1.85 | Δ |
| 2 | red | 1.97 | ○ |
| 3 | red | 1.81 | Δ |
| 4 | red | 1.92 | ○ |
| 5 | red | 1.88 | Δ |
| 6 | red | 1.73 | ○ |
| 7 | red | 1.84 | Δ |
| 8 | red | 1.89 | Δ |
| 9 | red | 1.88 | ○ |
| 10 | red | 1.83 | ○ |

__20-1-b K: —N=N—__

| 1 | red | 1.84 | ○ |
|---|---|---|---|
| 2 | red | 1.93 | ○ |
| 3 | red | 1.77 | ○ |
| 4 | red | 1.95 | ○ |
| 5 | red | 1.82 | Δ |
| 6 | red | 1.78 | ○ |
| 7 | red | 1.80 | ○ |
| 8 | red | 1.84 | Δ |
| 9 | red | 1.93 | Δ |
| 10 | red | 1.83 | Δ |

__20-1-c K: —N=N—__

| 1 | red | 1.71 | ○ |
|---|---|---|---|
| 2 | red | 1.78 | ○ |
| 3 | red | 1.73 | ○ |
| 4 | red | 1.82 | ○ |
| 5 | red | 1.79 | Δ |
| 6 | red | 1.65 | ○ |
| 7 | red | 1.74 | ○ |
| 8 | red | 1.73 | ○ |
| 9 | red | 1.84 | ○ |
| 10 | red | 1.85 | ○ |

__(20-2)__

| No. | R₁ | R₂ | R₃ | R₄ |
|---|---|---|---|---|
| 1 | —C₂H₅ | —C₂H₅ | —CH₃ | —CN |
| 2 | —C₂H₅ | —C₂H₅ | —NHCOCH₃ | —CN |
| 3 | —C₂H₅ | —C₂H₅ | —NHSO₂CH₃ | —CN |
| 4 | —C₂H₄OCH₃ | —C₂H₅ | —NHCOC₂H₅ | —CN |
| 5 | —C₂H₄CN | —C₂H₅ | —CH₃ | —CN |
| 6 | —C₂H₄OCOCH₃ | —C₂H₄CCOCH₃ | —NHCaCH₃ | —CN |

__20-2-a K: —N=N—__

| No. | hue | coloring density | light fastness |
|---|---|---|---|
| 1 | red | 1.92 | ○ |
| 2 | red | 2.13 | ○ |
| 3 | red | 2.04 | ○ |
| 4 | red | 2.02 | ○ |
| 5 | red | 1.97 | ○ |
| 6 | red | 1.92 | ○ |

__20-2-b K: —N=N—__

| 1 | red | 1.90 | Δ |
|---|---|---|---|
| 2 | red | 2.07 | ○ |
| 3 | red | 2.09 | ○ |
| 4 | red | 2.13 | ○ |
| 5 | red | 1.84 | ○ |
| 6 | red | 1.97 | ○ |

__20-2-c K: —N=N—__

| 1 | red | 1.89 | ○ |
|---|---|---|---|
| 2 | red | 2.03 | ○ |
| 3 | red | 2.04 | ○ |
| 4 | red | 2.03 | ○ |
| 5 | red | 1.91 | Δ |
| 6 | red | 1.94 | ○ |

__(20-3)__

| No. | R₁ | R₂ | R₃ | R₄ |
|---|---|---|---|---|
| 1 | —C₂H₅ | —C₂H₅ | —CH₃ | —CN |
| 2 | —C₂H₅ | —C₂H₅ | —NHCOCH₃ | —CN |
| 3 | —C₂H₅ | —C₂H₅ | —NHSO₂CH₃ | —CN |
| 4 | —C₂H₄OCOCH₃ | —C₂H₅ | —NHCOCH₃ | —CN |
| 5 | —C₂H₄OCOCH₃ | —C₂H₅ | —NHCOCH₃ | —SC₂H₅ |
| 6 | —C₂H₄OCH₃ | —C₂H₅ | —NHCOCH₃ | —CN |
| 7 | —C₂H₄OCH₃ | —C₂H₅ | —NHCOCH₃ | —SC₂H₅ |
| 8 | —C₂H₄OCOCH₃ | —C₂H₄OCOCH₃ | —NHCOCH₃ | —CN |

__20-3-a K: —N=N—__

| No. | hue | coloring density | light fastness |
|---|---|---|---|
| 1 | red | 1.74 | Δ |
| 2 | red | 1.81 | ○ |
| 3 | red | 1.77 | ○ |
| 4 | red | 1.79 | ○ |
| 5 | red | 1.78 | Δ |
| 6 | red | 1.75 | ○ |
| 7 | red | 1.70 | Δ |
| 8 | red | 1.68 | ○ |

__20-3-b K: —N=N—__

| 1 | red | 1.78 | ○ |
|---|---|---|---|
| 2 | red | 1.86 | ○ |

TABLE 20-continued
| | | | |
|---|---|---|---|
| 3 | red | 1.82 | ○ |
| 4 | red | 1.91 | ○ |
| 5 | red | 1.76 | ○ |
| 6 | red | 1.84 | ○ |
| 7 | red | 1.77 | ○ |
| 8 | red | 1.78 | ○ |
| 20-3-c K: —N=N— | | | |
| 1 | red | 1.81 | ○ |
| 2 | red | 1.92 | ○ |
| 3 | red | 1.88 | ○ |
| 4 | red | 1.87 | ○ |
| 5 | red | 1.82 | ○ |
| 6 | red | 1.92 | ○ |
| 7 | red | 1.82 | ○ |
| 8 | red | 1.84 | ○ |
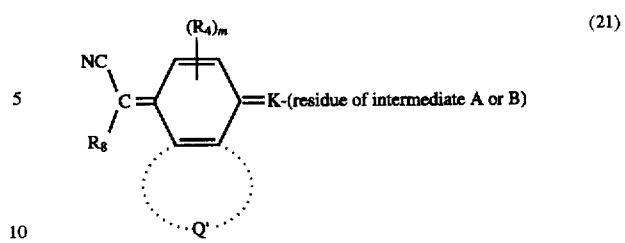
(21)
wherein K stands for —N=N—, Q' is absent or a ring comprising carbon, hydrogen, nitrogen, oxygen and sulfur and m is an integer of 0 to 4. Examples of the ring include the following.
(21) Dyes represented by the following structural formula:
TABLE 21
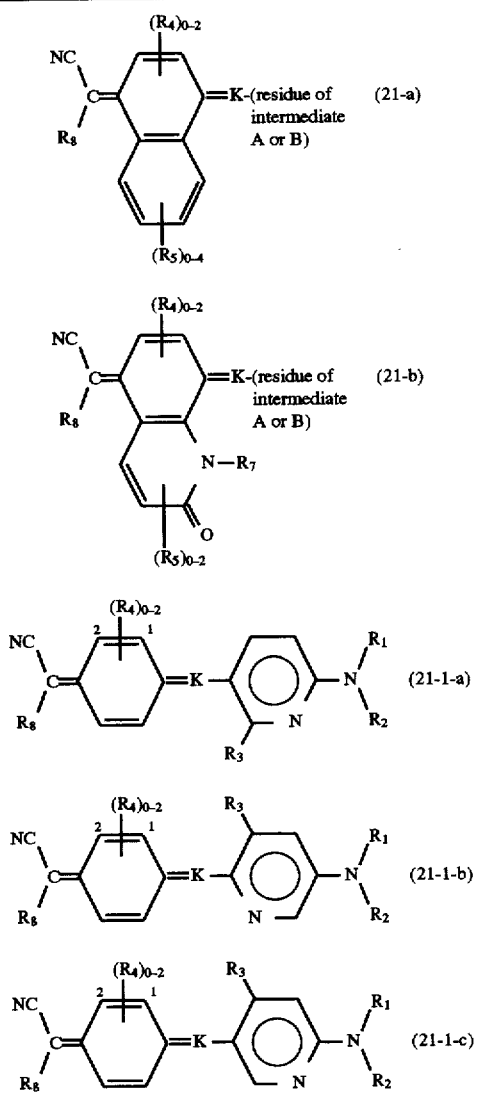
(21-a)
(21-b)
(21-1-a)
(21-1-b)
(21-1-c)

TABLE 21-continued
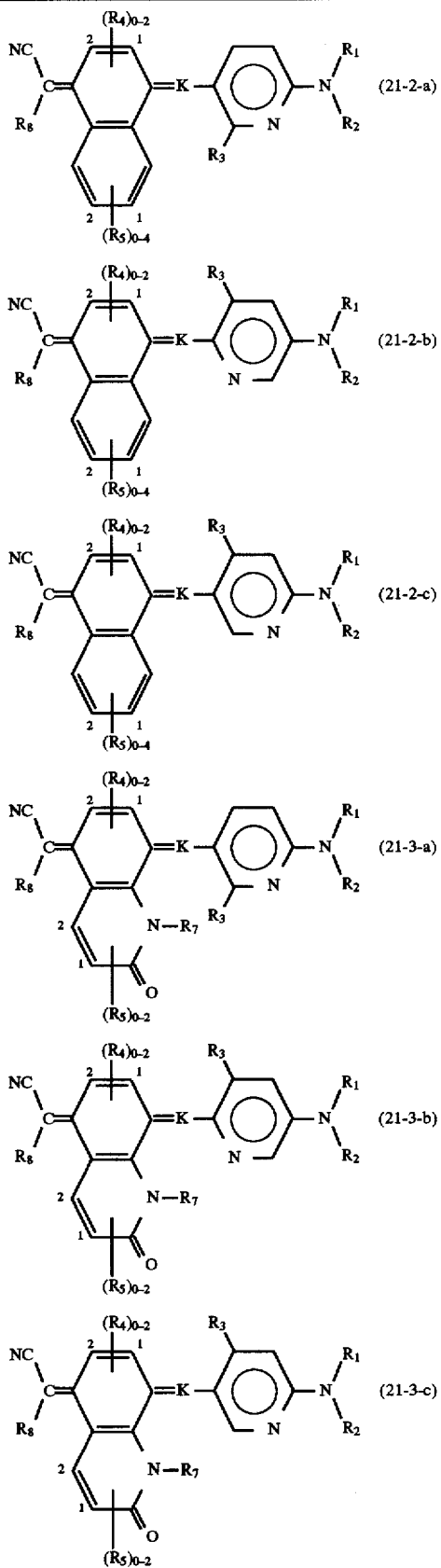

TABLE 21-continued

| No. | $R_1$ | $R_2$ | $R_3$ | $R_4$ | $R_8$ | hue | coloring density | light fastness |
|---|---|---|---|---|---|---|---|---|
| (21-1-a K: =N−) | | | | | | | | |
| 1 | $-C_2H_5$ | $-C_2H_5$ | $-H$ | $-H$ | $-CN$ | leek green | 1.58 | Δ |
| 2 | $-C_2H_5$ | $-C_2H_4OH$ | $-CH_3$ | $-H$ | $-H$ | leek green | 1.57 | Δ |
| 3 | $-C_2H_5$ | $-CH=CH_2$ | $-H$ | $-H$ | $-CH_3$ | leek green | 1.59 | Δ |
| 4 | $-C_2H_5$ | $-Ph$ | $-Cl$ | 1-$CH_3$ | $-CN$ | leek green | 1.65 | Δ |
| 5 | $-C_2H_5$ | $-CH=CHOCOCH_3$ | $-NHCOCH_3$ | 1-$CH_3$ | $-CN$ | leek green | 1.54 | O |
| 6 | $-C_2H_5$ | $-C_2H_4COOCH_3$ | $-OH$ | 1-$CH_3$ | $-CN$ | leek green | 1.53 | O |
| 7 | $-C_2H_5$ | $-C_2H_4OCOC_4H_7$ | $-NHSO_2CH_3$ | 1-$CH_3$ | $-H$ | leek green | 1.47 | O |
| 8 | $-C_2H_5$ | $-C_2H_4OCOOPh$ | $-NHCOCH_3$ | 1-$CH_3$ | $-CH_3$ | leek green | 1.56 | O |
| (21-1-b K: =N−) | | | | | | | | |
| 1 | $-C_2H_5$ | $-C_2H_5$ | $-H$ | $-H$ | $-CN$ | leek green | 1.54 | Δ |
| 2 | $-C_2H_5$ | $-C_2H_4OH$ | $-CH_3$ | $-H$ | $-H$ | leek green | 1.56 | Δ |
| 3 | $-C_2H_5$ | $-CH=CH_2$ | $-H$ | $-H$ | $-CH_3$ | leek green | 1.62 | Δ |
| 4 | $-C_2H_5$ | $-Ph$ | $-Cl$ | 1-$CH_3$ | $-CN$ | leek green | 1.63 | Δ |
| 5 | $-C_2H_5$ | $-CH=CHOCOCH_3$ | $-NHCOCH_3$ | 1-$CH_3$ | $-CN$ | leek green | 1.54 | O |
| 6 | $-C_2H_5$ | $-C_2H_4COOCH_3$ | $-OH$ | 1-$CH_3$ | $-CN$ | leek green | 1.51 | O |
| 7 | $-C_2H_5$ | $-C_2H_4OCOC_4H_7$ | $-NHSO_2CH_3$ | 1-$CH_3$ | $-H$ | leek green | 1.50 | O |
| 8 | $-C_2H_5$ | $-C_2H_4OCOOPh$ | $-NHCOCH_3$ | 2-$CH_3$ | $-CH_3$ | leek green | 1.47 | O |
| (21-1-c K: =N−) | | | | | | | | |
| 1 | $-C_2H_5$ | $-C_2H_5$ | $-H$ | $-H$ | $-CN$ | leek green | 1.61 | Δ |
| 2 | $-C_2H_5$ | $-C_2H_4OH$ | $-CH_3$ | $-H$ | $-H$ | leek green | 1.60 | Δ |
| 3 | $-C_2H_5$ | $-CH=CH_2$ | $-H$ | $-H$ | $-CH_3$ | leek green | 1.58 | Δ |
| 4 | $-C_2H_5$ | $-Ph$ | $-Cl$ | 1-$CH_3$ | $-CN$ | leek green | 1.59 | Δ |
| 5 | $-C_2H_5$ | $-CH=CHOCOCH_3$ | $-NHCOCH_3$ | 1-$CH_3$ | $-CN$ | leek green | 1.57 | O |
| 6 | $-C_2H_5$ | $-C_2H_4COOCH_3$ | $-OH$ | 1-$CH_3$ | $-CN$ | leek green | 1.51 | O |
| 7 | $-C_2H_5$ | $-C_2H_4OCOC_4H_7$ | $-NHSO_2CH_3$ | 1-$CH_3$ | $-H$ | leek green | 1.46 | O |
| 8 | $-C_2H_5$ | $-C_2H_4OCOOPh$ | $-NHCOCH_3$ | 1-$CH_3$ | $-CH_3$ | leek green | 1.50 | O |

| No. | $R_1$ | $R_2$ | $R_3$ | $R_4$ | $R_5$ | $R_7$ | $R_8$ | hue | coloring density | light fastness |
|---|---|---|---|---|---|---|---|---|---|---|
| (21-2-a K: =N−) | | | | | | | | | | |
| 1 | $-C_2H_5$ | $-C_2H_5$ | $-H$ | $-H$ | $-H$ | | $-CN$ | leek green | 1.52 | Δ |
| 2 | $-C_2H_5$ | $-C_2H_4OH$ | $-CH_3$ | $-H$ | $-H$ | | $-H$ | leek green | 1.51 | Δ |
| 3 | $-C_2H_5$ | $-CH=CH_2$ | $-H$ | $-H$ | 2-$CH_3$ | | $-H$ | leek green | 1.50 | Δ |
| 4 | $-C_2H_5$ | $-Ph$ | $-Cl$ | $-H$ | 1-Cl | | $-CN$ | leek green | 1.52 | Δ |
| 5 | $-C_2H_5$ | $-CH=CHOCOCH_3$ | $-NHCOCH_3$ | 2-$CH_3$ | $-H$ | | $-CN$ | leek green | 1.47 | O |
| 6 | $-C_2H_5$ | $-C_2H_4COOCH_3$ | $-OH$ | 2-$CH_3$ | $-H$ | | $-CN$ | leek green | 1.43 | O |
| 7 | $-C_2H_5$ | $-C_2H_4OCOC_4H_7$ | $-NHSO_2CH_3$ | 2-$CH_3$ | 1-Cl | | $-CN$ | leek green | 1.40 | O |
| 8 | $-C_2H_5$ | $-C_2H_4OCOOPh$ | $-NHCOCH_3$ | 2-$CH_3$ | 2-Cl | | $-CH_3$ | leek green | 1.41 | O |
| (21-2-b K: =N−) | | | | | | | | | | |
| 1 | $-C_2H_5$ | $-C_2H_5$ | $-H$ | $-H$ | $-H$ | | $-CN$ | leek green | 1.51 | Δ |
| 2 | $-C_2H_5$ | $-C_2H_4OH$ | $-CH_3$ | $-H$ | $-H$ | | $-H$ | leek green | 1.49 | Δ |
| 3 | $-C_2H_5$ | $-CH=CH_2$ | $-H$ | $-H$ | 2-$CH_3$ | | $-CN$ | leek green | 1.48 | Δ |
| 4 | $-C_2H_5$ | $-Ph$ | $-Cl$ | $-H$ | 1-Cl | | $-CN$ | leek green | 1.53 | Δ |
| 5 | $-C_2H_5$ | $-CH=CHOCOCH_3$ | $-NHCOCH_3$ | 2-$CH_3$ | $-H$ | | $-CN$ | leek green | 1.46 | O |
| 6 | $-C_2H_5$ | $-C_2H_4COOCH_3$ | $-OH$ | 2-$CH_3$ | $-H$ | | $-CN$ | leek green | 1.47 | O |
| 7 | $-C_2H_5$ | $-C_2H_4OCOC_4H_7$ | $-NHSO_2CH_3$ | 2-$CH_3$ | 1-Cl | | $-CN$ | leek green | 1.41 | O |
| 8 | $-C_2H_5$ | $-C_2H_4OCOOPh$ | $-NHCOCH_3$ | 2-$CH_3$ | 2-Cl | | $-CH_3$ | leek green | 1.42 | O |
| (21-2-c K: =N−) | | | | | | | | | | |
| 1 | $-C_2H_5$ | $-C_2H_5$ | $-H$ | $-H$ | $-H$ | | $-CN$ | leek green | 1.52 | Δ |
| 2 | $-C_2H_5$ | $-C_2H_4OH$ | $-CH_3$ | $-H$ | $-H$ | | $-H$ | leek green | 1.47 | Δ |
| 3 | $-C_2H_5$ | $-CH=CH_2$ | $-H$ | $-H$ | 2-$CH_3$ | | $-CN$ | leek green | 1.46 | Δ |
| 4 | $-C_2H_5$ | $-Ph$ | $-Cl$ | $-H$ | 1-Cl | | $-CN$ | leek green | 1.51 | Δ |
| 5 | $-C_2H_5$ | $-CH=CHOCOCH_3$ | $-NHCOCH_3$ | 2-$CH_3$ | $-H$ | | $-CN$ | leek green | 1.48 | O |
| 6 | $-C_2H_5$ | $-C_2H_4COOCH_3$ | $-OH$ | 2-$CH_3$ | $-H$ | | $-CN$ | leek green | 1.43 | O |
| 7 | $-C_2H_5$ | $-C_2H_4OCOC_4H_7$ | $-NHSO_2CH_3$ | 2-$CH_3$ | 1-Cl | | $-CN$ | leek green | 1.42 | O |
| 8 | $-C_2H_5$ | $-C_2H_4OCOOPh$ | $-NHCOCH_3$ | 2-$CH_3$ | 2-Cl | | $-CH_3$ | leek green | 1.44 | O |
| (21-3-a K: =N−) | | | | | | | | | | |
| 1 | $-C_2H_5$ | $-C_2H_5$ | $-H$ | $-H$ | $-H$ | $-H$ | $-CN$ | leek green | 1.60 | Δ |
| 2 | $-C_2H_5$ | $-C_2H_4OH$ | $-CH_3$ | $-H$ | $-H$ | $-H$ | $-H$ | leek green | 1.56 | Δ |
| 3 | $-C_2H_5$ | $-CH=CH_2$ | $-H$ | $-H$ | 2-$CH_3$ | $-H$ | $-CN$ | leek green | 1.67 | Δ |
| 4 | $-C_2H_5$ | $-Ph$ | $-Cl$ | $-H$ | 1-Cl | $-CH_3$ | $-CN$ | leek green | 1.62 | Δ |
| 5 | $-C_2H_5$ | $-CH=CHOCOCH_3$ | $-NHCOCH_3$ | 2-$CH_3$ | $-H$ | $-CH_3$ | $-CN$ | leek green | 1.51 | O |
| 6 | $-C_2H_5$ | $-C_2H_4COOCH_3$ | $-OH$ | 2-$CH_3$ | $-H$ | $-C_2H_4OC_2H_5$ | $-CN$ | leek green | 1.54 | O |
| 7 | $-C_2H_5$ | $-C_2H_4OCOC_4H_7$ | $-NHSO_2CH_3$ | 2-$CH_3$ | 1-Cl | $-H$ | $-CN$ | leek green | 1.50 | O |
| 8 | $-C_2H_5$ | $-C_2H_4OCOOPh$ | $-NHCOCH_3$ | 2-$CH_3$ | 2-Cl | $-CH_3$ | $-CH_3$ | leek green | 1.48 | O |

TABLE 21-continued (21-3-b K: =N—)

|   |        |              |          |       |        |            |        |           |      |   |
|---|--------|--------------|----------|-------|--------|------------|--------|-----------|------|---|
| 1 | —C₂H₅  | —C₂H₅        | —H       | —H    | —H     | —H         | —CN    | leek green | 1.57 | Δ |
| 2 | —C₂H₅  | —C₂H₄OH      | —CH₃     | —H    | —H     | —H         | —H     | leek green | 1.58 | Δ |
| 3 | —C₂H₅  | —CH=CH₂      | —H       | —H    | 2-CH₃  | —H         | —CN    | leek green | 1.62 | Δ |
| 4 | —C₂H₅  | —Ph          | —Cl      | —H    | 1-Cl   | —CH₃       | —CN    | leek green | 1.64 | Δ |
| 5 | —C₂H₅  | —CH=CHOCOCH₃ | —NHCOCH₃ | 2-CH₃ | —H     | —CH₃       | —CN    | leek green | 1.60 | ○ |
| 6 | —C₂H₅  | —C₂H₄COOCH₃  | —OH      | 2-CH₃ | —H     | —C₂H₄OC₂H₅ | —CN    | leek green | 1.58 | ○ |
| 7 | —C₂H₅  | —C₂H₄OCOC₄H₇ | —NHSO₂CH₃ | 2-CH₃ | 1-Cl  | —H         | —CN    | leek green | 1.49 | ○ |
| 8 | —C₂H₅  | —C₂H₄OCOOPh  | —NHCOCH₃ | 2-CH₃ | 2-Cl   | —CH₃       | —CH₃   | leek green | 1.53 | ○ |

(21-3-c K: =N—)

|   |        |              |          |       |        |            |        |           |      |   |
|---|--------|--------------|----------|-------|--------|------------|--------|-----------|------|---|
| 1 | —C₂H₅  | —C₂H₅        | —H       | —H    | —H     | —H         | —CN    | leek green | 1.54 | Δ |
| 2 | —C₂H₅  | —C₂H₄OH      | —CH₃     | —H    | —H     | —H         | —H     | leek green | 1.59 | Δ |
| 3 | —C₂H₅  | —CH=CH₂      | —H       | —H    | 2-CH₃  | —H         | —CN    | leek green | 1.58 | Δ |
| 4 | —C₂H₅  | —Ph          | —Cl      | —H    | 1-Cl   | —CH₃       | —CN    | leek green | 1.61 | Δ |
| 5 | —C₂H₅  | —CH=CHOCOCH₃ | —NHCOCH₃ | 2-CH₃ | —H     | —CH₃       | —CN    | leek green | 1.57 | ○ |
| 6 | —C₂H₅  | —C₂H₄COOCH₃  | —OH      | 2-CH₃ | —H     | —C₂H₄OC₂H₅ | —CN    | leek green | 1.56 | ○ |
| 7 | —C₂H₅  | —C₂H₄OCOC₄H₇ | —NHSO₂CH₃ | 2-CH₃ | 1-Cl  | —H         | —CN    | leek green | 1.50 | ○ |
| 8 | —C₂H₅  | —C₂H₄OCOOPh  | —NHCOCH₃ | 2-CH₃ | 2-Cl   | —CH₃       | —CH₃   | leek green | 1.49 | ○ |

The thermal transfer sheet of the present invention is characterized in that use is made of the above-described particular dyes. The other constitution may be the same as that in the conventional thermal transfer sheet.

The substrate sheet containing the above-described dye used in the thermal transfer sheet of the present invention may be any known one having a heat resistance and a strength to some extent. Examples of the substrate sheet include paper having a thickness in the range of from about 0.5 to 50 μm, preferably in the range of from about 3 to 10 μm, various types of converted paper, a polyester film, a polystyrene film, a polypropylene film, a polysulfone film, a polycarbonate film, an aramid film, a polyvinyl alcohol film and cellophane. A polyester film is particularly preferred.

The dye supporting layer provided on the surface of the above-described substrate sheet comprises a layer produced by supporting on the substrate sheet a dye selected from those represented by the general formula (I) by means of an arbitrary resin.

The binder resin for supporting the above-described dye may be any conventional one, and preferred examples thereof include cellulose resins such as ethyl cellulose, hydroxyethyl cellulose, ethylhydroxy cellulose, hydroxypropyl cellulose, methyl cellulose, cellulose acetate and cellulose acetate butyrate, and vinyl resins such as polyvinyl alcohol, polyvinyl acetate, polyvinyl butyral, polyvinyl acetoacetal, polyvinyl pyrrolidone and polyacrylamide. Among them, polyvinyl butyral and polyvinyl acetal are particularly preferred from the viewpoint of the heat resistance and the migration of a dye.

The dye supporting layer of the thermal transfer sheet of the present invention is basically comprised of the above-described material and, if necessary, additionally contains various additives known in the art.

The above-described dye supporting layer is preferably formed by adding the above-described dye, binder resin and optional components to a suitable solvent to dissolve or disperse the individual components in the solvent to prepare a coating solution or an ink for the formation of a supporting layer, coating the coating solution or ink on the substrate sheet and drying the resultant coating.

The thickness of the supporting layer thus formed is in the range of from about 0.2 to 5.0 μm, preferably in the range of from about 0.4 to 2.0 μm. The content of the dye in the supporting layer is preferably 5 to 70% by weight, still preferably 10 to 60 % by weight based on the weight of the supporting layer.

Although the thermal transfer sheet of the present invention, as such, is sufficiently useful for a thermal transfer application, it is also possible to further provide a surface tack eliminating layer, that is, a release layer, on the surface of the dye supporting layer. The provision of such a layer enables the tack adhesion of the thermal transfer sheet to the transfer material to be prevented during the thermal transfer, so that an image having a better density can be formed through the use of a higher thermal transfer temperature.

Regarding the release layer, a considerable effect can be attained by merely adhering an antitack inorganic powder. Further, for example, it is also possible to select a highly releasable resin, such as a silicone polymer, an acrylic polymer or a fluorinated polymer, and to provide a release layer of the selected resin having a thickness in the range of from 0.01 to 5 μm, preferably in the range of from 0.05 to 2 μm.

The inorganic powder or releasable polymer can exhibit a sufficient effect also when it is incorporated in the dye supporting layer.

Further, a heat resistant layer may be additionally provided on the back surface of the thermal transfer sheet for the purpose of preventing an adverse effect of heat from a thermal head.

The transfer material used for forming an image through the use of the above-described thermal transfer sheet may be any one as far as the recording face has a capability of accepting the above-described dye. When the transfer material is paper, a metal, glass, a synthetic resin or other material incapable of accepting the dye, a dye accepting layer may be formed on one surface such a material.

Means for applying a thermal energy used in the thermal transfer through the use of the thermal transfer sheet according to the present invention and the recording material may be any means known in the art. For example, a desired object can be sufficiently attained by applying a thermal energy of about 5 to 100 mJ/mm² through the control of a recording time by means of a recording device, for example, a thermal printer (for example, a video printer VY-100 manufactured by Hitachi, Limited).

The present invention will now be described in more detail with reference to the following Example and Comparative Example. In the Examples and Comparative Examples, "parts" is by weight unless otherwise specified.

EXAMPLE

An ink composition comprising the following components for the formation of a dye supporting layer was prepared, and the ink composition was coated on a 6 μm-thick polyethylene terephthalate film having a back surface subjected to tropicalization so that the coverage on a dry basis was 1.0 g/m². The resultant coating was dried to give the thermal transfer sheet of the present invention.

| Dye listed in Table A1 | 3 parts |
| Polyvinyl butyral resin | 4.5 parts |
| Methyl ethyl ketone | 46.25 parts |
| Toluene | 46.25 parts |

In the above-described composition, when the dye was insoluble, DMF, dioxane, chloroform or the like was properly used as a solvent, when the dye was not be sufficiently dissolved in the solvent, use was made of the filtrate.

Then, synthetic paper (Yupo FPG #150 manufactured by Oji-Yuka Synthetic Paper Co., Ltd.) was used as the substrate sheet, and a coating solution having the following composition was coated on one surface of the synthetic paper so that the coverage on a dry basis was 10.0 g/m². The resultant coating was dried at 100° C. for 30 min to give a thermal transfer sheet.

| Polyester resin (Vylon 200 manufactured by Toyobo Co., Ltd.) | 11.5 parts |
| Vinyl chloride/vinyl acetate copolymer (VYHH manufactured by UCC) | 5.0 parts |
| Amino modified silicone (KF-393) (manufactured by The Shin-Etsu Chemical Co., Ltd.) | 1.2 parts |
| Epoxy modified silicone (X-22-343) (manufactured by The Shin-Etsu Chemical Co., Ltd.) | 1.2 parts |
| Methyl ethyl ketone/toluene/cyclohexanone (weight ratio of 4:4:2) | 102.0 parts |

The above-described thermal transfer sheet of the present invention and the above-described transfer material were put on top of the other in such a manner that the dye supporting layer and the dye accepting surface faced each other. Recording was conducted by means of a thermal head from the back surface of the thermal transfer sheet under conditions of a head applied voltage of 11 V and a setting time of 14.0 msec. The results are given in the above-described tables.

Comparative Examples 1 to 5

The procedure of Example 1 was repeated, except that dyes listed in the following Table 22 were used instead of the dyes used in Example 1. The results are given in the following Table 22.

TABLE 22

| Comp. Ex. | Coloring density | Light fastness |
|---|---|---|
| 1 | 0.99 | × |
| 2 | 1.16 | Δ |
| 3 | 2.07 | × |
| 4 | 1.12 | Δ |
| 5 | 1.02 | × |

Note)
Comp. Ex. 1 = C.I. Disperse Blue 14

TABLE 22-continued

| Comp. Ex. | Coloring density | Light fastness |
|---|---|---|

Comp. Ex. 2 = C.I. Disperse Blue 134
Comp. Ex. 3 = C.I. Solvent Blue 63
Comp. Ex. 4 = C.I. Disperse Blue 26
Comp. Ex. 5 = C.I. Disperse Violet 4

The above-described recording density is a value measured by densitometer RD-918 manufactured by Macbeth, U.S.A.

The light fastness test was conducted by subjecting an image to irradiation by means of a xenon arc light (50 KLux) for 24 hr. When no change in the sharpness of the image was observed after this test, the light fastness was evaluated as "○"; when a slight deterioration in the sharpness of the image was observed, the light fastness was evaluated as "Δ"; and when a deterioration in the sharpness of the image was observed, the light fastness was evaluated as "X".

Mutagenic Test:

Ames test was conducted as an identical amest test with respect to representative examples of the intermediate of the present invention and control dyes having the same structure as that of the intermediate of the present invention, except that the ring was a pyridine ring instead of the phenyl ring.

The ames test was conducted in such a state that Salmonella TA1538 and TA98 were metabolically activated by a preincubation method (+x9mix). The dye was used in contentrations in five grades in the range of from 0 to 5 mg. Acetone was used as the solvent control. The toxicity was judged based on the maximum increase in the colony of the sample as compared with the solvent control. Specifically, when the increase in the reversion colony was twice or more as compared with that in the case of the control, the mutagenicity was judged as positive, while when the increase in the reversion colony was less than twice as compared with that in the case of the control, the mutagenicity was judged as negative. The results are given in the following Table.

TABLE 23

| Dye of the present invention | Increase (times) | Toxicity |
|---|---|---|
| (10-1-a K = —N=N— No. 1) | 1.5 | negative |
| (6-a No. 4) | 1.3 | negative |

TABLE 23-continued

| Dye of the present invention | Increase (times) | Toxicity |
|---|---|---|
| NHCOCH₃ structure (5-a No. 14) | 1.5 | negative |
| CH₃/Ph pyrazole azo structure | 2.2 | positive |
| CONNHC₃H₇ naphthoquinone structure | 5.2 | positive |
| NHCOCH₃ structure | 1.7 | negative |

As is apparent from the foregoing description, a thermal transfer sheet excellent in the coloring density, sharpness and light fastness can be provided through the use of an intermediate having a particular structure and a dye produced by making use of the intermediate as a starting compound.

What is claimed is:

1. An azomethine dye produced by coupling a pyridine derivative represented by the following formula A or B with a coupler capable of providing a C=N— linkage at Z of A or B:

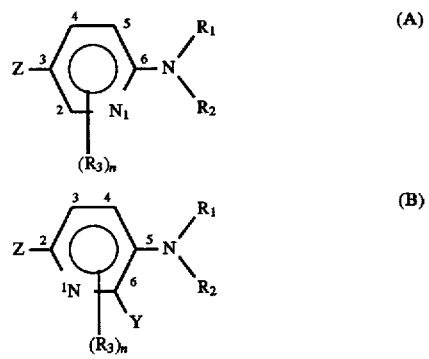

wherein

Z stands for an atom or atom group having a coupling capability selected from a hydrogen atom, an amino group, a halogen atom, a nitro group and a nitroso group;

$R_1$ and $R_2$ each independently stand for a hydrogen atom or a substituted or unsubstituted alkyl group having 1 to 8 carbon atoms, vinyl group, allyl group, aryl group, alkoxyalkyl group having 2 to 12 carbon atoms, aralkyl group, alkoxycarbonylalkyl group having 3 to 12 carbon atoms, carboxyalkyl group having 3 to 12 carbon atoms, alkoxycarboxyalkyl group having 3 to 12 carbon atoms, substituted or unsubstituted cycloalkyl group having 3 to 12 carbon atoms, substituted or unsubstituted acylamino group having 2 to 12 carbon atoms, substituted or unsubstituted alkylsulfonylamino group having 1 to 12 carbon atoms, substituted or unsubstituted oxycarbonyl group having 2 to 12 carbon atoms, substituted or unsubstituted ureido group having 1 to 8 carbon atoms, substituted or unsubstituted carbamoyl group having 2 to 12 carbon atoms, substituted or unsubstituted sulfamoyl group having 1 to 12 carbon atoms, substituted or unsubstituted heterocyclic group having 2 to 12 carbon atoms, substituted or unsubstituted acyl croup having 2 to 12 carbon atoms, substituted or unsubstituted amino group or substituted or unsubstituted sulfonyl group having 1 to 12 carbon atoms, provided that $R_1$ and $R_2$ may combine with each other to form a ring or $R_1$ and $R_2$ may bond at the 5 position on (A), or the 4 position on (B) and/or the 6 position on (B) to form a ring;

$R_3$ stands for hydroxyl group, a halogen atom, a cyano group or a substituted or unsubstituted alkyl group having 1 to 8 carbon atoms, alkylcarbonyl group having 2 to 8 carbon atoms, carbamoyl group, sulfamoyl group, amino group, carboxyl group, alkoxy group or unreido group; and n is an integer of 0 to 3.

2. An azomethin dye according to claim 1, which is represented by the following formula:

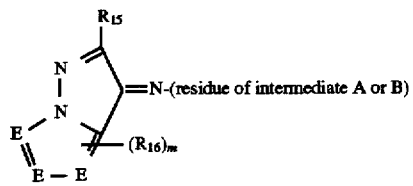

wherein $R_{15}$ and $R_{16}$ stand for a hydrogen atom, a halogen atom, a hydroxyl group, a cyano group, a nitro group or a substituted or unsubstituted alkyl group, aryl group, allyl group, aralkyl group, alkoxyalkyl group, alkoxy group, heterocyclic group, aralkylalkoxyalkyl group, carbamoyl group, sulfamonyl group, oxycarbonylalkyl group, oxycarbonyl group, carboxyalkyl group, formylamino group, sulfonylamino group, amino group or cycloalkyl group; E stands for a nitrogen atom or a carbon atom; and m is an integer of 0 to 3.

3. An azomethin dye according to claim 1, which is represented by the following general formula (1) or (2):

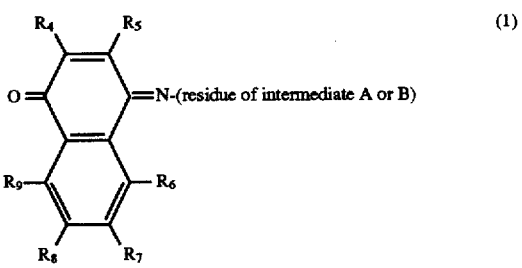

wherein $R_4$ to $R_9$ stand for a hydrogen atom, a halogen atom or a substituted or unsubstituted alkyl group, alkoxy group, amino group, ureido group, —CON($R_{10}$)($R_{11}$), —CSN($R_{10}$)($R_{11}$), —SO$_2$N($R_{10}$)($R_{11}$), —COOR$_{10}$ or —CSOR$_{10}$ wherein $R_{10}$ and $R_{11}$ stand for a hydrogen atom, a halogen atom or a substituted or unsubstituted alkyl group having 1 to 12 carbon atoms, cycloalkyl group having 3 to 8 carbon atoms, aryl group, vinyl group, ally group or aromatic heterocyclic group, provided that $R_{10}$ and $R_{11}$ may combine with each other to form a ring; or

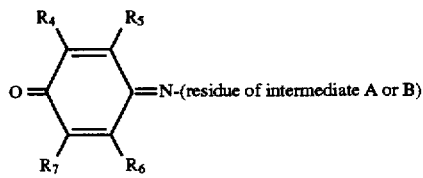
(2)

wherein $R_4$ stands for a hydrogen atom, a halogen atom or a substituted or unsubstituted alkyl group having 1 to 8 carbon atoms, alkoxy group having 1 to 8 carbon atoms, amino group, ureido group, carbamoyl group, sulfamoyl group, —NHCOR$_8$, —NHCSR$_8$, —NHCON($R_8$) ($R_9$), —NHCSN($R_8$)($R_9$), —NHCOOR$_8$, —NHCSOR$_8$, —NHCONHR$_8$, —NHCSNHR$_8$, —NHSO$_2$R$_8$ or —NHSO$_2$N($R_8$)($R_9$) wherein $R_8$ and $R_9$ stand for a hydrogen atom, a halogen atom or a substituted or unsubstituted alkyl group having 1 to 12 carbon atoms, aryl group, vinyl group, ally group, cycloalkyl group having 3 to 8 carbon atoms or aromatic heterocyclic group, provided that $R_8$ and $R_9$ may combine with each other to form a ring; and $R_5$ and $R_7$ stand for a hydrogen atom, a halogen atom or a substituted or unsubstituted alkyl group having 1 to 12 carbon atoms, alkoxy group having 1 to 8 carbon atoms, amino group, formylamino group, alkylformylamino group having 1 to 8 carbon atoms, sulfonylamino group, alkylsulfonylamino group having 1 to 8 carbon atoms, ureido group, carbamoyl group, sulfamoyl group or carboxyl group.

4. An azomethin dye according to claim 1, which is represented by the following structural formula (3) or (4):

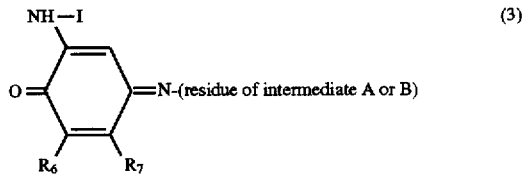
(3)

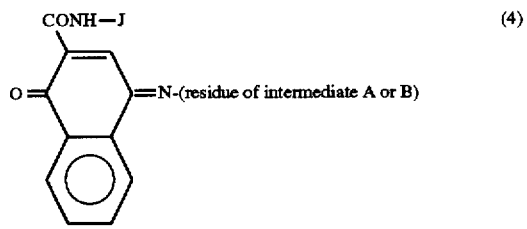
(4)

wherein I stands for —COJ, —CONHJ, —CONHCOJ, —SO$_2$J, —SO$_2$NHJ, —SO$_2$NHCOJ, —COOJ, —CSJ, —CSOJ or —CSNHJ wherein J stands for a hydrogen atom, a halogen atom or a substituted or unsubstituted alkyl group having 1 to 12 carbon atoms, aryl group, vinyl group, allyl group, cycloalkyl group having 3 to 8 carbon atoms, aralkyl group, alkenyl group or heterocyclic group.

* * * * *